US008802109B2

(12) United States Patent
Davido et al.

(10) Patent No.: US 8,802,109 B2
(45) Date of Patent: Aug. 12, 2014

(54) HERPES SIMPLEX VIRUS MUTANT ICP0

(75) Inventors: David Davido, Lawrence, KS (US); William Halford, Springfield, IL (US)

(73) Assignees: University of Kansas, Lawrence, KS (US); Southern Illinois University, Springfield, IL (US)

( * ) Notice: Subject to any disclaimer, the term of this patent is extended or adjusted under 35 U.S.C. 154(b) by 492 days.

(21) Appl. No.: 12/749,415

(22) Filed: Mar. 29, 2010

(65) Prior Publication Data

US 2010/0226940 A1    Sep. 9, 2010

Related U.S. Application Data

(63) Continuation-in-part of application No. 12/167,870, filed on Jul. 3, 2008, now Pat. No. 7,785,605.

(60) Provisional application No. 60/948,048, filed on Jul. 5, 2007.

(51) Int. Cl.
*C12N 7/00*    (2006.01)
*C12N 7/04*    (2006.01)

(52) U.S. Cl.
USPC ................ 424/205.1; 424/231.1; 435/235.1; 435/236

(58) Field of Classification Search
None
See application file for complete search history.

(56) References Cited

PUBLICATIONS

Cai et al (Journal of Virology 67:7501-7512, 1993).*
Halford, W.P. et. al., 'Herpes simplex virus 2 ICP0—mutant viruses are avirulent and immunogenic: Implications for a genital herpes vaccine. PLoS One, vol. 5, Issue.8, e12251, Aug. 17, 2010 See the whole document.
Halford, W.P. et. al., 'ICP0 antagonizes Stat 1-dependent repression of herpes simplex virus: implications for the regulation of viral latency.', Virology Journal, vol. 3, No. 44, Jun. 9, 2006 See Abstract; Table 1; Figure 2,4,9; pp. 17-18.
Minaker, R.L. et. al., 'Functional inaccessibility of quiescent herpes simplex virus genomes.', Virology Journal, vol. 2, No. 85, Nov. 21, 2005 See Abstract.
Kyratsous, C.A. et. al., 'Complementation of a herpes simplex virus ICP0 null mutant by varicella—zoster virus ORF61pV.' , Journal of Virology, vol .83, No. 20, pp. 10637-10643, Aug. 5, 2009 See Abstract; p. 10638; Fig.1.
Mossman, K.L. et. al. 'Herpes simplex virus ICP0 mutants are hypersensitive to interferon.', Journal of Virology, vol. 74, No. 4, pp. 2052-2056, Feb. 2000 See Abstract; Table.
PCT/US2011/030372, Dec. 23, 2011, International Search Report and Written Opinion.

* cited by examiner

*Primary Examiner* — Mary E Mosher
(74) *Attorney, Agent, or Firm* — Workman Nydegger

(57) ABSTRACT

A mutant herpesvirus that has a mutated gene that encodes a mutant infected cell protein 0 (ICP0) can be used in therapeutic methods as well as in diagnostics and research experiments. The encoded mutant ICP0 protein can be altered in one or more regions of ICP0 that are substantially conserved between two or more herpesviruses and/or within a phosphorylation region. The mutant herpesvirus can be substantially avirulent and immunogenic.

14 Claims, 54 Drawing Sheets

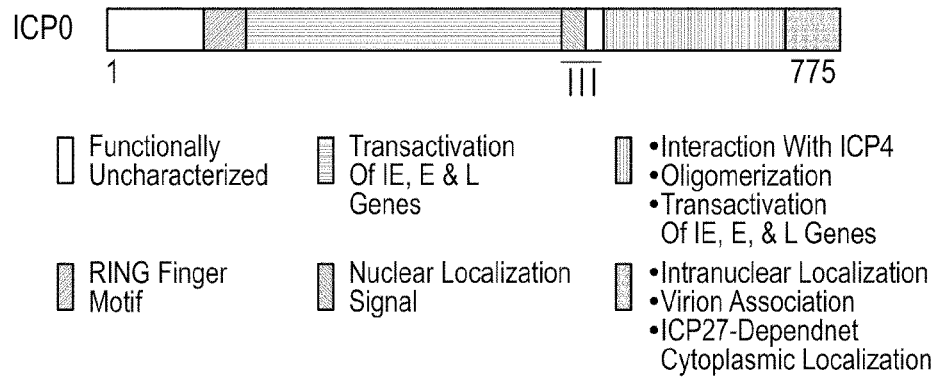
*Fig. 1A*
| Region | | Peptide Sequence | |
|---|---|---|---|
| III | 505 | RRGSGQENPSPQSTRPPLAPAGAK | 528 |
| | 508 | S CaM II, CKII, p70s6K, PKA, PKG | |
| | 514 | S CDK-1 or -2 | |
| | 517 | S PKC | |
| | 518 | T CKI | |
*Fig. 1B*
*Fig. 1C*

HSV-1s vs HSV-2s ICP0.apr

```
────────────────────────────────────────────────────────────────── Section 1
                        (1) 1         10        20        30        40        51
HSV-1 (Syn17+) ICP0     (1) MEPRPGASTRRPEGRPQREP---------APDVWVFPCDRDLPDSSDSEAE
HSV-2 (HG52) ICP0       (1) MEPRPGTSSRADPG-PERPPRQTPGTQPAAPHAWGMLNDMWQLASSDSEEE
           Consensus    (1) MEPRPG SSR    G P R P        AP  W   D    SSDSE E
────────────────────────────────────────────────────────────────── Section 2
                       (52) 52        60        70        80        90       102
HSV-1 (Syn17+) ICP0    (43) TEVGGRGDADHHDDDSASEADSTDTELFETGLLGPQGVDGGAVSG--GSPP
HSV-2 (HG52) ICP0      (51) TEVG--ISDDDLHRDSTSEAGSTDTEMFEAGLMDAATPPARPPAERQGSPT
           Consensus   (52) TEVG      D    DS SEA STDTELFE GLL       A    A GSP
────────────────────────────────────────────────────────────────── Section 3
                      (103) 103       110       120       130       140       153
HSV-1 (Syn17+) ICP0    (92) REEDPGSCGGAPP--REDGGSDEGDVCAVCTDEIAPHLRCDTFPCMHRFCI
HSV-2 (HG52) ICP0     (100) PADAQGSCGGGPVGEEEAEAGGGGDVCAVCTDETAPPLRCQSFPCLHPFCI
           Consensus  (103)    D GSCGGAP    E  A    GDVCAVCTDEIAP LRC SFPCLH FCI
────────────────────────────────────────────────────────────────── Section 4
                      (154) 154       160       170       180       190       204
HSV-1 (Syn17+) ICP0   (141) PCMKTWMQLRNTCPLCNAKLVYLIVGVTPSGSFSTIPIVNDPQTRMEAEEA
HSV-2 (HG52) ICP0     (151) PCMKTWIPLRNTCPLCNTPVAYLIVGVTASGSFSTIPIVNDPRTRVEAEAA
           Consensus  (154) PCMKTWI LRNTCPLCN   YLIVGVT SGSFSTIPIVNDP TRMEAE A
────────────────────────────────────────────────────────────────── Section 5
                      (205) 205       210       220       230       240       255
HSV-1 (Syn17+) ICP0   (192) VRAGTAVDFIWTGNQRFAPRYLTLGGHTVRALSPTHPEPTTDEDDDDLDDA
HSV-2 (HG52) ICP0     (202) VRAGTAVDFIWTGNPRTAPRSLSLGGHTVRALSPTPPWPGTDDEDDDLADV
           Consensus  (205) VRAGTAVDFIWTGN R APR LSLGGHTVRALSPT P P TDDDDDDL D
────────────────────────────────────────────────────────────────── Section 6
                      (256) 256       270       280       290       300       306
HSV-1 (Syn17+) ICP0   (243) DYVPPAPRRTPRAPPRRGAAAPPVTGGASHAAPQPAAARTAPPSAPIGPHG
HSV-2 (HG52) ICP0     (253) DYVPPAPRRAPRR-----GGGG---AGATRGTSQPAATRPAPPGAPRSSSS
           Consensus  (256) DYVPPAPRR PR         AAA   AGAS A  QPAA R APP  AP
────────────────────────────────────────────────────────────────── Section 7
                      (307) 307       320       330       340       350       357
HSV-1 (Syn17+) ICP0   (294) SSNHTTTTNSSGGGGSRQSRAAAPRGASGP--SGGVGVGVGVVEAEAGRPR
HSV-2 (HG52) ICP0     (296) GGAPLRAGVGSGSGGGPAVAAVVPRVASLPPAAGGGRAQARRVGEDAAAAE
           Consensus  (307)          SG GG     A  PR AS P  AGG        V DAA
────────────────────────────────────────────────────────────────── Section 8
                      (358) 358       370       380       390       400       408
HSV-1 (Syn17+) ICP0   (343) GRTGPLVNRPAPLANNRDPIVISDPPASPHRPPAAPMPGSAPR-------
HSV-2 (HG52) ICP0     (347) GRTPPAR---QPRAAQEPPIVISDPPPSPRRP-AGPGPLSFVSSSSAQVS
           Consensus  (358) GRT P      P  AN   PIVISDPP SP RP AAP P S
```

*Fig. 13A*

HSV-1s vs HSV-2s ICP0.apr

─────────────────────────────────────────────────────────── Section 9
                    (409) 409       420       430       440       459
HSV-1 (Syn17+) ICP0 (387) --PGPPASAAASG-PARPRAAVAPCVRAPP-----PGPGPRAPAPGAEPAA
HSV-2 (HG52) ICP0   (394) SGPGGGGLPQSSGRAARPRAAVAPRVRSPPRAAAAPVVSASADAAGPAPPA
Concensus           (409)   PG A  ASG ARPRAAVAP VRAPP     P     AAG PA
─────────────────────────────────────────────────────────── Section 10
                    (460) 460       470       480       490       500       510
HSV-1 (Syn17+) ICP0 (430) RPADARRVPQSHSSLAQAANQEQSLCRARATVARGSGGPGVEGGHGPSRGA
HSV-2 (HG52) ICP0   (445) VPVDAHRAPRSRMTQAQTDTQAQSLGRAGATDARGSGGPGAEGGPGVPRGT
Concensus           (460)  P DA R P S   S AQ   Q QSL RA AT ARGSGGPG EGG G RG
─────────────────────────────────────────────────────────── Section 11
                    (511) 511       520       530       540       550       561
HSV-1 (Syn17+) ICP0 (481) APSGAAPLPSAASVEQEAAVRPRKRRGSGQENPSPQSTRPPLAP-------
HSV-2 (HG52) ICP0   (496) NTPGAAPHAAEG-----AAAARPRKRRGSDSGPAASSSASSSAAPRSPLAPQ
Concensus           (511)   GAAP  A A       AA RPRKRRGS         A S    AP
─────────────────────────────────────────────────────────── Section12
                    (562) 562       570       580       590       600       612
HSV-1 (Syn17+) ICP0 (525) -AGAKRAATHPPSDSGPGGRGQG------GPGTPLTS-----SAASASSS
HSV-2 (HG52) ICP0   (542) GVGAKRAAPRRAPDSDSGDRGHGPLAPASAGAAPPSASPSSQAAVAAASSS
Concensus           (562)  GAKRAA     DS G RG G           GAP S      A AAASSS
─────────────────────────────────────────────────────────── Section13
                    (613) 613       620       630       640       650       683
HSV-1 (Syn17+) ICP0 (563) SASSSSAPTPAGAASSAAGAASSSASASS----------GGAVGALGGRQE
HSV-2 (HG52) ICP0   (593) SASSSSASSSSASSSSASSSSASSSSASSSSASSSAGGAGGSVASASGAGE
Concensus           (613) SASSSSA S  AAAASSAA AAASSASASS          GGAVAA  G E
─────────────────────────────────────────────────────────── Section 14
                    (664) 664       670       680       690       700       714
HSV-1 (Syn17+) ICP0 (604) --ETSLGPRAASGPRGPRKCARKTRHAETS----GAVPAGGLTRYLPISGV
HSV-2 (HG52) ICP0   (644) RRETSLGPRAAAP-RGPRKCARKTRHAEGGPEPGARDPAPGLTRYLPIAGV
Concensus           (664)   ETSLGPRAAA  RGPRKCARKTRHAE       A  PA GLTRYLPIAGV
─────────────────────────────────────────────────────────── Section 15
                    (715) 715       720       730       740       750       765
HSV-1 (Syn17+) ICP0 (649) SSVVALSPYVNKTITGDCLPILDMETGNIGAYVVLVDQTGNMATRLRAAVP
HSV-2 (HG52) ICP0   (694) SSVVALAPYVNKTVTGDCLPVLDMETGHIGAYVVLVDQTGNVADLLRAAAP
Concensus           (715) SSVVALAPYVNKTTGDCLP LDMETG IGAYVVLVDQTGN  LRAA P
─────────────────────────────────────────────────────────── Section 16
                    (766) 766       780       790       800       816
HSV-1 (Syn17+) ICP0 (700) GWSRRTLLPETAGNHVMPPEYPTAPASEWNSLWMTPVGNMLFDQGTLVGAL
HSV-2 (HG52) ICP0   (745) AWSRRTLLPEHARNCVRPPDYPTPPASEWNSLWMTPVGNMLFDQGTLVGAL
Concensus           (766) AWSRRTLLPE A N V PPDYPT PASEWNSLWMTPVGNMLFDQGTLVGAL
─────────────────────────────────────────────────────────── Section 17
                    (817) 817       830       846
HSV-1 (Syn17+) ICP0 (751) DFRSLRSRHPWSGEQGASTRDEGKQ-----
HSV-2 (HG52) ICP0   (796) DFHGLRSPHPWSREQGAPAPAGDAPAGHGE
Concensus           (817) DF  LRSRHPWS EQGA

*Fig. 13A*
Continued

HSV-1s vs HSV-2s ICP0.apr

```
──────────────────────────────────────────────────────────────── Section 1
                      (1)  1        10         20         30         40       52
HSV-1 (KOS) ICP0      (1)  MEPRPGASTRR---PEGRPQREP-----APDVWVFPCDRDLPDSSDSEAETE
HSV-2 (HG52) ICP0     (1)  MEPRPGTSSRADPGPERPPRQTPGTQPAAPHAWGMLNDMQWLASSDSEEETE
           Concensus  (1)  MEPRPG SSR   PE  P     P     AP W  D    SSDSE ETE
──────────────────────────────────────────────────────────────── Section 2
                     (53)  53       60         70         80         90      104
HSV-1 (KOS) ICP0     (45)  VGGRGDADHHDDDSASEADSTDTELFETGLLGPQGVDGG--AVSGGSPPREE
HSV-2 (HG52) ICP0    (53)  VG--ISDDDLHRDSTSEAGSTDTEMFEAGLMDAATPPARPPAERQGSPTPAD
           Concensus (53)  VG    D    DS SEA STDTELFE GLL    A   A  GSP    D
──────────────────────────────────────────────────────────────── Section 3
                    (105)  105      110        120        130        140     156
HSV-1 (KOS) ICP0    (95)   DPGSCGGAPPRED--GGSDEGDVCAVCTDEIAPHLRCDTFPCMHRFCIPCMK
HSV-2 (HG52) ICP0  (103)   AQGSCGGGPVGEEEAEAGGGGDVCAVCTDEIAPPLRCQSFPCLHPFCIPCMK
           Concensus(105)     GSCGGAP  ED    A   GDVCAVCTDEIAP LRC SFPCLH FCIPCMK
──────────────────────────────────────────────────────────────── Section 4
                    (157)  157      170        180        190        200     208
HSV-1 (KOS) ICP0   (145)   TWMQLRNTCPLCNAKLVYLIVGVTPSGSFSTIPIVNDPQTRMEAEEAVRAGT
HSV-2 (HG52) ICP0  (155)   TWIPLRNTCPLCNTPVAYLIVGVTASGSFSTIPIVNDPRTRVEAEAAVRAGT
           Concensus(157)  TWI LRNTCPLCN   L YLIVGVT SGSFSTIPIVNDP TR EAE AVRAGT
──────────────────────────────────────────────────────────────── Section 5
                    (209)  209      220        230        240        250     260
HSV-1 (KOS) ICP0   (197)   AVDFIWTGNQRFAPRYLTLGGHTVRALSPTHPEPTTDEDDDDLDDADYVPPA
HSV-2 (HG52) ICP0  (207)   AVDFIWTGNPRTAPRSLSLGGHTVRALSPTPPWPGTDDEDDDLADVDYVPPA
           Concensus(209)  AVDFIWTGN R APR LSLGGHTVRALSPT P P TDDDDDL D DYVPPA
──────────────────────────────────────────────────────────────── Section 6
                    (261)  261      270        280        290        300     312
HSV-1 (KOS) ICP0   (249)   PRRTPRAPPRRGAAAPPVTGGASHAAPQPAAARTAPPSAPIGPHGSSNTNTT
HSV-2 (HG52) ICP0  (259)   PRRAP----RRGGGG----AGATRGTSQPAATRPAPPGAPRSSSSGGAPLRA
           Concensus(261)  PRR P    RRGAAA     AGAS A QPAA R APP AP
──────────────────────────────────────────────────────────────── Section 7
                    (313)  313      320        330        340        350     364
HSV-1 (KOS) ICP0   (301)   TVSSGGGGSRQSRAAVPRGASGPSGGVG------VVEAEAGRPRGRTGPLVN
HSV-2 (HG52) ICP0  (303)   GVGSGSGGGPAVAAVVPRVASLPPAAGGGRAQARRVGEDAAAAEGRTPPAR-
           Concensus(313)       SG GG     A VPR AS P AA G      V  DAA   GRT P
──────────────────────────────────────────────────────────────── Section 8
                    (365)  365      370        380        390        400     416
HSV-1 (KOS) ICP0   (347)   RPAPLANNRDPIVISDSPPASPHRPP--------AAPMPGSAPRPGPPASAA
HSV-2 (HG52) ICP0  (354)   --QPRAAQEPPIVISDSPPSPRRPAGPGPLSFVSSSSAQVSSGPGGGGLPQ
           Concensus(365)     P  AN  PIVISDSPP SP RP         AA    A PG A
```

*Fig. 13B*

HSV-1s vs HSV-2s ICP0.apr

```
─────────────────────────────────────────────────────────────────── Section 9
              (417) 417         430         440         450         468
HSV-1 (KOS) ICP0 (391) ASG-PARPRAAVAPCVRAPP-----PGPGPRAPAPGAEPAARPADARRVPQS
HSV-2 (HG52) ICP0 (404) SSGRAARPRAAVAPRVRSPPRAAAAPVVSASADAAGPAPPAVPVDAHRAPRS
     Concensus (417) ASG ARPRAAVAP VRAPP     P      AAG PAP DA R P S
─────────────────────────────────────────────────────────────────── Section 10
              (469) 469         480         490         500         510         520
HSV-1 (KOS) ICP0 (437) HSSLAQAANQEQSLCRARATVARGSGGPGVEGGHGPSRGAAPSGAAPSGAPP
HSV-2 (HG52) ICP0 (456) RMTQAQTDTQAQSLGRAGATDARGSGGPGAEGGPGVPRGTNTPGAAPH-AA-
     Concensus (469)    S AQ  Q QSL RA AT ARGSGGPG EGG G  RG    GAAP  A
─────────────────────────────────────────────────────────────────── Section 11
              (521) 521         530         540         550         560         572
HSV-1 (KOS) ICP0 (489) LPSASVEQEAAVRPRKRRGS------GQENPSPQSTRPPLAP--AGAKRAAT
HSV-2 (HG52) ICP0 (506) -------EGAAARPRKRRGSDSGPAASSSASSSAAPRSPLAPQGVGAKRAAP
     Concensus (521)           AA RPRKRRGS          S  A R PLAP  GAKRAA
─────────────────────────────────────────────────────────────────── Section 12
              (573) 573         580         590         600         610         624
HSV-1 (KOS) ICP0 (533) HPPSDSGPGGRGQG-------GPGTPLTS----------SAASASSSSASSS
HSV-2 (HG52) ICP0 (551) RRAPDSDSGDRGHGPLAPASAGAAPPSASPSSQAAVAAASSSSASSSSASSS
     Concensus (573)       DS G RG G        GA P  S         SAASASSSSASSS
─────────────────────────────────────────────────────────────────── Section 13
              (625) 625         630         640         650         660         676
HSV-1 (KOS) ICP0 (568) SAPTPAGATSSATG--AASSSASASSGGAVGALG-----GRQEETSLGPRAA
HSV-2 (HG52) ICP0 (603) SASSSSASSSSASSSSASSSSASSSAGGAGGSVASASGAGERRETSLGPRAA
     Concensus (625) SA S  AAASSSAS   AASSSASASGGA GALA      G  ETSLGPRAA
─────────────────────────────────────────────────────────────────── Section 14
              (677) 677         690         700         710         728
HSV-1 (KOS) ICP0 (613) SGPRGPRKCARKTRHAETS----GAVPAGGLTRYLPISGVSSVVALSPYVNK
HSV-2 (HG52) ICP0 (655) AP-RGPRKCARKTRHAEGGPEPGARDPAPGLTRYLPIAGVSSVVALAPYVNK
     Concensus (677) A  RGPRKCARKTRHAE       A  PA GLTRYLPIAGVSSVVALAPYVNK
─────────────────────────────────────────────────────────────────── Section 15
              729) 729         740         750         760         770         780
HSV-1 (KOS) ICP0 (661) TITGDCLPILDMETGNIGAYVVLVDQTGNMATRLRAAVPGWSRRTLLPETAG
HSV-2 (HG52) ICP0 (706) TVTGDCLPVLDMETGHIGAYVVLVDQTGNVADLLRAAAPAWSRRTLLPEHAR
     Concensus (729) T TGDCLP LDMETG IGAYVVLVDQTGNMA  LRAA PAWSRRTLLPE A
─────────────────────────────────────────────────────────────────── Section 16
              (781) 781         790         800         810         820         832
HSV-1 (KOS) ICP0 (713) NHVTPPEYPTAPASEWNSLWMTPVGNMLFDQGTLVGALDFRSLRSRHPWSGE
HSV-2 (HG52) ICP0 (758) NCVRPPDYPTPPASEWNSLWMTPVGNMLFDQGTLVGALDFHGLRSRHPWSRE
     Concensus (781) N V PPDYPT PASEWNSLWMTPVGNMLFDQGTLVGALDF  LRSRHPWS E
─────────────────────────────────────────────────────────────────── Section 17
              (833) 833         848
HSV-1 (KOS) ICP0 (765) QGASTRDEGKQ-----
HSV-2 (HG52) ICP0 (810) QGAPAPAGDAPAGHGE
     Concensus (833) QGA
```

*Fig. 13B*
*Continued*

HSV-1's vs HSV-2's ICP0 Protein

1. RING finger region      87% homology
   • a.a. 113 - 242 in HSV-1 ICP0 / a.a. 123 - 252 in HSV-2 ICP0
2. Nuclear localization signal (NLS) region    65% homology
   • a.a. 453 - 531 in HSV-1 ICP0 / a.a. 468 - 549 in HSV-2 ICP0
3. Putative ICP4-binding domain (4BD) region      86% homology
   • a.a. 604 - 765 in HSV-1 ICP0 / a.a. 646 - 810 in HSV-2 ICP0
4. Unconserved regions (relative to HSV-2 ICP0)    43% homology
   • a.a. 1 - 122 → 58 / 122  [--] a.a. 253 - 467 → 85 / 212 [--] a.a. 550 - 645 → 42 / 96
   • a.a. 811 - 825 → 0 / 15  [--] total = 185 / 445

```
HSV-1 ICP0    1  MEPRPGASTRR---PEGRPQREP-----APDVWVFPCDRDLPDSSDSEAETEVGGRGDAD   52
                 MEPRPG S+R    PE P++ P     AP W  D    SSDSE ETEVG   D
HSV-2 ICP0    1  MEPRPGTSSRADPGPERPPRQTPGTQPAAPHAWGMLNDMQWLASSDSEEETEVGISDDDL   60

HSV-1 ICP0   53  HHDDDSASEADSTDTELFETGLLGPQGVDGGAVS--GGSPPREEDPGSCGGAP--PREDG  108
                  H D  S SEA STDTE+FE GL+            GSP   + GSCGG P    E
HSV-2 ICP0   61  HRD--STSEAGSTDTEMFEAGLMDAATPPARPPAERQGSPTPADAQGSCGGGPVGEEEAE  118

HSV-1 ICP0  109  GSDEGDVCAVCTDEIAPHLRCDIFPCMHRFCIPCMKTWMQLRNTCPLCNAKLVYLIVGVT  168
                      GDVCAVCTDEIAP LRC +FPC+H FCIPCMKTW+ LRNTCPLCN  + YLIVGVT
HSV-2 ICP0  119  AGGGGDVCAVCTDEIAPPLRCQSFPCLHPFCIPCMKTWIPLRNTCPLCNTPVAYLIVGVT  178

HSV-1 ICP0  169  PSGSFSTIPIVNDPQTRMEAEEAVRAGTAVDFIWTGNQRFAPRYLTLGGHTVRALSPTHP  228
                  SGSFSTIPIVNDP+TR+EAE AVRAGTAVDFIWTGN R APR L+LGGHTVRALSPT P
HSV-2 ICP0  179  ASGSFSTIPIVNDPRTRVEAEAAVRAGTAVDFIWTGNPRTAPRSLSLGGHTVRALSPTPP  238

HSV-1 ICP0  229  EPTTDEDDDDLDDADYVPPAPRRTPRAPPRRGAAAPPVTGGASHAAPQPAAARTAPPSAP  288
                  P TD++DDDL D DYVPPAPRR PR     A   +       QPAA R APP AP
HSV-2 ICP0  239  WPGTDDEDDDLADVDYVPPAPRRAPRRGGGGAGATRGTS--------QPAATRPAPPGAP  290

HSV-1 ICP0  289  IGPHGSSNTNTTTNSSGGGGSRQSRAAAPRGASGP--SGGVGVGVGVVEAEAGRPRGRTG  346
                          SG GG      A PR AS P  +GG      V  +A   GRT
HSV-2 ICP0  291  RSSSSGGAPLRAGVGSGSGGGPAVAAVVPRVASLPPAAGGGRAQARRVGEDAAAAEGRTP  350

HSV-1 ICP0  347  PLVNRPAPLANNRDPIVISDSPPAS--------PHRPPAAPMPGSAPRPGPPASAAASGP  398
                 P    PA   PIVISDSPP S        P    ++    + PG      +SG
HSV-2 ICP0  351  PARQ---PRAAQEPPIVISDSPPPSPRRPAGPGPLSFVSSSSAQVSSGPGGGGLPQSSGR  407

HSV-1 ICP0  399  ARPRAAVAPCVRAPPP------GPGPRAPAPGAEPAARPADARRVPQSHSSLAQAANQEQ  452
                 A   A    PP        AA G  PA P DA R P+S  + AQ    Q Q
HSV-2 ICP0  408  AARPRAAVAPRVRSPPRAAAAPVVSASADAAGPAPPAVPVDAHRAPRSRMTQAQTDTQAQ  467

HSV-1 ICP0  453  SLCRARATVARGSGGPGVEGGHGPSRGAAPSGAAPLPSAASVEQEAAVRPRKRRG-----  507
                 SL RA AT ARGSGGPG EGG G  RG    GAAP  +        AA RPRKRRG
HSV-2 ICP0  468  SLGRAGATDARGSGGPGAEGGPGVPRGTNTPGAAPHAAEG-----AAARPRKRRGSDSGP  522
```

*Fig. 14B*

HSV-1s vs HSV-2's ICP0 Protein

1. RING finger region    87% homology
    • a.a. 113 - 242 in HSV-1 ICP0 / a.a. 123 - 252 in HSV-2 ICP0
2. Nuclear localization signal (NLS) region    65% homology
    • a.a. 453 - 531 in HSV-1 ICP0 / a.a. 468 - 549 in HSV-2 ICP0
3. Putative ICP4-binding domain (4BD) region    86% homology
    • a.a. 604 - 765 in HSV-1 ICP0 / a.a. 646 - 810 in HSV-2 ICP0
4. Unconserved regions (relative to HSV-2 ICP0)    43% homology
    • a.a. 1 - 122 → 58 / 122  [--]  a.a. 253 - 467 → 85 / 212  [--]  a.a. 550 - 645 → 42 / 96
    • a.a. 811 - 825 → 0 / 15  [--] total = 185 / 445

```
HSV-1 ICP0  508   -SGQENPSPQSTRPPLAP---AGAKRAATHPPSDSGPGGRGQG------------------  546
                   +       S  + R PLAP   GAKRAA    DS  G RG G
HSV-2 ICP0  523   AASSSASSSAAPRSPLAPQGVGAKRAAPRRAPDSDSGDRGHGPLAPASAGAAPPSASPSS  582

HSV-1 ICP0  547   ------GPGTPLTSSAASASSSSASSSSAPTPAGATSSATGAASSSASASSGGAVGALGG  600
                        +  +SS+AS+SS+S+SS+S+  +  +  +++S++ A+SS+  A    A  +  G
HSV-2 ICP0  583   QAAVAAASSSSASSSSASSSSASSSSASSSSASSSSASSSSASSSAGGAGGSVASASGAG  642

HSV-1 ICP0  601   RQEETSLGPRAASGPRGPRKCARKTRHA-----ETSGAVPAGGLTRYLPISGVSSVVALSP  656
                   +  ETSLGPRAA+ PRGPRKCARKTRHA      E     PA GLTRYLPI+GVSSVVAL+P
HSV-2 ICP0  643   ERRETSLGPRAAA-PRGPRKCARKTRHAEGGPEPGARDPAPGLTRYLPIAGVSSVVALAP  701

HSV-1 ICP0  657   YVNKTITGDCLPILDMETGNIGAYVVLVDQTGNMATRLRAAVPGWSRRTLLPETAGNHVT  716
                   YVNKT+TGDCLP+LDMETG+IGAYVVLVDQTGN+A   LRAA P WSRRTLLPE A N V
HSV-2 ICP0  702   YVNKTVTGDCLPVLDMETGHIGAYVVLVDQTGNVADLLRAAAPAWSRRTLLPEHARNCVR  761

HSV-1 ICP0  717   PPEYPTAPASEWNSLWMTPVGNMLFDQGTLVGALDFRSLRSRHPWSGEQGASTRDEGKQ   775
                   PP+YPT PASEWNSLWMTPVGNMLFDQGTLVGALDF  LRSRHPWS EQGA
HSV-2 ICP0  762   PPDYPTPPASEWNSLWMTPVGNMLFDQGTLVGALDFHGLRSRHPWSREQGAPAPAGDAPAGHGE 825
```

*Fig. 14B*
*Continued* wild-type HSV-2

HSV-2 0ΔNLS

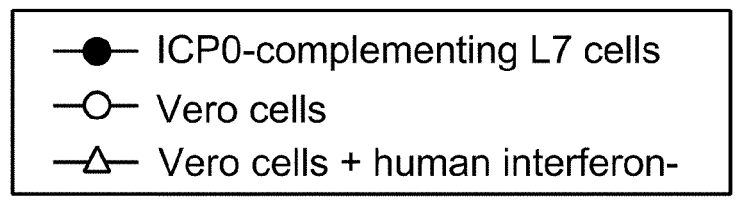
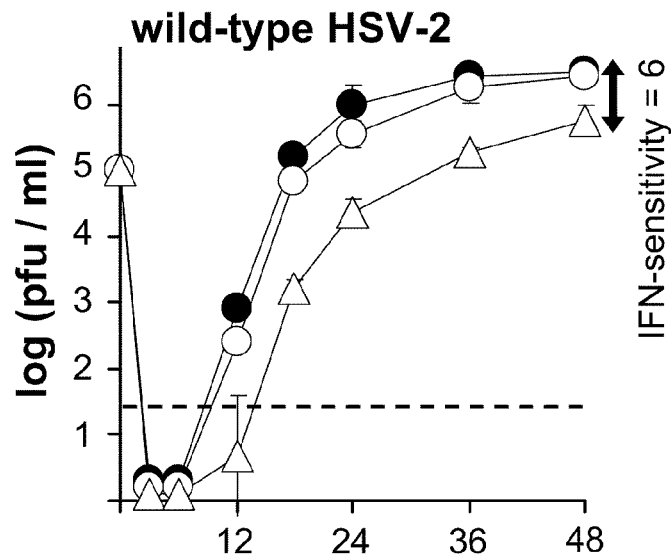
Fig. 18A
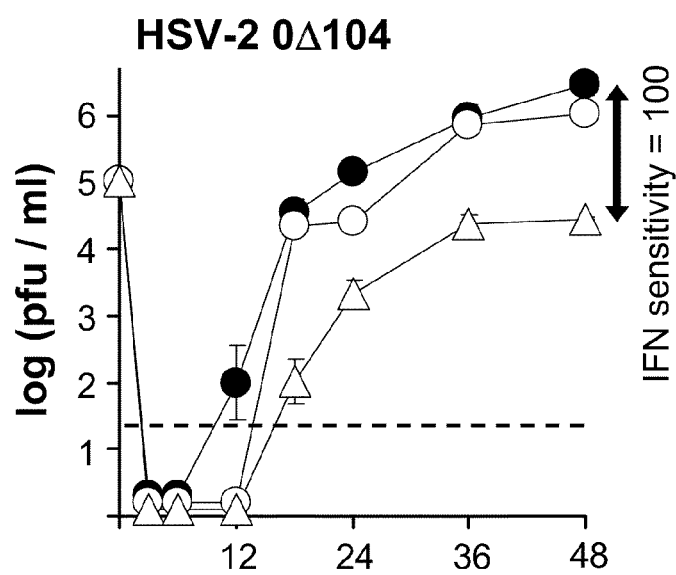
Fig. 18B

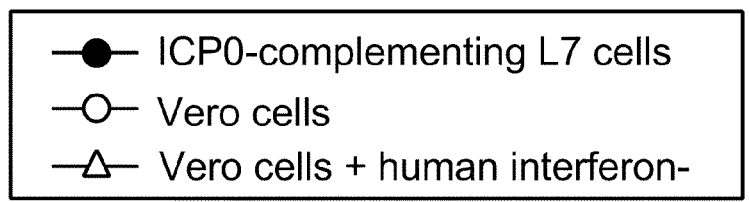
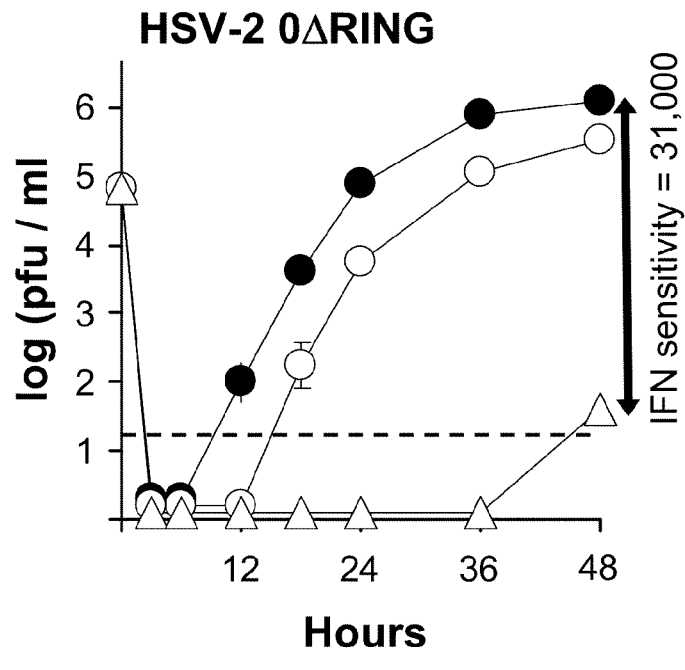
*Fig. 18C*
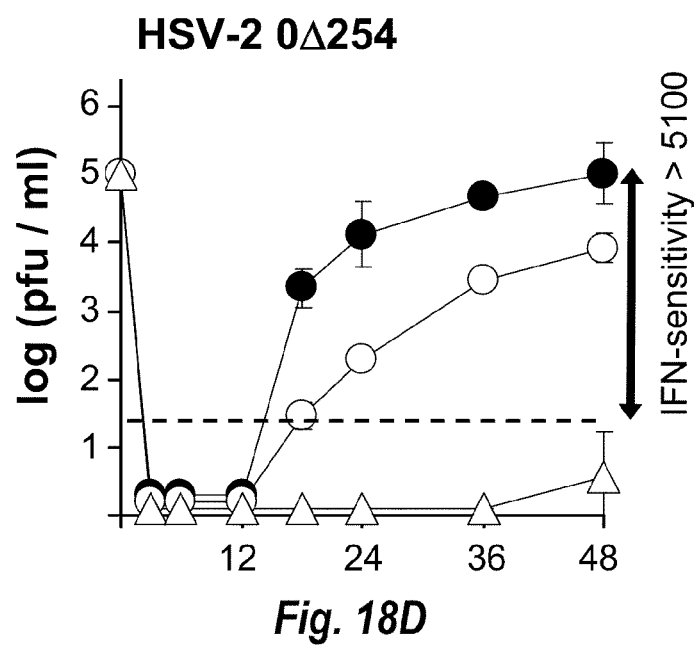
*Fig. 18D*

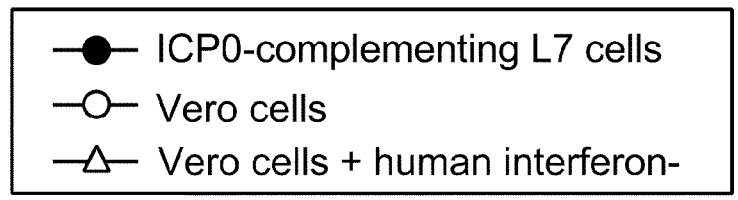
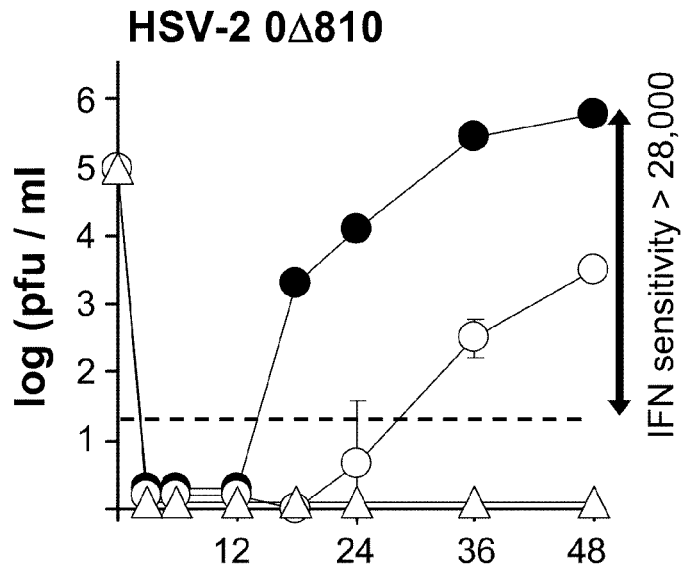
*Fig. 18E*
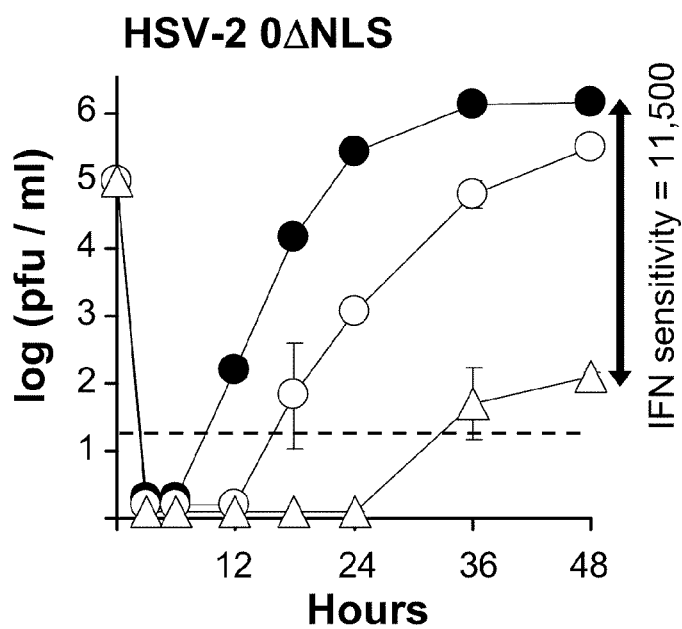
*Fig. 18F*

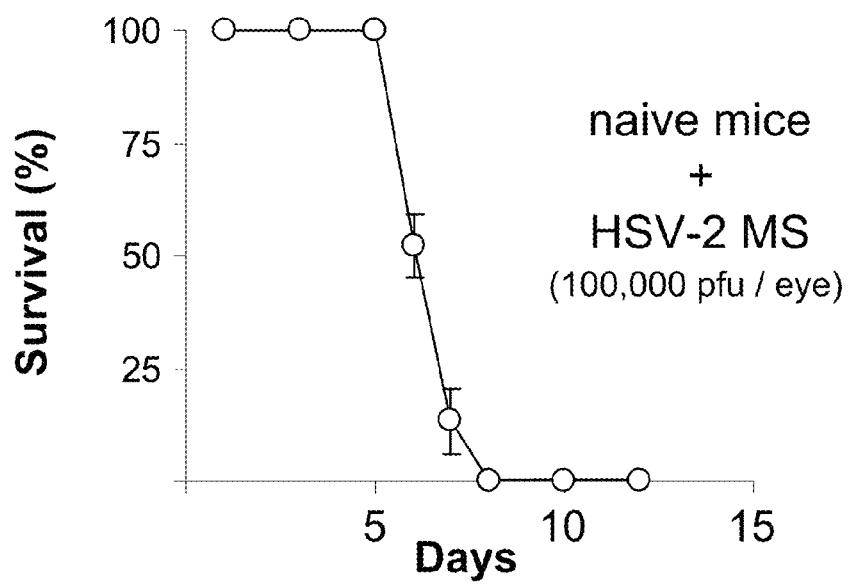
*Fig. 20A*
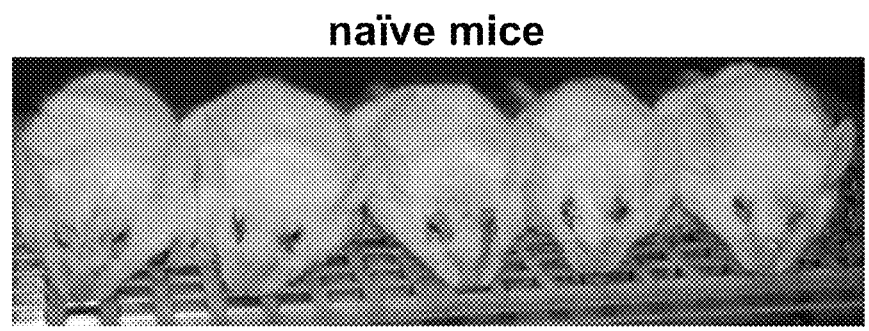
*Fig. 20B* mice challenged with
100,000 pfu / eye
HSV-2 MS luciferase

Protein Encoded By The ICP0 Gene Of HSV-2 0∆NLS

```
HSV-1 ICP0   1  MEPRPGASTRR---PEGR------------------------------------------  52
                MEPRPG S+R    PE
HSV-2 ICP0   1  MEPRPGTSSRADPGPERP---Green fluorescent protein---------------  60
(∆19-104)

HSV-1 ICP0  97  ------------------------------------------GSCGGAP--PREDG    108
                                                          GSCGG  P    E
HSV-2 ICP0 105  ------------------------------------------GSCGGGPVGEEEAE   118

HSV-1 ICP0 109  GSDEGDV CAVCTDEIAPHLRCDTFPCMHRFCIPCMKTWMQLRNTCPLC NAKLVYLIVGVT  168
                    GDV CAVCTDEIAP LRC +FPC+H FCIPCMKTW+ LRNTCPLC N   + YLIVGVT
HSV-2 ICP0 119  AGGGGDV CAVCTDEIAPPLRCQSFPCLHPFCIPCMKTWIPLRNTCPLC NTPVAYLIVGVT  178

HSV-1 ICP0 169  PSGSFSTIPIVNDPQTRMEAEEAVRAGTAVDFIWTGNQRFAPRYLTLGGHTVRALSPTHP    228
                 SGSFSTIPIVNDP+TR+EAE AVRAGTAVDFIWTGN R APR L+LGGHTVRALSPT P
HSV-2 ICP0 179  ASGSFSTIPIVNDPRTRVEAEAAVRAGTAVDFIWTGNPRTAPRSLSLGGHTVRALSPTPP    238

HSV-1 ICP0 229  EPTTDEDDDDLDDADYVPPAPRRTPRAPPRRGAAAPPVTGGASHAAPQPAAARTAPPSAP    288
                  P TD++DDDL D DYVPPAPRR  PR       A   +        QPAA R APP AP
HSV-2 ICP0 239  WPGTDDEDDDLADVDYVPPAPRRAPRRGGGGAGATRGTS--------QPAATRPAPPGAP    290

HSV-1 ICP0 289  IGPHGSSNTNTTTNSSGGGGSRQSRAAAPRGASGP--SGGVGVGVGVVEAEAGRPRGRTG   346
                              SG GG     A  PR AS P   +GG        V +A    GRT
HSV-2 ICP0 291  RSSSSGGAPLRAGVGSGSGGGPAVAAVVPRVASLPPAAGGGRAQARRVGEDAAAAEGRTP   350

HSV-1 ICP0 347  PLVNRPAPLANNRDPIVISDSPPAS--------PHRPPAAPMPGSAPRPGPPASAAASGP   398
                 P     P A    PIVISDSPP S        P      ++     +  PG     +SG
HSV-2 ICP0 351  PARQ---PRAAQEPPIVISDSPPPSPRRPAGPGPLSFVSSSSAQVSSGPGGGGLPQSSGR   407

HSV-1 ICP0 399  ARPRAAVAPCVRAPPP------GPGPRAPAPGAEPAARPADARRVPQSHSSLAQAANQEQ   452
                A  A        PP              A A G P A P DA R P+S   + AQ   Q Q
HSV-2 ICP0 408  AARPRAAVAPRVRSPPRAAAAPVVSASADAAGPAPPAVPVDAHRAPRSRMTQAQTDTQAQ   467

HSV-1 ICP0 453  SLCRARATVARGSGGPGVEGG---------------------------------       473
                SL RA AT ARGSGGPG EGG
HSV-2 ICP0 468  SLGRAGATDARGSGGPGAEGG-----------∆NLS mutation--------------   488
(∆489-695)

HSV-1 ICP0 508  -------------------------------------------------------       546

HSV-2 ICP0 523  -----------------------∆NLS mutation----------------------   582

HSV-1 ICP0 547  -------------------------------------------------------       600

HSV-2 ICP0 583  -----------------------∆NLS mutation----------------------   642
```

Fig. 29

Protein Encoded By The ICP0 Gene Of HSV-2 0ΔNLS

```
HSV-1 ICP0 651 ---------------------------------------------------------VVALSP 656
                                                                         VVAL+P
HSV-2 ICP0 696 --------------------ΔNLS mutation--------------------VVALAP 701

HSV-1 ICP0 657 YVNKTITGDCLPILDMETGNIGAYVVLVDQTGNMATRLRAAVPGWSRRTLLPETAGNHVT 716
               YVNKT+TGDCLP+LDMETG+IGAYVVLVDQTGN+A  LRAA P WSRRTLLPE A N V
HSV-2 ICP0 702 YVNKTVTGDCLPVLDMETGHIGAYVVLVDQTGNVADLLRAAAPAWSRRTLLPEHARNCVR 761

HSV-1 ICP0 717 PPEYPTAPASEWNSLWMTPVGNMLFDQGTLVGALDFRSLRSRHPWSGEQ----------  765
               PP+YPT PASEWNSLWMTPVGNMLFDQGTLVGALDF  LRSRHPWS EQ
HSV-2 ICP0 762 PPDYPTPPASEWNSLWMTPVGNMLFDQGTLVGALDFHGLRSRHPWSREQGAPAPAGDAPAGHGE 825
```

**Fig. 29
Continued**

Protein Encoded By The ICP0 Gene Of HSV-2 0△4BD

```
HSV-1 ICP0     1  MEPRPGASTRR---PEGR------------------------------------------  52
                  MEPRPG S+R   PE
HSV-2 ICP0     1  MEPRPGTSSRADPGPERP---Green fluorescent protein--------------  60
(△19-104)

HSV-1 ICP0    97  ----------------------------------------------GSCGGAP--PREDG 108
                                                                GSCGG P    E
HSV-2 ICP0   105  ----------------------------------------------GSCGGGPVGEEEAE 118

HSV-1 ICP0   109  GSDEGDVCAVCTDEIAPHLRCDTFPCMHRFCIPCMKTWMQLRNTCPLCNAKLVYLIVGVT  168
                       GDVCAVCTDEIAP LRC +FPC+H FCIPCMKTW+ LRNTCPLCN + YLIVGVT
HSV-2 ICP0   119  AGGGGDVCAVCTDEIAPPLRCQSFPCLHPFCIPCMKTWIPLRNTCPLCNTPVAYLIVGVT  178

HSV-1 ICP0   169  PSGSFSTIPIVNDPQTRMEAEEAVRAGTAVDFIWTGNQRFAPRYLTLGGHTVRALSPTHP  228
                   SGSFSTIPIVNDP+TR+EAE AVRAGTAVDFIWTGN R APR L+LGGHTVRALSPT P
HSV-2 ICP0   179  ASGSFSTIPIVNDPRTRVEAEAAVRAGTAVDFIWTGNPRTAPRSLSLGGHTVRALSPTPP  238

HSV-1 ICP0   229  EPTTDEDDDDLDDADYVPPAPRRTPRAPPRRGAAAPPVTGGASHAAPQPAAARTAPPSAP  288
                    P TD++DDDL D DYVPPAPRR  PR     A    +       QPAA R APP AP
HSV-2 ICP0   239  WPGTDDEDDDLADVDYVPPAPRRAPRRGGGGAGATRGTS--------QPAATRPAPPGAP  290

HSV-1 ICP0   289  IGPHGSSNTNTTTNSSGGGGSRQSRAAAPRGASGP--SGGVGVGVGVVEAEAGRPRGRTG  346
                            SG GG     A  PR AS P  +GG       V  +A   GRT
HSV-2 ICP0   291  RSSSSGGAPLRAGVGSGSGGGPAVAAVVPRVASLPPAAGGGRAQARRVGEDAAAAEGRTP  350

HSV-1 ICP0   347  PLVNRPAPLANNRDPIVISDSPPAS--------PHRPPAAPMPGSAPRPGPPASAAASGP  398
                  P     P A   PIVISDSPP S        P  ++     + PG   +SG
HSV-2 ICP0   351  PARQ---PRAAQEPPIVISDSPPPSPRRPAGPGPLSFVSSSSAQVSSGPGGGGLPQSSGR  407

HSV-1 ICP0   399  ARPRAAVAPCVRAPPP------GPGPRAPAPGAEPAARPADARRVPQSHSSLAQAANQEQ  452
                   A   A     PP          A A G PAP DA R P+S   + AQ   Q Q
HSV-2 ICP0   408  AARPRAAVAPRVRSPPRAAAAPVVSASADAAGPAPPAVPVDAHRAPRSRMTQAQTDTQAQ  467

HSV-1 ICP0   453  SLCRARATVARGSGGPGVEGGHGPSRGAAPSGAAPLPSAASVEQEAAVRPKKRRG-----  507
                  SL RA AT ARGSGGPG EGG G  RG    GAAP +        AA RPKRRG
HSV-2 ICP0   468  SLGRAGATDARGSGGPGAEGGPGVPRGTNTPGAAPHAAEG-----AAARPRKRRGSDSGP  522

HSV-1 ICP0   508  -SGQENPSPQSTRPPLAP--AGAKRAATHPPSDSGPGGRGQG------------------  546
                     +    S  +R PLAP    GAKRAA      DS G RG G
HSV-2 ICP0   523  AASSSASSSAAPRSPLAPQGVGAKRAAPRRAPDSDSGDRGHGPLAPASAGAAPPSASPSS  582

HSV-1 ICP0   547  ------GPGTPLTSSAASASSSSASSSSAPTPAGATSSATGAASSSASASSGGAVGALGG  600
                        +  +SS+AS+SS+S+SS+S+ + + +++S++ A+SS+  A    A   + G
HSV-2 ICP0   583  QAAVAAASSSSASSSSASSSSASSSSASSSSASSSSASSSSASSSSASSSAGGAGGSVASASGAG  642
```

*Fig. 30*

Protein Encoded By The ICP0 Gene Of HSV-2 0△4BD

```
HSV-1 ICP0  601  RQEETSLGPRAASGPRGPRKCARKTRHA----ETSGAVPAGGLTRYLPISGV-------- 648
                 + ETSLGPRAA+ PRGPRKCARKTRHA    E    PA GLTRYLPI+GV
HSV-2 ICP0  643  ERRETSLGPRAAA-PRGPRKCARKTRHAEGGPEPGARDPAPGLTRYLPIAGV-------- 694
(△695-810)

HSV-1 ICP0  657  ------------------------------------------------------------ 716

HSV-2 ICP0  702  ------------------△4BD mutation---------------------------- 761

HSV-1 ICP0  717  ---------------------------------------------------------- 765

HSV-2 ICP0  813  ------------------△4BD mutation--------------------GAPAPAGDAPAGHGE
                                                                              825
```

*Fig. 30*
*Continued*

Protein Encoded By The ICP0 Gene Of HSV-2 0△RING

```
HSV-1 ICP0   1  MEPRPGASTRR---PEGR----------------------------------------  52
                MEPRPG S+R    PE
HSV-2 ICP0   1  MEPRPGTSSRADPGPERP---Green fluorescent protein-------------  60

HSV-1 ICP0  97  ------------------------------------------------/---------- 108

HSV-2 ICP0 105  ------------------------------------------------/---△RING---- 118

HSV-1 ICP0 109  -----------------------------------------------CPLCNAKLVYLIVGVT 168
                                                                CPLCN + YLIVGVT
HSV-2 ICP0 119  ---------△RING-------------------------CPLCNTPVAYLIVGVT 178

HSV-1 ICP0 169  PSGSFSTIPIVNDPQTRMEAEEAVRAGTAVDFIWTGNQRFAPRYLTLGGHTVRALSPTHP 228
                SGSFSTIPIVNDP+TR+EAE AVRAGTAVDFIWTGN R APR L+LGGHTVRALSPT P
HSV-2 ICP0 179  ASGSFSTIPIVNDPRTRVEAEAAVRAGTAVDFIWTGNPRTAPRSLSLGGHTVRALSPTPP 238

HSV-1 ICP0 229  EPTTDEDDDDLDDADYVPPAPRRTPRAPPRRGAAAPPVTGGASHAAPQPAAARTAPPSAP 288
                 P TD++DDDL D DYVPPAPRR PR       A   +      QPAA R APP AP
HSV-2 ICP0 239  WPGTDDEDDDDLADVDYVPPAPRRAPRRGGGGAGATRGTS--------QPAATRPAPPGAP 290

HSV-1 ICP0 289  IGPHGSSNTNTTTNSSGGGGSRQSRAAAPRGASGP--SGGVGVGVGVVEAEAGRPRGRTG 346
                             SG GG   A  PR AS P  +GG      V +A   GRT
HSV-2 ICP0 291  RSSSSGGAPLRAGVGSGSGGGPAVAAVVPRVASLPPAAGGGRAQARRVGEDAAAAEGRTP 350

HSV-1 ICP0 347  PLVNRPAPLANNRDPIVISDSPPAS--------PHRPPAAPMPGSAPRPGPPASAAASGP 398
                P      P A    PIVISDSPP S         P     ++     + PG     +SG
HSV-2 ICP0 351  PARQ---PRAAQEPPIVISDSPPPSPRRPAGPGPLSFVSSSSAQVSSGPGGGGLPQSSGR 407

HSV-1 ICP0 399  ARPRAAVAPCVRAPPP------GPGPRAPAPGAEPAARPADARRVPQSHSSLAQAANQEQ 452
                A   A       PP           A A G   P AP  DA R P+S  + AQ    Q Q
HSV-2 ICP0 408  AARPRAAVAPRVRSPPRAAAAPVVSASADAAGPAPPAVPVDAHRAPRSRMTQAQTDTQAQ 467

HSV-1 ICP0 453  SLCRARATVARGSGGPGVEGGHGPSRGAAPSGAAPLPSAASVEQEAAVRPRKRRG----- 507
                SL RA AT ARGSGGPG EGG G  RG      GAAP   +       AA RPRKRRG
HSV-2 ICP0 468  SLGRAGATDARGSGGPGAEGGPGVPRGTNTPGAAPHAAEG-----AAARPRKRRGSDSGP 522

HSV-1 ICP0 508  -SGQENPSPQSTRPPLAP--AGAKRAATHPPSDSGPGGRGQG----------------- 546
                 +     S  + R PLAP   GAKRAA    DS   G RG G
HSV-2 ICP0 523  AASSSASSSAAPRSPLAPQGVGAKRAAPRRAPDSDSGDRGHGPLAPASAGAAPPSASPSS 582

HSV-1 ICP0 547  ------GPGTPLTSSAASASSSSASSSSAPTPAGATSSATGAASSSASASSGGAVGALGG 600
                      +  +SS+AS+SS+S+SS+S+ + +   +++S++ A+SS+ A   A   + G
HSV-2 ICP0 583  QAAVAAASSSSASSSSASSSSASSSSASSSSASSSSASSSSASSSAGGAGGSVASASGAG 642
```

Fig. 31

Protein Encoded By The ICP0 Gene Of HSV-2 0△RING

```
HSV-1 ICP0  601  RQEETSLGPRAASGPRGPRKCARKTRHA----ETSGAVPAGGLTRYLPISGVSSVVALSP  656
                 + ETSLGPRAA+ PRGPRKCARKTRHA    E    PA GLTRYLPI+GVSSVVAL+P
HSV-2 ICP0  643  ERRETSLGPRAAA-PRGPRKCARKTRHAEGGPEPGARDPAPGLTRYLPIAGVSSVVALAP  701

HSV-1 ICP0  657  YVNKTITGDCLPILDMETGNIGAYVVLVDQTGNMATRLRAAVPGWSRRTLLPETAGNHVT  716
                 YVNKT+TGDCLP+LDMETG+IGAYVVLVDQTGN+A  LRAA P WSRRTLLPE A N V
HSV-2 ICP0  702  YVNKTVTGDCLPVLDMETGHIGAYVVLVDQTGNVADLLRAAAPAWSRRTLLPEHARNCVR  761

HSV-1 ICP0  717  PPEYPTAPASEWNSLWMTPVGNMLFDQGTLVGALDFRSLRSRHPWSGEQGASTRDEGKQ   775
                 PP+YPT PASEWNSLWMTPVGNMLFDQGTLVGALDF  LRSRHPWS EQGA
HSV-2 ICP0  762  PPDYPTPPASEWNSLWMTPVGNMLFDQGTLVGALDFHGLRSRHPWSREQGAPAPAGDAPAGHGE  825
```

*Fig. 31*
Continued

Protein Encoded By The ICP0 Gene Of HSV-1 0△RING

```
HSV-1 ICP0    1  MEPRPGASTRR---PEGRPQREP-----APDVWVFPCDRDLPDSSDSEAETEVGGRGDAD   52
                 MEPRPG S+R    PE P++ P        AP W  D    SSDSE ETEVG   D
HSV-2 ICP0    1  MEPRPGTSSRADPGPERPPRQTPGTQPAAPHAWGMLNDMQWLASSDSEEETEVGISDDDL   60
```

```
HSV-1 ICP0   53  HHDDDSASEADSTDTELFETGLLGPQGVDGGAVS--GGSPPREEDPGSCGGAP--P      104
                 H D  S SEA STDTE+FE GL+             +  GSP  + GSCGG  P
HSV-2 ICP0   61  HRD--STSEAGSTDTEMFEAGLMDAATPPARPPAERQGSPTPADAQGSCGGGPVGE     114
```

```
HSV-1 ICP0  105  -------------green fluorescent protein /△RING-------------- 168
HSV-2 ICP0  115  ------------------------------------------------------------178
```

HSV-1 ICP0  169  ------------------------△RING------------------------VRALSPTHP  228
                                                                       VRALSPT P
HSV-2 ICP0  179  --------------------------------------------------VRALSPTPP  238

```
HSV-1 ICP0  229  EPTTDEDDDDLDDADYVPPAPRRTPRAPPRRGAAAPPVTGGASHAAPQPAAARTAPPSAP  288
                 P  TD++DDDL D DYVPPAPRR  PR       A   +        QPAA R APP AP
HSV-2 ICP0  239  WPGTDDEDDDLADVDYVPPAPRRAPRRGGGGAGATRGTS--------QPAATRPAPPGAP  290
```

```
HSV-1 ICP0  289  IGPHGSSNTNTTTNSSGGGGSRQSRAAAPRGASGP--SGGVGVGVGVVEAEAGRPRGRTG  346
                          SG GG      A  PR AS P   +GG        V  +A    GRT
HSV-2 ICP0  291  RSSSSGGAPLRAGVGSGSGGGPAVAAVVPRVASLPPAAGGGRAQARRVGEDAAAAEGRTP  350
```

```
HSV-1 ICP0  347  PLVNRPAPLANNRDPIVISDSPPAS--------PHRPPAAPMPGSAPRPGPPASAAASGP  398
                 P    P A   PIVISDSPP S        P   ++   + PG     +SG
HSV-2 ICP0  351  PARQ---PRAAQEPPIVISDSPPPSPRRPAGPGPLSFVSSSSAQVSSGPGGGGLPQSSGR  407
```

```
HSV-1 ICP0  399  ARPRAAVAPCVRAPPP------GPGPRAPAPGAEPAARPADARRVPQSHSSLAQAANQEQ  452
                 A   A       PP        A A G  P A P DA R P+S  + AQ    Q Q
HSV-2 ICP0  408  AARPRAAVAPRVRSPPRAAAAPVVSASADAAGPAPPAVPVDAHRAPRSRMTQAQTDTQAQ  467
```

```
HSV-1 ICP0  453  SLCRARATVARGSGGPGVEGGHGPSRGAAPSGAAPLPSAASVEQEAAVRPRKRRG-----  507
                 SL RA AT ARGSGGPG EGG G  RG    GAAP  +          AA RPRKRRG
HSV-2 ICP0  468  SLGRAGATDARGSGGPGAEGGPGVPRGTNTPGAAPHAAEG-----AAARPRKRRGSDSGP  522
```

```
HSV-1 ICP0  508  -SGQENPSPQSTRPPLAP--AGAKRAATHPPSDSGPGGRGQG-----------------  546
                  +    S + R PLAP    GAKRAA    DS G RG G
HSV-2 ICP0  523  AASSSASSSAAPRSPLAPQGVGAKRAAPRRAPDSDSGDRGHGPLAPASAGAAPPSASPSS  582
```

```
HSV-1 ICP0  547  ------GPGTPLTSSAASASSSSASSSSAPTPAGATSSATGAASSSASASSGGAVGALGG  600
                       +  +SS+AS+SS+S+SS+S+  + + +++S++ A+SS+   A      A + G
HSV-2 ICP0  583  QAAVAAASSSSASSSSASSSSASSSSASSSSASSSSASSSSASSSAGGAGGSVASASGAG  642
```

*Fig. 32*

Protein Encoded By The ICP0 Gene Of HSV-1 0△RING

```
HSV-1 ICP0  601  RQEETSLGPRAASGPRGPRKCARKTRHA----ETSGAVPAGGLTRYLPISGVSSVVALSP  656
                 + ETSLGPRAA+ PRGPRKCARKTRHA       E      PA GLTRYLPI+GVSSVVAL+P
HSV-2 ICP0  643  ERRETSLGPRAAA-PRGPRKCARKTRHAEGGPEPGARDPAPGLTRYLPIAGVSSVVALAP  701

HSV-1 ICP0  657  YVNKTITGDCLPILDMETGNIGAYVVLVDQTGNMATRLRAAVPGWSRRTLLPETAGNHVT  716
                 YVNKT+TGDCLP+LDMETG+IGAYVVLVDQTGN+A   LRAA P WSRRTLLPE A N V
HSV-2 ICP0  702  YVNKTVTGDCLPVLDMETGHIGAYVVLVDQTGNVADLLRAAAPAWSRRTLLPEHARNCVR  761

HSV-1 ICP0  717  PPEYPTAPASEWNSLWMTPVGNMLFDQGTLVGALDFRSLRSRHPWSGEQGASTRDEGKQ   775
                 PP+YPT PASEWNSLWMTPVGNMLFDQGTLVGALDF   LRSRHPWS EQGA
HSV-2 ICP0  762  PPDYPTPPASEWNSLWMTPVGNMLFDQGTLVGALDFHGLRSRHPWSREQGAPAPAGDAPAGHGE  825
```

Fig. 32
Continued

Protein Encoded By The ICP0 Gene Of HSV-1 0△NLS

```
HSV-1 ICP0    1  MEPRPGASTRR---PEGRPQREP-----APDVWVFPCDRDLPDSSDSEAETEVGGRGDAD   52
                 MEPRPG S+R    PE P++ P       AP W  D    SSDSE ETEVG   D
HSV-2 ICP0    1  MEPRPGTSSRADPGPERPPRQTPGTQPAAPHAWGMLNDMQWLASSDSEEETEVGISDDDL  60

HSV-1 ICP0   53  HHDDDSASEADSTDTELFETGLLGPQGVDGGAVS--GGSPPREEDPGSCGGAP--P     104
                 H D  S SEA STDTE+FE GL+        +    GSP    +  GSCGG  P
HSV-2 ICP0   61  HRD--STSEAGSTDTEMFEAGLMDAATPPARPPAERQGSPTPADAQGSCGGGPVGE    114

HSV-1 ICP0  105  ---green fluorescent protein (238 a.a. insertion)-------REDG 108
                                                                             E
HSV-2 ICP0  115  ----------------------------------------------------EEAE   118

HSV-1 ICP0  109  GSDEGDVCAVCTDEIAPHLRCDTFPCMHRFCIPCMKTWMQLRNTCPLCNAKLVYLIVGVT 168
                      GDVCAVCTDEIAP LRC +FPC+H FCIPCMKTW+ LRNTCPLCN  + YLIVGVT
HSV-2 ICP0  119  AGGGGDVCAVCTDEIAPPLRCQSFPCLHPFCIPCMKTWIPLRNTCPLCNTPVAYLIVGVT 178

HSV-1 ICP0  169  PSGSFSTIPIVNDPQTRMEAEEAVRAGTAVDFIWTGNQRFAPRYLTLGGHTVRALSPTHP 228
                 SGSFSTIPIVNDP+TR+EAE AVRAGTAVDFIWTGN R APR L+LGGHTVRALSPT P
HSV-2 ICP0  179  ASGSFSTIPIVNDPRTRVEAEAAVRAGTAVDFIWTGNPRTAPRSLSLGGHTVRALSPTPP 238

HSV-1 ICP0  229  EPTTDEDDDDLDDADYVPPAPRRTPRAPPRRGAAAPPVTGGASHAAPQPAAARTAPPSAP 288
                  P TD++DDDL D DYVPPAPRR  PR      A    +     QPAA R APP AP
HSV-2 ICP0  239  WPGTDDEDDDLADVDYVPPAPRRAPRRGGGGAGATRGTS--------QPAATRPAPPGAP 290

HSV-1 ICP0  289  IGPHGSSNTNTTTNSSGGGGSRQSRAAAPRGASGP--SGGVGVGVGVVEAEAGRPRGRTG 346
                                  SG GG    A   PR AS P  +GG     V  +A   GRT
HSV-2 ICP0  291  RSSSSGGAPLRAGVGSGSGGGPAVAAVVPRVASLPPAAGGGRAQARRVGEDAAAAEGRTP 350

HSV-1 ICP0  347  PLVNRPAPLANNRDPIVISDSPPAS--------PHRPPAAPMPGSAPRPGPPASAAASGP 398
                 P    P A   PIVISDSPP S        P    ++    + PG      +SG
HSV-2 ICP0  351  PARQ---PRAAQEPPIVISDSPPPSPRRPAGPGPLSFVSSSSAQVSSGPGGGGLPQSSGR 407

HSV-1 ICP0  399  ARPRAAVAPCVRAPPP------GPGPRAPAPGAEPAARPADARRVPQSHSSLAQAAN--- 449
                 A  A        PP          A  G  P AP DA R P+S  + AQ     Q Q
HSV-2 ICP0  408  AARPRAAVAPRVRSPPRAAAAPVVSASADAAGPAPPAVPVDAHRAPRSRMTQAQTDT--- 464

HSV-1 ICP0  457  △NLS-ARATVARGSGGPGVEGGHGPSRGAAPSGAAPLPSAASVEQEAA---△NLS------ 507
                      A AT ARGSGGPG EGG G  RG    GAAP +           AA
HSV-2 ICP0  472  -----AGATDARGSGGPGAEGGPGVPRGTNTPGAAPHAAEG-----AA--------SDSGP 522

HSV-1 ICP0  508  -SGQENPSPQSTRPPLAP--AGAKRAATHPPSDSGPGGRGQG---------------- 546
                  +    S  + R PLAP    GAKRAA     DS  G RG G
HSV-2 ICP0  523  AASSSASSSAAPRSPLAPQGVGAKRAAPRRAPDSDSGDRGHGPLAPASAGAAPPSASPSS 582
```

*Fig. 33*

Protein Encoded By The ICP0 Gene Of HSV-1 0△NLS

```
HSV-1 ICP0 547  ------GPGTPLTSSAASASSSSASSSSAPTPAGATSSATGAASSSASASSGGAVGALGG 600
                      +  +SS+AS+SS+S+SS+S+ + + +++S++ A+SS+  A    A  + G
HSV-2 ICP0 583  QAAVAAASSSSASSSSASSSSASSSSASSSSASSSSASSSSASSSAGGAGGSVASASGAG 642

HSV-1 ICP0 601  RQEETSLGPRAASGPRGPRKCARKTRHA----ETSGAVPAGGLTRYLPISGVSSVVALSP 656
                + ETSLGPRAA+ PRGPRKCARKTRHA    E     PA GLTRYLPI+GVSSVVAL+P
HSV-2 ICP0 643  ERRETSLGPRAAA-PRGPRKCARKTRHAEGGPEPGARDPAPGLTRYLPIAGVSSVVALAP 701

HSV-1 ICP0 657  YVNKTITGDCLPILDMETGNIGAYVVLVDQTGNMATRLRAAVPGWSRRTLLPETAGNHVT 716
                YVNKT+TGDCLP+LDMETG+IGAYVVLVDQTGN+A   LRAA P WSRRTLLPE A N V
HSV-2 ICP0 702  YVNKTVTGDCLPVLDMETGHIGAYVVLVDQTGNVADLLRAAAPAWSRRTLLPEHARNCVR 761

HSV-1 ICP0 717  PPEYPTAPASEWNSLWMTPVGNMLFDQGTLVGALDFRSLRSRHPWSGEQGASTRDEGKQ  775
                PP+YPT PASEWNSLWMTPVGNMLFDQGTLVGALDF  LRSRHPWS EQGA
HSV-2 ICP0 762  PPDYPTPPASEWNSLWMTPVGNMLFDQGTLVGALDFHGLRSRHPWSREQGAPAPAGDAPAGHGE 825
```

*Fig. 33*
*Continued*

Protein Encoded By The ICP0 Gene Of HSV-1 0△4BD

```
HSV-1 ICP0   1  MEPRPGASTRR---PEGRPQREP-----APDVWVFPCDRDLPDSSDSEAETEVGGRGDAD   52
                MEPRPG S+R    PE P++ P       AP W  D    SSDSE ETEVG   D
HSV-2 ICP0   1  MEPRPGTSSRADPGPERPPRQTPGTQPAAPHAWGMLNDMQWLASSDSEEETEVGISDDDL   60

HSV-1 ICP0  53  HHDDDSASEADSTDTELFETGLLGPQGVDGGAVS--GGSPPREEDPGSCGGAP--P      104
                H D   S SEA STDTE+FE GL+         +   GSP  +  GSCGG  P
HSV-2 ICP0  61  HRD--STSEAGSTDTEMFEAGLMDAATPPARPPAERQGSPTPADAQGSCGGGPVGE     114

HSV-1 ICP0 105  ---green fluorescent protein (238 a.a. insertion)-------REDG  108
                                                                        E
HSV-2 ICP0 115  ----------------------------------------------------------EEAE  118

HSV-1 ICP0 109  GSDEGDVCAVCTDEIAPHLRCDTFPCMHRFCIPCMKTWMQLRNTCPLCNAKLVYLIVGVT  168
                     GDVCAVCTDEIAP LRC +FPC+H FCIPCMKTW+ LRNTCPLCN  + YLIVGVT
HSV-2 ICP0 119  AGGGGDVCAVCTDEIAPPLRCQSFPCLHPFCIPCMKTWIPLRNTCPLCNTPVAYLIVGVT  178

HSV-1 ICP0 169  PSGSFSTIPIVNDPQTRMEAEEAVRAGTAVDFIWTGNQRFAPRYLTLGGHTVRALSPTHP  228
                 SGSFSTIPIVNDP+TR+EAE AVRAGTAVDFIWTGN R APR L+LGGHTVRALSPT P
HSV-2 ICP0 179  ASGSFSTIPIVNDPRTRVEAEAAVRAGTAVDFIWTGNPRTAPRSLSLGGHTVRALSPTPP  238

HSV-1 ICP0 229  EPTTDEDDDDLDDADYVPPAPRRTPRAPPRRGAAAPPVTGGASHAAPQPAAARTAPPSAP  288
                 P TD++DDDL D DYVPPAPRR PR       A    +      QPAA R APP AP
HSV-2 ICP0 239  WPGTDDEDDDLADVDYVPPAPRRAPRRGGGGAGATRGTS--------QPAATRPAPPGAP  290

HSV-1 ICP0 289  IGPHGSSNTNTTTNSSGGGGSRQSRAAAPRGASGP--SGGVGVGVGVVEAEAGRPRGRTG  346
                                SG GG    A  PR AS P  +GG        V   +A   GRT
HSV-2 ICP0 291  RSSSSGGAPLRAGVGSGSGGGPAVAAVVPRVASLPPAAGGGRAQARRVGEDAAAAEGRTP  350

HSV-1 ICP0 347  PLVNRPAPLANNRDPIVISDSPPAS--------PHRPPAAPMPGSAPRPGPPASAAASGP  398
                P       PA   PIVISDSPP S        P   ++    + PG       +SG
HSV-2 ICP0 351  PARQ---PRAAQEPPIVISDSPPPSPRRPAGPGPLSFVSSSSAQVSSGPGGGGLPQSSGR  407

HSV-1 ICP0 399  ARPRAAVAPCVRAPPP------GPGPRAPAPGAEPAARPADARRVPQSHSSLAQAAN---  449
                A  A        PP        AAG PAP DA R P+S  + AQ    Q Q
HSV-2 ICP0 408  AARPRAAVAPRVRSPPRAAAAPVVSASADAAGPAPPAVPVDAHRAPRSRMTQAQTDT---  464

HSV-1 ICP0 457  △NLS-ARATVARGSGGPGVEGGHGPSRGAAPSGAAPLPSAASVEQEAA---△NLS------  507
                     A AT ARGSGGPG EGG G  RG    GAAP  +     AA
HSV-2 ICP0 472  -----AGATDARGSGGPGAEGGPGVPRGTNTPGAAPHAAEG-----AA--------SDSGP  522

HSV-1 ICP0 508  -SGQENPSPQSTRPPLAP--AGAKRAATHPPSDSGPGGRGQG-----------------  546
                 +    S  + R PLAP    GAKRAA    DS  G RG G
HSV-2 ICP0 523  AASSSASSSAAPRSPLAPQGVGAKRAAPRRAPDSDSGDRGHGPLAPASAGAAPPSASPSS  582
```

Fig. 34

Protein Encoded By The ICP0 Gene Of HSV-1 0 △4BD

```
HSV-1 ICP0 547 ------GPGTPLTSSAASASSSSASSSSAPTPAGATSSATGAASSSASASSGGAVGALGG 600
                     +  +SS+AS+SS+S+SS+S+ + +  +++S++  A+SS+   A     A  +  G
HSV-2 ICP0 583 QAAVAAASSSSASSSSASSSSASSSSASSSSASSSSASSSSASSSSAGGAGGSVASASGAG 642

HSV-1 ICP0 601 RQEETSLGPRAASGPRGPRKCARKTRHA----ETSGAVPAGGLTRYLPISGVSSVVALSP 656
                + ETSLGPRAA+ PRGPRKCARKTRHA    E      PA GLTRYLPI+GVSSVVAL+P
HSV-2 ICP0 643 ERRETSLGPRAAA-PRGPRKCARKTRHAEGGPEPGARDPAPGLTRYLPIAGVSSVVALAP 701

HSV-1 ICP0 657 YVNKTITGDCLPILDMETGNIGAYV----------△4BD--------------GNHVT 716
                YVNKT+TGDCLP+LDMETG+IGAYV                             N V
HSV-2 ICP0 702 YVNKTVTGDCLPVLDMETGHIGAYV-------------------------------RNCVR 761

HSV-1 ICP0 717 PPEYPTAPASEWNSLWMTPVGNMLFDQGTLVGALDFRSLRSRHPWSGEQGASTRDEGKQ  775
                PP+YPT PASEWNSLWMTPVGNMLFDQGTLVGALDF  LRSRHPWS EQGA
HSV-2 ICP0 762 PPDYPTPPASEWNSLWMTPVGNMLFDQGTLVGALDFHGLRSRHPWSREQGAPAPAGDAPAGHGE 825
```

*Fig. 34*
*Continued*

Protein Encoded By The ICP0 Gene Of HSV-1 0 GFP

```
HSV-1 ICP0    1  MEPRPGASTRR---PEGRPQREP-----APDVWVFPCDRDLPDSSDSEAETEVGGRGDAD   52
                 MEPRPG S+R    PE  P++ P      AP  W   D     SSDSE ETEVG
HSV-2 ICP0    1  MEPRPGTSSRADPGPERPPRQTPGTQPAAPHAWGMLNDMQWLASSDSEEETEVGISDDDL  60

HSV-1 ICP0   53  HHDDDSASEADSTDTELFETGLLGPQGVDGGAVS--GGSPPREEDPGSCGGAP--P     104
                 H D  S SEA STDTE+FE GL+           +   GSP   + GSCGG P
HSV-2 ICP0   61  HRD--STSEAGSTDTEMFEAGLMDAATPPARPPAERQGSPTPADAQGSCGGGPVGE    114
```

HSV-1 ICP0 105 ---green fluorescent protein (238 a.a. insertion)----------- 108

HSV-2 ICP0 115 ----------------------------------------------------------- 118

HSV-1 ICP0 109 ----------------------------------------------------------- 168

HSV-2 ICP0 119 ----------------------------------------------------------- 178

HSV-1 ICP0 169 ----------------------------------------------------------- 228

HSV-2 ICP0 179 ----------------------------------------------------------- 238

HSV-1 ICP0 229 ----------------------------------------------------------- 288

HSV-2 ICP0 239 ----------------------------------------------------------- 290

HSV-1 ICP0 289 ----------------------------------------------------------- 346

HSV-2 ICP0 291 ----------------------------------------------------------- 350

HSV-1 ICP0 347 ----------------------------------------------------------- 398

HSV-2 ICP0 351 ----------------------------------------------------------- 407

HSV-1 ICP0 399 ----------------------------------------------------------- 449

HSV-2 ICP0 408 ----------------------------------------------------------- 464

HSV-1 ICP0 457 ----------------------------------------------------------- 507

HSV-2 ICP0 472 ----------------------------------------------------------- 522

HSV-1 ICP0 508 ----------------------------------------------------------- 546

HSV-2 ICP0 523 ----------------------------------------------------------- 582

*Fig. 35*

Protein Encoded By The ICP0 Gene Of HSV-1 0 GFP

HSV-1 ICP0 547 ---------------------------------------------------------------- 600

HSV-2 ICP0 583 ---------------------------------------------------------------- 642

HSV-1 ICP0 601 ---------------------------------------------------------------- 656

HSV-2 ICP0 643 ---------------------------------------------------------------- 701

HSV-1 ICP0 657 ---------------------------------------------------------------- 716

HSV-2 ICP0 702 ---------------------------------------------------------------- 761

HSV-1 ICP0 717 ---------------------------------------------------------------- 775

HSV-2 ICP0 762 ---------------------------------------------------------------- 825

*Fig. 35*
*Continued*

```
                          SEQUENCE LISTING

<160> NUMBER OF SEQ ID NOS: 45

<210> SEQ ID NO 1
<211> LENGTH: 3645
<212> TYPE: DNA
<213> ORGANISM: Herpes simplex virus 1
<220> FEATURE:
<221> NAME/KEY: CDS
<222> LOCATION: (3)..(59)
<220> FEATURE:
<221> NAME/KEY: CDS
<222> LOCATION: (825)..(1490)
<220> FEATURE:
<221> NAME/KEY: CDS
<222> LOCATION: (1627)..(3228)

<400> SEQUENCE: 1 cc atg gag ccc cgc ccc gga gcg agt acc cgc cgg cct gag ggc cgc         47
   Met Glu Pro Arg Pro Gly Ala Ser Thr Arg Arg Pro Glu Gly Arg
   1               5                   10                  15 ccc cag cgc gag gtgaggggcc gggcgccatg tctgggcgc catattgggg            99
Pro Gln Arg Glu ggcgccatat tgggggggcgc catgttgggg gacccccgac ccttacactg gaaccggccg    159
ccatgttggg ggaccccccac tcatacacgg gagccgggcg ccatgttggg gcgccatgtt    219
agggggcgtg gaacccccgtg acactatata tacagggacc gggggcgcca tgttagggg    279 tgcggaaccc cctgacccta tatatacagg gaccgggtc gccctgttgg gggtcgccat     339 gtgacccct gactttatat atacagaccc ccaacacata cacatggccc ctttgactca     399 gacgcaggc cggggtcgc cgtgggaccc cctgactcat acacagagac acgcccccac     459
aacaaacaca caaggaccgg ggtcgccgtg ttgggggcgt ggtccccact gactcatacg    519
caggcccccc ttactcacac gcatctaggg gggtggggag gagccgcccg ccatatttgg    579
gggacgccgt gggaccccccg actccggtgc gtctggaggg cgggagaaga gggaagaaga    639
```

-continued

```
ggggtcggga tccaaaggac ggacccagac caccttttggt tgcagacccc tttctccccc    699
ctcttccgag gccagcaggg gggcaggact ttgtgaggcg gggggggggag aggggggaact   759 cgtgggtgct gattgacgcg ggaaatcccc ccccattctt acccgccccc ctttttttccc   819
```

| cttag | ccc | gcc | ccg | gat | gtc | tgg | gtg | ttt | ccc | tgc | gac | cga | gac | ctg | ccg |        | 869 |
|-------|-----|-----|-----|-----|-----|-----|-----|-----|-----|-----|-----|-----|-----|-----|-----|--------|-----|
|       | Pro | Ala | Pro | Asp | Val | Trp | Val | Phe | Pro | Cys | Asp | Arg | Asp | Leu | Pro |        |     |
|       | 20  |     |     |     | 25  |     |     |     | 30  |     |     |     |     |     |     |        |     |

| gac | agc | agc | gac | tct | gag | gcg | gag | acc | gaa | gtg | ggg | ggg | cgg | ggg | gac | 917 |
|-----|-----|-----|-----|-----|-----|-----|-----|-----|-----|-----|-----|-----|-----|-----|-----|-----|
| Asp | Ser | Ser | Asp | Ser | Glu | Ala | Glu | Thr | Glu | Val | Gly | Gly | Arg | Gly | Asp |     |
| 35  |     |     |     | 40  |     |     |     | 45  |     |     |     | 50  |     |     |     |     |

| gcc | gac | cac | cat | gac | gac | gac | tcc | gcc | tcc | gag | gcg | gac | agc | acg | gac | 965 |
|-----|-----|-----|-----|-----|-----|-----|-----|-----|-----|-----|-----|-----|-----|-----|-----|-----|
| Ala | Asp | His | His | Asp | Asp | Asp | Ser | Ala | Ser | Glu | Ala | Asp | Ser | Thr | Asp |     |
|     |     |     | 55  |     |     |     | 60  |     |     |     |     | 65  |     |     |     |     |

| acg | gaa | ctg | ttc | gag | acg | ggg | ctg | ctg | ggg | ccg | cag | ggc | gtg | gat | ggg | 1013 |
|-----|-----|-----|-----|-----|-----|-----|-----|-----|-----|-----|-----|-----|-----|-----|-----|------|
| Thr | Glu | Leu | Phe | Glu | Thr | Gly | Leu | Leu | Gly | Pro | Gln | Gly | Val | Asp | Gly |      |
|     |     | 70  |     |     |     |     | 75  |     |     |     |     | 80  |     |     |     |      |

| ggg | gcg | gtc | tcg | ggg | ggg | agc | ccc | ccc | cgc | gag | gaa | gac | ccc | ggc | agt | 1061 |
|-----|-----|-----|-----|-----|-----|-----|-----|-----|-----|-----|-----|-----|-----|-----|-----|------|
| Gly | Ala | Val | Ser | Gly | Gly | Ser | Pro | Pro | Arg | Glu | Glu | Asp | Pro | Gly | Ser |      |
|     |     | 85  |     |     |     |     | 90  |     |     |     |     | 95  |     |     |     |      |

| tgc | ggg | ggc | gcc | ccc | cct | cga | gag | gac | ggg | ggg | agc | gac | gag | ggc | gac | 1109 |
|-----|-----|-----|-----|-----|-----|-----|-----|-----|-----|-----|-----|-----|-----|-----|-----|------|
| Cys | Gly | Gly | Ala | Pro | Pro | Arg | Glu | Asp | Gly | Gly | Ser | Asp | Glu | Gly | Asp |      |
| 100 |     |     |     |     | 105 |     |     |     |     | 110 |     |     |     |     |     |      |

| gtg | tgc | gcc | gtg | tgc | acg | gat | gag | atc | gcg | ccc | cac | ctg | cgc | tgc | gac | 1157 |
|-----|-----|-----|-----|-----|-----|-----|-----|-----|-----|-----|-----|-----|-----|-----|-----|------|
| Val | Cys | Ala | Val | Cys | Thr | Asp | Glu | Ile | Ala | Pro | His | Leu | Arg | Cys | Asp |      |
| 115 |     |     |     |     | 120 |     |     |     |     | 125 |     |     |     |     | 130 |      |

| acc | ttc | ccg | tgc | atg | cac | cgc | ttc | tgc | atc | ccg | tgc | atg | aaa | acc | tgg | 1205 |
|-----|-----|-----|-----|-----|-----|-----|-----|-----|-----|-----|-----|-----|-----|-----|-----|------|
| Thr | Phe | Pro | Cys | Met | His | Arg | Phe | Cys | Ile | Pro | Cys | Met | Lys | Thr | Trp |      |
|     |     |     |     | 135 |     |     |     |     | 140 |     |     |     |     | 145 |     |      |

| atg | caa | ttg | cgc | aac | acc | tgc | ccg | ctg | tgc | aac | gcc | aag | ctg | gtg | tac | 1253 |
|-----|-----|-----|-----|-----|-----|-----|-----|-----|-----|-----|-----|-----|-----|-----|-----|------|
| Met | Gln | Leu | Arg | Asn | Thr | Cys | Pro | Leu | Cys | Asn | Ala | Lys | Leu | Val | Tyr |      |
|     |     |     | 150 |     |     |     |     | 155 |     |     |     |     | 160 |     |     |      |

| ctg | ata | gtg | ggc | gtg | acg | ccc | agc | ggg | tcg | ttc | agc | acc | atc | ccg | atc | 1301 |
|-----|-----|-----|-----|-----|-----|-----|-----|-----|-----|-----|-----|-----|-----|-----|-----|------|
| Leu | Ile | Val | Gly | Val | Thr | Pro | Ser | Gly | Ser | Phe | Ser | Thr | Ile | Pro | Ile |      |
|     |     | 165 |     |     |     |     | 170 |     |     |     |     | 175 |     |     |     |      |

| gtg | aac | gac | ccc | cag | acc | cgc | atg | gag | gcc | gag | gag | gcc | gtc | agg | gcg | 1349 |
|-----|-----|-----|-----|-----|-----|-----|-----|-----|-----|-----|-----|-----|-----|-----|-----|------|
| Val | Asn | Asp | Pro | Gln | Thr | Arg | Met | Glu | Ala | Glu | Glu | Ala | Val | Arg | Ala |      |
|     | 180 |     |     |     |     | 185 |     |     |     |     | 190 |     |     |     |     |      |

| ggc | acg | gcc | gtg | gac | ttt | atc | tgg | acg | ggc | aat | cag | cgg | ttc | gcc | ccg | 1397 |
|-----|-----|-----|-----|-----|-----|-----|-----|-----|-----|-----|-----|-----|-----|-----|-----|------|
| Gly | Thr | Ala | Val | Asp | Phe | Ile | Trp | Thr | Gly | Asn | Gln | Arg | Phe | Ala | Pro |      |
| 195 |     |     |     | 200 |     |     |     |     | 205 |     |     |     |     | 210 |     |      |

| cgg | tac | ctg | acc | ctg | ggg | ggg | cac | acg | gtg | agg | gcc | ctg | tcg | ccc | acc | 1445 |
|-----|-----|-----|-----|-----|-----|-----|-----|-----|-----|-----|-----|-----|-----|-----|-----|------|
| Arg | Tyr | Leu | Thr | Leu | Gly | Gly | His | Thr | Val | Arg | Ala | Leu | Ser | Pro | Thr |      |
|     |     |     |     | 215 |     |     |     |     | 220 |     |     |     |     | 225 |     |      |

| cac | ccg | gag | ccc | acc | acg | gac | gag | gat | gac | gac | gac | ctg | gac | gac |     | 1490 |
|-----|-----|-----|-----|-----|-----|-----|-----|-----|-----|-----|-----|-----|-----|-----|-----|------|
| His | Pro | Glu | Pro | Thr | Thr | Asp | Glu | Asp | Asp | Asp | Asp | Leu | Asp | Asp |     |      |
|     |     |     | 230 |     |     |     |     | 235 |     |     |     |     | 240 |     |     |      |

```
ggtgaggcgg ggggcggcaa ggaccctggg ggaggaggag gaggagggggg ggggagggag   1550 gaataggcgg gcgggcgagg aaagggcggg ccggggaggg ggcgtaacct gatcgcgccc   1610
```

| cccgttgtct | cttgca | gca | gac | tac | gta | ccg | ccc | gcc | ccc | cgc | cgg | acg | ccc | 1662 |
|------------|--------|-----|-----|-----|-----|-----|-----|-----|-----|-----|-----|-----|-----|------|
|            |        | Ala | Asp | Tyr | Val | Pro | Pro | Ala | Pro | Arg | Arg | Thr | Pro |      |
|            |        |     |     |     | 245 |     |     |     |     | 250 |     |     |     |      |

| cgc | gcc | ccc | cca | cgc | aga | ggc | gcc | gcc | gcg | ccc | ccc | gtg | acg | ggc | ggg | 1710 |
|-----|-----|-----|-----|-----|-----|-----|-----|-----|-----|-----|-----|-----|-----|-----|-----|------|
| Arg | Ala | Pro | Pro | Arg | Arg | Gly | Ala | Ala | Ala | Pro | Pro | Val | Thr | Gly | Gly |      |
|     | 255 |     |     |     |     | 260 |     |     |     |     | 265 |     |     |     |     |      |

| gcg | tct | cac | gca | gcc | ccc | cag | ccg | gcc | gcg | gct | cgg | aca | gcc | ccc | ccc | 1758 |
|-----|-----|-----|-----|-----|-----|-----|-----|-----|-----|-----|-----|-----|-----|-----|-----|------|
| Ala | Ser | His | Ala | Ala | Pro | Gln | Pro | Ala | Ala | Ala | Arg | Thr | Ala | Pro | Pro |      |
| 270 |     |     |     |     | 275 |     |     |     |     | 280 |     |     |     |     | 285 |      |

-continued

| | | |
|---|---|---|
| tcg gcg ccc atc ggg cca cac ggc agc agt aac acc aac acc acc acc<br>Ser Ala Pro Ile Gly Pro His Gly Ser Ser Asn Thr Asn Thr Thr Thr<br>290                                295                     300 | 1806 |
| aac agc agc ggc ggc ggc ggc tcc cgc cag tcg cga gcc gcg gcg ccg<br>Asn Ser Ser Gly Gly Gly Gly Ser Arg Gln Ser Arg Ala Ala Ala Pro<br>305                       310                       315 | 1854 |
| cgg ggg gcg tct ggc ccc tcc ggg ggg gtt ggg gtt ggg gtt ggg gtt<br>Arg Gly Ala Ser Gly Pro Ser Gly Gly Val Gly Val Gly Val Gly Val<br>320                     325                      330 | 1902 |
| gtt gaa gcg gag gcg ggg cgg ccg agg ggc cgg acg ggc ccc ctt gtc<br>Val Glu Ala Glu Ala Gly Arg Pro Arg Gly Arg Thr Gly Pro Leu Val<br>335                       340                     345 | 1950 |
| aac aga ccc gcc ccc ctt gca aac aac aga gac ccc ata gtg atc agc<br>Asn Arg Pro Ala Pro Leu Ala Asn Asn Arg Asp Pro Ile Val Ile Ser<br>350                   355                     360                    365 | 1998 |
| gac tcc ccc ccg gcc tct ccc cac agg ccc ccc gcg gcg ccc atg cca<br>Asp Ser Pro Pro Ala Ser Pro His Arg Pro Pro Ala Ala Pro Met Pro<br>                370                     375                     380 | 2046 |
| ggc tcc gcc ccc cgc ccc ggg ccc ccc gcg tcc gcg gcc gcg tcg gga<br>Gly Ser Ala Pro Arg Pro Gly Pro Pro Ala Ser Ala Ala Ala Ser Gly<br>385                       390                      395 | 2094 |
| ccc gcg cgc ccc cgc gcg gcc gtg gcc ccg tgc gtg cga gcg ccg cct<br>Pro Ala Arg Pro Arg Ala Ala Val Ala Pro Cys Val Arg Ala Pro Pro<br>        400                     405                     410 | 2142 |
| ccg ggg ccc ggc ccc cgc gcc ccg gcc ccc ggg gcg gag ccg gcc gcc<br>Pro Gly Pro Gly Pro Arg Ala Pro Ala Pro Gly Ala Glu Pro Ala Ala<br>415                     420                      425 | 2190 |
| cgc ccc gcg gac gcg cgc cgt gtg ccc cag tcg cac tcg tcc ctg gct<br>Arg Pro Ala Asp Ala Arg Arg Val Pro Gln Ser His Ser Ser Leu Ala<br>430                       435                      440                    445 | 2238 |
| cag gcc gcg aac caa gaa cag agt ctg tgc cgg gcg cgt gcg acg gtg<br>Gln Ala Ala Asn Gln Glu Gln Ser Leu Cys Arg Ala Arg Ala Thr Val<br>                 450                     455                    460 | 2286 |
| gcg cgc ggc tcg ggg ggg ccg ggc gtg gag ggt ggg cac ggg ccc tcc<br>Ala Arg Gly Ser Gly Gly Pro Gly Val Glu Gly Gly His Gly Pro Ser<br>                 465                     470                     475 | 2334 |
| cgc ggc gcc gcc ccc tcc ggc gcc gcc ccg ctc ccc tcc gcc gcc tct<br>Arg Gly Ala Ala Pro Ser Gly Ala Ala Pro Leu Pro Ser Ala Ala Ser<br>        480                     485                     490 | 2382 |
| gtc gag cag gag gcg gcg gtg cgt ccg agg aag agg cgc ggg tcg ggc<br>Val Glu Gln Glu Ala Ala Val Arg Pro Arg Lys Arg Arg Gly Ser Gly<br>495                       500                      505 | 2430 |
| cag gaa aac ccc tcc ccc cag tcc acg cgt ccc ccc ctc gcg ccg gca<br>Gln Glu Asn Pro Ser Pro Gln Ser Thr Arg Pro Pro Leu Ala Pro Ala<br>510                   515                     520                    525 | 2478 |
| ggg gcc aag agg gcg gcg acg cac ccc ccc tcc gac tca ggg ccg ggg<br>Gly Ala Lys Arg Ala Ala Thr His Pro Pro Ser Asp Ser Gly Pro Gly<br>                 530                     535                    540 | 2526 |
| ggg cgc ggc cag ggt ggg ccc ggg acc ccc ctg acg tcc tcg gcg gcc<br>Gly Arg Gly Gln Gly Gly Pro Gly Thr Pro Leu Thr Ser Ser Ala Ala<br>545                       550                       555 | 2574 |
| tcc gcc tct tcc tcc tct gcc tct tcc tcg gcc ccg acc ccc gcg<br>Ser Ala Ser Ser Ser Ala Ser Ser Ser Ala Pro Thr Pro Ala<br>        560                     565                     570 | 2622 |
| ggg gcc gcc tct tcc gcc gcc ggg gcc gcg tcc tcc tcc gct tcc gcc<br>Gly Ala Ala Ser Ser Ala Ala Gly Ala Ala Ser Ser Ser Ala Ser Ala<br>575                       580                      585 | 2670 |
| tcc tcg ggc ggg gcc gtc ggt gcc ctg gga ggg aga caa gag gaa acc<br>Ser Ser Gly Gly Ala Val Gly Ala Leu Gly Gly Arg Gln Glu Glu Thr<br>590                     595                     600                    605 | 2718 |

| | | | | | | | | | | | | | | | |
|---|---|---|---|---|---|---|---|---|---|---|---|---|---|---|---|
| tcc | ctc | ggc | ccc | cgc | gct | gct | tct | ggg | ccg | cgg | ggg | ccg | agg | aag | tgt | 2766 |
| Ser | Leu | Gly | Pro | Arg | Ala | Ala | Ser | Gly | Pro | Arg | Gly | Pro | Arg | Lys | Cys |
| | | | 610 | | | | | 615 | | | | 620 | | | | gcc cgg aag acg cgc cac gcg gag act tcc ggg gcc gtc ccc gcg ggc 2814
Ala Arg Lys Thr Arg His Ala Glu Thr Ser Gly Ala Val Pro Ala Gly
            625                 630                 635 ggc ctc acg cgc tac ctg ccc atc tcg ggg gtc tct agc gtg gtc gcc 2862
Gly Leu Thr Arg Tyr Leu Pro Ile Ser Gly Val Ser Ser Val Val Ala
        640                 645                 650 ctg tcg cct tac gtg aac aag act atc acg ggg gac tgc ctg ccc atc 2910
Leu Ser Pro Tyr Val Asn Lys Thr Ile Thr Gly Asp Cys Leu Pro Ile
    655                 660                 665 ctg gac atg gag acg ggg aac atc ggg gcg tac gtg gtc ctg gtg gac 2958
Leu Asp Met Glu Thr Gly Asn Ile Gly Ala Tyr Val Val Leu Val Asp
670                 675                 680                 685 cag acg gga aac atg gcg acc cgg ctg cgg gcc gcg gtc ccc ggc tgg 3006
Gln Thr Gly Asn Met Ala Thr Arg Leu Arg Ala Ala Val Pro Gly Trp
                690                 695                 700 agc cgc cgc acc ctg ctc ccc gag acc gcg ggt aac cac gtg atg ccc 3054
Ser Arg Arg Thr Leu Leu Pro Glu Thr Ala Gly Asn His Val Met Pro
            705                 710                 715 ccc gag tac ccg acg gcc ccc gcg tcg gag tgg aac agc ctc tgg atg 3102
Pro Glu Tyr Pro Thr Ala Pro Ala Ser Glu Trp Asn Ser Leu Trp Met
        720                 725                 730 acc ccc gtg ggg aac atg ctg ttc gac cag ggc acc cta gtg ggc gcc 3150
Thr Pro Val Gly Asn Met Leu Phe Asp Gln Gly Thr Leu Val Gly Ala
    735                 740                 745 ctg gac ttc cgc agc ctg cgg tct cgg cac ccg tgg tcc ggg gag cag 3198
Leu Asp Phe Arg Ser Leu Arg Ser Arg His Pro Trp Ser Gly Glu Gln
750                 755                 760                 765 ggg gcg tcg acc cgg gac gag gga aaa caa taagggacgc cccccgtgtt 3248
Gly Ala Ser Thr Arg Asp Glu Gly Lys Gln
                770                 775 tgtggggagg gggggggtcgg gcgctgggtg gtctctggcc gcgcccacta caccagccaa 3308 tccgtgtcgg ggagggggaaa agtgaaagac acgggcacca cacaccagcg ggtcttttgt 3368 gttggcccta ataaaaaaaa actcagggga ttttgctgt ctgttgggaa ataaggttt 3428 acttttgtat cttttccctg tctgtgttgg atgtatcgcg gggatgcgtg ggagtggggg 3488 tgcgtgggag tgggggtgcg tgggagtggg ggtgcgtggg agtgggggtg cgtgggagtg 3548 ggggtgcgtg ggagtggggg tgcgtgggag tgggggtgcg tgggagtggg ggtgcgtggg 3608 agtgggggtg ccatgttggg caggctctgg tgttaac 3645

<210> SEQ ID NO 2
<211> LENGTH: 775
<212> TYPE: PRT
<213> ORGANISM: Herpes simplex virus 1

<400> SEQUENCE: 2

Met Glu Pro Arg Pro Gly Ala Ser Thr Arg Arg Pro Glu Gly Arg Pro
1               5                   10                  15

Gln Arg Glu Pro Ala Pro Asp Val Trp Val Phe Pro Cys Asp Arg Asp
            20                  25                  30

Leu Pro Asp Ser Ser Asp Ser Glu Ala Glu Thr Glu Val Gly Gly Arg
        35                  40                  45

Gly Asp Ala Asp His His Asp Asp Asp Ser Ala Ser Glu Ala Asp Ser
    50                  55                  60

```
Thr Asp Thr Glu Leu Phe Glu Thr Gly Leu Leu Gly Pro Gln Gly Val
 65                  70                  75                  80

Asp Gly Gly Ala Val Ser Gly Gly Ser Pro Pro Arg Glu Glu Asp Pro
                 85                  90                  95

Gly Ser Cys Gly Gly Ala Pro Pro Arg Glu Asp Gly Gly Ser Asp Glu
            100                 105                 110

Gly Asp Val Cys Ala Val Cys Thr Asp Glu Ile Ala Pro His Leu Arg
            115                 120                 125

Cys Asp Thr Phe Pro Cys Met His Arg Phe Cys Ile Pro Cys Met Lys
    130                 135                 140

Thr Trp Met Gln Leu Arg Asn Thr Cys Pro Leu Cys Asn Ala Lys Leu
145                 150                 155                 160

Val Tyr Leu Ile Val Gly Val Thr Pro Ser Gly Ser Phe Ser Thr Ile
                165                 170                 175

Pro Ile Val Asn Asp Pro Gln Thr Arg Met Glu Ala Glu Glu Ala Val
                180                 185                 190

Arg Ala Gly Thr Ala Val Asp Phe Ile Trp Thr Gly Asn Gln Arg Phe
                195                 200                 205

Ala Pro Arg Tyr Leu Thr Leu Gly Gly His Thr Val Arg Ala Leu Ser
    210                 215                 220

Pro Thr His Pro Glu Pro Thr Thr Asp Glu Asp Asp Asp Leu Asp
225                 230                 235                 240

Asp Ala Asp Tyr Val Pro Ala Pro Arg Arg Thr Pro Arg Ala Pro
                245                 250                 255

Pro Arg Arg Gly Ala Ala Ala Pro Pro Val Thr Gly Gly Ala Ser His
    260                 265                 270

Ala Ala Pro Gln Pro Ala Ala Arg Thr Ala Pro Pro Ser Ala Pro
    275                 280                 285

Ile Gly Pro His Gly Ser Ser Asn Thr Asn Thr Thr Asn Ser Ser
    290                 295                 300

Gly Gly Gly Gly Ser Arg Gln Ser Arg Ala Ala Ala Pro Arg Gly Ala
305                 310                 315                 320

Ser Gly Pro Ser Gly Gly Val Gly Val Gly Val Gly Val Val Glu Ala
                325                 330                 335

Glu Ala Gly Arg Pro Arg Gly Arg Thr Gly Pro Leu Val Asn Arg Pro
            340                 345                 350

Ala Pro Leu Ala Asn Asn Arg Asp Pro Ile Val Ile Ser Asp Ser Pro
    355                 360                 365

Pro Ala Ser Pro His Arg Pro Ala Ala Pro Met Pro Gly Ser Ala
    370                 375                 380

Pro Arg Pro Gly Pro Pro Ala Ser Ala Ala Ser Gly Pro Ala Arg
    385                 390                 395                 400

Pro Arg Ala Ala Val Ala Pro Cys Val Arg Ala Pro Pro Gly Pro
                405                 410                 415

Gly Pro Arg Ala Pro Ala Pro Gly Ala Glu Pro Ala Ala Arg Pro Ala
                420                 425                 430

Asp Ala Arg Arg Val Pro Gln Ser His Ser Ser Leu Ala Gln Ala Ala
                435                 440                 445

Asn Gln Glu Gln Ser Leu Cys Arg Ala Arg Ala Thr Val Ala Arg Gly
    450                 455                 460

Ser Gly Gly Pro Gly Val Glu Gly Gly His Gly Pro Ser Arg Gly Ala
465                 470                 475                 480

Ala Pro Ser Gly Ala Ala Pro Leu Pro Ser Ala Ala Ser Val Glu Gln
```

|       |       |       |       |       |       | 485 |       |       |       |       |       | 490 |       |       |       |       |       | 495 |       |       |
|-------|-------|-------|-------|-------|-------|-----|-------|-------|-------|-------|-------|-----|-------|-------|-------|-------|-------|-----|-------|-------|

```
                                485                 490                 495
        Glu Ala Ala Val Arg Pro Arg Lys Arg Arg Gly Ser Gly Gln Glu Asn
                500                 505                 510

Pro Ser Pro Gln Ser Thr Arg Pro Leu Ala Pro Gly Ala Lys
            515                 520                 525

Arg Ala Ala Thr His Pro Pro Ser Asp Ser Gly Pro Gly Arg Gly
            530                 535                 540

Gln Gly Gly Pro Gly Thr Pro Leu Thr Ser Ser Ala Ala Ser Ala Ser
        545                 550                 555                 560

Ser Ser Ser Ala Ser Ser Ser Ala Pro Thr Pro Ala Gly Ala Ala
                        565                 570                 575

Ser Ser Ala Ala Gly Ala Ala Ser Ser Ala Ser Ala Ser Ser Gly
                        580                 585                 590

Gly Ala Val Gly Ala Leu Gly Gly Arg Gln Glu Glu Thr Ser Leu Gly
                        595                 600                 605

Pro Arg Ala Ala Ser Gly Pro Arg Gly Pro Arg Lys Cys Ala Arg Lys
                        610                 615                 620

Thr Arg His Ala Glu Thr Ser Gly Ala Val Pro Ala Gly Gly Leu Thr
        625                 630                 635                 640

Arg Tyr Leu Pro Ile Ser Gly Val Ser Val Val Ala Leu Ser Pro
                        645                 650                 655

Tyr Val Asn Lys Thr Ile Thr Gly Asp Cys Leu Pro Ile Leu Asp Met
                        660                 665                 670

Glu Thr Gly Asn Ile Gly Ala Tyr Val Val Leu Val Asp Gln Thr Gly
                        675                 680                 685

Asn Met Ala Thr Arg Leu Arg Ala Val Pro Gly Trp Ser Arg Arg
        690                 695                 700

Thr Leu Leu Pro Glu Thr Ala Gly Asn His Val Met Pro Pro Glu Tyr
        705                 710                 715                 720

Pro Thr Ala Pro Ala Ser Glu Trp Asn Ser Leu Trp Met Thr Pro Val
                        725                 730                 735

Gly Asn Met Leu Phe Asp Gln Gly Thr Leu Val Gly Ala Leu Asp Phe
                        740                 745                 750

Arg Ser Leu Arg Ser Arg His Pro Trp Ser Gly Glu Gln Gly Ala Ser
                        755                 760                 765

Thr Arg Asp Glu Gly Lys Gln
                        770                 775

<210> SEQ ID NO 3
<211> LENGTH: 3298
<212> TYPE: DNA
<213> ORGANISM: Herpes simplex virus 1
<220> FEATURE:
<221> NAME/KEY: CDS
<222> LOCATION: (3)..(59)
<220> FEATURE:
<221> NAME/KEY: CDS
<222> LOCATION: (866)..(1531)
<220> FEATURE:
<221> NAME/KEY: CDS
<222> LOCATION: (1670)..(3271)

<400> SEQUENCE: 3 cc atg gag ccc cgc ccc gga gcg agt acc cgc cgg cct gag ggc cgc          47
   Met Glu Pro Arg Pro Gly Ala Ser Thr Arg Arg Pro Glu Gly Arg
    1               5                   10                  15 ccc cag cgc gag gtgaggggcc gggcgccatg tctggggcgc catgtctggg             99
Pro Gln Arg Glu
```

```
gcgccatgtc tggggcgcca tgtctggggc gccatgttgg ggggcgccat gttgggggc        159 gccatgttgg gggaccccg acccttacac tggaaccggc cgccatgttg gggaccccc         219 actcatacac gggagccggg cgcccatgtt ggggcgccat gttaggggc gtggaacccc         279 gtgacactat atatacaggg accggggcg ccatgttagg gggcgcggaa cccctgacc          339 ctatatatac agggaccggg gtcgccctgt tagggtcgc catgtgaccc cctgacttta         399
tatatacaga cccccaacac ctacacatgg ccccttttgac tcagacgcag ggcccggggt      459
cgccgtggga cccccctgac tcatacacag agacacgccc cacaacaaa cacacaggga        519 ccggggtcgc cgtgttgggg gcgtggtccc cactgactca tacgcaggc cccttactc         579 acacgcatct aggggggtgg ggaggagccg cccgccatat ttgggggacg ccgtgggacc       639
cccgactccg gtgcgtctgg agggcggag aagagggaag aagaggggtc gggatccaaa       699
ggacggaccc agaccacctt tggttgcaga ccccttttctc ccccctcttc cgaggccagc     759 agggggcag gactttgtga ggcggggggg ggaggggaa ctcgtgggcg ctgattgacg        819
cgggaaatcc ccccattctt acccgccccc cctttttcc cctcag ccc gcc ccg          874
                                                   Pro Ala Pro
                                                        20 gat gtc tgg gtg ttt ccc tgc gac cga gac ctg ccg gac agc agc gac        922
Asp Val Trp Val Phe Pro Cys Asp Arg Asp Leu Pro Asp Ser Ser Asp
         25                  30                  35 tcg gag gcg gag acc gaa gtg ggg ggg cgg ggg gac gcc gac cac cat        970
Ser Glu Ala Glu Thr Glu Val Gly Gly Arg Gly Asp Ala Asp His His
 40                  45                  50 gac gac gac tcc gcc tcc gag gcg gac agc acg gac acg gaa ctg ttc       1018
Asp Asp Asp Ser Ala Ser Glu Ala Asp Ser Thr Asp Thr Glu Leu Phe
 55                  60                  65                  70 gag acg ggg ctg ctg ggg ccg cag ggc gtg gat ggg ggg gcg gtc tcg       1066
Glu Thr Gly Leu Leu Gly Pro Gln Gly Val Asp Gly Gly Ala Val Ser
                 75                  80                  85 ggg ggg agc ccc ccc cgc gag gaa gac ccc ggc agt tgc ggg ggc gcc       1114
Gly Gly Ser Pro Pro Arg Glu Glu Asp Pro Gly Ser Cys Gly Gly Ala
             90                  95                 100 ccc cct cga gag gac ggg ggg agc gac gag ggc gac gtg tgc gcc gtg       1162
Pro Pro Arg Glu Asp Gly Gly Ser Asp Glu Gly Asp Val Cys Ala Val
        105                 110                 115 tgc acg gat gag atc gcg ccc cac ctg cgc tgc gac acc ttc ccg tgc       1210
Cys Thr Asp Glu Ile Ala Pro His Leu Arg Cys Asp Thr Phe Pro Cys
    120                 125                 130 atg cac cgc ttc tgc atc ccg tgc atg aaa acc tgg atg caa ttg cgc       1258
Met His Arg Phe Cys Ile Pro Cys Met Lys Thr Trp Met Gln Leu Arg
135                 140                 145                 150 aac acc tgc ccg ctg tgc aac gcc aag ctg gtg tac ctg ata gtg ggc       1306
Asn Thr Cys Pro Leu Cys Asn Ala Lys Leu Val Tyr Leu Ile Val Gly
                155                 160                 165 gtg acg ccc agc ggg tcg ttc agc acc atc ccg atc gtg aac gac ccc       1354
Val Thr Pro Ser Gly Ser Phe Ser Thr Ile Pro Ile Val Asn Asp Pro
            170                 175                 180 cag acc cgc atg gag gcc gag gag gcc gtc agg gcg ggc acg gcc gtg       1402
Gln Thr Arg Met Glu Ala Glu Glu Ala Val Arg Ala Gly Thr Ala Val
       185                 190                 195 gac ttt atc tgg acg ggc aat cag cgg ttc gcc ccg cgg tac ctg acc       1450
Asp Phe Ile Trp Thr Gly Asn Gln Arg Phe Ala Pro Arg Tyr Leu Thr
   200                 205                 210 ctg ggg ggg cac acg gtg agg gcc ctg tcg ccc acc cac cct gag ccc       1498
Leu Gly Gly His Thr Val Arg Ala Leu Ser Pro Thr His Pro Glu Pro
```

```
                215                 220                 225                 230
acc acg gac gag gat gac gac gac ctg gac gac ggtgaggcgg ggggcggcg         1551
Thr Thr Asp Glu Asp Asp Asp Asp Leu Asp Asp
                    235                 240 aggaccctgg gggaggagga ggaggggggg ggagggagga ataggcgggc gggcgggcga        1611
ggaaagggcg ggccggggag ggggcgtaac ctgatcgcgc ccccgttgt tcttgca            1669 gca gac tac gta ccg ccc gcc ccc cgc cgg acg ccc cgc gcc ccc cca         1717
Ala Asp Tyr Val Pro Pro Ala Pro Arg Arg Thr Pro Arg Ala Pro Pro
                245                 250                 255 cgc aga ggc gcc gcc gcg ccc ccc gtg acg ggc ggg gcg tct cac gca         1765
Arg Arg Gly Ala Ala Ala Pro Pro Val Thr Gly Gly Ala Ser His Ala
            260                 265                 270 gcc ccc cag ccg gcc gcg gct cgg aca gcc ccc tcg gcg ccc atc             1813
Ala Pro Gln Pro Ala Ala Ala Arg Thr Ala Pro Pro Ser Ala Pro Ile
275                 280                 285 ggg cca cac ggc agc agt aac act aac acc acc acc aac agc agc ggc         1861
Gly Pro His Gly Ser Ser Asn Thr Asn Thr Thr Thr Asn Ser Ser Gly
290                 295                 300                 305 ggc ggc ggc tcc cgc cag tcg cga gcc gcg gtg ccg cgg ggg gcg tct         1909
Gly Gly Gly Ser Arg Gln Ser Arg Ala Ala Val Pro Arg Gly Ala Ser
                310                 315                 320 ggc ccc tcc ggg ggg gtt ggg gtt gtt gaa gcg gag gcg ggg cgg ccg         1957
Gly Pro Ser Gly Gly Val Gly Val Val Glu Ala Glu Ala Gly Arg Pro
            325                 330                 335 agg ggc cgg acg ggc ccc ctt gtc aac aga ccc gcc ccc ctt gca aac         2005
Arg Gly Arg Thr Gly Pro Leu Val Asn Arg Pro Ala Pro Leu Ala Asn
        340                 345                 350 aac aga gac ccc ata gtg atc agc gac tcc ccc ccg gcc tct ccc cac         2053
Asn Arg Asp Pro Ile Val Ile Ser Asp Ser Pro Pro Ala Ser Pro His
355                 360                 365 agg ccc ccc gcg gcg ccc atg cca ggc tcc gcc ccc cgc ccc ggt ccc         2101
Arg Pro Pro Ala Ala Pro Met Pro Gly Ser Ala Pro Arg Pro Gly Pro
370                 375                 380                 385 ccc gcg tcc gcg gcc gcg tcg ggc ccc gcg cgc ccc cgc gcg gcc gtg         2149
Pro Ala Ser Ala Ala Ala Ser Gly Pro Ala Arg Pro Arg Ala Ala Val
                390                 395                 400 gcc ccg tgt gtg cgg gcg ccg cct ccg ggg ccc ggc ccc cgc gcc ccg         2197
Ala Pro Cys Val Arg Ala Pro Pro Pro Gly Pro Gly Pro Arg Ala Pro
            405                 410                 415 gcc ccc ggg gcg gag ccg gcc gcc cgc ccc gcg gac gcg cgc cgt gtg         2245
Ala Pro Gly Ala Glu Pro Ala Ala Arg Pro Ala Asp Ala Arg Arg Val
        420                 425                 430 ccc cag tcg cac tcg tcc ctg gct cag gcc gcg aac caa gaa cag agt         2293
Pro Gln Ser His Ser Ser Leu Ala Gln Ala Ala Asn Gln Glu Gln Ser
435                 440                 445 ctg tgc cgg gcg cgt gcg acg gtg gcg cgc ggc tcg ggg ggg ccg ggc         2341
Leu Cys Arg Ala Arg Ala Thr Val Ala Arg Gly Ser Gly Gly Pro Gly
450                 455                 460                 465 gtg gag ggt gga cac ggg ccc tcc cgc ggc gcc gcc ccc tcc ggc gcc         2389
Val Glu Gly Gly His Gly Pro Ser Arg Gly Ala Ala Pro Ser Gly Ala
                470                 475                 480 gcc ccc tcc ggc gcc ccc ccg ctc ccc tcc gcc tct gtc gag cag gag         2437
Ala Pro Ser Gly Ala Pro Pro Leu Pro Ser Ala Ser Val Glu Gln Glu
            485                 490                 495 gcg gcg gtg cgt ccg agg aag agg cgc ggg tcg ggc cag gaa aac ccc         2485
Ala Ala Val Arg Pro Arg Lys Arg Arg Gly Ser Gly Gln Glu Asn Pro
        500                 505                 510 tcc ccg cag tcc acg cgt ccc ccc ctc gcg ccg gca ggg gcc aag agg         2533
```

```
Ser Pro Gln Ser Thr Arg Pro Pro Leu Ala Pro Ala Gly Ala Lys Arg
    515                 520                 525 gcg gcg acg cac ccc ccc tcc gac tca ggg ccg ggg ggg cgc ggc cag    2581
Ala Ala Thr His Pro Pro Ser Asp Ser Gly Pro Gly Gly Arg Gly Gln
530                 535                 540                 545 gga ggg ccc ggg acc ccc ctg acg tcc tcg gcg gcc tcc gcc tct tcc    2629
Gly Gly Pro Gly Thr Pro Leu Thr Ser Ser Ala Ala Ser Ala Ser Ser
                550                 555                 560 tcc tcc gcc tct tcc tcc tcg gcc ccg act ccc gcg ggg gcc acc tct    2677
Ser Ser Ala Ser Ser Ser Ser Ala Pro Thr Pro Ala Gly Ala Thr Ser
                565                 570                 575 tcc gcc acc ggg gcc gcg tcc tcc tcc gct tcc gcc tcc tcg ggc ggg    2725
Ser Ala Thr Gly Ala Ala Ser Ser Ser Ala Ser Ala Ser Ser Gly Gly
            580                 585                 590 gcc gtc ggt gcc ctg gga ggg aga caa gag gaa acc tcc ctc ggc ccc    2773
Ala Val Gly Ala Leu Gly Gly Arg Gln Glu Glu Thr Ser Leu Gly Pro
        595                 600                 605 cgc gct gct tct ggg ccg cgg ggg ccg agg aag tgt gcc cgg aag acg    2821
Arg Ala Ala Ser Gly Pro Arg Gly Pro Arg Lys Cys Ala Arg Lys Thr
610                 615                 620                 625 cgc cac gcg gag act tcc ggg gcc gtc ccc gcg ggc ggc ctc acg cgc    2869
Arg His Ala Glu Thr Ser Gly Ala Val Pro Ala Gly Gly Leu Thr Arg
                630                 635                 640 tac ctg ccc atc tcg ggg gtc tct agc gtg gtc gcc ctg tcg cct tac    2917
Tyr Leu Pro Ile Ser Gly Val Ser Ser Val Val Ala Leu Ser Pro Tyr
                645                 650                 655 gtg aac aag acg atc acg ggg gac tgc ctg ccc atc ctg gac atg gag    2965
Val Asn Lys Thr Ile Thr Gly Asp Cys Leu Pro Ile Leu Asp Met Glu
            660                 665                 670 acg ggg aac atc ggg gcg tac gtg gtc ctg gtg gac cag acg gga aac    3013
Thr Gly Asn Ile Gly Ala Tyr Val Val Leu Val Asp Gln Thr Gly Asn
        675                 680                 685 atg gcg acc cgg ctg cgg gcc gcg gtc ccc ggc tgg agc cgc cgc acc    3061
Met Ala Thr Arg Leu Arg Ala Ala Val Pro Gly Trp Ser Arg Arg Thr
690                 695                 700                 705 ctg ctc ccc gag acc gcg ggt aac cac gtg acg ccc ccc gag tac ccg    3109
Leu Leu Pro Glu Thr Ala Gly Asn His Val Thr Pro Pro Glu Tyr Pro
                710                 715                 720 acg gcc ccc gcg tcg gag tgg aac agc ctc tgg atg acc ccc gtg ggg    3157
Thr Ala Pro Ala Ser Glu Trp Asn Ser Leu Trp Met Thr Pro Val Gly
                725                 730                 735 aac atg ctg ttc gac cag ggc acc cta gtg ggc gcc ctg gac ttc cgc    3205
Asn Met Leu Phe Asp Gln Gly Thr Leu Val Gly Ala Leu Asp Phe Arg
            740                 745                 750 agc ctg cgg tct cgg cac ccg tgg tcc ggg gag cag ggg gcg tcg acc    3253
Ser Leu Arg Ser Arg His Pro Trp Ser Gly Glu Gln Gly Ala Ser Thr
        755                 760                 765 cgg gac gag gga aaa caa taagggacgc ccccgtgttt gtgggga             3298
Arg Asp Glu Gly Lys Gln
770                 775

<210> SEQ ID NO 4
<211> LENGTH: 775
<212> TYPE: PRT
<213> ORGANISM: Herpes simplex virus 1

<400> SEQUENCE: 4

Met Glu Pro Arg Pro Gly Ala Ser Thr Arg Arg Pro Glu Gly Arg Pro
1               5                   10                  15

Gln Arg Glu Pro Ala Pro Asp Val Trp Val Phe Pro Cys Asp Arg Asp
```

-continued

```
                20                  25                  30
Leu Pro Asp Ser Ser Asp Ser Glu Ala Glu Thr Glu Val Gly Gly Arg
            35                  40                  45
Gly Asp Ala Asp His His Asp Asp Ser Ala Ser Glu Ala Asp Ser
50                  55                  60
Thr Asp Thr Glu Leu Phe Glu Thr Gly Leu Leu Gly Pro Gln Gly Val
65                  70                  75                  80
Asp Gly Gly Ala Val Ser Gly Gly Ser Pro Pro Arg Glu Glu Asp Pro
                85                  90                  95
Gly Ser Cys Gly Gly Ala Pro Pro Arg Glu Asp Gly Gly Ser Asp Glu
            100                 105                 110
Gly Asp Val Cys Ala Val Cys Thr Asp Glu Ile Ala Pro His Leu Arg
            115                 120                 125
Cys Asp Thr Phe Pro Cys Met His Arg Phe Cys Ile Pro Cys Met Lys
            130                 135                 140
Thr Trp Met Gln Leu Arg Asn Thr Cys Pro Leu Cys Asn Ala Lys Leu
145                 150                 155                 160
Val Tyr Leu Ile Val Gly Val Thr Pro Ser Gly Ser Phe Ser Thr Ile
                165                 170                 175
Pro Ile Val Asn Asp Pro Gln Thr Arg Met Glu Ala Glu Glu Ala Val
            180                 185                 190
Arg Ala Gly Thr Ala Val Asp Phe Ile Trp Thr Gly Asn Gln Arg Phe
            195                 200                 205
Ala Pro Arg Tyr Leu Thr Leu Gly Gly His Thr Val Arg Ala Leu Ser
            210                 215                 220
Pro Thr His Pro Glu Pro Thr Thr Asp Glu Asp Asp Asp Leu Asp
225                 230                 235                 240
Asp Ala Asp Tyr Val Pro Pro Ala Pro Arg Arg Thr Pro Arg Ala Pro
                245                 250                 255
Pro Arg Arg Gly Ala Ala Ala Pro Pro Val Thr Gly Gly Ala Ser His
            260                 265                 270
Ala Ala Pro Gln Pro Ala Ala Arg Thr Ala Pro Pro Ser Ala Pro
            275                 280                 285
Ile Gly Pro His Gly Ser Ser Asn Thr Asn Thr Thr Asn Ser Ser
            290                 295                 300
Gly Gly Gly Gly Ser Arg Gln Ser Arg Ala Ala Val Pro Arg Gly Ala
305                 310                 315                 320
Ser Gly Pro Ser Gly Gly Val Gly Val Val Glu Ala Glu Ala Gly Arg
                325                 330                 335
Pro Arg Gly Arg Thr Gly Pro Leu Val Asn Arg Pro Ala Pro Leu Ala
            340                 345                 350
Asn Asn Arg Asp Pro Ile Val Ile Ser Asp Ser Pro Pro Ala Ser Pro
            355                 360                 365
His Arg Pro Pro Ala Ala Pro Met Pro Gly Ser Ala Pro Arg Pro Gly
            370                 375                 380
Pro Pro Ala Ser Ala Ala Ala Ser Gly Pro Ala Arg Pro Arg Ala Ala
385                 390                 395                 400
Val Ala Pro Cys Val Arg Ala Pro Pro Gly Pro Gly Pro Arg Ala
                405                 410                 415
Pro Ala Pro Gly Ala Glu Pro Ala Ala Arg Pro Ala Asp Ala Arg Arg
            420                 425                 430
Val Pro Gln Ser His Ser Ser Leu Ala Gln Ala Ala Asn Gln Glu Gln
            435                 440                 445
```

Ser Leu Cys Arg Ala Arg Ala Thr Val Ala Arg Gly Ser Gly Gly Pro
    450                 455                 460

Gly Val Glu Gly Gly His Gly Pro Ser Arg Gly Ala Ala Pro Ser Gly
465                 470                 475                 480

Ala Ala Pro Ser Gly Ala Pro Pro Leu Pro Ser Ala Ser Val Glu Gln
                485                 490                 495

Glu Ala Ala Val Arg Pro Arg Lys Arg Arg Gly Ser Gly Gln Glu Asn
            500                 505                 510

Pro Ser Pro Gln Ser Thr Arg Pro Pro Leu Ala Pro Gly Ala Lys
        515                 520                 525

Arg Ala Ala Thr His Pro Pro Ser Asp Ser Gly Pro Gly Gly Arg Gly
    530                 535                 540

Gln Gly Gly Pro Gly Thr Pro Leu Thr Ser Ser Ala Ala Ser Ala Ser
545                 550                 555                 560

Ser Ser Ser Ala Ser Ser Ser Ala Pro Thr Pro Ala Gly Ala Thr
                565                 570                 575

Ser Ser Ala Thr Gly Ala Ala Ser Ser Ala Ser Ala Ser Ser Gly
            580                 585                 590

Gly Ala Val Gly Ala Leu Gly Gly Arg Gln Glu Glu Thr Ser Leu Gly
    595                 600                 605

Pro Arg Ala Ala Ser Gly Pro Arg Gly Pro Arg Lys Cys Ala Arg Lys
    610                 615                 620

Thr Arg His Ala Glu Thr Ser Gly Ala Val Pro Ala Gly Gly Leu Thr
625                 630                 635                 640

Arg Tyr Leu Pro Ile Ser Gly Val Ser Ser Val Ala Leu Ser Pro
                645                 650                 655

Tyr Val Asn Lys Thr Ile Thr Gly Asp Cys Leu Pro Ile Leu Asp Met
            660                 665                 670

Glu Thr Gly Asn Ile Gly Ala Tyr Val Val Leu Val Asp Gln Thr Gly
            675                 680                 685

Asn Met Ala Thr Arg Leu Arg Ala Ala Val Pro Gly Trp Ser Arg Arg
    690                 695                 700

Thr Leu Leu Pro Glu Thr Ala Gly Asn His Val Thr Pro Pro Glu Tyr
705                 710                 715                 720

Pro Thr Ala Pro Ala Ser Glu Trp Asn Ser Leu Trp Met Thr Pro Val
                725                 730                 735

Gly Asn Met Leu Phe Asp Gln Gly Thr Leu Val Gly Ala Leu Asp Phe
            740                 745                 750

Arg Ser Leu Arg Ser Arg His Pro Trp Ser Gly Glu Gln Gly Ala Ser
    755                 760                 765

Thr Arg Asp Glu Gly Lys Gln
    770                 775

<210> SEQ ID NO 5
<211> LENGTH: 78
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctgggggggc acacggtgag ggccctagcg ccggcccacc ctgagccggc cgcggacgag    60
gatgacgacg acctggac                                                 78

<210> SEQ ID NO 6
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcaaacaaca gagacccat agtgatcgcc gatgccccc cggccgctcc cacaggcccc        60
ccgcggcgcc c                                                          71

<210> SEQ ID NO 7
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcggtgcgtc cgaggaagag gcgcggggcc ggccaggaaa accccgcccc gcaggccgcg      60 cgtcccccc tcgcgccggc agggg                                            85

<210> SEQ ID NO 8
<211> LENGTH: 825
<212> TYPE: PRT
<213> ORGANISM: Herpes simplex virus 2

<400> SEQUENCE: 8

Met Glu Pro Arg Pro Gly Thr Ser Ser Arg Ala Asp Pro Gly Pro Glu
1               5                   10                  15

Arg Pro Pro Arg Gln Thr Pro Gly Thr Gln Pro Ala Ala Pro His Ala
            20                  25                  30

Trp Gly Met Leu Asn Asp Met Gln Trp Leu Ala Ser Ser Asp Ser Glu
        35                  40                  45

Glu Glu Thr Glu Val Gly Ile Ser Asp Asp Asp Leu His Arg Asp Ser
    50                  55                  60

Thr Ser Glu Ala Gly Ser Thr Asp Thr Glu Met Phe Glu Ala Gly Leu
65                  70                  75                  80

Met Asp Ala Ala Thr Pro Pro Ala Arg Pro Pro Ala Glu Arg Gln Gly
                85                  90                  95

Ser Pro Thr Pro Ala Asp Ala Gln Gly Ser Cys Gly Gly Gly Pro Val
            100                 105                 110

Gly Glu Glu Glu Ala Glu Ala Gly Gly Gly Asp Val Cys Ala Val
            115                 120                 125

Cys Thr Asp Glu Ile Ala Pro Pro Leu Arg Cys Gln Ser Phe Pro Cys
        130                 135                 140

Leu His Pro Phe Cys Ile Pro Cys Met Lys Thr Trp Ile Pro Leu Arg
145                 150                 155                 160

Asn Thr Cys Pro Leu Cys Asn Thr Pro Val Ala Tyr Leu Ile Val Gly
                165                 170                 175

Val Thr Ala Ser Gly Ser Phe Ser Thr Ile Pro Ile Val Asn Asp Pro
            180                 185                 190

Arg Thr Arg Val Glu Ala Glu Ala Val Arg Ala Gly Thr Ala Val
        195                 200                 205

Asp Phe Ile Trp Thr Gly Asn Pro Arg Thr Ala Pro Arg Ser Leu Ser
    210                 215                 220

```
Leu Gly Gly His Thr Val Arg Ala Leu Ser Pro Thr Pro Pro Trp Pro
225                 230                 235                 240

Gly Thr Asp Asp Glu Asp Asp Leu Ala Asp Val Asp Tyr Val Pro
        245                 250                 255

Pro Ala Pro Arg Arg Ala Pro Arg Arg Gly Gly Gly Ala Gly Ala
            260                 265                 270

Thr Arg Gly Thr Ser Gln Pro Ala Ala Thr Arg Pro Ala Pro Pro Gly
        275                 280                 285

Ala Pro Arg Ser Ser Ser Ser Gly Gly Ala Pro Leu Arg Ala Gly Val
290                 295                 300

Gly Ser Gly Ser Gly Gly Gly Pro Ala Val Ala Ala Val Val Pro Arg
305                 310                 315                 320

Val Ala Ser Leu Pro Pro Ala Ala Gly Gly Arg Ala Gln Ala Arg
            325                 330                 335

Arg Val Gly Glu Asp Ala Ala Ala Ala Glu Gly Arg Thr Pro Pro Ala
            340                 345                 350

Arg Gln Pro Arg Ala Ala Gln Glu Pro Pro Ile Val Ile Ser Asp Ser
            355                 360                 365

Pro Pro Pro Ser Pro Arg Arg Pro Ala Gly Pro Gly Pro Leu Ser Phe
370                 375                 380

Val Ser Ser Ser Ala Gln Val Ser Ser Gly Pro Gly Gly Gly
385                 390                 395                 400

Leu Pro Gln Ser Ser Gly Arg Ala Ala Arg Pro Arg Ala Ala Val Ala
            405                 410                 415

Pro Arg Val Arg Ser Pro Pro Arg Ala Ala Ala Pro Val Val Ser
            420                 425                 430

Ala Ser Ala Asp Ala Ala Gly Pro Ala Pro Ala Val Pro Val Asp
            435                 440                 445

Ala His Arg Ala Pro Arg Ser Arg Met Thr Gln Ala Gln Thr Asp Thr
            450                 455                 460

Gln Ala Gln Ser Leu Gly Arg Ala Gly Ala Thr Asp Ala Arg Gly Ser
465                 470                 475                 480

Gly Gly Pro Gly Ala Glu Gly Gly Pro Gly Val Pro Arg Gly Thr Asn
            485                 490                 495

Thr Pro Gly Ala Ala Pro His Ala Ala Glu Gly Ala Ala Ala Arg Pro
            500                 505                 510

Arg Lys Arg Arg Gly Ser Asp Ser Gly Pro Ala Ala Ser Ser Ser Ala
            515                 520                 525

Ser Ser Ser Ala Ala Pro Arg Ser Pro Leu Ala Pro Gln Gly Val Gly
530                 535                 540

Ala Lys Arg Ala Ala Pro Arg Arg Ala Pro Asp Ser Asp Ser Gly Asp
545                 550                 555                 560

Arg Gly His Gly Pro Leu Ala Pro Ala Ser Gly Ala Ala Pro Pro
            565                 570                 575

Ser Ala Ser Pro Ser Ser Gln Ala Ala Val Ala Ala Ala Ser Ser Ser
            580                 585                 590

Ser Ala Ser Ser Ser Ser Ala Ser Ser Ser Ala Ser Ser Ser
            595                 600                 605

Ala Ser Ser Ser Ser Ala Ser Ser Ser Ala Ser Ser Ser Ala
            610                 615                 620

Ser Ser Ser Ala Gly Gly Ala Gly Gly Ser Val Ala Ser Ala Ser Gly
625                 630                 635                 640
```

```
Ala Gly Glu Arg Arg Glu Thr Ser Leu Gly Pro Arg Ala Ala Ala Pro
            645                 650                 655

Arg Gly Pro Arg Lys Cys Ala Arg Lys Thr Arg His Ala Glu Gly Gly
        660                 665                 670

Pro Glu Pro Gly Ala Arg Asp Pro Ala Pro Gly Leu Thr Arg Tyr Leu
    675                 680                 685

Pro Ile Ala Gly Val Ser Val Val Ala Leu Ala Pro Tyr Val Asn
690                 695                 700

Lys Thr Val Thr Gly Asp Cys Leu Pro Val Leu Asp Met Glu Thr Gly
705                 710                 715                 720

His Ile Gly Ala Tyr Val Val Leu Val Asp Gln Thr Gly Asn Val Ala
                725                 730                 735

Asp Leu Leu Arg Ala Ala Ala Pro Ala Trp Ser Arg Arg Thr Leu Leu
            740                 745                 750

Pro Glu His Ala Arg Asn Cys Val Arg Pro Pro Asp Tyr Pro Thr Pro
        755                 760                 765

Pro Ala Ser Glu Trp Asn Ser Leu Trp Met Thr Pro Val Gly Asn Met
    770                 775                 780

Leu Phe Asp Gln Gly Thr Leu Val Gly Ala Leu Asp Phe His Gly Leu
785                 790                 795                 800

Arg Ser Arg His Pro Trp Ser Arg Glu Gln Gly Ala Pro Ala Pro Ala
                805                 810                 815

Gly Asp Ala Pro Ala Gly His Gly Glu
            820                 825
```

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccgagcggcc gctgagcaag ggcgaggagc tgt        33

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccacaggatc ccagctcgtc catgccgaga g        31

<210> SEQ ID NO 11
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
tttggatccg gatgtgccgt gtgcacggac gagatcgccc cgcccctgcg ctgccagagt        60
tttccctgcc tgcacccctt ctgcatcccg tgcatgaaga cctggattcc gttgcgcaac        120
acgtgcatca        130

<210> SEQ ID NO 12
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
tttggatccg gagtgtgcac ggacgagatc gccccgcccc tgcgctgcca gagttttccc      60
tgcctgcacc ccttctgcat cccgtgcatg aagacctgga ttccgttgcg caacacgtgc     120
atca                                                                  124

<210> SEQ ID NO 13
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
tttggatccg gaacggacga gatcgccccg ccctgcgct gccagagttt ccctgcctg       60 caccccttct gcatcccgtg catgaagacc tggattccgt tgcgcaacac gtgcatca      118

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ccctgggatc cctagactag tctagctgca gtggac                               36

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcgcgggcgc gcccagctcg tccatgccga g                                    31

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgaaggtcgt cgtcagagat tcccacctcg gtctcctcct                           40

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
atagacgttg tggctgttgt agttgtactc cagcttgtgc                                40

<210> SEQ ID NO 18
<211> LENGTH: 24
<212> TYPE: PRT
<213> ORGANISM: Herpes simplex virus 1

<400> SEQUENCE: 18

Arg Arg Gly Ser Gly Gln Glu Asn Pro Ser Pro Gln Ser Thr Arg Pro
1               5                   10                  15

Pro Leu Ala Pro Ala Gly Ala Lys
            20

<210> SEQ ID NO 19
<211> LENGTH: 775
<212> TYPE: PRT
<213> ORGANISM: Herpes simplex virus 1

<400> SEQUENCE: 19

Met Glu Pro Arg Pro Gly Ala Ser Thr Arg Arg Pro Glu Gly Arg Pro
1               5                   10                  15

Gln Arg Glu Pro Ala Pro Asp Val Trp Val Phe Pro Cys Asp Arg Asp
            20                  25                  30

Leu Pro Asp Ser Ser Asp Ser Glu Ala Glu Thr Glu Val Gly Gly Arg
        35                  40                  45

Gly Asp Ala Asp His His Asp Asp Ser Ala Ser Glu Ala Asp Ser
    50                  55                  60

Thr Asp Thr Glu Leu Phe Glu Thr Gly Leu Leu Gly Pro Gln Gly Val
65                  70                  75                  80

Asp Gly Gly Ala Val Ser Gly Ser Pro Pro Arg Glu Glu Asp Pro
                85                  90                  95

Gly Ser Cys Gly Gly Ala Pro Pro Arg Glu Asp Gly Gly Ser Asp Glu
            100                 105                 110

Gly Asp Val Cys Ala Val Cys Thr Asp Glu Ile Ala Pro His Leu Arg
        115                 120                 125

Cys Asp Thr Phe Pro Cys Met His Arg Phe Cys Ile Pro Cys Met Lys
    130                 135                 140

Thr Trp Met Gln Leu Arg Asn Thr Cys Pro Leu Cys Asn Ala Lys Leu
145                 150                 155                 160

Val Tyr Leu Ile Val Gly Val Thr Pro Ser Gly Ser Phe Ser Thr Ile
                165                 170                 175

Pro Ile Val Asn Asp Pro Gln Thr Arg Met Glu Ala Glu Ala Val
            180                 185                 190

Arg Ala Gly Thr Ala Val Asp Phe Ile Trp Thr Gly Asn Gln Arg Phe
        195                 200                 205

Ala Pro Arg Tyr Leu Thr Leu Gly Gly His Thr Val Arg Ala Leu Ser
    210                 215                 220

Pro Thr His Pro Glu Pro Thr Thr Asp Glu Asp Asp Asp Leu Asp
225                 230                 235                 240

Asp Ala Asp Tyr Val Pro Pro Ala Pro Arg Arg Thr Pro Arg Ala Pro
                245                 250                 255

Pro Arg Arg Gly Ala Ala Ala Pro Pro Val Thr Gly Gly Ala Ser His
            260                 265                 270

Ala Ala Pro Gln Pro Ala Ala Ala Arg Thr Ala Pro Pro Ser Ala Pro

```
                     275                 280                 285
Ile Gly Pro His Gly Ser Ser Asn Thr Asn Thr Thr Thr Asn Ser Ser
    290                 295                 300
Gly Gly Gly Gly Ser Arg Gln Ser Arg Ala Ala Pro Arg Gly Ala
305                 310                 315                 320
Ser Gly Pro Ser Gly Val Gly Val Gly Val Val Glu Ala
                325                 330                 335
Glu Ala Gly Arg Pro Arg Gly Arg Thr Gly Pro Leu Val Asn Arg Pro
            340                 345                 350
Ala Pro Leu Ala Asn Asn Arg Asp Pro Ile Val Ile Ser Asp Ser Pro
                355                 360                 365
Pro Ala Ser Pro His Arg Pro Pro Ala Ala Pro Met Pro Gly Ser Ala
        370                 375                 380
Pro Arg Pro Gly Pro Pro Ala Ser Ala Ala Ala Ser Gly Pro Ala Arg
385                 390                 395                 400
Pro Arg Ala Ala Val Ala Pro Cys Val Arg Ala Pro Pro Gly Pro
                405                 410                 415
Gly Pro Arg Ala Pro Ala Pro Gly Ala Glu Pro Ala Ala Arg Pro Ala
                420                 425                 430
Asp Ala Arg Arg Val Pro Gln Ser His Ser Ser Leu Ala Gln Ala Ala
            435                 440                 445
Asn Gln Glu Gln Ser Leu Cys Arg Ala Arg Ala Thr Val Ala Arg Gly
    450                 455                 460
Ser Gly Gly Pro Gly Val Glu Gly Gly His Gly Pro Ser Arg Gly Ala
465                 470                 475                 480
Ala Pro Ser Gly Ala Ala Pro Leu Pro Ser Ala Ala Ser Val Glu Gln
                485                 490                 495
Glu Ala Ala Val Arg Pro Arg Lys Arg Gly Ser Gly Gln Glu Asn
                500                 505                 510
Pro Ser Pro Gln Ser Thr Arg Pro Pro Leu Ala Pro Gly Ala Lys
            515                 520                 525
Arg Ala Ala Thr His Pro Pro Ser Asp Ser Gly Pro Gly Arg Gly
        530                 535                 540
Gln Gly Gly Pro Gly Thr Pro Leu Thr Ser Ala Ala Ser Ala Ser
545                 550                 555                 560
Ser Ser Ser Ala Ser Ser Ser Ala Pro Thr Pro Ala Gly Ala Thr
                565                 570                 575
Ser Ser Ala Thr Gly Ala Ala Ser Ser Ser Ala Ser Ala Ser Ser Gly
            580                 585                 590
Gly Ala Val Gly Ala Leu Gly Gly Arg Gln Glu Glu Thr Ser Leu Gly
        595                 600                 605
Pro Arg Ala Ala Ser Gly Pro Arg Gly Pro Arg Lys Cys Ala Arg Lys
    610                 615                 620
Thr Arg His Ala Glu Thr Ser Gly Ala Val Pro Ala Gly Gly Leu Thr
625                 630                 635                 640
Arg Tyr Leu Pro Ile Ser Gly Val Ser Ser Val Ala Leu Ser Pro
                645                 650                 655
Tyr Val Asn Lys Thr Ile Thr Gly Asp Cys Leu Pro Ile Leu Asp Met
            660                 665                 670
Glu Thr Gly Asn Ile Gly Ala Tyr Val Val Leu Val Asp Gln Thr Gly
        675                 680                 685
Asn Met Ala Thr Arg Leu Arg Ala Ala Val Pro Gly Trp Ser Arg Arg
    690                 695                 700
```

```
Thr Leu Leu Pro Glu Thr Ala Gly Asn His Val Thr Pro Pro Glu Tyr
705                 710                 715                 720

Pro Thr Ala Pro Ala Ser Glu Trp Asn Ser Leu Trp Met Thr Pro Val
            725                 730                 735

Gly Asn Met Leu Phe Asp Gln Gly Thr Leu Val Gly Ala Leu Asp Phe
        740                 745                 750

Arg Ser Leu Arg Ser Arg His Pro Trp Ser Gly Glu Gln Gly Ala Ser
    755                 760                 765

Thr Arg Asp Glu Gly Lys Gln
    770                 775
```

<210> SEQ ID NO 20
<211> LENGTH: 15
<212> TYPE: PRT
<213> ORGANISM: Herpes simplex virus 1

<400> SEQUENCE: 20

```
Met Glu Pro Arg Pro Gly Ala Ser Thr Arg Arg Pro Glu Gly Arg
1               5                   10                  15
```

<210> SEQ ID NO 21
<211> LENGTH: 377
<212> TYPE: PRT
<213> ORGANISM: Herpes simplex virus 1

<400> SEQUENCE: 21

```
Gly Ser Cys Gly Gly Ala Pro Pro Arg Glu Asp Gly Gly Ser Asp Glu
1               5                   10                  15

Gly Asp Val Cys Ala Val Cys Thr Asp Glu Ile Ala Pro His Leu Arg
            20                  25                  30

Cys Asp Thr Phe Pro Cys Met His Arg Phe Cys Ile Pro Cys Met Lys
        35                  40                  45

Thr Trp Met Gln Leu Arg Asn Thr Cys Pro Leu Cys Asn Ala Lys Leu
    50                  55                  60

Val Tyr Leu Ile Val Gly Val Thr Pro Ser Gly Ser Phe Ser Thr Ile
65                  70                  75                  80

Pro Ile Val Asn Asp Pro Gln Thr Arg Met Glu Ala Glu Glu Ala Val
                85                  90                  95

Arg Ala Gly Thr Ala Val Asp Phe Ile Trp Thr Gly Asn Gln Arg Phe
            100                 105                 110

Ala Pro Arg Tyr Leu Thr Leu Gly Gly His Thr Val Arg Ala Leu Ser
        115                 120                 125

Pro Thr His Pro Glu Pro Thr Thr Asp Glu Asp Asp Asp Asp Leu Asp
    130                 135                 140

Asp Ala Asp Tyr Val Pro Pro Ala Pro Arg Arg Thr Pro Arg Ala Pro
145                 150                 155                 160

Pro Arg Arg Gly Ala Ala Ala Pro Pro Val Thr Gly Gly Ala Ser His
                165                 170                 175

Ala Ala Pro Gln Pro Ala Ala Ala Arg Thr Ala Pro Ser Ala Pro
            180                 185                 190

Ile Gly Pro His Gly Ser Ser Asn Thr Asn Thr Thr Asn Ser Ser
        195                 200                 205

Gly Gly Gly Gly Ser Arg Gln Ser Arg Ala Ala Ala Pro Arg Gly Ala
    210                 215                 220

Ser Gly Pro Ser Gly Gly Val Gly Val Gly Val Gly Val Val Glu Ala
225                 230                 235                 240
```

```
Glu Ala Gly Arg Pro Arg Gly Arg Thr Gly Pro Leu Val Asn Arg Pro
                245                 250                 255

Ala Pro Leu Ala Asn Asn Arg Asp Pro Ile Val Ile Ser Asp Ser Pro
            260                 265                 270

Pro Ala Ser Pro His Arg Pro Pro Ala Ala Pro Met Pro Gly Ser Ala
        275                 280                 285

Pro Arg Pro Gly Pro Pro Ala Ser Ala Ala Ser Gly Pro Ala Arg
    290                 295                 300

Pro Arg Ala Ala Val Ala Pro Cys Val Arg Ala Pro Pro Gly Pro
305                 310                 315                 320

Gly Pro Arg Ala Pro Ala Pro Gly Ala Glu Pro Ala Ala Arg Pro Ala
                325                 330                 335

Asp Ala Arg Arg Val Pro Gln Ser His Ser Ser Leu Ala Gln Ala Ala
            340                 345                 350

Asn Gln Glu Gln Ser Leu Cys Arg Ala Arg Ala Thr Val Ala Arg Gly
        355                 360                 365

Ser Gly Gly Pro Gly Val Glu Gly Gly
    370                 375

<210> SEQ ID NO 22
<211> LENGTH: 115
<212> TYPE: PRT
<213> ORGANISM: Herpes simplex virus 1

<400> SEQUENCE: 22

Val Val Ala Leu Ser Pro Tyr Val Asn Lys Thr Ile Thr Gly Asp Cys
1               5                   10                  15

Leu Pro Ile Leu Asp Met Glu Thr Gly Asn Ile Gly Ala Tyr Val Val
            20                  25                  30

Leu Val Asp Gln Thr Gly Asn Met Ala Thr Arg Leu Arg Ala Ala Val
        35                  40                  45

Pro Gly Trp Ser Arg Arg Thr Leu Leu Pro Glu Thr Ala Gly Asn His
    50                  55                  60

Val Thr Pro Pro Glu Tyr Pro Thr Ala Pro Ala Ser Glu Trp Asn Ser
65                  70                  75                  80

Leu Trp Met Thr Pro Val Gly Asn Met Leu Phe Asp Gln Gly Thr Leu
                85                  90                  95

Val Gly Ala Leu Asp Phe Arg Ser Leu Arg Ser Arg His Pro Trp Ser
            100                 105                 110

Gly Glu Gln
        115

<210> SEQ ID NO 23
<211> LENGTH: 18
<212> TYPE: PRT
<213> ORGANISM: Herpes simplex virus 2

<400> SEQUENCE: 23

Met Glu Pro Arg Pro Gly Thr Ser Ser Arg Ala Asp Pro Gly Pro Glu
1               5                   10                  15

Arg Pro

<210> SEQ ID NO 24
<211> LENGTH: 384
<212> TYPE: PRT
<213> ORGANISM: Herpes simplex virus 2
```

<400> SEQUENCE: 24

```
Gly Ser Cys Gly Gly Gly Pro Val Gly Glu Glu Ala Glu Ala Gly
1               5                   10                  15
Gly Gly Gly Asp Val Cys Ala Val Cys Thr Asp Glu Ile Ala Pro Pro
            20                  25                  30
Leu Arg Cys Gln Ser Phe Pro Cys Leu His Pro Phe Cys Ile Pro Cys
            35                  40                  45
Met Lys Thr Trp Ile Pro Leu Arg Asn Thr Cys Pro Leu Cys Asn Thr
50                  55                  60
Pro Val Ala Tyr Leu Ile Val Gly Val Thr Ala Ser Gly Ser Phe Ser
65                  70                  75                  80
Thr Ile Pro Ile Val Asn Asp Pro Arg Thr Arg Val Glu Ala Glu Ala
                85                  90                  95
Ala Val Arg Ala Gly Thr Ala Val Asp Phe Ile Trp Thr Gly Asn Pro
            100                 105                 110
Arg Thr Ala Pro Arg Ser Leu Ser Leu Gly Gly His Thr Val Arg Ala
            115                 120                 125
Leu Ser Pro Thr Pro Pro Trp Pro Gly Thr Asp Asp Glu Asp Asp Asp
130                 135                 140
Leu Ala Asp Val Asp Tyr Val Pro Pro Ala Pro Arg Arg Ala Pro Arg
145                 150                 155                 160
Arg Gly Gly Gly Gly Ala Gly Ala Thr Arg Gly Thr Ser Gln Pro Ala
            165                 170                 175
Ala Thr Arg Pro Ala Pro Pro Gly Ala Pro Arg Ser Ser Ser Ser Gly
            180                 185                 190
Gly Ala Pro Leu Arg Ala Gly Val Gly Ser Gly Ser Gly Gly Gly Pro
            195                 200                 205
Ala Val Ala Ala Val Val Pro Arg Val Ala Ser Leu Pro Pro Ala Ala
210                 215                 220
Gly Gly Gly Arg Ala Gln Ala Arg Arg Val Gly Glu Asp Ala Ala Ala
225                 230                 235                 240
Ala Glu Gly Arg Thr Pro Pro Ala Arg Gln Pro Arg Ala Ala Gln Glu
            245                 250                 255
Pro Pro Ile Val Ile Ser Asp Ser Pro Pro Ser Pro Arg Arg Pro
            260                 265                 270
Ala Gly Pro Gly Pro Leu Ser Phe Val Ser Ser Ser Ala Gln Val
            275                 280                 285
Ser Ser Gly Pro Gly Gly Gly Leu Pro Gln Ser Ser Gly Arg Ala
            290                 295                 300
Ala Arg Pro Arg Ala Ala Val Ala Pro Arg Val Arg Ser Pro Arg
305                 310                 315                 320
Ala Ala Ala Ala Pro Val Val Ser Ala Ser Ala Asp Ala Gly Pro
                325                 330                 335
Ala Pro Pro Ala Val Pro Val Asp Ala His Arg Ala Pro Arg Ser Arg
            340                 345                 350
Met Thr Gln Ala Gln Thr Asp Thr Gln Ala Gln Ser Leu Gly Arg Ala
            355                 360                 365
Gly Ala Thr Asp Ala Arg Gly Ser Gly Gly Pro Gly Ala Glu Gly Gly
            370                 375                 380
```

<210> SEQ ID NO 25
<211> LENGTH: 130
<212> TYPE: PRT
<213> ORGANISM: Herpes simplex virus 2

<400> SEQUENCE: 25

Val Val Ala Leu Ala Pro Tyr Val Asn Lys Thr Val Thr Gly Asp Cys
1               5                   10                  15

Leu Pro Val Leu Asp Met Glu Thr Gly His Ile Gly Ala Tyr Val Val
            20                  25                  30

Leu Val Asp Gln Thr Gly Asn Val Ala Asp Leu Leu Arg Ala Ala Ala
            35                  40                  45

Pro Ala Trp Ser Arg Arg Thr Leu Leu Pro Glu His Ala Arg Asn Cys
            50                  55                  60

Val Arg Pro Pro Asp Tyr Pro Thr Pro Pro Ala Ser Glu Trp Asn Ser
65                  70                  75                  80

Leu Trp Met Thr Pro Val Gly Asn Met Leu Phe Asp Gln Gly Thr Leu
                85                  90                  95

Val Gly Ala Leu Asp Phe His Gly Leu Arg Ser Arg His Pro Trp Ser
            100                 105                 110

Arg Glu Gln Gly Ala Pro Ala Pro Ala Gly Asp Ala Pro Ala Gly His
            115                 120                 125

Gly Glu
    130

<210> SEQ ID NO 26
<211> LENGTH: 552
<212> TYPE: PRT
<213> ORGANISM: Herpes simplex virus 1

<400> SEQUENCE: 26

Gly Ser Cys Gly Gly Ala Pro Pro Arg Glu Asp Gly Gly Ser Asp Glu
1               5                   10                  15

Gly Asp Val Cys Ala Val Cys Thr Asp Glu Ile Ala Pro His Leu Arg
            20                  25                  30

Cys Asp Thr Phe Pro Cys Met His Arg Phe Cys Ile Pro Cys Met Lys
            35                  40                  45

Thr Trp Met Gln Leu Arg Asn Thr Cys Pro Leu Cys Asn Ala Lys Leu
            50                  55                  60

Val Tyr Leu Ile Val Gly Val Thr Pro Ser Gly Ser Phe Ser Thr Ile
65                  70                  75                  80

Pro Ile Val Asn Asp Pro Gln Thr Arg Met Glu Ala Glu Glu Ala Val
                85                  90                  95

Arg Ala Gly Thr Ala Val Asp Phe Ile Trp Thr Gly Asn Gln Arg Phe
            100                 105                 110

Ala Pro Arg Tyr Leu Thr Leu Gly Gly His Thr Val Arg Ala Leu Ser
            115                 120                 125

Pro Thr His Pro Glu Pro Thr Thr Asp Glu Asp Asp Asp Leu Asp
            130                 135                 140

Asp Ala Asp Tyr Val Pro Pro Ala Pro Arg Arg Thr Pro Arg Ala Pro
145                 150                 155                 160

Pro Arg Arg Gly Ala Ala Ala Pro Val Thr Gly Gly Ala Ser His
            165                 170                 175

Ala Ala Pro Gln Pro Ala Ala Arg Thr Ala Pro Pro Ser Ala Pro
            180                 185                 190

Ile Gly Pro His Gly Ser Ser Asn Thr Asn Thr Thr Asn Ser Ser
            195                 200                 205

Gly Gly Gly Gly Ser Arg Gln Ser Arg Ala Ala Pro Arg Gly Ala
            210                 215                 220

```
Ser Gly Pro Ser Gly Gly Val Gly Val Gly Val Val Glu Ala
225                 230                 235                 240

Glu Ala Gly Arg Pro Arg Gly Arg Thr Gly Pro Leu Val Asn Arg Pro
            245                 250                 255

Ala Pro Leu Ala Asn Asn Arg Asp Pro Ile Val Ile Ser Asp Ser Pro
        260                 265                 270

Pro Ala Ser Pro His Arg Pro Ala Ala Pro Met Pro Gly Ser Ala
    275                 280                 285

Pro Arg Pro Gly Pro Pro Ala Ser Ala Ala Ser Gly Pro Ala Arg
290                 295                 300

Pro Arg Ala Ala Val Ala Pro Cys Val Arg Ala Pro Pro Gly Pro
305                 310                 315                 320

Gly Pro Arg Ala Pro Ala Pro Gly Ala Glu Pro Ala Ala Arg Pro Ala
            325                 330                 335

Asp Ala Arg Arg Val Pro Gln Ser His Ser Ser Leu Ala Gln Ala Ala
            340                 345                 350

Asn Gln Glu Gln Ser Leu Cys Arg Ala Arg Ala Thr Val Ala Arg Gly
        355                 360                 365

Ser Gly Gly Pro Gly Val Glu Gly Gly His Gly Pro Ser Arg Gly Ala
370                 375                 380

Ala Pro Ser Gly Ala Ala Pro Leu Pro Ser Ala Ala Ser Val Glu Gln
385                 390                 395                 400

Glu Ala Ala Val Arg Pro Arg Lys Arg Arg Gly Ser Gly Gln Glu Asn
            405                 410                 415

Pro Ser Pro Gln Ser Thr Arg Pro Pro Leu Ala Pro Ala Gly Ala Lys
            420                 425                 430

Arg Ala Ala Thr His Pro Pro Ser Asp Ser Gly Pro Gly Gly Arg Gly
            435                 440                 445

Gln Gly Gly Pro Gly Thr Pro Leu Thr Ser Ser Ala Ala Ser Ala Ser
450                 455                 460

Ser Ser Ser Ala Ser Ser Ser Ala Pro Thr Pro Ala Gly Ala Thr
465                 470                 475                 480

Ser Ser Ala Thr Gly Ala Ala Ser Ser Ala Ser Ala Ser Ser Gly
            485                 490                 495

Gly Ala Val Gly Ala Leu Gly Gly Arg Gln Glu Glu Thr Ser Leu Gly
        500                 505                 510

Pro Arg Ala Ala Ser Gly Pro Arg Gly Pro Arg Lys Cys Ala Arg Lys
    515                 520                 525

Thr Arg His Ala Glu Thr Ser Gly Ala Val Pro Ala Gly Gly Leu Thr
            530                 535                 540

Arg Tyr Leu Pro Ile Ser Gly Val
545                 550
```

<210> SEQ ID NO 27
<211> LENGTH: 589
<212> TYPE: PRT
<213> ORGANISM: Herpes simplex virus 2

<400> SEQUENCE: 27

```
Gly Ser Cys Gly Gly Gly Pro Val Gly Glu Glu Ala Glu Ala Gly
1               5                   10                  15

Gly Gly Gly Asp Val Cys Ala Val Cys Thr Asp Glu Ile Ala Pro Pro
            20                  25                  30

Leu Arg Cys Gln Ser Phe Pro Cys Leu His Pro Phe Cys Ile Pro Cys
```

```
                35                  40                  45
Met Lys Thr Trp Ile Pro Leu Arg Asn Thr Cys Pro Leu Cys Asn Thr
 50                  55                  60

Pro Val Ala Tyr Leu Ile Val Gly Val Thr Ala Ser Gly Ser Phe Ser
 65                  70                  75                  80

Thr Ile Pro Ile Val Asn Asp Pro Arg Thr Arg Val Glu Ala Glu Ala
                 85                  90                  95

Ala Val Arg Ala Gly Thr Ala Val Asp Phe Ile Trp Thr Gly Asn Pro
                100                 105                 110

Arg Thr Ala Pro Arg Ser Leu Ser Leu Gly Gly His Thr Val Arg Ala
                115                 120                 125

Leu Ser Pro Thr Pro Trp Pro Gly Thr Asp Asp Glu Asp Asp Asp
130                 135                 140

Leu Ala Asp Val Asp Tyr Val Pro Pro Ala Pro Arg Arg Ala Pro Arg
145                 150                 155                 160

Arg Gly Gly Gly Gly Ala Gly Ala Thr Arg Gly Thr Ser Gln Pro Ala
                165                 170                 175

Ala Thr Arg Pro Ala Pro Pro Gly Ala Pro Arg Ser Ser Ser Ser Gly
                180                 185                 190

Gly Ala Pro Leu Arg Ala Gly Val Gly Ser Gly Ser Gly Gly Gly Pro
                195                 200                 205

Ala Val Ala Ala Val Val Pro Arg Val Ala Ser Leu Pro Pro Ala Ala
210                 215                 220

Gly Gly Gly Arg Ala Gln Ala Arg Arg Val Gly Glu Asp Ala Ala Ala
225                 230                 235                 240

Ala Glu Gly Arg Thr Pro Pro Ala Arg Gln Pro Arg Ala Ala Gln Glu
                245                 250                 255

Pro Pro Ile Val Ile Ser Asp Ser Pro Pro Ser Pro Arg Arg Pro
                260                 265                 270

Ala Gly Pro Gly Pro Leu Ser Phe Val Ser Ser Ser Ala Gln Val
                275                 280                 285

Ser Ser Gly Pro Gly Gly Gly Leu Pro Gln Ser Ser Gly Arg Ala
290                 295                 300

Ala Arg Pro Arg Ala Ala Val Ala Pro Arg Val Arg Ser Pro Pro Arg
305                 310                 315                 320

Ala Ala Ala Ala Pro Val Val Ser Ala Ser Ala Asp Ala Ala Gly Pro
                325                 330                 335

Ala Pro Pro Ala Val Pro Val Asp Ala His Arg Ala Pro Arg Ser Arg
                340                 345                 350

Met Thr Gln Ala Gln Thr Asp Thr Gln Ala Gln Ser Leu Gly Arg Ala
                355                 360                 365

Gly Ala Thr Asp Ala Arg Gly Ser Gly Gly Pro Gly Ala Glu Gly Gly
                370                 375                 380

Pro Gly Val Pro Arg Gly Thr Asn Thr Pro Gly Ala Ala Pro His Ala
385                 390                 395                 400

Ala Glu Gly Ala Ala Ala Arg Pro Arg Lys Arg Arg Gly Ser Asp Ser
                405                 410                 415

Gly Pro Ala Ala Ser Ser Ser Ala Ser Ser Ala Ala Pro Arg Ser
                420                 425                 430

Pro Leu Ala Pro Gln Gly Val Gly Ala Lys Arg Ala Ala Pro Arg Arg
                435                 440                 445

Ala Pro Asp Ser Asp Ser Gly Asp Arg Gly His Gly Pro Leu Ala Pro
                450                 455                 460
```

```
Ala Ser Ala Gly Ala Ala Pro Pro Ser Ala Ser Pro Ser Ser Gln Ala
465                 470                 475                 480

Ala Val Ala Ala Ala Ser Ser Ser Ala Ser Ser Ser Ser Ala Ser
            485                 490                 495

Ser Ser Ser Ala Ser Ser Ser Ser Ala Ser Ser Ser Ala Ser Ser
            500                 505                 510

Ser Ser Ala Ser Ser Ser Ser Ala Ser Ser Ser Ala Gly Gly Ala Gly
            515                 520                 525

Gly Ser Val Ala Ser Ala Ser Gly Ala Gly Glu Arg Arg Glu Thr Ser
530                 535                 540

Leu Gly Pro Arg Ala Ala Ala Pro Arg Gly Pro Arg Lys Cys Ala Arg
545                 550                 555                 560

Lys Thr Arg His Ala Glu Gly Gly Pro Glu Pro Gly Ala Arg Asp Pro
                565                 570                 575

Ala Pro Gly Leu Thr Arg Tyr Leu Pro Ile Ala Gly Val
            580                 585

<210> SEQ ID NO 28
<211> LENGTH: 15
<212> TYPE: PRT
<213> ORGANISM: Herpes simplex virus 2

<400> SEQUENCE: 28

Gly Ala Pro Ala Pro Ala Gly Asp Ala Pro Ala Gly His Gly Glu
1               5                   10                  15

<210> SEQ ID NO 29
<211> LENGTH: 623
<212> TYPE: PRT
<213> ORGANISM: Herpes simplex virus 1

<400> SEQUENCE: 29

Cys Pro Leu Cys Asn Ala Lys Leu Val Tyr Leu Ile Val Gly Val Thr
1               5                   10                  15

Pro Ser Gly Ser Phe Ser Thr Ile Pro Ile Val Asn Asp Pro Gln Thr
            20                  25                  30

Arg Met Glu Ala Glu Ala Val Arg Ala Gly Thr Ala Val Asp Phe
        35                  40                  45

Ile Trp Thr Gly Asn Gln Arg Phe Ala Pro Arg Tyr Leu Thr Leu Gly
    50                  55                  60

Gly His Thr Val Arg Ala Leu Ser Pro Thr His Pro Glu Pro Thr Thr
65                  70                  75                  80

Asp Glu Asp Asp Asp Asp Leu Asp Asp Ala Asp Tyr Val Pro Pro Ala
                85                  90                  95

Pro Arg Arg Thr Pro Arg Ala Pro Pro Arg Arg Gly Ala Ala Ala Pro
            100                 105                 110

Pro Val Thr Gly Gly Ala Ser His Ala Ala Pro Gln Pro Ala Ala Ala
            115                 120                 125

Arg Thr Ala Pro Pro Ser Ala Pro Ile Gly Pro His Gly Ser Ser Asn
130                 135                 140

Thr Asn Thr Thr Thr Asn Ser Ser Gly Gly Gly Ser Arg Gln Ser
145                 150                 155                 160

Arg Ala Ala Ala Pro Arg Gly Ala Ser Gly Pro Ser Gly Gly Val Gly
                165                 170                 175

Val Gly Val Gly Val Val Glu Ala Glu Ala Gly Arg Pro Arg Gly Arg
            180                 185                 190
```

```
Thr Gly Pro Leu Val Asn Arg Pro Ala Pro Leu Ala Asn Asn Arg Asp
        195                 200                 205

Pro Ile Val Ile Ser Asp Ser Pro Ala Ser Pro His Arg Pro Pro
210                 215                 220

Ala Ala Pro Met Pro Gly Ser Ala Pro Arg Pro Gly Pro Pro Ala Ser
225                 230                 235                 240

Ala Ala Ala Ser Gly Pro Ala Arg Pro Arg Ala Ala Val Ala Pro Cys
                245                 250                 255

Val Arg Ala Pro Pro Gly Pro Gly Pro Arg Ala Pro Ala Pro Gly
            260                 265                 270

Ala Glu Pro Ala Ala Arg Pro Ala Asp Ala Arg Arg Val Pro Gln Ser
        275                 280                 285

His Ser Ser Leu Ala Gln Ala Ala Asn Gln Glu Gln Ser Leu Cys Arg
        290                 295                 300

Ala Arg Ala Thr Val Ala Arg Gly Ser Gly Pro Gly Val Glu Gly
305                 310                 315                 320

Gly His Gly Pro Ser Arg Gly Ala Ala Pro Ser Gly Ala Ala Pro Leu
                325                 330                 335

Pro Ser Ala Ala Ser Val Glu Gln Glu Ala Ala Val Arg Pro Arg Lys
            340                 345                 350

Arg Arg Gly Ser Gly Gln Glu Asn Pro Ser Pro Gln Ser Thr Arg Pro
        355                 360                 365

Pro Leu Ala Pro Ala Gly Ala Lys Arg Ala Ala Thr His Pro Pro Ser
    370                 375                 380

Asp Ser Gly Pro Gly Gly Arg Gly Gln Gly Pro Gly Thr Pro Leu
385                 390                 395                 400

Thr Ser Ser Ala Ala Ser Ala Ser Ser Ser Ala Ser Ser Ser Ser
                405                 410                 415

Ala Pro Thr Pro Ala Gly Ala Thr Ser Ser Ala Thr Gly Ala Ala Ser
            420                 425                 430

Ser Ser Ala Ser Ala Ser Gly Gly Ala Val Gly Ala Leu Gly Gly
        435                 440                 445

Arg Gln Glu Glu Thr Ser Leu Gly Pro Arg Ala Ala Ser Gly Pro Arg
    450                 455                 460

Gly Pro Arg Lys Cys Ala Arg Lys Thr Arg His Ala Glu Thr Ser Gly
465                 470                 475                 480

Ala Val Pro Ala Gly Gly Leu Thr Arg Tyr Leu Pro Ile Ser Gly Val
                485                 490                 495

Ser Ser Val Val Ala Leu Ser Pro Tyr Val Asn Lys Thr Ile Thr Gly
            500                 505                 510

Asp Cys Leu Pro Ile Leu Asp Met Glu Thr Gly Asn Ile Gly Ala Tyr
        515                 520                 525

Val Val Leu Val Asp Gln Thr Gly Asn Met Ala Thr Arg Leu Arg Ala
530                 535                 540

Ala Val Pro Gly Trp Ser Arg Arg Thr Leu Leu Pro Glu Thr Ala Gly
545                 550                 555                 560

Asn His Val Thr Pro Pro Glu Tyr Pro Thr Ala Pro Ala Ser Glu Trp
                565                 570                 575

Asn Ser Leu Trp Met Thr Pro Val Gly Asn Met Leu Phe Asp Gln Gly
            580                 585                 590

Thr Leu Val Gly Ala Leu Asp Phe Arg Ser Leu Arg Ser Arg His Pro
        595                 600                 605
```

```
Trp Ser Gly Glu Gln Gly Ala Ser Thr Arg Asp Glu Gly Lys Gln
    610                 615                 620
```

<210> SEQ ID NO 30
<211> LENGTH: 663
<212> TYPE: PRT
<213> ORGANISM: Herpes simplex virus 2

<400> SEQUENCE: 30

```
Cys Pro Leu Cys Asn Thr Pro Val Ala Tyr Leu Ile Val Gly Val Thr
1               5                   10                  15

Ala Ser Gly Ser Phe Ser Thr Ile Pro Ile Val Asn Asp Pro Arg Thr
            20                  25                  30

Arg Val Glu Ala Glu Ala Ala Val Arg Ala Gly Thr Ala Val Asp Phe
        35                  40                  45

Ile Trp Thr Gly Asn Pro Arg Thr Ala Pro Arg Ser Leu Ser Leu Gly
    50                  55                  60

Gly His Thr Val Arg Ala Leu Ser Pro Thr Pro Pro Trp Pro Gly Thr
65                  70                  75                  80

Asp Asp Glu Asp Asp Leu Ala Asp Val Asp Tyr Val Pro Ala
                85                  90                  95

Pro Arg Arg Ala Pro Arg Arg Gly Gly Gly Ala Gly Ala Thr Arg
                100                 105                 110

Gly Thr Ser Gln Pro Ala Ala Thr Arg Pro Ala Pro Gly Ala Pro
            115                 120                 125

Arg Ser Ser Ser Gly Gly Ala Pro Leu Arg Ala Gly Val Gly Ser
    130                 135                 140

Gly Ser Gly Gly Gly Pro Ala Val Ala Val Val Pro Arg Val Ala
145                 150                 155                 160

Ser Leu Pro Pro Ala Ala Gly Gly Gly Arg Ala Gln Ala Arg Arg Val
                165                 170                 175

Gly Glu Asp Ala Ala Ala Ala Glu Gly Arg Thr Pro Pro Ala Arg Gln
            180                 185                 190

Pro Arg Ala Ala Gln Glu Pro Pro Ile Val Ile Ser Asp Ser Pro Pro
        195                 200                 205

Pro Ser Pro Arg Arg Pro Ala Gly Pro Gly Pro Leu Ser Phe Val Ser
    210                 215                 220

Ser Ser Ser Ala Gln Val Ser Ser Gly Pro Gly Gly Gly Leu Pro
225                 230                 235                 240

Gln Ser Ser Gly Arg Ala Ala Arg Pro Arg Ala Ala Val Ala Pro Arg
                245                 250                 255

Val Arg Ser Pro Pro Arg Ala Ala Ala Pro Val Val Ser Ala Ser
            260                 265                 270

Ala Asp Ala Ala Gly Pro Ala Pro Pro Ala Val Pro Val Asp Ala His
        275                 280                 285

Arg Ala Pro Arg Ser Arg Met Thr Gln Ala Gln Thr Asp Thr Gln Ala
    290                 295                 300

Gln Ser Leu Gly Arg Ala Gly Ala Thr Asp Ala Arg Gly Ser Gly Gly
305                 310                 315                 320

Pro Gly Ala Glu Gly Gly Pro Gly Val Pro Arg Gly Thr Asn Thr Pro
                325                 330                 335

Gly Ala Ala Pro His Ala Ala Glu Gly Ala Ala Arg Pro Arg Lys
            340                 345                 350

Arg Arg Gly Ser Asp Ser Gly Pro Ala Ala Ser Ser Ala Ser Ser
    355                 360                 365
```

```
Ser Ala Ala Pro Arg Ser Pro Leu Ala Pro Gln Gly Val Gly Ala Lys
    370                 375                 380
Arg Ala Ala Pro Arg Arg Ala Pro Asp Ser Asp Ser Gly Asp Arg Gly
385                 390                 395                 400
His Gly Pro Leu Ala Pro Ala Ser Ala Gly Ala Ala Pro Pro Ser Ala
                405                 410                 415
Ser Pro Ser Ser Gln Ala Ala Val Ala Ala Ala Ser Ser Ser Ser Ala
                420                 425                 430
Ser Ser Ser Ser Ala Ser Ser Ser Ala Ser Ser Ser Ser Ala Ser
            435                 440                 445
Ser Ser Ser Ala Ser Ser Ser Ala Ser Ser Ser Ala Ser Ser
    450                 455                 460
Ser Ala Gly Gly Ala Gly Gly Ser Val Ala Ser Ala Ser Gly Ala Gly
465                 470                 475                 480
Glu Arg Arg Glu Thr Ser Leu Gly Pro Arg Ala Ala Pro Arg Gly
                485                 490                 495
Pro Arg Lys Cys Ala Arg Lys Thr Arg His Ala Glu Gly Gly Pro Glu
                500                 505                 510
Pro Gly Ala Arg Asp Pro Ala Pro Gly Leu Thr Arg Tyr Leu Pro Ile
                515                 520                 525
Ala Gly Val Ser Ser Val Val Ala Leu Ala Pro Tyr Val Asn Lys Thr
                530                 535                 540
Val Thr Gly Asp Cys Leu Pro Val Leu Asp Met Glu Thr Gly His Ile
545                 550                 555                 560
Gly Ala Tyr Val Val Leu Val Asp Gln Thr Gly Asn Val Ala Asp Leu
                565                 570                 575
Leu Arg Ala Ala Ala Pro Ala Trp Ser Arg Arg Thr Leu Leu Pro Glu
                580                 585                 590
His Ala Arg Asn Cys Val Arg Pro Pro Asp Tyr Pro Thr Pro Pro Ala
                595                 600                 605
Ser Glu Trp Asn Ser Leu Trp Met Thr Pro Val Gly Asn Met Leu Phe
                610                 615                 620
Asp Gln Gly Thr Leu Val Gly Ala Leu Asp Phe His Gly Leu Arg Ser
625                 630                 635                 640
Arg His Pro Trp Ser Arg Glu Gln Gly Ala Pro Ala Pro Ala Gly Asp
                645                 650                 655
Ala Pro Ala Gly His Gly Glu
                660

<210> SEQ ID NO 31
<211> LENGTH: 104
<212> TYPE: PRT
<213> ORGANISM: Herpes simplex virus 1

<400> SEQUENCE: 31

Met Glu Pro Arg Pro Gly Ala Ser Thr Arg Arg Pro Glu Gly Arg Pro
1               5                   10                  15
Gln Arg Glu Pro Ala Pro Asp Val Trp Val Phe Pro Cys Asp Arg Asp
                20                  25                  30
Leu Pro Asp Ser Ser Asp Ser Glu Ala Glu Thr Glu Val Gly Gly Arg
                35                  40                  45
Gly Asp Ala Asp His His Asp Asp Ser Ala Ser Glu Ala Asp Ser
        50                  55                  60
Thr Asp Thr Glu Leu Phe Glu Thr Gly Leu Leu Gly Pro Gln Gly Val
```

```
                    65                  70                  75                  80
Asp Gly Gly Ala Val Ser Gly Ser Pro Pro Arg Glu Glu Asp Pro
                85                  90                  95

Gly Ser Cys Gly Gly Ala Pro Pro
                100
```

```
<210> SEQ ID NO 32
<211> LENGTH: 556
<212> TYPE: PRT
<213> ORGANISM: Herpes simplex virus 1

<400> SEQUENCE: 32

Val Arg Ala Leu Ser Pro Thr His Pro Glu Pro Thr Thr Asp Glu Asp
1               5                   10                  15

Asp Asp Asp Leu Asp Asp Ala Asp Tyr Val Pro Pro Ala Pro Arg Arg
                20                  25                  30

Thr Pro Arg Ala Pro Pro Arg Arg Gly Ala Ala Ala Pro Pro Val Thr
            35                  40                  45

Gly Gly Ala Ser His Ala Ala Pro Gln Pro Ala Ala Ala Arg Thr Ala
        50                  55                  60

Pro Pro Ser Ala Pro Ile Gly Pro His Gly Ser Ser Asn Thr Asn Thr
65                  70                  75                  80

Thr Thr Asn Ser Ser Gly Gly Gly Ser Arg Gln Ser Arg Ala Ala
                85                  90                  95

Ala Pro Arg Gly Ala Ser Gly Pro Ser Gly Val Gly Val Gly Val
                100                 105                 110

Gly Val Val Glu Ala Glu Ala Gly Arg Pro Arg Gly Arg Thr Gly Pro
            115                 120                 125

Leu Val Asn Arg Pro Ala Pro Leu Ala Asn Asn Arg Asp Pro Ile Val
        130                 135                 140

Ile Ser Asp Ser Pro Pro Ala Ser Pro His Arg Pro Pro Ala Ala Pro
145                 150                 155                 160

Met Pro Gly Ser Ala Pro Arg Pro Gly Pro Pro Ala Ser Ala Ala Ala
                165                 170                 175

Ser Gly Pro Ala Arg Pro Arg Ala Ala Val Ala Pro Cys Val Arg Ala
                180                 185                 190

Pro Pro Pro Gly Pro Gly Pro Arg Ala Pro Ala Pro Gly Ala Glu Pro
            195                 200                 205

Ala Ala Arg Pro Ala Asp Ala Arg Arg Val Pro Gln Ser His Ser Ser
        210                 215                 220

Leu Ala Gln Ala Ala Asn Gln Glu Gln Ser Leu Cys Arg Ala Arg Ala
225                 230                 235                 240

Thr Val Ala Arg Gly Ser Gly Gly Pro Gly Val Glu Gly Gly His Gly
                245                 250                 255

Pro Ser Arg Gly Ala Ala Pro Ser Gly Ala Ala Pro Leu Pro Ser Ala
                260                 265                 270

Ala Ser Val Glu Gln Glu Ala Ala Val Arg Pro Arg Lys Arg Arg Gly
            275                 280                 285

Ser Gly Gln Glu Asn Pro Ser Pro Gln Ser Thr Arg Pro Pro Leu Ala
        290                 295                 300

Pro Ala Gly Ala Lys Arg Ala Ala Thr His Pro Pro Ser Asp Ser Gly
305                 310                 315                 320

Pro Gly Gly Arg Gly Gln Gly Pro Gly Thr Pro Leu Thr Ser Ser
                325                 330                 335
```

-continued

```
Ala Ala Ser Ala Ser Ser Ser Ala Ser Ser Ser Ala Pro Thr
            340                 345                 350

Pro Ala Gly Ala Thr Ser Ser Ala Thr Gly Ala Ala Ser Ser Ser Ala
        355                 360                 365

Ser Ala Ser Ser Gly Gly Ala Val Gly Ala Leu Gly Gly Arg Gln Glu
    370                 375                 380

Glu Thr Ser Leu Gly Pro Arg Ala Ala Ser Gly Pro Arg Gly Pro Arg
385                 390                 395                 400

Lys Cys Ala Arg Lys Thr Arg His Ala Glu Thr Ser Gly Ala Val Pro
                405                 410                 415

Ala Gly Gly Leu Thr Arg Tyr Leu Pro Ile Ser Gly Val Ser Ser Val
            420                 425                 430

Val Ala Leu Ser Pro Tyr Val Asn Lys Thr Ile Thr Gly Asp Cys Leu
        435                 440                 445

Pro Ile Leu Asp Met Glu Thr Gly Asn Ile Gly Ala Tyr Val Val Leu
    450                 455                 460

Val Asp Gln Thr Gly Asn Met Ala Thr Arg Leu Arg Ala Ala Val Pro
465                 470                 475                 480

Gly Trp Ser Arg Arg Thr Leu Leu Pro Glu Thr Ala Gly Asn His Val
                485                 490                 495

Thr Pro Pro Glu Tyr Pro Thr Ala Pro Ala Ser Glu Trp Asn Ser Leu
            500                 505                 510

Trp Met Thr Pro Val Gly Asn Met Leu Phe Asp Gln Gly Thr Leu Val
        515                 520                 525

Gly Ala Leu Asp Phe Arg Ser Leu Arg Ser Arg His Pro Trp Ser Gly
    530                 535                 540

Glu Gln Gly Ala Ser Thr Arg Asp Glu Gly Lys Gln
545                 550                 555

<210> SEQ ID NO 33
<211> LENGTH: 114
<212> TYPE: PRT
<213> ORGANISM: Herpes simplex virus 2

<400> SEQUENCE: 33

Met Glu Pro Arg Pro Gly Thr Ser Ser Arg Ala Asp Pro Gly Pro Glu
1               5                   10                  15

Arg Pro Pro Arg Gln Thr Pro Gly Thr Gln Pro Ala Ala Pro His Ala
            20                  25                  30

Trp Gly Met Leu Asn Asp Met Gln Trp Leu Ala Ser Ser Asp Ser Glu
        35                  40                  45

Glu Glu Thr Glu Val Gly Ile Ser Asp Asp Asp Leu His Arg Asp Ser
    50                  55                  60

Thr Ser Glu Ala Gly Ser Thr Asp Thr Glu Met Phe Glu Ala Gly Leu
65                  70                  75                  80

Met Asp Ala Ala Thr Pro Pro Ala Arg Pro Pro Ala Glu Arg Gln Gly
                85                  90                  95

Ser Pro Thr Pro Ala Asp Ala Gln Gly Ser Cys Gly Gly Gly Pro Val
            100                 105                 110

Gly Glu

<210> SEQ ID NO 34
<211> LENGTH: 596
<212> TYPE: PRT
<213> ORGANISM: Herpes simplex virus 2
```

```
<400> SEQUENCE: 34

Val Arg Ala Leu Ser Pro Thr Pro Pro Trp Pro Gly Thr Asp Asp Glu
1               5                   10                  15

Asp Asp Asp Leu Ala Asp Val Asp Tyr Val Pro Pro Ala Pro Arg Arg
            20                  25                  30

Ala Pro Arg Arg Gly Gly Gly Ala Gly Ala Thr Arg Gly Thr Ser
        35                  40                  45

Gln Pro Ala Ala Thr Arg Pro Ala Pro Gly Ala Pro Arg Ser Ser
50                  55                  60

Ser Ser Gly Gly Ala Pro Leu Arg Ala Gly Val Gly Ser Gly Ser Gly
65              70                  75                  80

Gly Gly Pro Ala Val Ala Ala Val Pro Arg Val Ala Ser Leu Pro
                85                  90                  95

Pro Ala Ala Gly Gly Gly Arg Ala Gln Ala Arg Val Gly Glu Asp
            100                 105                 110

Ala Ala Ala Ala Glu Gly Arg Thr Pro Pro Ala Arg Gln Pro Arg Ala
            115                 120                 125

Ala Gln Glu Pro Pro Ile Val Ile Ser Asp Ser Pro Pro Ser Pro
130                 135                 140

Arg Arg Pro Ala Gly Pro Gly Pro Leu Ser Phe Val Ser Ser Ser Ser
145                 150                 155                 160

Ala Gln Val Ser Ser Gly Pro Gly Gly Gly Leu Pro Gln Ser Ser
            165                 170                 175

Gly Arg Ala Ala Arg Pro Arg Ala Ala Val Ala Pro Arg Val Arg Ser
            180                 185                 190

Pro Pro Arg Ala Ala Ala Pro Val Val Ser Ala Ser Ala Asp Ala
            195                 200                 205

Ala Gly Pro Ala Pro Pro Val Pro Val Asp Ala His Arg Ala Pro
210                 215                 220

Arg Ser Arg Met Thr Gln Ala Gln Thr Asp Thr Gln Ala Gln Ser Leu
225                 230                 235                 240

Gly Arg Ala Gly Ala Thr Asp Ala Arg Gly Ser Gly Gly Pro Gly Ala
            245                 250                 255

Glu Gly Gly Pro Gly Val Pro Arg Gly Thr Asn Thr Pro Gly Ala Ala
            260                 265                 270

Pro His Ala Ala Glu Gly Ala Ala Arg Pro Arg Lys Arg Arg Gly
            275                 280                 285

Ser Asp Ser Gly Pro Ala Ala Ser Ser Ala Ser Ser Ser Ala Ala
            290                 295                 300

Pro Arg Ser Pro Leu Ala Pro Gln Gly Val Gly Ala Lys Arg Ala Ala
305                 310                 315                 320

Pro Arg Arg Ala Pro Asp Ser Asp Ser Gly Asp Arg Gly His Gly Pro
            325                 330                 335

Leu Ala Pro Ala Ser Ala Gly Ala Ala Pro Ser Ala Ser Pro Ser
            340                 345                 350

Ser Gln Ala Ala Val Ala Ala Ser Ser Ser Ala Ser Ser Ser
            355                 360                 365

Ser Ala Ser Ser Ser Ser Ala Ser Ser Ser Ala Ser Ser Ser
            370                 375                 380

Ala Ser Ser Ser Ala Ser Ser Ser Ala Ser Ser Ser Ala Gly
385                 390                 395                 400

Gly Ala Gly Gly Ser Val Ala Ser Ala Ser Gly Ala Gly Glu Arg Arg
            405                 410                 415
```

```
Glu Thr Ser Leu Gly Pro Arg Ala Ala Pro Arg Gly Pro Arg Lys
            420                 425                 430

Cys Ala Arg Lys Thr Arg His Ala Glu Gly Pro Glu Pro Gly Ala
            435                 440                 445

Arg Asp Pro Ala Pro Gly Leu Thr Arg Tyr Leu Pro Ile Ala Gly Val
    450                 455                 460

Ser Ser Val Val Ala Leu Ala Pro Tyr Val Asn Lys Thr Val Thr Gly
465                 470                 475                 480

Asp Cys Leu Pro Val Leu Asp Met Glu Thr Gly His Ile Gly Ala Tyr
                485                 490                 495

Val Val Leu Val Asp Gln Thr Gly Asn Val Ala Asp Leu Leu Arg Ala
            500                 505                 510

Ala Ala Pro Ala Trp Ser Arg Arg Thr Leu Leu Pro Glu His Ala Arg
            515                 520                 525

Asn Cys Val Arg Pro Pro Asp Tyr Pro Thr Pro Pro Ala Ser Glu Trp
            530                 535                 540

Asn Ser Leu Trp Met Thr Pro Val Gly Asn Met Leu Phe Asp Gln Gly
545                 550                 555                 560

Thr Leu Val Gly Ala Leu Asp Phe His Gly Leu Arg Ser Arg His Pro
                565                 570                 575

Trp Ser Arg Glu Gln Gly Ala Pro Ala Pro Ala Gly Asp Ala Pro Ala
            580                 585                 590

Gly His Gly Glu
            595

<210> SEQ ID NO 35
<211> LENGTH: 449
<212> TYPE: PRT
<213> ORGANISM: Herpes simplex virus 1

<400> SEQUENCE: 35

Met Glu Pro Arg Pro Gly Ala Ser Thr Arg Arg Pro Glu Gly Arg Pro
1               5                   10                  15

Gln Arg Glu Pro Ala Pro Asp Val Trp Val Phe Pro Cys Asp Arg Asp
            20                  25                  30

Leu Pro Asp Ser Ser Asp Ser Glu Ala Glu Thr Glu Val Gly Gly Arg
        35                  40                  45

Gly Asp Ala Asp His His Asp Asp Ser Ala Ser Glu Ala Asp Ser
    50                  55                  60

Thr Asp Thr Glu Leu Phe Glu Thr Gly Leu Leu Gly Pro Gln Gly Val
65                  70                  75                  80

Asp Gly Gly Ala Val Ser Gly Gly Ser Pro Pro Arg Glu Glu Asp Pro
                85                  90                  95

Gly Ser Cys Gly Gly Ala Pro Pro Arg Glu Asp Gly Gly Ser Asp Glu
            100                 105                 110

Gly Asp Val Cys Ala Val Cys Thr Asp Glu Ile Ala Pro His Leu Arg
            115                 120                 125

Cys Asp Thr Phe Pro Cys Met His Arg Phe Cys Ile Pro Cys Met Lys
    130                 135                 140

Thr Trp Met Gln Leu Arg Asn Thr Cys Pro Leu Cys Asn Ala Lys Leu
145                 150                 155                 160

Val Tyr Leu Ile Val Gly Val Thr Pro Ser Gly Ser Phe Ser Thr Ile
                165                 170                 175

Pro Ile Val Asn Asp Pro Gln Thr Arg Met Glu Ala Glu Glu Ala Val
            180                 185                 190
```

```
Arg Ala Gly Thr Ala Val Asp Phe Ile Trp Thr Gly Asn Gln Arg Phe
        195                 200                 205

Ala Pro Arg Tyr Leu Thr Leu Gly Gly His Thr Val Arg Ala Leu Ser
    210                 215                 220

Pro Thr His Pro Glu Pro Thr Thr Asp Glu Asp Asp Asp Leu Asp
225                 230                 235                 240

Asp Ala Asp Tyr Val Pro Pro Ala Pro Arg Arg Thr Pro Arg Ala Pro
                245                 250                 255

Pro Arg Arg Gly Ala Ala Ala Pro Pro Val Thr Gly Gly Ala Ser His
            260                 265                 270

Ala Ala Pro Gln Pro Ala Ala Ala Arg Thr Ala Pro Pro Ser Ala Pro
        275                 280                 285

Ile Gly Pro His Gly Ser Ser Asn Thr Asn Thr Thr Thr Asn Ser Ser
        290                 295                 300

Gly Gly Gly Gly Ser Arg Gln Ser Arg Ala Ala Ala Pro Arg Gly Ala
305                 310                 315                 320

Ser Gly Pro Ser Gly Gly Val Gly Val Gly Val Val Glu Ala
                325                 330                 335

Glu Ala Gly Arg Pro Arg Gly Arg Thr Gly Pro Leu Val Asn Arg Pro
            340                 345                 350

Ala Pro Leu Ala Asn Asn Arg Asp Pro Ile Val Ile Ser Asp Ser Pro
        355                 360                 365

Pro Ala Ser Pro His Arg Pro Ala Ala Pro Met Pro Gly Ser Ala
        370                 375                 380

Pro Arg Pro Gly Pro Pro Ala Ser Ala Ala Ala Ser Gly Pro Ala Arg
385                 390                 395                 400

Pro Arg Ala Ala Val Ala Pro Cys Val Arg Ala Pro Pro Gly Pro
                405                 410                 415

Gly Pro Arg Ala Pro Ala Pro Gly Ala Glu Pro Ala Ala Arg Pro Ala
            420                 425                 430

Asp Ala Arg Arg Val Pro Gln Ser His Ser Ser Leu Ala Gln Ala Ala
        435                 440                 445

Asn

<210> SEQ ID NO 36
<211> LENGTH: 43
<212> TYPE: PRT
<213> ORGANISM: Herpes simplex virus 1

<400> SEQUENCE: 36

Ala Arg Ala Thr Val Ala Arg Gly Ser Gly Gly Pro Gly Val Glu Gly
1               5                   10                  15

Gly His Gly Pro Ser Arg Gly Ala Ala Pro Ser Gly Ala Ala Pro Leu
            20                  25                  30

Pro Ser Ala Ala Ser Val Glu Gln Glu Ala Ala
        35                  40

<210> SEQ ID NO 37
<211> LENGTH: 268
<212> TYPE: PRT
<213> ORGANISM: Herpes simplex virus 1
```

<400> SEQUENCE: 37

```
Ser Gly Gln Glu Asn Pro Ser Pro Gln Ser Thr Arg Pro Pro Leu Ala
1               5                   10                  15

Pro Ala Gly Ala Lys Arg Ala Ala Thr His Pro Pro Ser Asp Ser Gly
            20                  25                  30

Pro Gly Gly Arg Gly Gln Gly Gly Pro Gly Thr Pro Leu Thr Ser Ser
        35                  40                  45

Ala Ala Ser Ala Ser Ser Ser Ala Ser Ser Ser Ala Pro Thr
    50                  55                  60

Pro Ala Gly Ala Thr Ser Ser Ala Thr Gly Ala Ala Ser Ser Ser Ala
65                  70                  75                  80

Ser Ala Ser Ser Gly Gly Ala Val Gly Ala Leu Gly Gly Arg Gln Glu
                85                  90                  95

Glu Thr Ser Leu Gly Pro Arg Ala Ala Ser Gly Pro Arg Gly Pro Arg
            100                 105                 110

Lys Cys Ala Arg Lys Thr Arg His Ala Glu Thr Ser Gly Ala Val Pro
        115                 120                 125

Ala Gly Gly Leu Thr Arg Tyr Leu Pro Ile Ser Gly Val Ser Ser Val
    130                 135                 140

Val Ala Leu Ser Pro Tyr Val Asn Lys Thr Ile Thr Gly Asp Cys Leu
145                 150                 155                 160

Pro Ile Leu Asp Met Glu Thr Gly Asn Ile Gly Ala Tyr Val Val Leu
                165                 170                 175

Val Asp Gln Thr Gly Asn Met Ala Thr Arg Leu Arg Ala Ala Val Pro
            180                 185                 190

Gly Trp Ser Arg Arg Thr Leu Leu Pro Glu Thr Ala Gly Asn His Val
        195                 200                 205

Thr Pro Pro Glu Tyr Pro Thr Ala Pro Ala Ser Glu Trp Asn Ser Leu
    210                 215                 220

Trp Met Thr Pro Val Gly Asn Met Leu Phe Asp Gln Gly Thr Leu Val
225                 230                 235                 240

Gly Ala Leu Asp Phe Arg Ser Leu Arg Ser Arg His Pro Trp Ser Gly
                245                 250                 255

Glu Gln Gly Ala Ser Thr Arg Asp Glu Gly Lys Gln
            260                 265
```

<210> SEQ ID NO 38
<211> LENGTH: 464
<212> TYPE: PRT
<213> ORGANISM: Herpes simplex virus 2

<400> SEQUENCE: 38

```
Met Glu Pro Arg Pro Gly Thr Ser Ser Arg Ala Asp Pro Gly Pro Glu
1               5                   10                  15

Arg Pro Pro Arg Gln Thr Pro Gly Thr Gln Pro Ala Ala Pro His Ala
            20                  25                  30

Trp Gly Met Leu Asn Asp Met Gln Trp Leu Ala Ser Ser Asp Ser Glu
        35                  40                  45

Glu Glu Thr Glu Val Gly Ile Ser Asp Asp Asp Leu His Arg Asp Ser
    50                  55                  60

Thr Ser Glu Ala Gly Ser Thr Asp Thr Glu Met Phe Glu Ala Gly Leu
65                  70                  75                  80

Met Asp Ala Ala Thr Pro Pro Ala Arg Pro Pro Ala Glu Arg Gln Gly
                85                  90                  95
```

Ser Pro Thr Pro Ala Asp Ala Gln Gly Ser Cys Gly Gly Pro Val
            100                 105                 110

Gly Glu Glu Glu Ala Glu Ala Gly Gly Gly Asp Val Cys Ala Val
        115                 120                 125

Cys Thr Asp Glu Ile Ala Pro Pro Leu Arg Cys Gln Ser Phe Pro Cys
        130                 135                 140

Leu His Pro Phe Cys Ile Pro Cys Met Lys Thr Trp Ile Pro Leu Arg
145                 150                 155                 160

Asn Thr Cys Pro Leu Cys Asn Thr Pro Val Ala Tyr Leu Ile Val Gly
                165                 170                 175

Val Thr Ala Ser Gly Ser Phe Ser Thr Ile Pro Ile Val Asn Asp Pro
                180                 185                 190

Arg Thr Arg Val Glu Ala Glu Ala Val Arg Ala Gly Thr Ala Val
        195                 200                 205

Asp Phe Ile Trp Thr Gly Asn Pro Arg Thr Ala Pro Arg Ser Leu Ser
        210                 215                 220

Leu Gly Gly His Thr Val Arg Ala Leu Ser Pro Thr Pro Pro Trp Pro
225                 230                 235                 240

Gly Thr Asp Asp Glu Asp Asp Asp Leu Ala Asp Val Asp Tyr Val Pro
                245                 250                 255

Pro Ala Pro Arg Arg Ala Pro Arg Arg Gly Gly Gly Ala Gly Ala
        260                 265                 270

Thr Arg Gly Thr Ser Gln Pro Ala Ala Thr Arg Pro Ala Pro Pro Gly
                275                 280                 285

Ala Pro Arg Ser Ser Ser Gly Gly Ala Pro Leu Arg Ala Gly Val
        290                 295                 300

Gly Ser Gly Ser Gly Gly Pro Ala Val Ala Ala Val Val Pro Arg
305                 310                 315                 320

Val Ala Ser Leu Pro Pro Ala Ala Gly Gly Arg Ala Gln Ala Arg
                325                 330                 335

Arg Val Gly Glu Asp Ala Ala Ala Ala Glu Gly Arg Thr Pro Pro Ala
        340                 345                 350

Arg Gln Pro Arg Ala Ala Gln Glu Pro Pro Ile Val Ile Ser Asp Ser
        355                 360                 365

Pro Pro Pro Ser Pro Arg Arg Pro Ala Gly Pro Gly Pro Leu Ser Phe
        370                 375                 380

Val Ser Ser Ser Ala Gln Val Ser Ser Gly Pro Gly Gly Gly
385                 390                 395                 400

Leu Pro Gln Ser Ser Gly Arg Ala Ala Arg Pro Arg Ala Ala Val Ala
                405                 410                 415

Pro Arg Val Arg Ser Pro Pro Arg Ala Ala Ala Pro Val Val Ser
        420                 425                 430

Ala Ser Ala Asp Ala Ala Gly Pro Ala Pro Pro Ala Val Pro Val Asp
        435                 440                 445

Ala His Arg Ala Pro Arg Ser Arg Met Thr Gln Ala Gln Thr Asp Thr
        450                 455                 460

<210> SEQ ID NO 39
<211> LENGTH: 38
<212> TYPE: PRT
<213> ORGANISM: Herpes simplex virus 2

<400> SEQUENCE: 39

```
Ala Gly Ala Thr Asp Ala Arg Gly Ser Gly Gly Pro Gly Ala Glu Gly
1               5                   10                  15

Gly Pro Gly Val Pro Arg Gly Thr Asn Thr Pro Gly Ala Ala Pro His
            20                  25                  30

Ala Ala Glu Gly Ala Ala
        35
```

<210> SEQ ID NO 40
<211> LENGTH: 308
<212> TYPE: PRT
<213> ORGANISM: Herpes simplex virus 2

<400> SEQUENCE: 40

```
Ser Asp Ser Gly Pro Ala Ala Ser Ser Ala Ser Ser Ser Ala Ala
1               5                   10                  15

Pro Arg Ser Pro Leu Ala Pro Gln Gly Val Gly Ala Lys Arg Ala Ala
            20                  25                  30

Pro Arg Arg Ala Pro Asp Ser Asp Ser Gly Asp Arg His Gly Pro
            35                  40                  45

Leu Ala Pro Ala Ser Ala Gly Ala Ala Pro Pro Ser Ala Ser Pro Ser
    50                  55                  60

Ser Gln Ala Ala Val Ala Ala Ala Ser Ser Ser Ala Ser Ser Ser
65                  70                  75                  80

Ser Ala Ser Ser Ser Ala Ser Ser Ser Ala Ser Ser Ser
                85                  90                  95

Ala Ser Ser Ser Ala Ser Ser Ser Ala Ser Ser Ser Ala Gly
                100                 105                 110

Gly Ala Gly Gly Ser Val Ala Ser Ala Ser Gly Ala Gly Glu Arg Arg
            115                 120                 125

Glu Thr Ser Leu Gly Pro Arg Ala Ala Ala Pro Arg Gly Pro Arg Lys
130                 135                 140

Cys Ala Arg Lys Thr Arg His Ala Glu Gly Gly Pro Glu Pro Gly Ala
145                 150                 155                 160

Arg Asp Pro Ala Pro Gly Leu Thr Arg Tyr Leu Pro Ile Ala Gly Val
                165                 170                 175

Ser Ser Val Val Ala Leu Ala Pro Tyr Val Asn Lys Thr Val Thr Gly
            180                 185                 190

Asp Cys Leu Pro Val Leu Asp Met Glu Thr Gly His Ile Gly Ala Tyr
            195                 200                 205

Val Val Leu Val Asp Gln Thr Gly Asn Val Ala Asp Leu Leu Arg Ala
    210                 215                 220

Ala Ala Pro Ala Trp Ser Arg Arg Thr Leu Leu Pro Glu His Ala Arg
225                 230                 235                 240

Asn Cys Val Arg Pro Pro Asp Tyr Pro Thr Pro Pro Ala Ser Glu Trp
                245                 250                 255

Asn Ser Leu Trp Met Thr Pro Val Gly Asn Met Leu Phe Asp Gln Gly
            260                 265                 270

Thr Leu Val Gly Ala Leu Asp Phe His Gly Leu Arg Ser Arg His Pro
        275                 280                 285

Trp Ser Arg Glu Gln Gly Ala Pro Ala Pro Ala Gly Asp Ala Pro Ala
    290                 295                 300

Gly His Gly Glu
305
```

```
<210> SEQ ID NO 41
<211> LENGTH: 174
<212> TYPE: PRT
<213> ORGANISM: Herpes simplex virus 1

<400> SEQUENCE: 41
```

Ser Gly Gln Glu Asn Pro Ser Pro Gln Ser Thr Arg Pro Pro Leu Ala
1               5                   10                  15

Pro Ala Gly Ala Lys Arg Ala Ala Thr His Pro Pro Ser Asp Ser Gly
            20                  25                  30

Pro Gly Gly Arg Gly Gln Gly Gly Pro Gly Thr Pro Leu Thr Ser Ser
        35                  40                  45

Ala Ala Ser Ala Ser Ser Ser Ala Ser Ser Ser Ala Pro Thr
    50                  55                  60

Pro Ala Gly Ala Thr Ser Ser Ala Thr Gly Ala Ala Ser Ser Ser Ala
65                  70                  75                  80

Ser Ala Ser Ser Gly Gly Ala Val Gly Ala Leu Gly Gly Arg Gln Glu
                85                  90                  95

Glu Thr Ser Leu Gly Pro Arg Ala Ala Ser Gly Pro Arg Gly Pro Arg
            100                 105                 110

Lys Cys Ala Arg Lys Thr Arg His Ala Glu Thr Ser Gly Ala Val Pro
        115                 120                 125

Ala Gly Gly Leu Thr Arg Tyr Leu Pro Ile Ser Gly Val Ser Ser Val
    130                 135                 140

Val Ala Leu Ser Pro Tyr Val Asn Lys Thr Ile Thr Gly Asp Cys Leu
145                 150                 155                 160

Pro Ile Leu Asp Met Glu Thr Gly Asn Ile Gly Ala Tyr Val
                165                 170

```
<210> SEQ ID NO 42
<211> LENGTH: 64
<212> TYPE: PRT
<213> ORGANISM: Herpes simplex virus 1

<400> SEQUENCE: 42
```

Gly Asn His Val Thr Pro Pro Glu Tyr Pro Thr Ala Pro Ala Ser Glu
1               5                   10                  15

Trp Asn Ser Leu Trp Met Thr Pro Val Gly Asn Met Leu Phe Asp Gln
            20                  25                  30

Gly Thr Leu Val Gly Ala Leu Asp Phe Arg Ser Leu Arg Ser Arg His
        35                  40                  45

Pro Trp Ser Gly Glu Gln Gly Ala Ser Thr Arg Asp Glu Gly Lys Gln
    50                  55                  60

```
<210> SEQ ID NO 43
<211> LENGTH: 209
<212> TYPE: PRT
<213> ORGANISM: Herpes simplex virus 2

<400> SEQUENCE: 43
```

Ser Asp Ser Gly Pro Ala Ala Ser Ser Ala Ser Ser Ser Ala Ala
1               5                   10                  15

Pro Arg Ser Pro Leu Ala Pro Gln Gly Val Gly Ala Lys Arg Ala Ala
            20                  25                  30

Pro Arg Arg Ala Pro Asp Ser Asp Ser Gly Asp Arg Gly His Gly Pro
        35                  40                  45

Leu Ala Pro Ala Ser Ala Gly Ala Ala Pro Pro Ser Ala Ser Pro Ser
    50                  55                  60

```
Ser Gln Ala Ala Val Ala Ala Ser Ser Ser Ser Ala Ser Ser Ser
 65                  70                  75                  80

Ser Ala Ser Ser Ser Ser Ala Ser Ser Ser Ala Ser Ser Ser Ser
                 85                  90                  95

Ala Ser Ser Ser Ala Ser Ser Ser Ser Ala Ser Ser Ser Ala Gly
            100                 105                 110

Gly Ala Gly Gly Ser Val Ala Ser Ala Ser Gly Ala Gly Glu Arg Arg
        115                 120                 125

Glu Thr Ser Leu Gly Pro Arg Ala Ala Pro Arg Gly Pro Arg Lys
        130                 135                 140

Cys Ala Arg Lys Thr Arg His Ala Glu Gly Gly Pro Glu Pro Gly Ala
145                 150                 155                 160

Arg Asp Pro Ala Pro Gly Leu Thr Arg Tyr Leu Pro Ile Ala Gly Val
                165                 170                 175

Ser Ser Val Val Ala Leu Ala Pro Tyr Val Asn Lys Thr Val Thr Gly
                180                 185                 190

Asp Cys Leu Pro Val Leu Asp Met Glu Thr Gly His Ile Gly Ala Tyr
                195                 200                 205

Val

<210> SEQ ID NO 44
<211> LENGTH: 69
<212> TYPE: PRT
<213> ORGANISM: Herpes simplex virus 2

<400> SEQUENCE: 44

Arg Asn Cys Val Arg Pro Pro Asp Tyr Pro Thr Pro Pro Ala Ser Glu
  1               5                  10                  15

Trp Asn Ser Leu Trp Met Thr Pro Val Gly Asn Met Leu Phe Asp Gln
                 20                  25                  30

Gly Thr Leu Val Gly Ala Leu Asp Phe His Gly Leu Arg Ser Arg His
            35                  40                  45

Pro Trp Ser Arg Glu Gln Gly Ala Pro Ala Pro Ala Gly Asp Ala Pro
     50                  55                  60

Ala Gly His Gly Glu
 65

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 45

His His His His His His
  1               5
```

HERPES SIMPLEX VIRUS MUTANT ICP0

CROSS-REFERENCE TO RELATED APPLICATIONS

This application is a continuation-in-part of U.S. patent application Ser. No. 12/167,870, filed Jul. 3, 2008, which claims the benefit of U.S. Provisional Patent Application No. 60/948,048, filed on Jul. 5, 2007, the disclosures of these applications are incorporated herein by specific reference in their entirety.

This invention was made with government support under Grant Numbers CA20260 and AI81072 awarded by the National Institute of Health. The government has certain rights in the invention.

SEQUENCE LISTING

The instant application contains a Sequence Listing which has been submitted via EFS-Web and is hereby incorporated by reference in its entirety. Said ASCII copy, created on Apr. 14, 2010, is named 16994111.txt and is 118,526 bytes in size.

BACKGROUND OF THE INVENTION

1. The Field of the Invention

The present invention relates to a mutant herpes simplex virus (HSV) encoding for or having a mutated ICP0 protein. More particularly, the present invention relates to a mutant HSV, mutant gene encoding ICP0, mutant ICP0 protein, a vaccine or other composition having the mutant HSV, assay systems and reagents with the mutant HSV and/or mutant ICP0, and methods of making and using the same.

2. The Relevant Technology

Herpes simplex virus 1 and 2 (HSV-1 and HSV-2) are two species of the herpesvirus family, herpesviridae, which cause infections in humans. Members of herpesviridae infect humans to cause a variety of illnesses including cold sores, chickenpox or varicella, shingles or herpes zoster (VZV), cytomegalovirus (CMV), and various cancers, and can cause brain inflammation (encephalitis). All viruses in the herpes family produce life-long infections. HSV-1 and HSV-2 are also called Human Herpesvirus 1 and 2 (HHV-1 and HHV-2) and belong to the sub-family of neurotropic herpesviruses, which are conventionally referred to as the alpha-herpesviruses Like all alpha-herpesviruses, HSV-1 and HSV-2 enter the body and hide in the nervous system of their animal host, hence accounting for their ability to persist. HSV-1 is commonly associated with recurrent herpes outbreaks of the face known as cold sores or fever blisters, whereas HSV-2 is more often associated with recurrent genital herpes.

An infection by a herpes simplex virus (HSV) is marked by watery blisters in the skin or mucous membranes of the mouth, lips, or genitals. Lesions heal with a scab characteristic of herpetic disease. However, the infection is persistent and symptoms may recur periodically as outbreaks of sores near the site of original infection. After the initial, or primary, infection, HSV becomes latent in the cell bodies of nerves in the area. Some infected people experience sporadic episodes of viral reactivation, followed by transportation of the virus via the nerve's axon to the skin, where virus replication and shedding occurs. Herpes is contagious if the carrier is producing and shedding the virus. This is especially likely during an outbreak, but possible at other times. There is no cure yet, but there are treatments which reduce the likelihood of viral shedding.

HSV is a common and significant human pathogen which causes a variety of diseases, ranging from cold sores to potentially blinding ocular infections and life-threatening encephalitis. HSV establishes lifelong latent infections in neuronal cells, which reactivate periodically. The HSV lifecycle can be described in two specific stages of infection: latent and productive. Latent infection is defined as a lack of production of infectious virus at the site. Productive infection can be characterized by the expression of nearly all (about 100) viral genes in epithelial cells and fibroblasts at the periphery and the sensory neurons that innervate the site of infection. One of the important HSV-1 and HSV-2 proteins in this process is Infected Cell Protein 0 (ICP0).

Infected Cell Protein 0 (ICP0) is a nuclear phosphoprotein, and is one of the first HSV-1 proteins to be expressed upon infection of cells in culture. ICP0 is a key determinant in the switch between latent and productive infections of HSV viruses. ICP0 is a potent transactivator of HSV gene expression, and can be considered essential for efficient viral replication, especially at low multiplicities. ICP0 transactivates all classes of HSV genes, immediately-early (IE), early, and late, as well as numerous cellular genes and genes of other viruses. ICP0 is an immediately-early (IE) transactivator, and E3 ubiquitin ligase, which disrupts nuclear domain 10 and inhibits the cellular interferon response. Due to these features, HSV-1, HSV-2, and ICP0 have been studied for indications of the pathogenesis of the viral infection. Research of ICP0 has shown that phosphorylation is important for ICP0 to function in the viral pathway.

BRIEF SUMMARY OF THE INVENTION

In one embodiment, the present invention can include a mutant herpesvirus having a mutated gene that encodes a mutant infected cell protein 0 (ICP0) that is altered in one or more regions of ICP0 that are substantially conserved between two or more herpesviruses, wherein the mutant herpesvirus is substantially avirulent and immunogenic.

In one embodiment, the present invention can include an immunogenic composition that has a pharmaceutically acceptable carrier and a mutant herpesvirus gene. The mutant herpesvirus gene can encode a mutant infected cell protein 0 (ICP0) that is altered in one or more regions of ICP0 that are substantially conserved between two or more herpesviruses, wherein the mutant herpesvirus is substantially avirulent and immunogenic. Optionally, the gene can be located within a mutant herpesvirus.

In one embodiment, the present invention can include a method of immunizing a subject. Such a method can include administering to the subject an immunogenic composition having a mutant herpesvirus gene that encodes a mutant infected cell protein 0 (ICP0) that is altered in one or more regions of ICP0 that are substantially conserved between two or more herpesviruses, wherein the mutant herpesvirus is substantially avirulent and immunogenic. Optionally, the mutant ICP0 gene can be located within a mutant herpesvirus.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIGS. 1A-1C illustrate the locations of ICP0 functional domains, phosphorylation sites, and phosphorylation site mutants. FIG. 1B discloses SEQ ID NO: 18.

FIG. 13A is a sequence alignment of the ICP0 of HSV-1 strain 17 (SEQ ID NO: 2) an HSV-2 strain HG52 (SEQ ID NO: 8).

FIG. 13B is a sequence alignment of the ICP0 of HSV-1 strain KOS (SEQ ID NO: 4) an HSV-2 strain HG52 (SEQ ID NO: 8).

FIGS. 14A-14B show conserved regions of HSV-1 and HSV-2 ICP0 protein. FIG. 14A is a schematic of conserved regions of HSV-1 versus HSV-2 ICP0. FIG. 14B is an amino acid alignment showing which amino acids constitute the conserved RING finger region, nuclear localization signal region, and ICP4-binding domain of HSV-1 (SEQ ID NO: 19) and HSV-2 (SEQ ID NO: 8) ICP0 protein.

FIG. 15B is a Southern blot analysis of the wild-type and mutant alleles of the ICP0 genes in HSV-2 MS, HSV-20Δ104, HSV-20ΔRING, HSV-20ΔNLS, HSV-20Δ254, and HSV-20Δ810. Southern blots show an oligonucleotide specific for ICP0 exon 2 or GFP hybridized to a Sac I-Stu I fragment of the wild-type or mutant alleles of the ICP0 gene.

FIG. 16B is a Western blot analysis of proteins harvested from cells that were uninfected (UI) or were inoculated with 2.5 pfu per cell of HSV-2 MS, HSV-2 MS-GFP, HSV-2 0Δ104, HSV-2 0ΔRING, HSV-2 0ΔNLS, HSV-2 0Δ254, or HSV-2 0Δ810. GFP or chimeric ICP0 proteins bearing a GFP tag were labeled with rabbit polyclonal GFP-specific antibody. Molecular weight markers are shown on the right.

FIG. 17C shows results of interferon-sensitivity testing of a panel of HSV-2 ICP0-viruses. The results represent reductions in plaque formation in interferon-β-treated Vero cells relative to ICP0-complementing L7 cells.

FIGS. 18A-18F are graphs that show HSV-2 0ΔRING, HSV-2 0Δ254, HSV-2 0Δ810, and HSV-2 0ΔNLS fail to efficiently replicate in cells treated with human interferon-β. Three sets of replicate cultures of ICP0-complementing L7 cells (closed circles), Vero cells (open circles), or Vero cells treated with human inteferon-β (open triangles) were inoculated with 0.1 pfu per cell of (FIG. 18A) wild-type HSV-2 MS, (FIG. 18B) HSV-2 0Δ104, (FIG. 18C) HSV-2 0ΔRING, (FIG. 18D) HSV-2 0Δ254, (FIG. 18E) HSV-2 0Δ810, or (FIG. 18F) HSV-2 0ΔNLS. Following inoculation, cultures were incubated at 37° C. for 3, 6, 12, 18, 24, 36, or 48 hours prior to freezing at −80° C. Upon thawing, the titer of infectious virus in each culture well was determined by a microtiter plaque assay. Arrows on the right of each graph represent the antilogarithm ($10^x$) of the following value: log (pfu/ml) in L7 cells$_{48\ hours}$–log (pfu/ml) in interferon-β-treated Vero cells$_{48\ hours}$.

FIG. 19A shows viral shedding from the right eyes of mice inoculated with 100,000 pfu/eye of wild-type HSV-2 MS which were untreated or were treated with the antiviral drug acyclovir (ACV) versus viral shedding from mice inoculated with 100,000 pfu/eye of HSV-2 0Δ254 or HSV-2 0Δ810. FIG. 19B shows viral shedding from the right eyes of mice inoculated with 100,000 pfu/eye of HSV-2 0Δ104, HSV-2 0ΔRING, or HSV-2 0Δ810. FIG. 19C shows direct visualization of sites of HSV-2 ICP0-mutant viral replication in the right corneas of mice, which appear as tracts of GFP+ (bright spots in eye) cells due to the expression of GFP-tagged ICP0 mutant proteins in cells infected with HSV-2 0Δ254, HSV-2 0Δ810, HSV-2 0Δ104, HSV-2 0ΔRING, or HSV-2 0ΔNLS. Of the various mouse eyes that were photographed, a representative image shows the average extent of HSV-2 spread observed at 60 hours p.i., and the percentage in each image represents the frequency with which tracts of GFP+ cells were observed in mouse eyes in two experiments. FIG. 19D shows the frequency of survival of mice until 30 days after inoculation of the right eye with a dose of 100,000 pfu/eye of HSV-2 MS, HSV-2 0Δ104, HSV-2 0ΔRING, HSV-2 0Δ254, HSV-2 0Δ810, or HSV-2 0ΔNLS. Mice inoculated with HSV-2 MS that survived due to the antiviral drug acyclovir (ACV) were specifically treated with 30 mg/kg of acyclovir delivered intraperitoneally on days −1, 0, 1, and 3 p.i. and in addition were given acyclovir in their drinking water (1 mg/ml) from days −3 to 20 p.i.

FIG. 20A shows the summated results of six independent experiments in which naïve mice were challenged with 100,000 pfu/eye of HSV-2 MS, and uniformly succumbed to HSV-2 infection in the following 6 to 8 days. FIG. 20B shows the frequency of survival of mice until 30 days post-challenge (100 days post-vaccination) following inoculation of the left eye with a dose of 100,000 pfu/eye of HSV-2 MS based on 2 independent challenge experiments. A single asterisk, *, denotes significant protection against HSV-2 MS challenge relative to naïve mice. A double asterisk, **, denotes highly significant protection relative to naïve mice.

FIG. 21A shows the duration of survival of naïve mice following ocular inoculation with 8, 4, 20, or 100 thousand pfu/eye of HSV-2 MS. FIG. 21B shows the duration of survival of naïve mice following ocular inoculation with 8, 4, 20, or 100 thousand pfu/eye of HSV-2 0ΔNLS.

FIG. 23A shows ocular shedding of HSV-2 MS challenge virus in the eyes of naïve mice versus HSV-2 0ΔNLS-vaccinated mice between 24 and 72 hours post-challenge. FIG. 23B shows vaginal shedding of HSV-2 MS challenge virus in the vaginas of naïve mice versus HSV-2 0ΔNLS-vaccinated mice between 48 and 144 hours post-challenge. FIGS. 23C-23D show the frequency of survival of mice challenged with HSV-2 MS in the (FIG. 23C) eyes or (FIG. 23D) vagina until Day 30 post-challenge (Day 100 post-vaccination). Asterisks, *, denote groups in which 0ΔNLS vaccination induced highly significant protection against HSV-2 MS-induced death relative to naïve controls.

FIG. 25A shows ocular shedding of HSV-2 MS luciferase virus at 24 hours post-challenge. FIGS. 25B-25C are photographs that show the distribution of HSV-2 MS luciferase viral infection on (FIG. 25B) Day 2 or (FIG. 25C) Day 6 post-ocular-challenge in mice vaccinated with the HSV-2 0ΔNLS virus versus the gD protein subunit vaccine. In these figures, the stippling density provides an indication of infection, with more stipple showing more infection. The negative controls in this experiment are the mice that were injected with complete DMEM (naïve) or an irrelevant antigen (GFP). The positive-control in this experiment was a mouse that was asymptomatically infected with wild-type HSV-2 MS virus, which is known to renders animals highly resistant to infection with a second, exogenous HSV-2 virus (i.e., animals may only be colonized by a single HSV-2 virus). Finally, an animal that was not infected with HSV-2 MS luciferase was included to verify that an uninfected animal did not spontaneously break down the luciferin substrate, and thus the background noise of the experimental measurement was negligible. Hence, all light emission measurements provided a faithful measurement of the distribution of HSV-2 MS luciferase infection in mice.

FIG. 26A shows vaginal shedding of HSV-2 MS luciferase virus at 48 hours post-challenge. FIGS. 26B-26C show the distribution of HSV-2 MS luciferase viral infection on (FIG. 26B) Day 2 or (FIG. 26C) Day 6 post-vaginal-challenge in mice vaccinated with the HSV-2 0ΔNLS virus versus the gD protein subunit vaccine. In these figures, the stippling density provides an indication of infection, with more stipple showing more infection. The relevance of the other four control animals is explained in the legend to FIG. 25.

On Day 70 post-vaccination of the left and right, rear footpads (no booster shot was given; just a single immunization on Day 0), mice were challenged with 100,000 pfu/eye of HSV-2 MS-luciferase. The distribution of HSV-2 MS luciferase viral infection is compared on Days 2, 4, and 6 post-challenge in naïve mice versus mice vaccinated with the HSV-2 0ΔNLS virus or the HSV-2 0Δ4BD virus.

Figure 28:
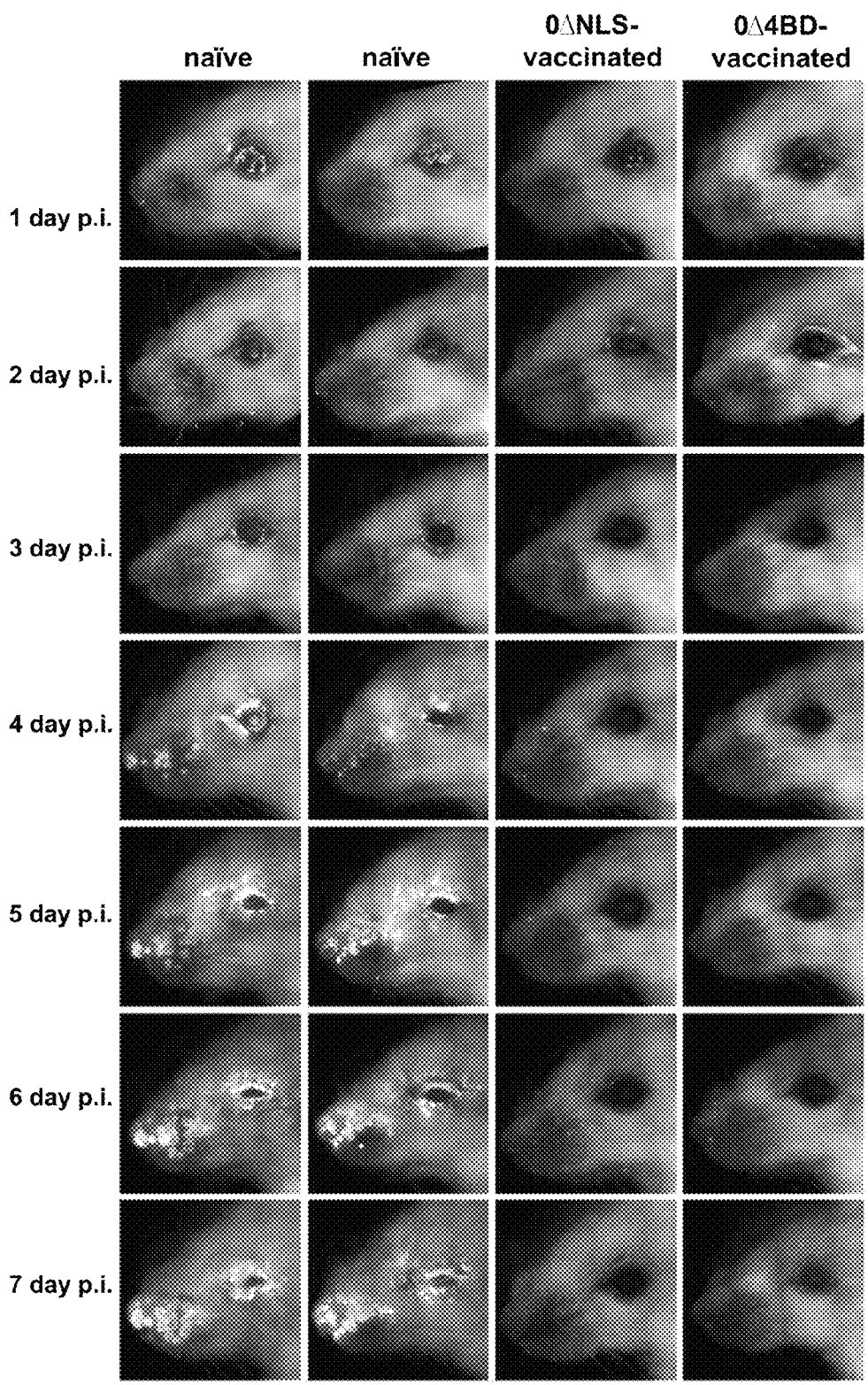

FIG. 28 shows that mice exposed to HSV-2 0ΔNLS or HSV-2 0Δ4BD virus acquire potent immunity to the spread of a 'green' HSV-2 MS GFP virus from an ocular site of challenge. On Day 70 post-vaccination of the left and right, rear footpads (no booster shot was given; just a single immunization on Day 0), mice were challenged with 100,000 pfu/eye of HSV-2 MS-GFP. The distribution of HSV-2 MS-GFP viral infection is compared on the faces of naïve versus vaccinated mice on Days 1-7 post-challenge.

FIG. 29 presents the amino acid sequence of the mutant ICP0 protein encoded by HSV-2 0ΔNLS to illustrate that (1) green-fluorescent protein replaces amino acids 19 to 104 of the native HSV-2 ICP0 protein, and (2) amino acids 489-695 have been removed from the native HSV-2 ICP0 protein. The mutant HSV-2 ICP0 protein (SEQ ID NOS 23-25, respectively, in order of appearance) is aligned with HSV-1's ICP0 protein (SEQ ID NOS 20-22, respectively, in order of appearance) to illustrate that deletion of amino acids 489-695 removes the NLS region which is conserved between HSV-1 ICP0 and HSV-2 ICP0.

FIG. 30 presents the amino acid sequence of the mutant ICP0 protein encoded by HSV-2 0Δ4BD to illustrate that (1) green-fluorescent protein replaces amino acids 19 to 104 of the native HSV-2 ICP0 protein, and (2) amino acids 696-810 have been removed from the native HSV-2 ICP0 protein. The mutant HSV-2 ICP0 protein (SEQ ID NOS 23 and 27-28 respectively, in order of appearance) is aligned with HSV-1's ICP0 protein (SEQ ID NOS 20 and 26, respectively, in order of appearance) to illustrate that deletion of amino acids 696-810 removes the potential ICP4-binding domain (4BD)/oligomerization domain which is conserved between HSV-1 ICP0 and HSV-2 ICP0.

FIG. 31 presents the amino acid sequence of the mutant ICP0 protein encoded by HSV-2 0ΔRING to illustrate that (1) green-fluorescent protein replaces amino acids 19 to 104 of the native HSV-2 ICP0 protein, and (2) amino acids 105-162 have been removed from the native HSV-2 ICP0 protein. The mutant HSV-2 ICP0 protein (SEQ ID NOS 23 and 30, respectively, in order of appearance) is aligned with HSV-1's ICP0 protein (SEQ ID NOS 20 and 29, respectively, in order of appearance) to illustrate that deletion of amino acids 105-162 removes a portion of the RING finger domain which is conserved between HSV-1 ICP0 and HSV-2 ICP0.

FIG. 32 presents the amino acid sequence of the mutant ICP0 protein encoded by HSV-1 0ΔRING to illustrate that (1) green-fluorescent protein has been inserted between amino acids 104 and 105 of the native HSV-1 ICP0 protein, and (2) amino acids 105-219 have been removed from the native HSV-1 ICP0 protein. The mutant HSV-1 ICP0 protein (SEQ ID NOS 31-32, respectively, in order of appearance) is aligned with HSV-2's ICP0 protein (SEQ ID NOS 33-34, respectively, in order of appearance) to illustrate that deletion of amino acids 105-219 removes most of the RING finger domain which is conserved between HSV-1 ICP0 and HSV-2 ICP0.

FIG. 33 presents the amino acid sequence of the mutant ICP0 protein encoded by HSV-1 0ΔRING to illustrate that (1) green-fluorescent protein has been inserted between amino acids 104 and 105 of the native HSV-1 ICP0 protein, and (2) amino acids 450-456 and 500-507 have been removed from the native HSV-1 ICP0 protein. The mutant HSV-1 ICP0 protein (SEQ ID NOS 35-37, respectively, in order of appearance) is aligned with HSV-2's ICP0 protein (SEQ ID NOS 38-40, respectively, in order of appearance) to illustrate that deletion of amino acids 500-507 removes the perfectly conserved, basic nuclear localization signal present in HSV-1 ICP0 and HSV-2 ICP0.

FIG. 34 presents the amino acid sequence of the mutant ICP0 protein encoded by HSV-1 0Δ4BD to illustrate that (1) green-fluorescent protein has been inserted between amino acids 104 and 105 of the native HSV-1 ICP0 protein, and (2) amino acids 682-711 have been removed from the native HSV-1 ICP0 protein. The mutant HSV-1 ICP0 protein (SEQ ID NOS 35-36 and 41-42, respectively, in order of appearance) is aligned with HSV-2's ICP0 protein (SEQ ID NOS 38-39 and 43-44, respectively, in order of appearance) to illustrate that deletion of amino acids 682-711 removes a portion of the conserved, potential ICP4-binding domain (4BD)/oligomerization domain present in HSV-1 ICP0 and HSV-2 ICP0.

FIG. 35 presents the amino acid sequence of the mutant ICP0 protein encoded by HSV-1 $0^-$GFP to illustrate that (1) green-fluorescent protein has been inserted between amino acids 104 and 105 of the native HSV-1 ICP0 protein, and (2) a translational stop codon occurs after the green-fluorescent protein coding sequence such that HSV-1 $0^-$GFP's ICP0 protein lacks amino acids 105-775. The mutant HSV-1 ICP0 protein (SEQ ID NO: 31) is aligned with HSV-2's ICP0 protein (SEQ ID NO: 33) to illustrate that failure to encode amino acids 105-775 removes all three of the conserved domains present in both HSV-1 ICP0 and HSV-2 ICP0.

DETAILED DESCRIPTION OF THE PREFERRED EMBODIMENTS

Herpes simplex virus (HSV) type 1 (HSV-1) or type 2 (HSV-1) include an infected cell protein 0 (ICP0) as an immediate-early (IE) transactivator and E3 ubiquitin (Ub) ligase, which disrupts nuclear domain 10 (ND10) and inhibits the cellular interferon response. Cellular functions of ICP0 are involved in viral gene expression, viral replication, and reactivation from latency. ICP0 is a nuclear protein that is phosphorylated, a post-translational modification that acts as a key regulator of many viral and cellular proteins.

ICP0 is the product of gene IE-1 (or α0), which is in the repeated sequences bounding the long unique segment of the HSV genome. The primary transcript of the IE-1 gene is one of the few produced by HSV that is spliced. The ICP0 protein product of HSV-1 strain 17 contains 775 amino acids and HSV-2 contains 825 amino acids. This protein has been named as Vmw110 or IE110 in many older publications, but now the designation ICP0 has been almost universally adopted.

It has now been found that mutation of phosphorylation sites of viral regulatory proteins, such as ICP0, in HSV can alter their DNA replication activity, affecting both their biochemical and biological functions. It has been demonstrated that phosphorylation is an important modulator of the functions of infected cell proteins (ICPs). Mutant viruses having mutations that affect an ICP's transactivating activity to replicate, establish latency, and reactivate from latency may be inefficient for infection and are sensitive to the cellular antiviral factors, interferon. Although early studies demonstrated that ICPs are phosphorylated, the location of specific phosphorylation sites on ICPs, and the kinases that phosphorylate ICPs and the functional relevance of ICP phosphorylation to HSV replication have been largely unknown. Previous studies demonstrated a link between ICP0's posttranslational modification state and HSV transactivating activity, which includes posttranslational phosphorylation. In addition, the kinase UL13 has been shown to be required to achieve maximal levels of ICP0 phosphorylation during viral infection, and can phosphorylated ICP0 in vitro.

It has also been found that a mutation in a conserved region of ICP0 that occurs in the gene encoding ICP0 for both the HSV-1 and HSV-2 may result in an avirulent mutant virus. The mutations within conserved regions may alter DNA replication activity, affecting both their biochemical and biological functions in a manner similar to mutations to phosphorylation regions. However, the conserved regions are much larger than the phosphorylation regions and can provide greater flexibility in designing a mutant HSV that is avirulent.

Additionally, regions that are conserved in the ICP0 protein between HSV-1 and HSV-2 may also be conserved in about 20 other α-herpesviruses, and thereby mutations to the conserved regions of the α-herpesviruses may also produce avirulent α-herpesviruses. Examples of some of these α-herpesviruses can include bovine herpesviruses 1 or 5 (BHV-1 or BHV-5), equid herpesviruses 1, 4, or 9 (EHV-1, EHV-4, or EHV-9), suid herpesvirus 1 or pseudorabiesvirus (PRV), varicella zoster virus (VZV), canid herpesvirus 1 (CHV-1), felid herpesvirus 1 (FHV-1), macropodid herpesvirus 1 (MHV-1), cercopithecine herpesviruses 2 or 9 (CpHV-2 or CpHV-9), macacine herpesvirus 1 which is commonly known as the herpes B virus, or papiine herpesvirus 2 (PHV-2). This is not an exhaustive list of all herpesviruses that encode an ICP0-like protein, but rather is meant to illustrate that herpesviruses exist throughout the animal kingdom and are known to rely on an ICP0-like protein for their ability to replicate efficiently and cause disease in their animal hosts ICP0 Phosphorylation Regions In one embodiment, the present invention includes a mutant HSV-1 that encodes for a mutant ICP0 that is mutated to reduce or inhibit posttranslational phosphorylation. Accordingly, the mutant HSV-1 can include a mutant gene that encodes for the mutant ICP0. The mutant HSV-1 can be grown in an ICP0-complementing cell line where the wild-type ICP0 protein is provided by the host cell and thus allows for the efficient growth of the HSV-1 ICP0 mutant virus. The mutant HSV-1 can be avirulent, have inhibited replication and inhibited reactivation in comparison with wild-type HSV-1, and be immunogenic. The mutant HSV-1 can have inhibited or reduced replication or reactivation in both peripheral and central nervous systems. Such a mutant HSV-1 with a genome mutated in respect to ICP0 can protect a susceptible species immunized therewith against infection by the corresponding wild-type HSV-1. Thus, the mutant HSV-1 encoding for a mutant ICP0 can be used in an immunogenic composition to inhibit wild-type HSV-1 replication, and thereby treat and/or prevent diseases caused by wild-type HSV-1.

Phosphorylation is a critical regulator of HSV-1 ICP0 function in cell culture, and likely in other herpesviruses. FIGS. 1A-1C show that there are three phosphorylated regions on ICP0 that were identified and designated in regions I, II, and III: Region I is referred to as the Phos1 region and includes amino acids 224-232; Region II is referred to as the Phos2 region and includes amino acids 365-371; and Region III is referred to as the Phos3 region and includes amino acids 508-518. In the Phos1 region, at least amino acids at S224, T226, T231, and T232 (i.e., Phos1 phosphorylated amino acids) can be mutated to inhibit phosphorylation. In the Phos2 region, at least amino acids at S365, S367, and S371 (i.e., Phos2 phosphorylated amino acids) can be mutated to inhibit phosphorylation. In the Phos3 region, at least amino acids at S508, S514, S517, and T518 (i.e., Phos3 phosphorylated amino acids) can be mutated to inhibit phosphorylation. Additionally, other amino acids within the Phos1, Phos2, and/or Phos3 regions can be mutated to inhibit phosphorylation. Also, such mutations can result in a virus encoding the ICP0 protein to be avirulent and immunogenic. In some instances, the mutations in these regions may also result in the virus encoding for the mutation to have inhibited replication.

Mutant HSV-1 viruses carrying mutations within the genetic code for each region (Phos1, Phos2, and Phos3) of the mutant ICP0 protein have been constructed. In cell culture studies, the plating efficiencies of HSV-1 Phos1 and HSV-1 Phos3 are distinct from that of wild-type virus, in that both exhibit reduced efficiency of plaque formation. Notably, for HSV-1 Phos3, this defect is apparent only in the presence of interferon-beta. All three Phos viral mutants have reduced reactivation efficiencies, and HSV-1 Phos1 and HSV-1 Phos3 have significantly reduced pathogenicities compared to wild-type HSV-1. The greatest decline in viral pathogenicity is observed with HSV-1 Phos3, whose mutations overlap the nuclear localization signal of ICP0.

The mutation in the HSV-1 gene encoding for ICP0 can result in an ICP0 protein having the selected mutations, which include mutations in the ICP0 protein being amino acid insertions, deletions, or substitutions. Accordingly, reference to mutations of selected regions or amino acids within the ICP0 protein may also refer to corresponding mutations to the gene encoding ICP0 such that the resulting ICP0 has the amino acid insertions, deletions, or substitutions. The mutations can be in the Phos1, Phos2, and/or Phos3 regions so as to inhibit phosphorylation of one or more amino acids in these regions. Such inhibition of phosphorylation in ICP0 can result in a virus encoding the mutant ICP0 to be considered avirulent. As used herein, the term "avirulent" is meant to refer to a mutant virus that is unable to cause disease or significantly inhibited from causing disease. For example, an "avirulent" virus can be considered to be replication-impaired, repression-prone, and/or interferon-sensitive. Additionally, the mutations to Phos1, Phos2, and/or Phos3 regions can result in a virus encoding the mutant ICP0 to be immunogenic. As used herein, the term "immunogenic" is meant to refer to a mutant virus that is capable of causing or producing an immune response. For example, an "immunogenic" virus may be useful in an immunogenic composition, such as a vaccine.

In one aspect, the mutation of HSV-1 encodes for a mutant ICP0 protein having an amino acid substitution, insertion, deletion, or combination thereof. The mutant ICP0 can have a mutant within the Phos1, Phos2, and/or Phos3 regions, or the specific phosphorylated amino acids contained therein. The mutation can be a substation of at least one serine and/or threonine amino with a different amino acid. For example, the different amino acid can be alanine. The mutation can cause the HSV-1 to be avirulent and immunogenic.

Of the viral mutants, mutations in the Phos3 region can have the greatest effect on all phases of the HSV-1 life-cycle in vivo. In contrast to the ICP0 null mutant HSV-1 7134, HSV-1 Phos3 has reduced or inhibited replication in neurons of the trigeminal ganglia (TG) during acute infection, days 1-9 post infection (p.i.). The mutant HSV-1 Phos3 can have reduced or inhibited replication in TG during the initial stage of HSV-1 infection. This reduction or inhibition of replication can produce no or significantly reduced visible signs of viral pathogenesis and an impaired reactivation phenotype. HSV-1 Phos1 can have inhibited replication and reduced pathogenesis, although its defects may be less pronounced as those of HSV-1 Phos3. HSV-1 Phos2 may be considered the least attenuated mutant of the three mutant HSV-1 Phos viruses.

Accordingly, Phos1 mutations in the gene encoding for ICP0 can impair acute replication in eyes and TG and reactivation from latency. Phos2 mutations in the gene encoding for ICP0 can impair acute replication in TG and reactivation from latency. Phos3 mutations in the gene encoding for ICP0 can impair ocular replication, completely inhibit acute TG replication, and significantly reduce reactivation. As such, Phos3 shows the greatest diminution of the three mutant HSV-1 Phos viruses. Also, all three ICP0 phosphorylation regions may be required for efficient viral replication and reactivation from latency, and a mutation to one or more of the regions can reduce or inhibit replication. The Phos3 mutant form of ICP0 appears to interfere with a viral or cellular function essential for viral growth in neurons.

In one embodiment, the mutation in HSV-1 could be introduced by site-directed mutagenesis. However, any method known or developed for preparing a mutant HSV-1 and/or mutant ICP0 as described herein can be used for preparing the mutant HSV-1 and/or mutant ICP0 of the present invention.

Conserved ICP0 Regions

HSV-1 and HSV-2 both encode an ICP0 protein. Sequence alignments were prepared between ICP0 proteins from HSV-1 strain KOS and HSV-2 strain HG52 (FIG. 13B), and HSV-1 strain 17 and HSV-2 strain HG52 (FIG. 13A). The sequence alignments indicate that a mutant HSV-2 and/or mutant HSV-2 ICP0 can be prepared as described in connection with mutant HSV-1 and/or mutant HSV-1 ICP0. The ICP0 phosphorylation sites in HSV-1 from amino acids 508-518 appears to be homologous to HSV-2 amino acids 518-531, depending on the alignment. HSV-1 ICP0 serine 508 is conserved as HSV-2 ICP0 serine 518. Depending on the strain used in the alignment, either HSV-1 ICP0 serine 514 is conserved as HSV-2 ICP0 serine 530 (with strain KOS) or HSV-1 ICP0 serine 517 is conserved as HSV-2 ICP0 serine 530 (with strain 17). Also, for HSV-1 ICP0, there are 3 serines and 1 threonine from amino acid 508-518, and for HSV-2 ICP0, there are 8 serines from amino acid 518-531.

Additional sequence alignments were performed with standard HSV-1 and HSV-2 sequences available in databases (see FIGS. 14B, 29 and 30). These sequence alignments also show highly conserved regions between HSV-1 and HSV-2. With the sequence similarities, it is thought that HSV-2 ICP0 protein will have similar properties of the HSV-1 ICP0 protein; and thereby the mutations to HSV-1 for an avirulent virus with a mutant ICP0 may be applied to a mutant HSV-2, and vice versa.

Figure 14A:
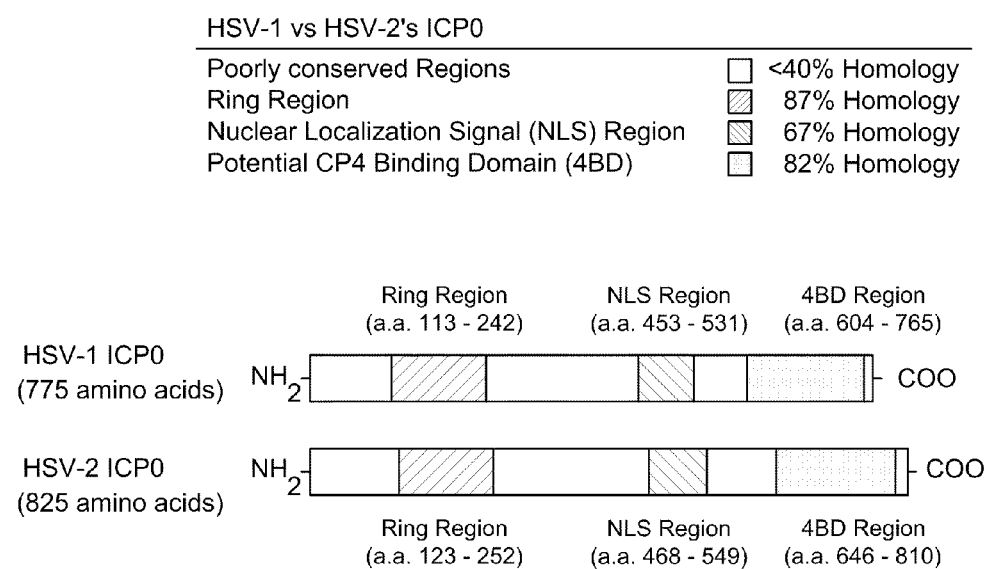

Approximately one-half of the ICP0 proteins of HSV-1 and HSV-2 are not particularly well conserved (FIG. 14A-14B). However, three regions of ICP0 are highly conserved between these two viruses, which are thought to have diverged from a common ancestral virus millions of years ago. The portions of HSV-1 and HSV-2 ICP0 protein that are conserved are the: 1. N-terminal RING finger domain that is necessary for ICP0's E3 ligase activity (FIGS. 14A, 14B); 2. a nuclear localization signal (NLS) region near the middle of the protein (FIGS. 14A, 14B); and 3. a conserved C-terminal portion that appears to function as an ICP0 multimerization domain and/or a putative ICP4-binding domain (4BD) (FIGS. 14A, 14B). While the 4BD region is suspected to be an ICP4-binding domain, it is not established, and thereby is putative. In any event, this region is referred to as the 4BD region. Accordingly, the putative 4BD region is a stretch of highly conserved amino acids near the carboxy-terminus of the ICP0 protein as described herein.

Mutant HSV-2 viruses were prepared with a deletion mutation in each one of the conserved regions, and are referred to as: HSV-2 0ΔRING; HSV-2 0ΔNLS; and HSV-2 0Δ4BD. Additional mutant HSV-2 viruses were prepared as controls and are: HSV-2 0Δ104; HSV-2 0Δ254; and HSV-2 0Δ810. Information regarding the deleted amino acids and ICP0 protein are shown in Table 1 below.

TABLE 1

| HSV-2 virus | Deleted amino acids | ICP0 protein encoded |
| --- | --- | --- |
| Wild-type HSV-2 | | $ICP0_{aminoacids\ (a.a.)\ 1-825}$ |
| HSV-2 0Δ104 | Δ19-104 | $ICP0_{a.a.\ 1-18} \rightarrow GFP \rightarrow ICP0_{a.a.\ 105-825}$ |
| HSV-2 0ΔRING | Δ19-162 | $ICP0_{a.a.\ 1-18} \rightarrow GFP \rightarrow ICP0_{a.a.\ 163-825}$ |
| HSV-2 0ΔNLS | Δ19-104, Δ489-695 | $ICP0_{a.a.\ 1-18} \rightarrow GFP \rightarrow ICP0_{a.a.\ 105-488--\Delta---a.a\ 696-825}$ |
| HSV-2 0Δ4BD | Δ19-104, Δ695-810 | $ICP0_{a.a.\ 1-18} \rightarrow GFP \rightarrow ICP0_{a.a.\ 105-694--\Delta--a.a.\ 811-825}$ |
| HSV-2 0Δ254 | Δ19-825 | $ICP0_{a.a.\ 1-18} \rightarrow GFP - COOH$ |
| HSV-2 0Δ810 | Δ19-810 | $ICP0_{a.a.\ 1-18} \rightarrow GFP \rightarrow ICP0_{a.a.\ 811-825}$ |

GFP = green fluorescent protein

The RING finger region is about 87% conserved in amino acid homology between HSV-1 and HSV-2, and is referred to as conserved region 1. As such, the RING finger region of HSV-1 is referred to as RING-1 and occurs between amino acid 113 and 242 of the ICP0 protein. The RING finger region of HSV-2 is referred to as RING-2 and occurs between amino acid 123 and 252 of the ICP0 protein. Accordingly, the RING-1 and RING-2 regions overlap with the Phos1 region.

The nuclear localization signal (NLS) region is about 65% conserved in amino acid homology between HSV-1 and HSV-2, and is referred to as conserved region 2. As such, the NLS region of HSV-1 is referred to as NLS-1 and occurs between amino acid 453 and 531 of the ICP0 protein. The NLS region of HSV-2 is referred to as NLS-2 and occurs between amino acid 468 and 549 of the ICP0 protein. Accordingly, the NLS-1 and NLS-2 regions overlap with the Phos3 region.

The putative 4BD region is about 86% conserved in amino acid homology between HSV-1 and HSV-2, and is referred to as conserved region 3. As such, the 4BD region of HSV-1 is referred to as 4BD-1 and occurs between amino acid 604 and 765 of the ICP0 protein. The 4BD region of HSV-2 is referred to as 4BD-2 and occurs between amino acid 646 and 810 of the ICP0 protein. Accordingly, the 4BD-1 and 4BD-2 regions do not overlap with any of the Phos regions.

Additionally, HSV-2 0Δ254 encodes for a mutant ICP0 having a deletion between amino acids 19 to 825, and is avirulent and may be useful as a live virus for an immunogenic composition. HSV-2 0Δ810 encodes for a mutant ICP0 having a deletion between amino acids 19 to 810, and yields the desired attenuation and potential to function as a live HSV-2 vaccine strain. Likewise, a mutant HSV virus having one or more deletions in any one of the three conserved regions of ICP0 protein may yield a mutant virus with similar properties, which may be used as live, attenuated HSV vaccine strain. Data also shows that HSV-1 0⁻GFP encodes a truncated ICP0 protein that lacks amino acids 105 to 775 (86% of the protein) and which has the desired properties of a live HSV-1 vaccine strain (e.g., attenuated in disease-causing potential and protective against disease caused by wild-type HSV-1).

It has been found, as shown in the data provided herein, that a genetic mutation that produces an ICP0 protein with a mutation in any of these conserved regions can result in a HSV-2 virus that is avirulent and immunogenic. As such, one or more of the conserved regions of ICP0 can be mutated with substitutions, deletions, insertions, or combinations thereof in order to obtain an avirulent and immunogenic HSV-2 virus encoding the mutant ICP0. A mutation in any one of the three conserved regions of the ICP0 protein can render the virus: (1) interferon-sensitive, (2) avirulent in animals, and (3) still highly immunogenic as is shown by HSV-2 0ΔNLS and HSV-2 0Δ4BD. Mutations that remove all three of the conserved regions of the ICP0 protein as shown by HSV-2 0delta254 and HSV-2 0delta810 render the HSV-2 virus: (1) interferon-sensitive, (2) avirulent in animals, and (3) weakly immunogenic.

However, mutations in poorly conserved regions have been found to have little effect on the virulence of the HSV-2 virus. This is shown in HSV-2 0Δ104, which is missing amino acids 19-104 of ICP0, and yet replicates and kills animals similarly to the wild-type HSV-2. The comparison of ICP0 having a mutation in a conserved region compared to a non-conserved region are shown in Table 2 below, where a "+" indicates a conserved region is included in the wild-type or mutant ICP0 protein, and a "−" indicates a conserved region is deleted from the mutant ICP0 protein. Bolding is used to show that a conserved domain has been deleted from the ICP0 encoded by the mutant virus.

TABLE 2

| HSV-2 virus | Conserved domains | Produce disease in animals? |
|---|---|---|
| Wild-type HSV-2 | RING+, NLS+, 4BD+ | Yes |
| HSV-2 0Δ104 | RING+, NLS+, 4BD+ | Yes |
| HSV-2 0ΔRING | RING−, NLS+, 4BD+ | No |
| HSV-2 0ΔNLS | RING+, NLS−, 4BD+ | No |
| HSV-2 0ΔBD | RING+, NLS+, 4BD− | No |
| HSV-2 0Δ254 | RING−, NLS−, 4BD− | No |
| HSV-2 0Δ810 | RING−, NLS−, 4BD− | No |

For comparison, mutant HSV-1 viruses were prepared that had deletions in the conserved regions as shown in Table 3. Also, Table 4 shows that the mutant HSV-1 viruses with deletion in any one the conserved regions were not virulent. Accordingly, it is established that mutations within a conserved region of ICP0 can inhibit a mutant virus from being virulent.

TABLE 3

| Mutant HSV-1 virus | ICP0 protein encoded |
|---|---|
| Wild-type HSV-1 | ICP0$_{amino\ acids\ (a.a.)\ 1\text{-}775}$ |
| HSV-1 0ΔRING | ICP0$_{a.a.\ 1\text{-}104}$ → GFP → ICP0$_{a.a\ 220\text{-}775}$ |
| HSV-1 0ΔNLS | ICP0$_{a.a.\ 1\text{-}104}$ → GFP → ICP0$_{a.a\ 105\text{-}494\text{--}\Delta\text{---}a.a\ 512\text{-}775}$ |
| HSV-1 0Δ4BD | ICP0$_{a.a.\ 1\text{-}104}$ → GFP → ICP0$_{a.a\ 105\text{-}499\text{--}\Delta\text{--}a.a.\ 508\text{-}775}$ |
| HSV-1 0−GFP | ICP0$_{a.a.\ 1\text{-}104}$ → GFP |

TABLE 4

| Mutant HSV-1 virus | Conserved domains | Produce disease in animals? |
|---|---|---|
| Wild-type HSV-1 | RING+, NLS+, 4BD+ | Yes |
| HSV-1 0ΔRING | RING−, NLS+, 4BD+ | No |

TABLE 4-continued

| Mutant HSV-1 virus | Conserved domains | Produce disease in animals? |
|---|---|---|
| HSV-1 0ΔNLS | RING+, NLS−, 4BD+ | No |
| HSV-1 0ΔBD | RING+, NLS+, 4BD− | No |
| HSV-1 0−GFP | RING−, NLS−, 4BD− | No |

In view of the data, it has been found that HSV-2 viruses that encode mutant ICP0 proteins lacking any one, two, or three of the ICP0 conserved regions elicit protective immunity against herpetic diseases caused by wild-type HSV-2. Also, it has been determined that: HSV-2 0ΔNLS and HSV-2 0Δ4BD are lead candidates for an immunogenic composition; HSV-2 0ΔRING is another candidate for an immunogenic composition but may be less effective; and HSV-2 0Δ254 HSV-2 0Δ810 may also be candidates that are safe albeit possibly less effective compared to the RING, NLS, and 4BD mutations. These conserved regions may also be mutated in HSV-1 viral mutants for candidates for immunogenic compositions.

The homology between ICP0 proteins in HSV-1 strains and HSV-2 strains provides an indication that the mutations of ICP0 described in connection with HSV-1 can also be applied to HSV-2 and vice versa, as well as to other alpha-herpesviruses. As such, any herpesvirus can be mutated in substantially the same manner as the mutant HSV-1 and/or mutant HSV-2 as described herein. The mutation in the HSV-1 or HSV-2 gene that encodes ICP0 can include amino acid insertions, deletions, substitutions, and like mutations introduced at the Phos regions and/or the conserved regions.

With regard to the Phos regions, the mutations of HSV-2 can correlate with phosphorylation sites in HSV-2 ICP0 amino acids 518-531. For example, the mutation can be at the serine or threonine in the following: HSV-2 ICP0 at amino acid 518; HSV-2 ICP0 at amino acid 530; HSV-2 ICP0 at amino acid 530; and/or any of the 8 serines from amino acids 518-531 or HSV-2 ICP0.

Mutant HSV

In one embodiment, the present invention includes a mutant virus of any HSV (e.g., HSV-1 or HSV-2) encoding for a mutant ICP0. The mutant HSV encoding mutant ICP0 produces a mutant ICP0 that has a mutation in at least one phosphorylation region of the ICP0 protein or a mutation within at least one conserved region. The mutant HSV encoding mutant ICP0 protein can be used in vaccines, pharmaceutical compositions, and other compositions, such as those used in diagnostics or screening assays. Additionally, the present invention includes the methods of mutating the HSV encoding ICP0 and methods of manufacturing mutant HSV encoding for mutant ICP0 or having the mutant ICP0. Moreover, the present invention includes methods of using the mutant HSV encoding mutant ICP0 in the treatment and/or prevention of HSV infection, and in assays for studying HSV infection.

A mutant HSV virus encoding for a mutated ICP0 protein can be used in a therapeutic composition to inhibit HSV replication in sites that are common place for HSV replication. The animal studies have shown that the mutant ICP0 protein impairs replication of HSV in the eyes, and substantially no infectious HSV virus has been detected in the neurons of the animals infected with the mutant HSV virus in the initial stages of infection. Mice that have been infected with the mutant HSV virus that includes a mutated ICP0 protein visually look like uninfected mice. Thus, the studies, which are discussed in more detail herein, have shown that the mutant HSV virus that includes a mutated ICP0 protein is avirulent, apathogenic or exhibits reduced levels of viral replication in animals as well as being immunogenic. HSV ICP0-mutant viruses exhibit limited or reduced replication in animals, which is useful for immunogenic compositions.

A mutant HSV can be dominant-negative, and thereby inhibit the interaction of the mutant ICP0 with other proteins that normally interact with the ICP0 protein in HSV replication. That is, the expressed mutant ICP0 can block binding to another protein, such as a cellular protein or other HSV protein in the replication pathway. For example, the mutant ICP0 protein can inhibit binding with such other proteins in the replication cycle, thereby providing a dominant/negative characteristic. As such, the mutant ICP0 can inhibit other proteins, to which ICP0 typically associates, from performing normal replication functions because the mutant ICP0 protein inhibits normal function. As such, the mutant virus can be introduced into an infected site and/or potentially infected site and the dominant/negative characteristic can inhibit replication the wild type virus, if present at that site. Thus, the mutant ICP0 protein inhibits other proteins from functioning, which can be used as a treatment of prophylactic with respect to HSV infections or other disease states associated with HSV infection.

The mutant HSV virus encoding a mutant ICP0 can exhibit greatly reduced replication in neurons during the initial stages of the infection. A control HSV that is substantially devoid of expressing the ICP0 protein is still capable of replicating in neuronal cells; however, a genetic mutation to the encoded ICP0 protein inhibits replication in neuronal cells. As such, the mutant HSV can function as a type of dominant/negative because of significantly reduced replication in neuron cells. Also the mutant HSV can also reduce or inhibit blepharitis (eyelid disease), keratitis (corneal opacity), and latency.

Mutant alpha-herpesviruses may also be used that encode for a mutant ICP0 or ICP0-like protein. These mutant alpha-herpesviruses can be used substantially as the mutant HSV-1 and/or mutant HSV-2.

Immunogenic Compositions

In accordance with the discussions of mutant HSV-1 and/or mutant HSV-2, either the mutant HSV-1 and/or mutant HSV-1 as well as any mutant alpha-herpesvirus can be used in an immunogenic composition such as a vaccine. Methods of preparing vaccines to include a mutant virus are well established in the art of vaccines. References to HSV should be considered to also refer to any of the alpha-herpesviruses that encode an ICP0-like protein.

In one embodiment, the mutant HSV can be used in a vaccine or other composition to inhibit wild-type HSV replication, and thereby inhibit or prevent the diseases caused by HSV infections. Data for the mutant HSV viruses encoding for mutant ICP0 indicate that alterations of ICP0 at one or more of the phosphorylation regions or conserved regions inhibits HSV replication in comparison with wild-type HSV-1, while still being immunogenic. Also, the mutant HSV-1 encoding mutant ICP0 was shown to exhibit a reduced capacity to replicate in neurons.

In one embodiment, the mutant HSV encoding the mutant ICP0 protein can be introduced into an individual that has been infected or may become infected with a HSV virus. Thus, the mutant HSV can treat, limit, and/or prevent wild-type HSV infections as well as disease states caused by wild-type HSV. For example, mutant HSV-1 viruses can be used to prevent wild-type HSV-1 infections and mutant HSV-2 viruses can be used to prevent wild-type HSV-2 infections. Likewise, any mutant alpha-herpesvirus that encodes a mutant ICP0 protein can be used to prevent infection of animals with its corresponding wild-type alpha-herpesvirus.

A vaccine can be prepared which includes mutant HSV-1 and/or mutant HSV-2 with one or more excipients and/or adjuvants. The mutant HSV viral genome encoding for mutant ICP0 may be included in a vaccine. The vaccine can contain genetic material, such as a heterologous gene insert expressing the mutant protein. In such a case, the mutant ICP0 can be expressed in cells of a susceptible species immunized with the vaccine containing mutant HSV-1 and/or mutant HSV-2. Immunity against wild type HSV-1 and/or HSV-2 can thereby be conferred in a species and/or tissue normally susceptible to HSV-1 and/or HSV-2 infection. Also, a vaccine that contains a mutant HSV-1 and/or mutant HSV-2 may be taken by subjects who are already infected by HSV-1 and/or HSV-2 to impair or inhibit its replication and thereby impair or prevent recurrent outbreaks of herpetic disease.

The vaccine can be a pharmaceutical preparation as is standard in the art. The vaccine can be administrable subcutaneously, intra-muscularly, intra-dermally, epithelially, nasally, vaginally, or orally and can comprise excipient(s) suitable for the selected administration route. The pharmaceutical preparation can be capable of protecting a patient immunized therewith against infection or the consequences of infection by a corresponding wild-type virus.

Also, the present invention can include an assembly comprising a pharmaceutical for prophylaxis or for therapy as described herein in a container. The container can contain the mutant HSV-1 and/or mutant HSV-2. The container can be a pre-filled syringe or glass vial/ampoule with printed instructions on or accompanying the container concerning the administration of the pharmaceutical to a patient to prevent or treat conditions caused by infection with wild-type HSV-1 and/or HSV-2.

A vaccine or other pharmaceutical preparation containing the mutant HSV-1 and/or mutant HSV-2 as described can be prepared in accordance with methods well known in the art wherein the mutant HSV is combined in admixture with a suitable vehicle. Suitable vehicles include, for example, saline solutions, or other additives recognized in the art for use in compositions applied to prevent viral infections. Such vaccines will contain an effective amount of the mutant HSV as hereby provided and a suitable amount of vehicle in order to prepare a vaccine useful for effective administration to the host.

Dosage rates of the vaccine can be determined according to known methods. For example, dosage rate may be determined by measuring the optimum amount of antibodies directed against a mutant HSV resulting from administration of varying amounts of the mutant HSV in vaccine preparations. Suitable vehicles and their formulation are described in 'Remington's Pharmaceutical Sciences' (Mack Publishing Co, Easton, Pa., ed. A R Gennaro), by E W Martin, and by F Rola, which is incorporated herein by specific reference. Such compositions contain an effective amount of the mutant HSV-1 and/or mutant HSV-2 with a suitable amount of carrier vehicle in order to prepare therapeutically acceptable compositions suitable for effective administration to the host.

Vaccines can be prepared with excipients which are pharmaceutically acceptable and compatible with the active ingredient. Suitable excipients are, for example, water, saline, dextrose, glycerol, trehalose, or the like and combinations thereof. In addition, if desired, the vaccine may contain minor amounts of auxiliary substances such as other stabilizers and/or pH buffering agents, which enhance the stability and thus the effectiveness of the vaccine.

Vaccines may be configured to be administered parenterally, by injection, for example, subcutaneously, intraepithelially (with or without scarification). Additional formulations which are suitable for other modes of administration, such as oral, vaginal and nasal formulations are also provided. Oral formulations include such normally employed excipients as, for example, pharmaceutical grades of trehalose, mannitol, lactose, starch, magnesium stearate, sodium saccharine, cellulose, magnesium carbonate, and the like. The compositions may take the form of solutions, suspensions, tablets, pills, capsules sustained release formulations or powders.

Vaccines can be administered in a manner compatible with the dosage formulation, and in such amount as will be prophylactically effective. The quantity to be administered will have been predetermined from preclinical and clinical (phase I) studies to provide the optimum immunological response.

The vaccine may be given in a single dose schedule or in a multiple dose schedule, as needed or desired. A multiple dose schedule is one in which a primary course of vaccination with 1-3 separate doses elicits an immune response, and is followed by other doses given at subsequent time intervals that maintain, reinforce, and/or boost the immune response to HSV. For example, at 1-4 months for a second dose, and if needed, a subsequent dose(s) after several months. The dosage regimen will also, have been determined from preclinical and clinical studies as maintaining the optimum immunological response over time.

The vaccine including the mutant HSV-1 and/or mutant HSV-2 may be taken by subjects during primary or secondary infections with wild-type HSV to curtail the severity and duration of symptoms. The vaccine including mutant HSV-1 and/or mutant HSV-2 may also reduce the frequency and severity of recurrent herpetic disease. Single injection of mutant HSV encoding mutant ICP0 may provide life-long protection against recurrent outbreaks of the corresponding wild-type HSV virus. However, multiple administrations may be utilized. The vaccine of the present invention can improve treatment and prevention of HSV infections and other disease states related to HSV infection. The present invention may be applied to a subject during latent infection of HSV to impair or prevent recurrent herpetic disease, as well as reduce their rate of infectious HSV shedding. Thus, the vaccine can also reduce the relative risk that an HSV carrier will transmit the infection to other persons.

Additionally, the mutant HSV-1 and/or mutant HSV-2 can also be included in vaccines, as well as methods of treatment and/or prevention, to reduce or inhibit blepharitis (eyelid disease), keratitis (corneal opacity), and latency. Methods of treating and/or preventing blepharitis (eyelid disease), keratitis (corneal opacity), and latency can include providing the mutant HSV-1 and/or mutant HSV-2 to a subject.

Cell Having Mutant HSV or Mutant ICP0 Protein

The present invention also provides a cell having a mutant HSV and/or mutant ICP0. This can include cells that include genetic material that encodes for the production of the mutant HSV and/or mutant ICP0. The cell can be any type of cell; however, it can be preferable for the cell to be a cell type that is infected with wild type HSV-1 and/or HSV-2. Also, the cell can be a cell type for use in preparing the mutant HSV-1 and/or mutant HSV-2. Such cells are well known in the art. For example, the cell can be a host cell, such as a recombinant eukaryotic cell line containing the gene(s) encoding mutant HSV-1 and/or mutant HSV-2. A cell which includes or provides the mutant HSV-1 and/or mutant HSV-2 can be used to grow the mutant HSV-1 and/or mutant HSV-2 in tissue culture.

In one embodiment, the cell having mutant HSV-1 and/or mutant HSV-2 or genetic material encoding the same can be a Vero cell or L7 cell. Vero cells, an African green monkey kidney cell line, can be obtained from the American Type Cell Culture (ATCC, Manassas, Va.) and propagated in Dulbecco's modified Eagle's medium (DMEM) supplemented with 10% fetal bovine serum (FBS) as described previously in the art. Vero cells can be stably transformed with the gene(a) encoding for mutant HSV-1 and/or mutant ICP0, and passaged as described in the art.

Screening Assays

In one embodiment, the mutant HSV-1 and/or the mutant HSV-2 can be used in screening and/or developing therapeutic agents that treat and/or prevent HSV-1 infection or HSV-2 infection as well as other disease states associated with HSV. An example of screening can include: providing a first and second cell of the same cell type that is capable of being infected with HSV; introducing a mutant HSV encoding for a mutant ICP0 into the first cell, introducing a corresponding wild type HSV encoding wild type ICP0 into the second cell; introducing an agent to be screened for activity that inhibits replication of the wild type HSV into the second cell; and comparing the replication of the mutant HSV and the wild type HSV, wherein the replication of mutant HSV and the wild type HSV being similar is an indication that the agent is an active agent that inhibits replication of wild type HSV. Additionally, studies can be conducted to determine avirulence and/or immunogenicity of the mutant HSV. Also, the mutant HSV-1 and/or the mutant HSV-2 can be used in other screening techniques.

Also, biological studies with the mutant HSV and/or mutant ICP0 can be used in screening and/or developing active agents that can inhibit phosphorylation of ICP0 and/or can be used as anti-HSV drugs. For example, drug screens can be established to identify small molecules or other active agents that inhibit the action of viral and cellular kinases that inhibit phosphorylation at these sites on the ICP0 protein. Inhibition of ICP0 phosphorylation can inhibit HSV replication, and thereby inhibit HSV infections.

The screening assays can be used with various compounds from a library of compounds. The library of compounds can be screened so as to determine which compounds are effective in inhibiting phosphorylation of ICP0. Also, the library of compounds can be screened so as to determine which compounds are effective in inhibiting replication of HSV-1.

Polynucleotide/Polypeptide Sequences

In one embodiment, the present invention includes a polynucleotide sequence, such as a plasmid or gene or RNA, which encodes for the production of mutant HSV and/or mutant ICP0. Also, the present invention can include a polypeptide sequence of a mutant ICP0. Examples of such polynucleotide and polypeptide sequences related to mutant HSV and/or mutant ICP0 are included in the Sequence Listing.

EXEMPLARY EMBODIMENTS

The mutant herpesviruses described herein as well as the mutant gene encoding for a mutant ICP0 can be useful in therapeutic methods, diagnostic methods, as well as in research science. As such, embodiments of inventions related to the mutant herpesvirus are provided.

In one embodiment, the present invention can include a mutant herpesvirus having a mutated gene that encodes a mutant infected cell protein 0 (ICP0) that is altered in one or more regions of ICP0 that are substantially conserved between two or more herpesviruses, wherein the mutant herpesvirus is substantially avirulent and immunogenic. The mutation in ICP0 can be an amino acid substitution, insertion, deletion, or combination thereof in the encoded mutant.

In one embodiment, the mutant ICP0 can be altered in one or more regions that are substantially conserved between herpes simplex virus 1 (HSV-1) and herpes simplex virus 2 (HSV-2). Also, the mutant ICP0 can be altered in one or more regions that are substantially conserved between herpes simplex virus 1 (HSV-1) and/or herpes simplex virus 2 (HSV-2) and an alpha-herpesvirus.

In one embodiment, the two or more herpesviruses can be selected from herpes simplex virus 1 (HSV-1), herpes simplex virus 2 (HSV-2), and/or an alpha-herpesvirus. The alpha-herpesvirus can be selected from bovine herpesviruses 1 or 5 (BHV-1 or BHV-5), equid herpesviruses 1, 4, or 9 (EHV-1, EHV-4, or EHV-9), suid herpesvirus 1 or pseudorabiesvirus (PRV), varicella zoster virus (VZV), canid herpesvirus 1 (CHV-1), felid herpesvirus 1 (FHV-1), macropodid herpesvirus 1 (MHV-1), cercopithecine herpesviruses 2 or 9 (CpHV-2 or CpHV-9), macacine herpesvirus 1 which is commonly known as the herpes B virus, or papiine herpesvirus 2 (PHV-2), or the like.

In one embodiment, the mutation in the encoded mutant ICP0 can be in one or more conserved regions selected from a RING finger region, a nuclear localization signal (NLS) region, or a putative infected cell protein 4 binding domain (4BD) region. When the mutation is in the RING finger region of ICP0, it can be between: amino acids corresponding to about amino acid 113 to about amino acid 242 of HSV-1 ICP0; or amino acids corresponding to about amino acid 123 to about amino acid 252 of HSV-2 ICP0. When the mutation is in the NLS region of ICP0, it can be between: amino acids corresponding to about amino acid 453 to about amino acid 531 of HSV-1 ICP0; or amino acids corresponding to about amino acid 468 to about amino acid 549 of HSV-2 ICP0. When the mutation is in the putative 4BD region of ICP0, it can be between: amino acids corresponding to about amino acid 604 to about amino acid 765 of HSV-1 ICP0; or amino acids corresponding to about amino acid 646 to about amino acid 810 of HSV-2 ICP0.

In one embodiment, the mutation can inhibit phosphorylation of one or more amino acids in one or more of the conserved regions. The region can be one of the conserved Phos regions.

In one embodiment, the mutant herpesvirus can be derived from a herpes simplex virus type 1 (HSV-1). Alternatively, the mutant herpesvirus can be derived from a herpes simplex virus type 2 (HSV-2). In yet another alternative, the mutant herpesvirus can be an alpha herpesvirus.

In one embodiment, an immunogenic composition can include a mutant herpesvirus.

In one embodiment, the present invention can include an immunogenic composition that has a pharmaceutically acceptable carrier and a mutant herpesvirus gene. The mutant herpesvirus gene can encode a mutant infected cell protein 0 (ICP0) that is altered in one or more regions of ICP0 that are substantially conserved between two or more herpesviruses, wherein the mutant herpesvirus is substantially avirulent and immunogenic. Optionally, the gene can be located within a mutant herpesvirus. Optionally, the immunogenic composition can include a mutant herpesvirus that is derived from a herpes simplex virus type 1 (HSV-1) having the mutant herpesvirus gene and/or a mutant herpesvirus that is derived from a herpes simplex virus type 2 (HSV-2) having the mutant herpesvirus gene. Pharmaceutically acceptable carries are well known in the art.

In one embodiment, the present invention can include a method of immunizing a subject. Such a method can include administering to the subject an immunogenic composition having a mutant herpesvirus gene that encodes a mutant infected cell protein 0 (ICP0) that is altered in one or more regions of ICP0 that are substantially conserved between two or more herpesviruses, wherein the mutant herpesvirus is substantially avirulent and immunogenic. Optionally, the gene can be located within a mutant herpesvirus. The mutation can be sufficient to impair replication of the herpesvirus. Also, the mutation can reduce clinical severity of a herpesvirus infection and/or herpesvirus-mediated diseases.

In one embodiment, the immunogenic composition can administered to the subject in a therapeutically effective amount to induce an immunological response to the mutant herpesvirus. The immunological response can be sufficient to provide immunity to a corresponding wild-type herpesvirus. It is possible that the immunity can be for life of the subject, or possibly for a limited number of years.

In the instance that immunity may not be for life of the subject, the immunization method can include administering a booster dose of an immunogenic composition having a mutant herpesvirus gene that encodes a mutant infected cell protein 0 (ICP0) that is altered in one or more regions of ICP0 that are substantially conserved between two or more herpesviruses, wherein the mutant herpesvirus is substantially avirulent and immunogenic.

The immunogenic composition can be administered in a method for treating, inhibiting, and/or preventing a herpesvirus infection. For example, the immunogenic composition can be administered for a method of treating, inhibiting, and/or preventing genital herpes, cold sores, or any other animal disease or condition caused by an alpha-herpesvirus.

In one embodiment, the mutant herpesvirus can have a mutation in a gene encoding for a mutant ICP0 that has at least one phosphorylation site involved in replication in order to inhibit phosphorylation of the site. The inhibition of phosphorylation can prohibit or impair replication of the herpesvirus. Also, the inhibition of phosphorylation can reduce clinical severity of a herpesvirus infection and/or herpesvirus-mediated diseases.

In one embodiment, a mutant herpesvirus as described herein can include the mutant ICP0 protein. Such a mutant virus can be obtained from a cell infected with a mutant herpesvirus that encodes for such a mutant ICP0. The mutant herpesvirus having the mutant ICP0 protein can be useful in diagnostics and research science as well as in immunogenic compositions.

In one embodiment, the invention can include a mutant gene encoding for a mutant ICP0.

In one embodiment, the invention can include a mutant ICP0 protein.

In one embodiment, the mutant herpesvirus, mutant gene encoding for mutant ICP0, or a mutant ICP0 protein can be used in diagnostic assays, screening assays, or other assays of research science related to herpesviruses. The mutant herpesvirus, mutant gene, or mutant ICP0 can be used in screening and/or developing anti-herpesvirus therapeutic agents. Such therapeutic agents can be specific for a selected herpesvirus, such as HSV-1 or HSV-2. A therapeutic agent can interact with a conserved region so that the conserved region does not participate or is inhibited from participating in a normal biological function.

In one embodiment, the present invention can include a method of mutating a herpesvirus. Such a method can include mutating a gene that encodes for ICP0, and forming the mutant virus to have the mutated gene encoding for mutant ICP0. The gene mutation can be within the DNA coding sequence for at least one region of ICP0 that is substantially conserved between herpes simplex virus 1 (HSV-1) and herpes simplex virus 2 (HSV-2), or with other alpha-herpesviruses. The mutant herpesvirus can be substantially avirulent and immunogenic.

In one embodiment, the present invention can include preparing an immunogenic composition having a mutant herpesvirus encoding for a mutant ICP0 or having a mutant herpesvirus gene encoding for a mutant ICP0. The method can include combining a therapeutically acceptable carrier with the mutant herpesvirus and/or the mutant herpesvirus gene that encodes for mutant ICP0.

In one embodiment, the present invention can be a mutant alpha-herpesvirus that encodes for a mutant ICP0 or mutant ICP0-like protein such that the mutant alpha-herpesvirus is substantially avirulent and immunogenic. The mutant alpha-herpesvirus can encode for a mutant ICP0 homolog that is altered in the equivalent of HSV-1 and HSV-2 ICP0s conserved RING finger region, NLS region, or 4BD region, or any combination thereof.

In one embodiment, a mutant herpesvirus encodes for a mutant ICP0 that has a mutation in one or more amino acids corresponding with HSV-2 ICP0 between amino acid 19 and amino acid 810 such that the mutant virus is avirulent and immunogenic. Such a mutation can be a substitution, insertion, deletion, or combination thereof, which alters the NLS region, RING finger region, and/or putative 4BD region of ICP0.

In one embodiment, the present invention is a gene that encodes for a mutant ICP0 and/or an actual mutant ICP0 protein having one or more amino acids mutated (e.g., deleted, inserted, or substitution) between amino acids 19 and 810. This mutant gene or mutant ICP0 can be included in a mutant herpesvirus as well as within an immunogenic composition. Preferably, the mutation is a deletion between amino acids 19 and 810.

In one embodiment, the present invention is a gene that encodes for a mutant ICP0 and/or an actual mutant ICP0 protein having one or more amino acids mutated (e.g., deleted, inserted, or substitution) between amino acids 105 and 775. This mutant gene or mutant ICP0 can be included in a mutant herpesvirus as well as within an immunogenic composition. Preferably, the mutation is a deletion between amino acids 105 and 775.

EXAMPLES

Example 1

To identify the sites on ICP0 that are phosphorylated, μLC-MS/MS analysis was performed on ICP0 partially purified from HSV-1-infected cells. ICP0 synthesized after removal of CHX block was immunoprecipitated from extracts of $8 \times 10^6$ cells and separated by standard SDS-PAGE. ICP0 was digested with trypsin and chymotrypsin in gel and subjected to μLC-MS/MS analysis.

FIG. 1A shows the 775 amino acids of ICP0 and the location of its major functional domains. One region of ICP0 phosphorylation is indicated by bars below its structure. FIG. 1B shows the location of putative phosphorylation sites (4 in total) in region III and probable cellular kinases that target each site. The codon numbers of the putatively phosphorylated serine (S) and threonine (T) residues are listed beneath the peptide sequence in each region. To the right of each S or T are listed the cellular kinases that most likely phosphorylate each residue, as determined by computer-based modeling with NetPhos2.0, ScanProsite, and MacVector 7.1.1. Kinases include calmodulin kinase II (CaM II), protein kinase A (PKA), cyclin-dependent kinase 1 (cdk-1) and 2, casein kinase I (CKI), casein kinase II (CKII), p70S6K kinase, protein kinase G (PKG), and protein kinase C (PKC). FIG. 1C shows ICP0 phosphorylation site mutant Phos3 contains mutations. Serines and threonine in this region have been mutated to alanine at S508, S514, S517, and T518.

Mutations in Phos3 overlap the nuclear localization signal of ICP0 (FIG. 1A), whereas mutations in Phos1 and Phos2 are in a large proline-rich region of ICP0 that is important for its transactivating activity (FIG. 1A). Thus, Phos3 mutations may control the nuclear import and/or accumulation of nuclear ICP0 (Table 5), especially in neurons. Furthermore, HSV Phos3 replication is sensitive to the effects of interferon-beta in cell culture, which also likely influences its growth in vivo. Mutations in Phos1 have been shown to impair the E3 Ub ligase, ND10 disrupting, and transactivating activities (Table 5). Mutated residues in Phos2 differentially affect the staining of ND10-associated proteins (Table 5). Alteration in these activities of ICP0 may well contribute to the in vivo phenotypes observed with Phos1 and 2.

TABLE 5

Properties of ICP0

| Form of ICP0 | Transient Transfection Assays | | | | virus Impaired Replication |
|---|---|---|---|---|---|
| | Subcellular Localization | E3 Ub Ligase Activity | Dissociation of ND10 Proteins | Transactivating activity | |
| WT ICP0 | Nuclear | Yes | Yes | +++ | No |
| Phos1 | Nuclear | No | Yes & No | + | Yes & w/ IFN |
| Phos2 | Nuclear | Yes | Yes & No | +++ | No |
| Phos3 | Nuclear & Cytoplasmic | Yes | Yes | ++ | Only w/ IFN |

*IFN = interferon-β

Phosphorylation is a universal post-translational modification that alters the activities of many viral regulatory proteins. The mutation on the phosphorylation sites in ICP0 may decrease ICP0's transactivating activity, and thereby impair or inhibit the replication of HSV-1 and/or the clinical severity of HSV-1-mediated diseases.

Example 2

To determine the effects of these phosphorylation site mutations on acute infection, latency, and reactivation in vivo, mice were ocularly infected with wild-type HSV-1, the HSV-1 Phos mutants, and their marker-rescued counterparts, and viral replication was monitored by plaque assays.
Experimental Design The purpose of this study is to understand the impact the mutation of Phos1, Phos2, and Phos3 regions have on HSV-1 acute replication, pathogenesis, latency, and reactivation. The mouse model of HSV-1 latency was used to determine the relative in vivo replication efficiencies for the Phos mutants and their marker-rescuants (MRs) compared to an ICP0 null mutant (HSV-1 7134) and a wild-type strain (HSV-1 KOS). For each viral group, mice were ocularly infected with 1-2× $10^5$ PFU (plaque forming unit) per eye after corneal scarification. On days 1, 3, 5, 7, and 9 post-infection (p.i.), mice from each group were sacrificed, and eye swabs and trigeminal ganglia (TG) were collected. Samples were titered either on Vero or L7 (ICP0-expressing Vero cells) monolayers, and the PFUs/sample were determined. Pathogenicity scores for each viral group were taken on day 9 or 10 p.i. On days 28-30 p.i., TG were removed, cut into 8 pieces, and co-cultured on Vero cell monolayers. Media was assayed daily for the presence of infectious virus.

Ocular Replication

Figure 2A:
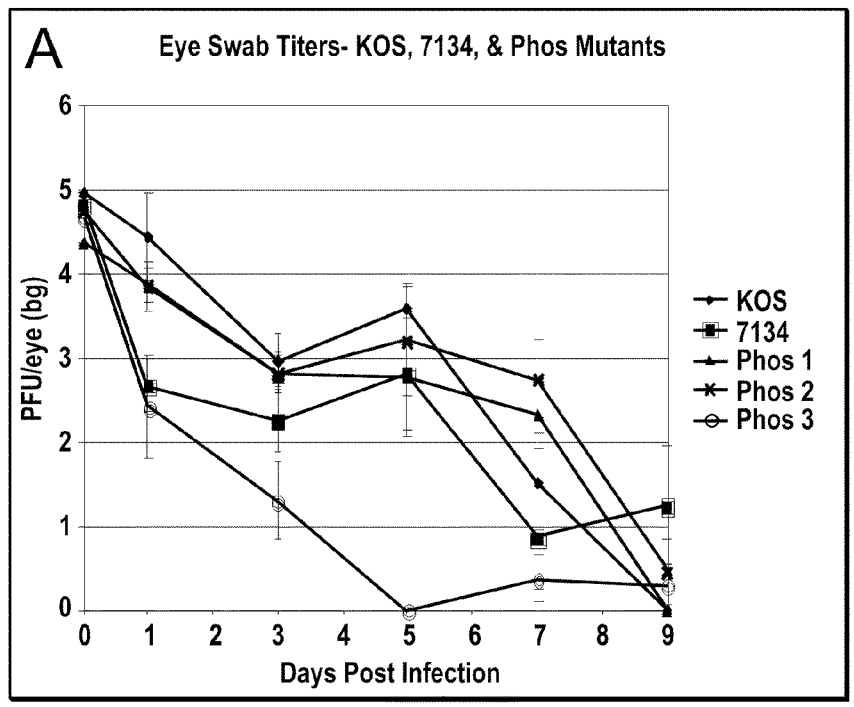
FIGS. 2A-2B include graphs that illustrate eye swab titers of wild-type (HSV-1 KOS), ICP0 null mutant (HSV-1 7134), phosphorylation site mutants (HSV-1 Phos1, HSV-1 Phos2, and HSV-1 Phos3), and their marker-rescue (MR) viruses during acute infection of mice.
Figure 2B:
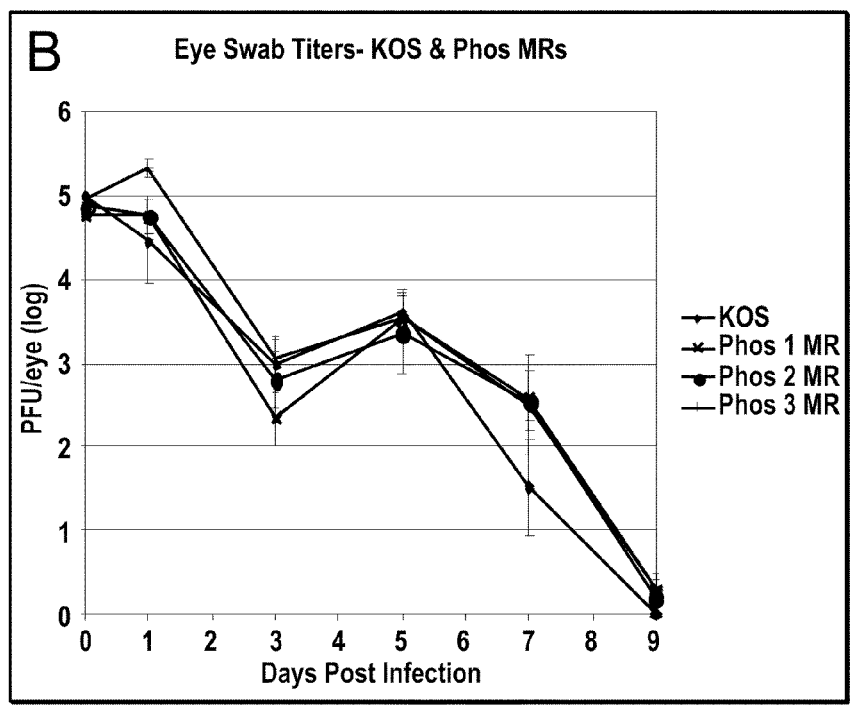

To determine peripheral replication efficiencies of the HSV-1 Phos mutants, acute eye swab samples were taken. HSV-1 KOS and HSV-1 7134 were included as controls in these studies. FIGS. 2A-2B show eye swab titers of wild-type (HSV-1 KOS), ICP0 null mutant (HSV-1 7134), phosphorylation site mutants (FIG. 2A), and their marker-rescue (MR) viruses (FIG. 2B) during acute infection of mice. For each viral group, seventeen female CD-1 mice were infected in both eyes after corneal scarification. On days 1, 3, 5, 7, and 9 p.i., eyes were swabbed as described in experimental design. KOS and marker-rescue viruses were tittered on Vero cells, and HSV-1 7134 and the phosphorylation site mutants were titered on L7 cell monolayers. Results shown are logarithmic means, with the error bars indicating the standard error of the mean. The experiment was performed simultaneously for all groups, but the results are separated for ease of interpretation.

The replication of HSV-1 Phos1 was slightly reduced relative to HSV-1 KOS on days 1 and 5 p.i., with the greatest difference observed on day 5 (7-fold reduction) (FIG. 2A). The replication of HSV-1 Phos2 was similar to HSV-1 KOS on all days tested (FIG. 2A). Of all the mutants, HSV-1 Phos3 showed the greatest reduction in viral replication compared to HSV-1 KOS. Days 1 and 3 showed reduction of approximately 100-fold and 50-fold, respectively. On day 5, no infectious HSV-1 Phos3 virus was detected (a ~4100-fold decrease), which was followed by a 15-fold reduction on day 7 (FIG. 2A). Notably, the replication of HSV-1 Phos3 was more impaired than HSV-1 7134. As expected, the marker-rescuants showed replication that was similar to HSV-1 KOS (FIG. 2B). It was concluded that mutations in Phos1 and 3 ICP0 protein may have mutated amino acid sites in the ICP0 protein that may be required for efficient viral replication in eyes, with HSV-1 Phos3 showing the greatest impairment of the HSV-1 Phos mutants.

Relative to wild-type virus, eye titers of HSV-1 Phos1 and HSV-1 Phos3 were reduced as much as 7- and 4100-fold, respectively, on days 1-9 post-infection. HSV-1 Phos2 titers were similar to wild-type virus. Thus, HSV-1 Phos3 may effectively impair HSV-1 peripheral replication.

Trigeminal Ganglia (TG) Replication

Figure 3A:
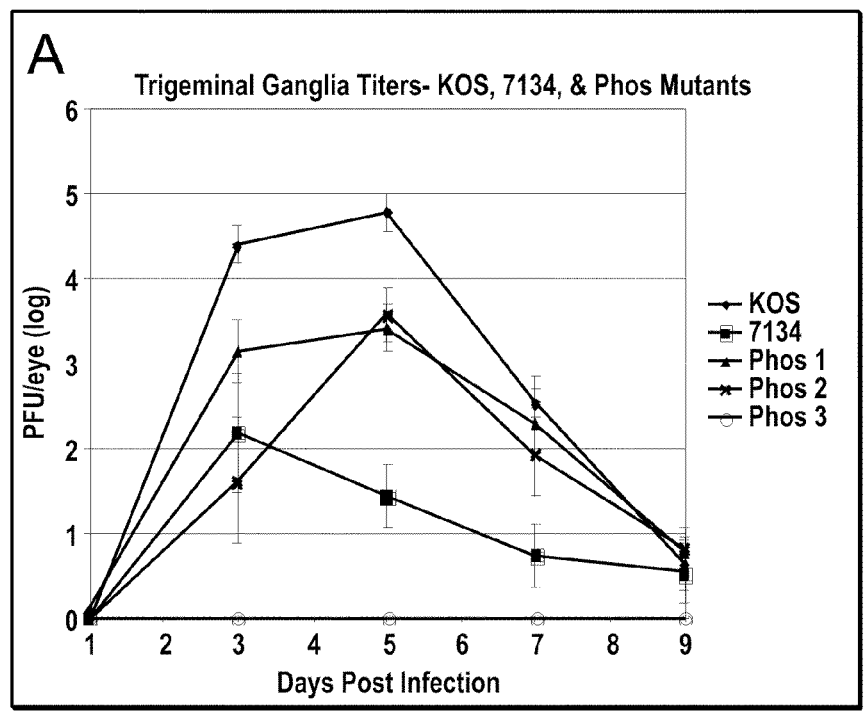
FIGS. 3A-3B include graphs that illustrate trigeminal ganglia (TG) titers of wild-type (HSV-1 KOS), ICP0 null mutant (HSV-1 7134), phosphorylation site mutants (Phos1, 2, and 3), and their marker-rescue (MR) viruses during acute infection of mice.
Figure 3B:
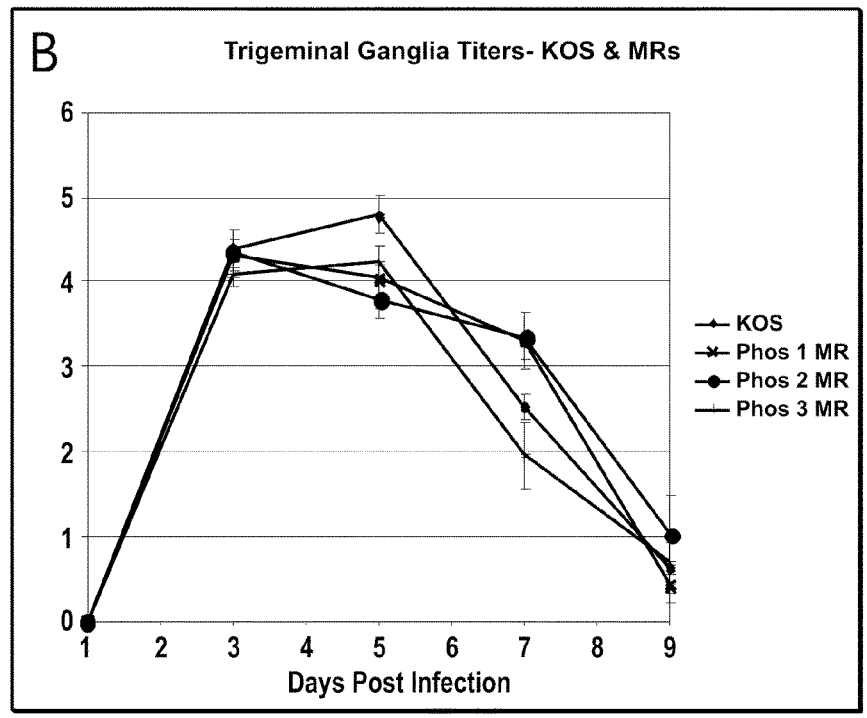

To note differences in viral replication in sensory neurons, TG samples were collected and titered. FIGS. 3A-3B show trigeminal ganglia (TG) titers of wild-type (HSV-1 KOS), ICP0 null mutant (HSV-1 7134), phosphorylation site mutants (FIG. 3A), and their marker-rescue (MR) viruses (FIG. 3B) during acute infection of mice. For each viral group, seventeen female CD-1 mice were infected in both eyes after corneal scarification. On days 1, 3, 5, 7, and 9 p.i., TG were collected and processed as described in experimental design. HSV-1 KOS and marker-rescue viruses were tittered on Vero cells, and HSV-1 7134 and the mutant HSV-1 Phos1, HSV-1 Phos2, and HSV-1 Phos3 were tittered on L7 cell monolayers. Results shown are logarithmic mans, with the error bars indicating the standard error of the mean. The experiment was performed simultaneously for all groups, but the results are separated for ease of interpretation.

TG titers showed similar trends to the eye swab titers. On days 3 and 5 p.i., HSV-1 Phos1 replication was diminished 20- and 25-fold, respectively (FIG. 3A). For HSV-1 Phos2, viral titers were reduced 615-fold (day 3 p.i.) and 20-fold (day 5 p.i.) (FIG. 3A). Remarkably, no HSV-1 Phos3 infectious virus was detected in TG during the course of infection, unlike the ICP0 null mutant HSV-1 7134 (FIG. 3A). Marker-rescue viruses replicated at levels comparable to HSV-1 KOS (FIG. 3B). The results indicate that HSV-1 Phos1 and HSV-1 Phos2 mutations impaired acute viral replication in the TG, whereas HSV-1 Phos3 mutations completely inhibited viral replication.

Trigeminal ganglia (TG) titers of HSV-1 Phos1 and HSV-1 Phos2 were reduced as much as 25- and 615-fold, respectively, on days 1-9 post-infection, whereas no infectious virus was detected in acute TG of HSV-1 Phos3-infected mice. Thus, HSV-1 Phos3 may effectively impair HSV-1 replication in sensory neurons.

Pathogenesis

Figure 4:
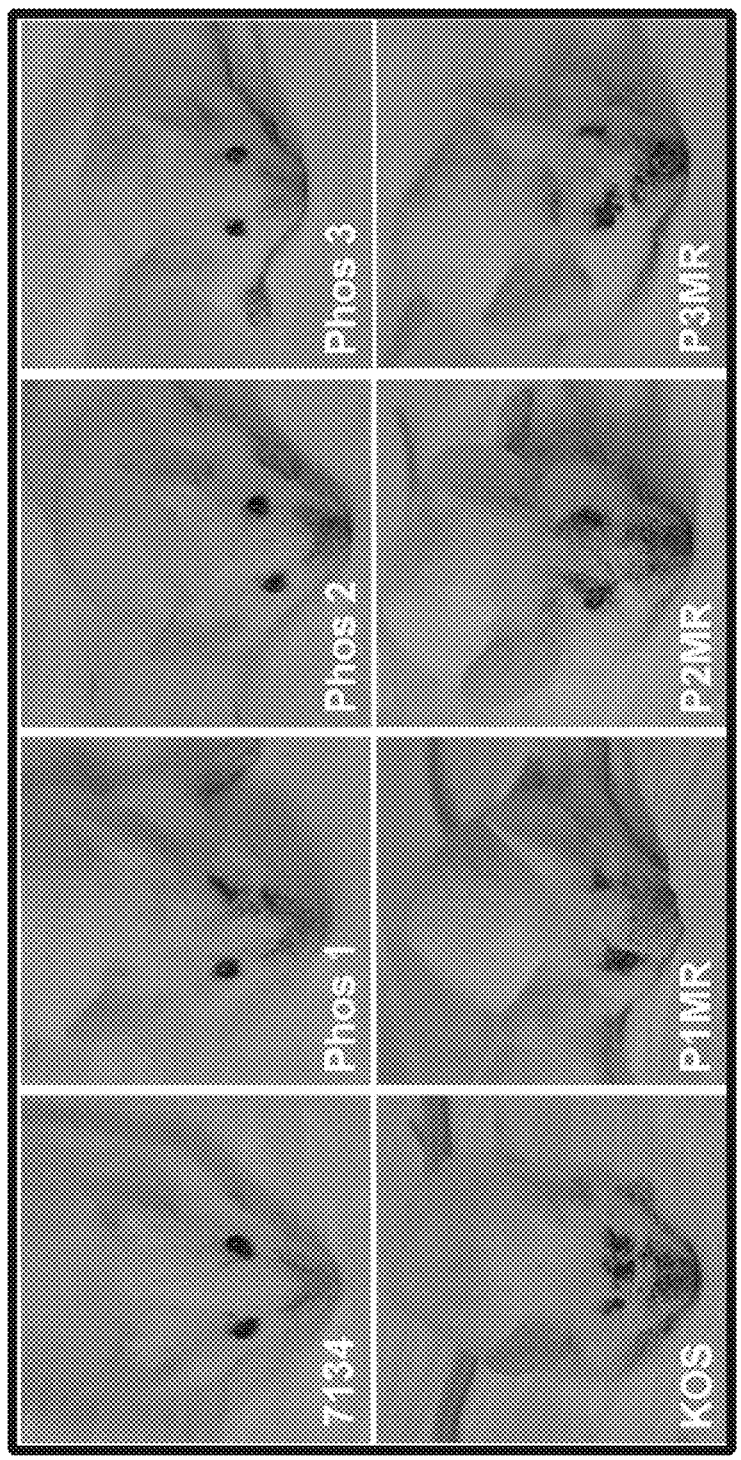
FIG. 4 includes images of infected mice (9 days p.i.) of wild-type (KOS), ICP0 null mutant (7134), phosphorylation site mutants (HSV-1 Phos1, HSV-1 Phos2, and HSV-1 Phos3), and their marker-rescue (MR) viruses.

To establish whether acute replication altered viral pathogenesis, clinical pathology scores were taken on either day 9 or 10 p.i. The physiological severity of infection was ranked on a scale of 0-4 for each viral group, where a score of zero indicates no apparent infection, and a score of 4 indicates complete removal of the hair from between the eyes due to scratching. FIG. 4 shows various images of infected mice (9 days p.i.) of wild-type (HSV-1 KOS), ICP0-null mutant (HSV-1 7134), phosphorylation site mutants (HSV-1 Phos1, HSV-1 Phos2, HSV-1 Phos3), and their marker-rescue (MR) viruses. For each group, mice were infected in both eyes with virus after corneal scarification.

Table 6 shows average pathogenicity scores of wild-type (HSV-1 KOS), ICP0-null mutant (HSV-1 7134), phosphorylation site mutants (HSV-1 Phos1, HSV-1 Phos2, HSV-1 Phos3), and their marker-rescue (MR) viruses. For each group, mice were infected in both eyes with virus after corneal scarification.

Two of the three Phos mutants showed reduced pathogenicity on days 9 and 10 p.i. (FIG. 4 and Table 6). Notably, HSV-1 Phos3-infected mice displayed no signs of disease, similar to HSV-1 7134 (FIG. 4 and Table 6). Marker-rescue viruses had pathologies comparable to or slightly greater than HSV-1 KOS (FIG. 4 and Table 6). Thus, HSV-1 Phos3 may effectively treat, limit or prevent HSV-1 infection.

In Table 6, average pathogenicity scores of wild-type (HSV-1 KOS), ICP0-null mutant (HSV-1 7134), phosphorylation site mutants (HSV-1 Phos1, HSV-1 Phos2, HSV-1 Phos3), and their marker-rescue (MR) viruses.

TABLE 6

|  | KOS | 7134 | Phos 1 | Phos 1 MR | Phos 2 | Phos 2 MR | Phos 3 | Phos 3 MR | Sample size per group |
|---|---|---|---|---|---|---|---|---|---|
| Expt 1 t = 9 d.p.i. | $2.67 \pm 0.41^a$ | $0.2 \pm 0.22$ | $1.2 \pm 0.42$ | $2.25 \pm 0.55$ | $1 \pm 0$ | $2.67 \pm 0.41$ | $0 \pm 0$ | $2.5 \pm 0.33$ | n = 3-5 |
| Expt 2 t = 10 d.p.i. | $1.38 \pm 0.30$ | N.D. | $0.6 \pm 0.16$ | $2.16 \pm 0.26$ | $1 \pm 0.53$ | $2.25 \pm 0.37$ | $0 \pm 0$ | $1.31 \pm 0.21$ | n = 13-16 |

Reactivation

Figure 5A:
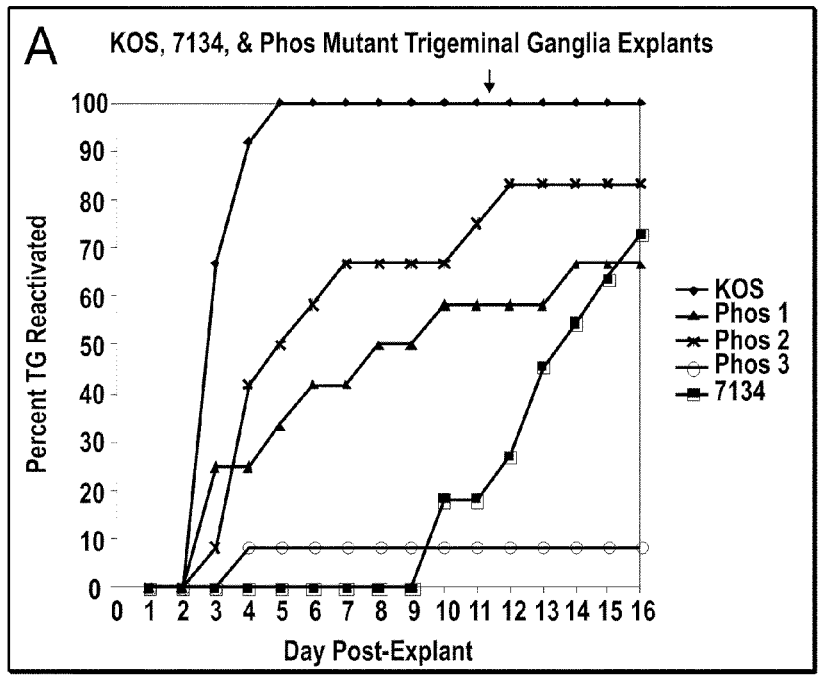
FIGS. 5A-5B include graphs that illustrate reactivation efficiency of wild-type (HSV-1 KOS), ICP0-nul mutant (HSV-1 7134), phosphorylation site mutants (HSV-1 Phos1, HSV-1 Phos2, and HSV-1 Phos3), and their marker-rescue (MR) viruses from TG explants.
Figure 5B:
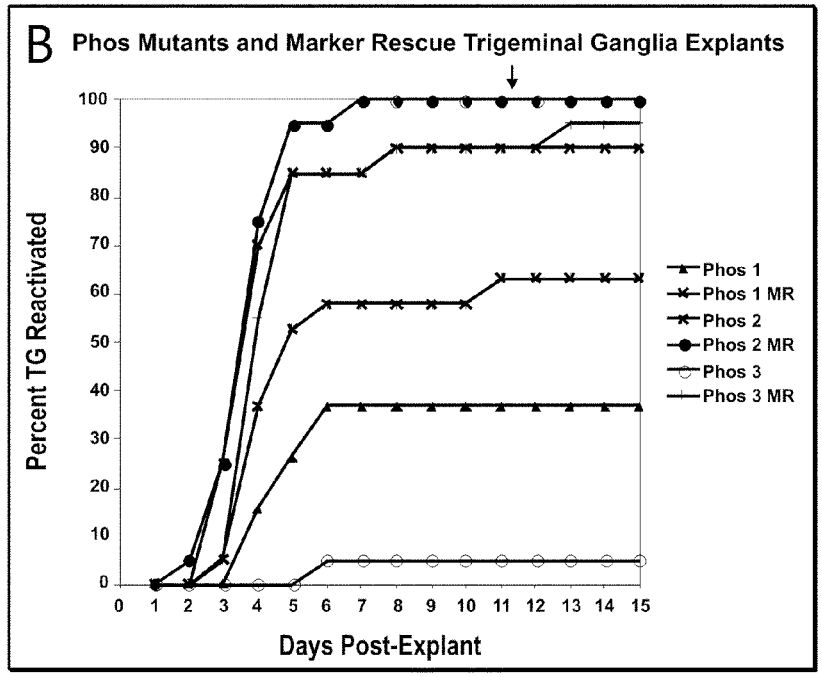

To ascertain the efficiencies of reactivation of the viral groups, explant co-cultivations on latently infected TG (28-30 days p.i.) were performed. FIGS. 5A-5B show reactivation efficiencies of wild-type (HSV-1 KOS), ICP0-null mutant (HSV-1 7134), phosphorylation site mutants (HSV-1 Phos1, HSV-1 Phos2, HSV-1 Phos3), and their marker-rescue (MR) viruses from TG explants. FIG. A shows HSV-1 KOS, HSV-1 7134, and phosphorylation site mutants (HSV-1 Phos1, HSV-1 Phos2, HSV-1 Phos3). FIG. B shows phosphorylation site mutants (HSV-1 Phos1, HSV-1 Phos2, HSV-1 Phos3) and marker-rescue viruses. The arrows at the top of both graphs indicate that after day 11, samples were heat shocked at 43° C. for 3 hours. For each viral group, mice were infected in both eyes after corneal scarification. On day 28-30 p.i., TGs were collected as described in experimental design. Culture medium was assayed daily for the presence of infectious virus. Each time point represents the cumulative percentage of reactivating samples. The figure shows two independent experiments.

In the initial study, rates of reactivation of the Phos mutants (HSV-1 Phos1, HSV-1 Phos2, HSV-1 Phos3) were compared to HSV-1 KOS and HSV-1 7134. HSV-1 KOS began to reactivate on day 3 post-explant (p.e.) at 66% and reached 100% reactivation by day 5 p.e. (FIG. 5A). HSV-1 Phos1 and HSV-1 Phos2 showed steady reactivation throughout the study, achieving 66% and 83%, on days 14 p.e. and 12 p.e., respectively (FIG. 5A). HSV-1 Phos3 reactivation peaked at day 4 p.e., maintaining a reactivation efficiency of 8% (FIG. 5A). HSV-1 7134 started to reactivate on day 10 p.e., reaching its highest levels (73%) on day 16 p.e. (FIG. 5A). In a second study, the reactivation efficiencies of the Phos mutants (HSV-1 Phos1, HSV-1 Phos2, HSV-1 Phos3) relative to their rescuants were examined. The marker-rescue viruses behaved as expected, rapidly reactivating from days 2-5 p.e., eventually reaching efficiencies of 85-95% by day 5 p.e. (FIG. 5B). In contrast, HSV-1 Phos1 reached a peak efficiency of 37% by day 6 p.e.; HSV-1 Phos2 was at 58% by day 6 p.e., reaching a peak of 63% by day 11 p.e.; and HSV-1 Phos3 reactivated at 5% on day 6 p.e., and remained so through day 15 p.e. (FIG. 5B). These reactivation studies showed that the frequencies and kinetics of reactivation were altered for the HSV-1 Phos mutants, with HSV-1 Phos3 showing the greatest deficiency, followed by HSV-1 Phos1, and finally HSV-1 Phos2. Thus, HSV-1 Phos3 may effectively impair or prevent HSV-1 reactivation.

DISCUSSION

In this study, it is shown that three ICP0 phosphorylation site mutant viruses are impaired for replication and reactivation in vivo. Of the viral mutants tested, mutations in the Phos3 region of ICP0 had the greatest effect on all phases of the HSV-1 life-cycle that were examined in vivo. In contrast to the ICP0 null mutant HSV-1 7134, HSV-1 Phos3 did not replicate in neurons of the TG during acute infection on days 1-9 p.i. Thus, the sites mutated in the Phos3 region of ICP0 may be required for replication in TG during the initial stage of HSV-1 infection. This inhibition resulted in no visible signs of viral pathogenesis and an impaired reactivation phenotype. HSV-1 Phos1 also affected viral replication and pathogenesis, although its defects were not as pronounced as those of HSV-1 Phos3. HSV-1 Phos2 was the least attenuated mutant of the three viruses tested. Notably, mutations in HSV-1 Phos2 did not affect ocular replication. Thus, the phosphorylation sites in the Phos2 region of ICP0 may not be necessary to ICP0 function and HSV-1 replication in eyes.

Previous reports have shown that the level of acute replication in neurons directly influences the establishment of and reactivation from latency. Because the Phos viral mutants show reduced reactivation and ICP0 is important for establishing an efficient latent infection, it is plausible that the Phos viral mutants may not have established latency at sufficient levels. For all three phosphorylation site mutant viruses, inclusion of the marker-rescue viruses confirmed that the phenotypes observed with the Phos viral mutants are due to the phosphorylation site mutations in the ICP0 protein and not from secondary mutations present in the viral genome. Taken together, these data strongly support a model in which ICP0 phosphorylation may be essential for efficient HSV-1 replication in vivo.

SUMMARY

Phos1 viral mutations impair acute replication in eyes and TG, and reactivation from latency. Phos2 viral mutations impair acute replication in TG and reactivation from latency. Phos3 viral mutations impair ocular replication, completely inhibit acute TG replication, and significantly reduce reactivation. Phos3 viral mutants show the greatest diminution of the three mutant viruses. Mutations in the Phos3 region of the ICP0 protein overlap the nuclear localization signal of the ICP0 protein, whereas mutations in the Phos1 and Phos2 regions of the ICP0 protein are in a large proline-rich region of ICP0 that is important for its transactivating activity. Thus, Phos3 mutations to the ICP0 protein may control the nuclear import and/or accumulation of nuclear ICP0 (Table 5), especially in neurons.

All three ICP0 phosphorylation regions may be required for efficient viral replication and reactivation from latency. However, the Phos3 mutant form of ICP0 appears to interfere with a viral or cellular function essential for viral growth in neurons. Furthermore, Phos3 mutant virus replication is sensitive to the effects of interferon-beta in cell culture, which also likely influences its growth in vivo. Mutations in the Phos1 region of ICP0 have been shown to impair the E3 Ub ligase, ND10 disrupting, and transactivating activities (Table 5). Mutated residues in the Phos2 region of ICP0 differentially affect the staining of ND10-associated proteins (Table 5). Alteration in these activities of ICP0 may well contribute to the in vivo phenotypes observed with Phos1 and 2 mutant viruses.

Example 3

Experimental Design

To assess relative capacity to replicate in neural tissue, groups of 4 mice were inoculated by the intracranial (i.c.) route with $1\times10^3$ PFU of virus. Brain tissue was removed after 24 hours, homogenized, and viral titer was determined on L7 cells. ICP0 helps HSV-1 to counteract the host type I IFN response. On the theory that HSV-1 Phos3 is attenuated for replication in neural tissue because its mutant ICP0 protein cannot block the type I IFN response, mice deficient in the type I IFN receptor were similarly inoculated with HSV-1 7134, HSV-1 Phos3, HSV-1 Phos3MR, or HSV-1 KOS.

The mouse model of prophylactic vaccination against HSV-1 corneal challenge was used to determine the in vivo efficacy of HSV-1 Phos3 relative to a replication-competent ICP0 null mutant (HSV-1 7134) and a replication-defective mutant (HSV-1 1D461) in generating immune responses that protect against ocular disease caused by HSV-1.

The HSV-1 1D461 control is an engineered mutant virus derived from the HSV-1 KOS strain. It has been manipulated in three ways with the goal of making an optimally safe and effective live vaccine. First, it is replication-defective due to a deletion in the UL29 gene encoding ICP8, a viral protein essential for replication of the viral DNA. Second, this virus also contains a deletion in the UL41 gene encoding the virion host shutoff protein. Vhs is known to help HSV-1 counteract the host immune response, and its deletion improves the immunogenicity and protective capacity of an ICP8⁻ replication-defective virus. Third, we have inserted the mouse CD86 gene encoding B7-2 co-stimulation molecules into the thymidine kinase locus. B7-2 is a second signal that, along with the first signal provided by viral antigen presented on MHC molecules, stimulates naïve T cells to orchestrate an antiviral immune response (or vaccine-induced immunity). Thus, 1D461 cannot replicate and spread in a vaccine (hence optimal safety), and yet produces numerous other virus proteins and host co-stimulation molecules (to stimulate antiviral immunity), and has an important viral inhibitor of immune responses disabled (hence increasing its immunogenicity).

For each viral group, 10 mice were immunized subcutaneously in the hind flanks with $5\times10^5$ PFU (high dose), $1\times10^5$ PFU (medium dose) or $2\times10^4$ PFU (low dose) of HSV-1 Phos3, HSV-1 7134, or HSV-1 1D461. An amount of supernatant from uninfected cells (control supernatant) equivalent to the high dose concentration was a negative control. On day 21 after immunization, mice were bled and serum was used to determine HSV-specific antibody titers by ELISA. On day 30 after immunization, mice were infected with $4\times10^5$ PFU per eye HSV-1 strain mP after corneal scarification. On days 0.2, 1, 2, 3, and 4 post-challenge (p.c.), the eyes of mice were swabbed for determination of virus titer shed in the tear film. Mice were individually weighed and scored for blepharitis in masked fashion on days 0 through 12 p.c. Keratitis was assessed on days 9 and 14 p.c. in masked fashion. On days 28-29 p.c. TG were removed and frozen for determination of viral genome load by real-time PCR.

Replication in Brain

Figure 6:
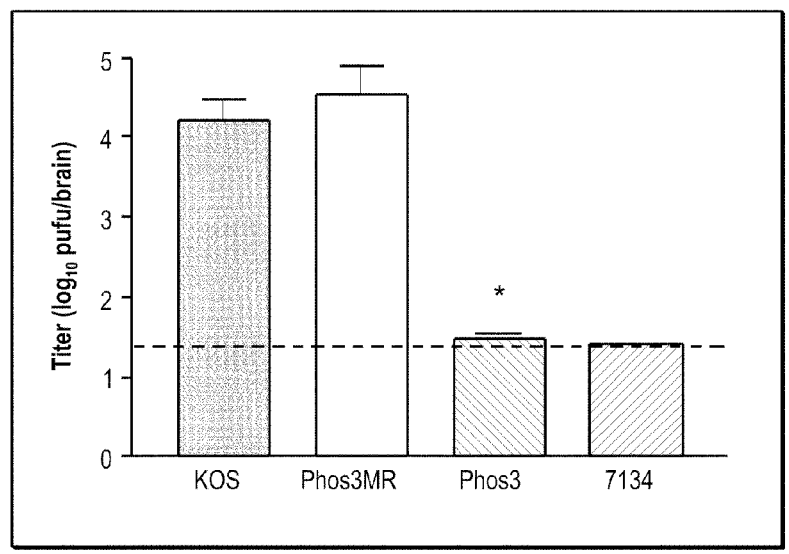
FIG. 6 includes a graph that illustrates replication of virus in the brains after direct inoculation by wild-type (HSV-1 KOS), ICP0-nul mutant (HSV-1 7134), phosphorylation site mutant (HSV-1 Phos3), and it marker-rescue (MR) virus.

To determine capacity of HSV-1 Phos3 to replicate in the nervous system, mouse brain tissue was taken after direct i.c. inoculation of virus. The HSV-1 viruses 7134, Phos3MR and wild-type KOS were included as controls in these studies. FIG. 6 shows replication of virus in the brain after direct inoculation. Groups of 4 mice lacking the type I IFN receptor were inoculated i.c. with $1\times10^3$ PFU of the indicated virus. After 24 hours the brain tissue was removed and virus titer was determined by standard plaque assay. Neither HSV-1 Phos3 nor HSV-1 7134 could be detected in the brain tissue of wild-type mice 24 hours after infection.

HSV-1 Phos3 and HSV-1 7134 were rarely detected even in brain tissue of mice that lacked the type I IFN receptor (FIG. 6), in contrast to the robust replication of HSV-1 KOS and HSV-1 Phos3MR. This result provides strong evidence that HSV-1 Phos3 is defective for replication in the nervous system. It was determined that phosphorylations at region III (Phos3 region in ICP0 protein) are important for efficient replication of HSV-1 in neural tissue. This is surprising because a mutation in the Phos3 region of ICP0 protein, or genetic code encoding ICP0, may impair or prohibit replication of HSV-1 in nervous system.

Antibody Titers

Figure 7:
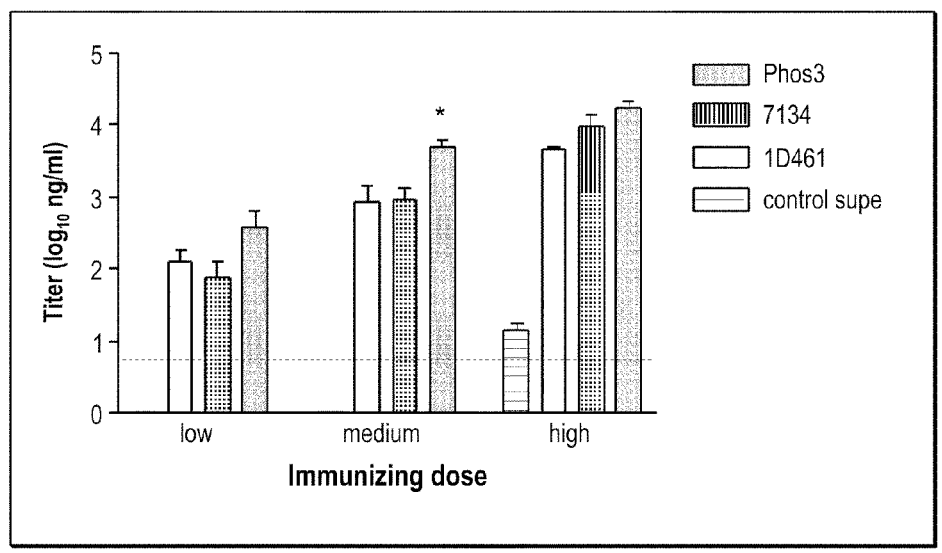
FIG. 7 includes a graph that illustrates titer of HSV-specific antibody in mice after immunized with ICP0-null mutant (HSV-1 7134), phosphorylation site mutant (HSV-1 Phos3), control virus (HSV-1 1D416), and control supernatant.

To determine whether HSV-1 Phos3 can stimulate a strong immune response, mice were immunized with HV-1 Phos3. HSV-1 7134 and HSV-1 1D16 viruses were replication-competent and defective controls, respectively. FIG. 7 shows titer of HSV-specific antibody in immunized mice. Groups of 6 mice were immunized with high, medium or low doses of the indicated viruses and 1 group of 6 mice was immunized with control supernatant as a negative control. Blood was collected on 21 days post-immunization and HSV-specific serum IgG was quantified by ELISA. HSV-1 Phos3 induced a stronger HSV-specific antibody response than HSV-1 7134 or HSV-1 1D461 at all immunizing doses, particularly at the medium dose (FIG. 7).

It was concluded that HSV-1 Phos3 is immunogenic and stimulates a stronger immune response than the less attenuated ICP0 null virus. Thus, HSV-1 Phos3 surprisingly may be more effective in impairing or preventing HSV-1 infection than the ICP0 null virus.

Protection from HSV-1 Corneal Infection and Disease

To determine how effectively immunization with HSV-1 Phos3 could protect mice from ocular HSV-1 infection, corneal challenge was perform. After corneal scarification mice were infected with a virulent strain of HSV-1.

Body Weight Change

Figure 8A:
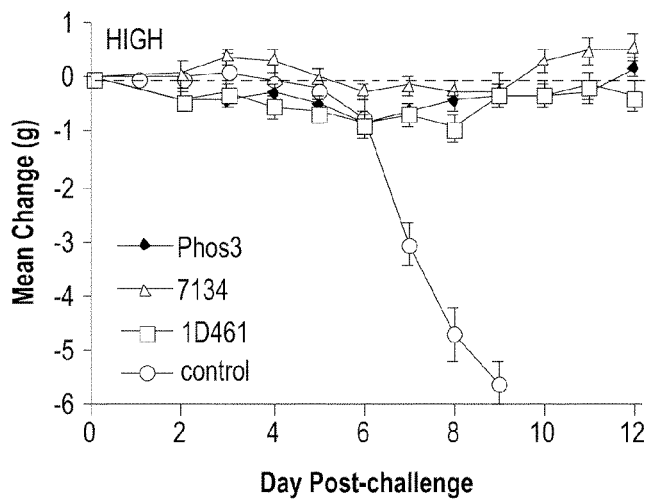
FIGS. 8A-8C include graphs that illustrate body weight of immunized mice after corneal challenge with HSV-1 when the mice were immunized with high (FIG. 8A), medium (FIG. 8B), or low (FIG. 8C) doses of ICP0-null mutant (HSV-1 7134), phosphorylation site mutant (HSV-1 Phos3), HSV-1 1D416, and control supernatant FIGS. 9A-9C include graphs that illustrate protection of mice from blepharitis after corneal challenge with HSV-1 when the mice were immunized with high (FIG. 9A), medium (FIG. 9B), or low (FIG. 9C) doses of ICP0-null mutant (HSV-1 7134), phosphorylation site mutant (HSV-1 Phos3), HSV-1 1D416, and control supernatant.
Figure 8B:
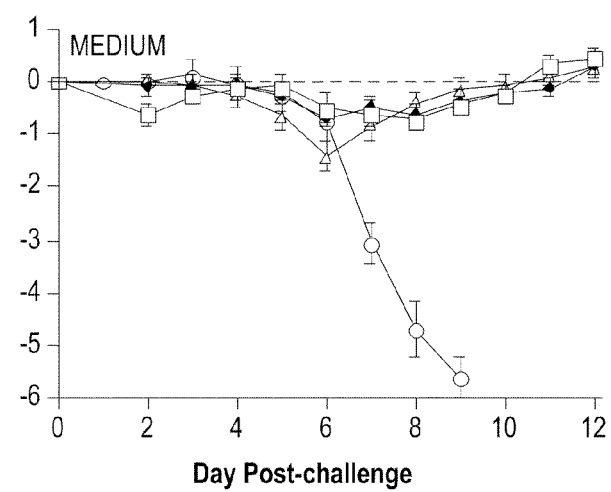
Figure 8C:
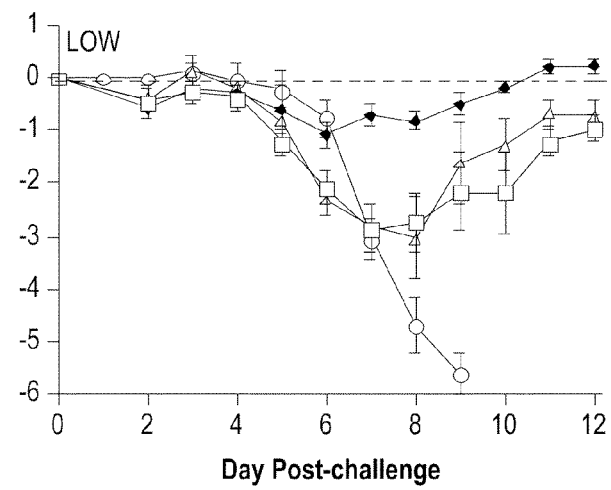

To determine how well the general health of mice is preserved after challenge, the mice were weighed daily for two weeks. FIG. 8 shows body weight change of immunized mice after corneal challenge with HSV-1. Groups of 10 mice immunized with high, medium or low doses of the indicated viruses and 1 group of mice immunized with control supernatant were challenged by corneal infection with HSV-1 and monitored daily for change in weight. Previous immunization with any dose of HSV-1 Phos3 allowed the mice to maintain body weight (FIG. 8), whereas mice immunized with the low dose of HSV-1 7134 or replication-defective virus lost an average of 3 grams (approximately 15% of their body weight). Thus, compared to HSV-1 7134 and replication-defective virus, HSV-1 Phos3 vaccine may preserve the general health of immunized subjects.

Protection from Eyelid Swelling and Disease (Blepharitis)

Figure 9A:
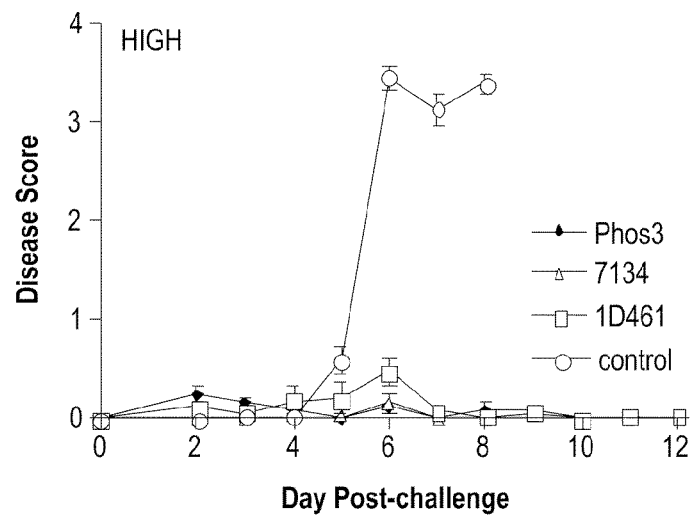
Figure 9B:
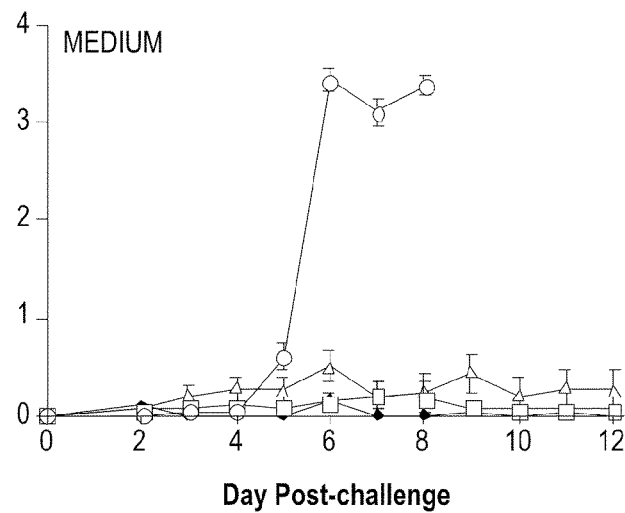
Figure 9C:
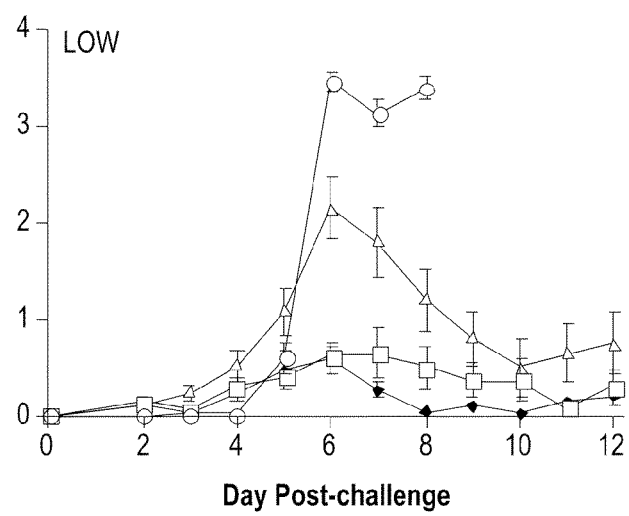

To determine how well previously immunized mice are protected from eyelid swelling and disease (blepharitis) after challenge, blepharitis was scored for each eye using a scale of 1 to 4. Scoring was performed by an observer masked to the experimental groups. Experiments were performed as described in experimental design. FIG. 9 shows protection of mice from blepharitis after corneal challenge. Groups of 10 mice immunized with high, medium or low doses of the indicated viruses and 1 group of mice immunized with control supernatant were challenged by corneal infection with HSV-1 and scored daily for signs of eyelid disease.

HSV-1 Phos3 almost completely protected mice from developing blepharitis when given at the high or medium doses (FIG. 9). Mice immunized with the lowest dose of HSV-1 Phos3 developed only mild and transient swelling of the eyelid. In contrast, mild swelling was prolonged in mice immunized with the replication-defective control virus, and blepharitis was much more severe in mice previously immunized with HSV-1 7134. Thus, HSV-1 Phos3 may effectively impair or prevent subjects from eyelid swelling and diseases.

Protection from Opacification of the Cornea (Keratitis)

Figure 10A:
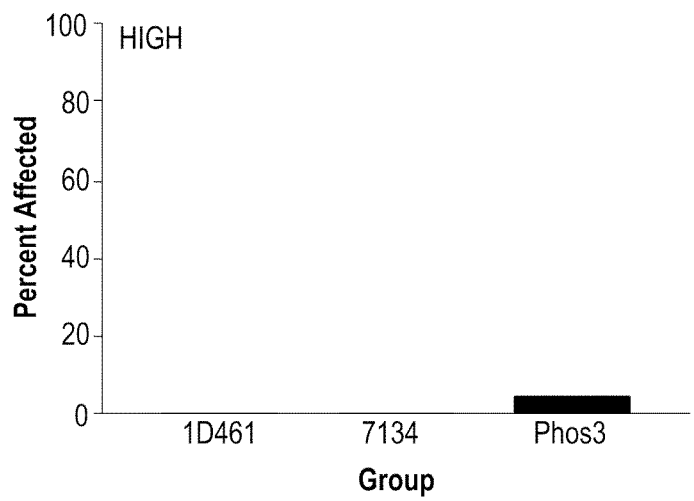
FIGS. 10A-10C include graphs that illustrate protection of mice from severe keratitis after corneal challenge with HSV-1 when the mice were immunized with high (FIG. 10A), medium (FIG. 10B), or low (FIG. 10C) doses of ICP0-null mutant (HSV-1 7134), phosphorylation site mutant (HSv-1 Phos3) and HSV-1 1D416.
Figure 10B:
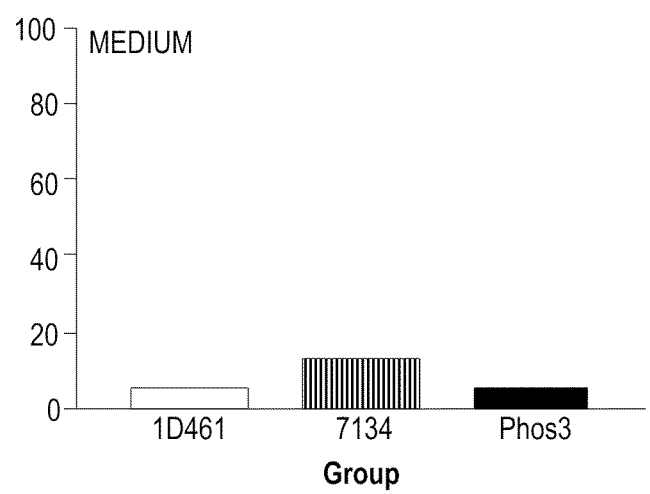
Figure 10C:
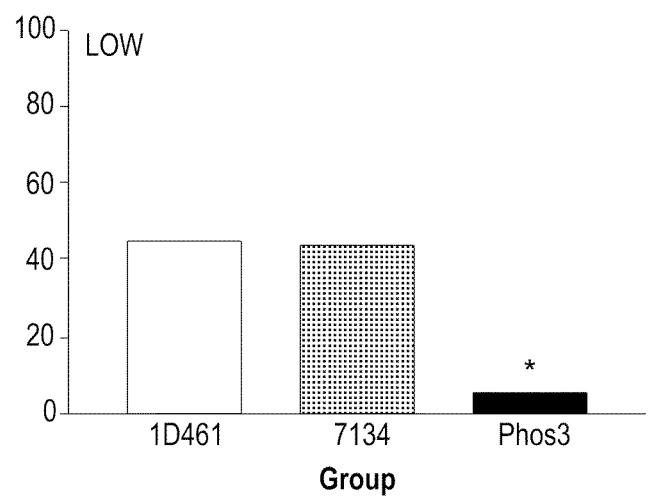

Keratitis, or opacification of the cornea, was evaluated in all immunization groups after challenge (except those receiving control supernatant, which did not survive). FIG. 10 shows Protection of mice from severe keratitis after corneal challenge. Groups of 10 mice immunized with high, medium or low doses of the indicated viruses and 1 group of mice immunized with control supernatant were challenged by corneal infection with HSV-1. At 14 days after challenge the eyes were examined for signs of severe keratitis. Values represent the percentage of eyes from surviving mice with a score of 3 or 4 (sight-impairing). All immunizing viruses significantly protected mice when given at the high or medium doses, but only HSV-1 Phos3 continued to protect the majority of eyes from severe (sight impairing) keratitis at the low immunizing dose (FIG. 10). Thus, HSV-1 Phos3 may effectively impair or prevent subjects from opacification of the cornea.

Protection from Lethal Infection

Figure 11:
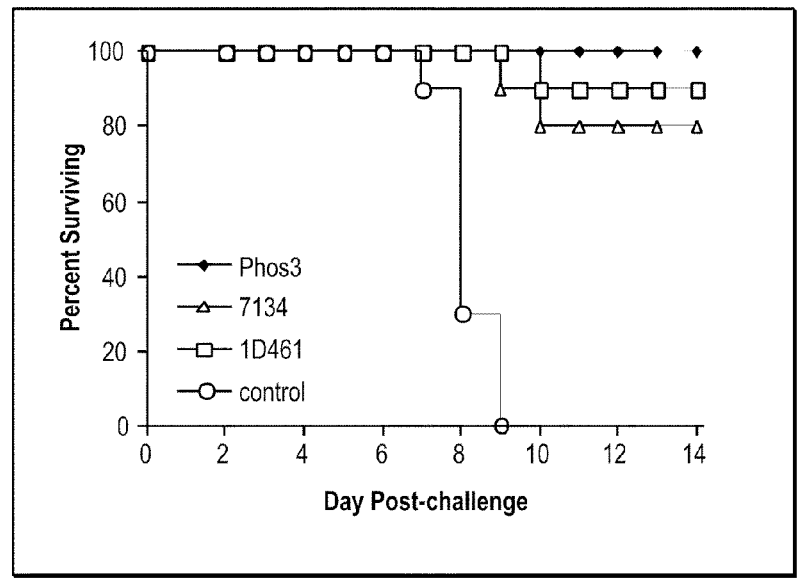
FIG. 11 includes a graph that illustrates survival of mice after corneal challenge with HSV-1 when the mice were immunized with low dose of ICP0-null mutant (HSv-1 7134), phosphorylation site mutants (HSV-1 Phos3), HSV-1 1D416, and control supernatant.

To determine whether immunization could protect mice from lethal infection, survival was monitored over time post-challenge. FIG. 11 shows survival of mice after corneal challenge. Groups of 10 mice immunized with the low dose of the indicated virus were challenged on the scarified corneas with HSV-1, and their survival was monitored daily. All mice immunized with control supernatant succumbed by day 9 post-challenge (FIG. 11). Deaths also occurred after challenge in groups immunized with the low dose of HSV-1 7134 or replication-defective control virus, but all mice immunized with HSV-1 Phos3 survived. Thus, HSV-1 Phos3 may effectively protect subjects from lethal infection.

SUMMARY

Collectively, the results of corneal challenge of immunized mice indicate that prior vaccination with HSV-1 Phos3 provides significant protection against HSV-1-mediated disease of the eyelid and eye, even at a very low immunizing dose. Surprisingly, this protective effect was stronger for HSV-1 Phos3 than either a less attenuated ICP0 null virus or a replication-defective control virus.

Example 4

Virus Titers in the Tear Film of Immunized Mice for 30 Days During the Period of Acute Replication after Corneal Challenge Female 6-week-old BALB/c mice (National Cancer Institute) were immunized with $4\times10^4$, $2\times10^5$, or $1\times10^6$ PFU of each virus or control cell extract, in a 20 μL volume subcutaneously near the base of the tail, using a 26-gauge needle. Four weeks after primary immunization, all mice were challenged by inoculation of $4\times10^5$ PFU of HSV-1 strain mP per eye after corneal scarification in inoculum of 5 μL. This dose produces encephalitis in 100% of non-immune BALB/c mice and represents 10 to 30 times the minimum dose. Results shown are for mice immunized with HSV-1 Phos3, HSV-1 7134 (ICP0 null mutant), HSV-1 1D461 (control virus), and control supernatant (cell extract). Description for methods was modified as previously described. Immunization with replication-defective mutants of herpes simplex virus type 1: sites of immune intervention in pathogenesis of challenge virus infection. Morrison L A, Knipe D M. J. Virol. 1994 February; 68(2):689-96.)

Mice immunized at the high dose ($1\times10^6$ PFU) of HSV-1 Phos3 and HSV-1 7134 had lower titers of virus in eye swabs on days 1-4 after challenge; HSV-1 1D461 had lower titers on days 2-4 post challenge compared to the control supernatant. At the medium dose ($2\times10^5$ PFU), HSV-1 Phos3, HSV-1 7134, and HSV-1 1D461 had lower titers 1-4 post challenge compared to the control supernatant. At the low dose ($4\times10^4$ PFU), HSV-1 1D461 titers were lower on days 1-4 post challenge compared, whereas HSV-1 Phos3 and HSV-1 7134 titers were lower on 2-4 days post challenge relative to the control supernatant. Notably, immunization with HSV-1 Phos3 significantly decreased shedding of virus on either day 3 (high dose) or day 4 (medium and low doses) compared to all other viral groups during primary replication. Thus, HSV-1 Phos3 vaccine may impair or prevent HSV-1 replication or infection in eyes.

Figure 12A:
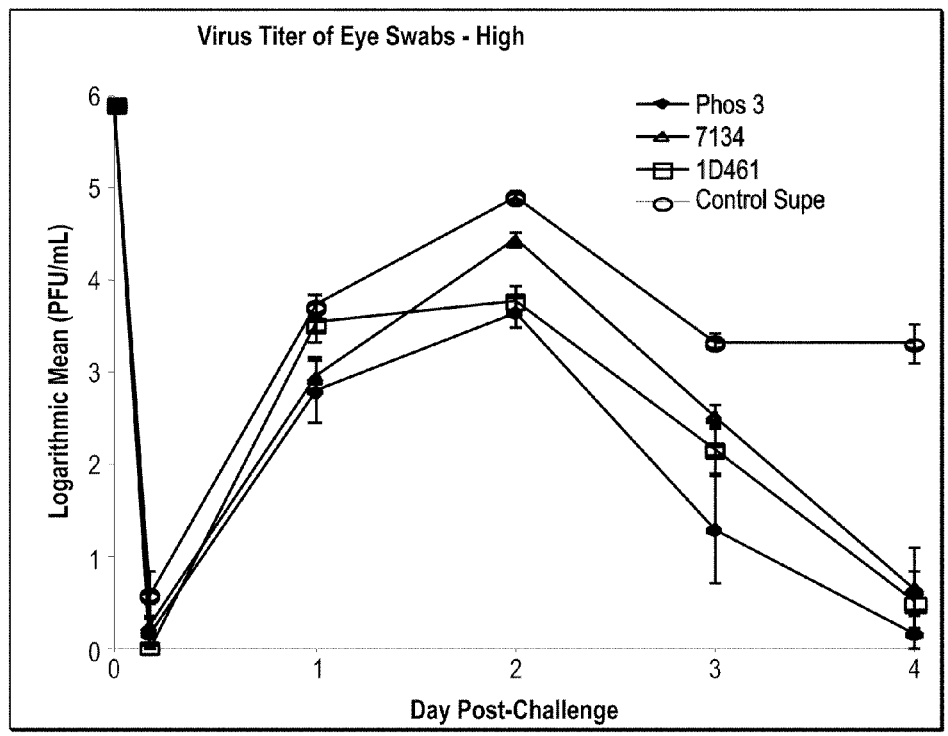
FIGS. 12A-12C include graphs that illustrate viral titer of eye swabs after corneal challenge with HSV-1 when the mice were immunized with high (FIG. 12A), medium (FIG. 12B), or low (FIG. 12C) doses of ICP0-null mutant (HSV-1 7134), phosphorylation site mutant (HSV-1 Phos3), control virus (HSV-1 1D416), and cell extract (control supernatant).
Figure 12B:
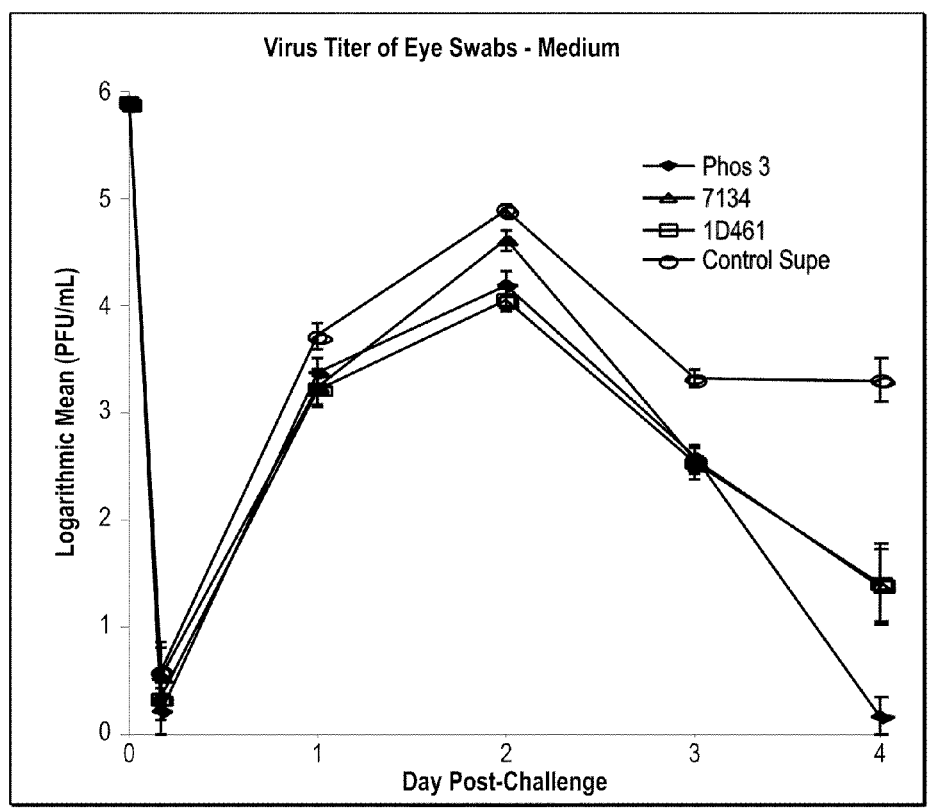
Figure 12C:
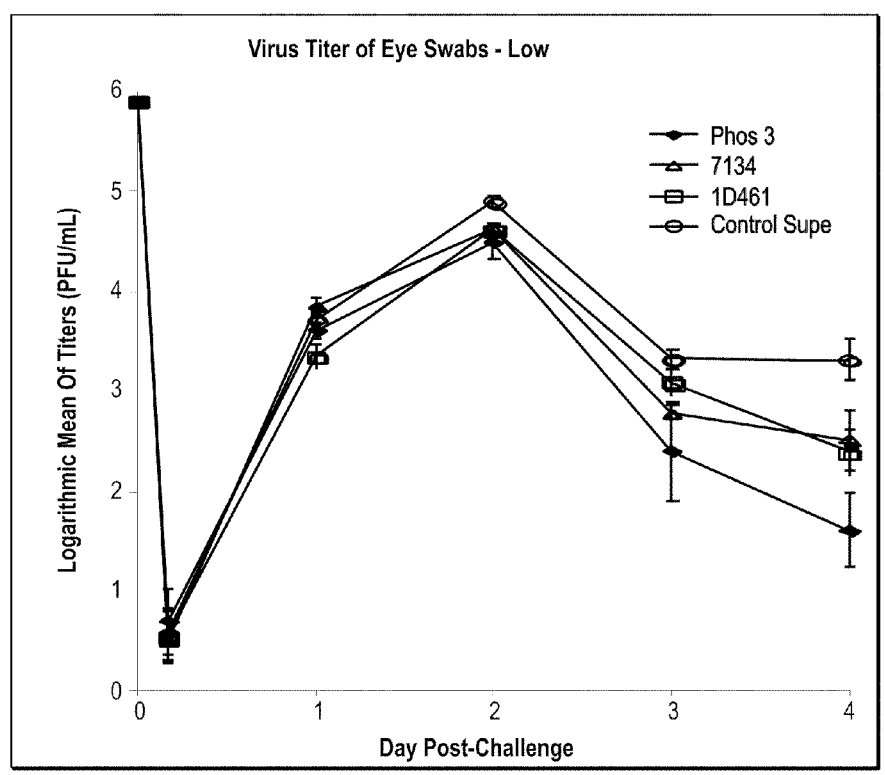

FIGS. 12A-12C show viral titer of eye swabs after corneal challenge with HSV-1 when the mice were immunized with high (12A), medium (12B) or low (12C) doses of ICP0-null mutant (HSV-1 7134), phosphorylation site mutant (HSV-1 Phos3), control virus (HSV-1 1D416), and cell extract (control supernatant).

Example 5

Phosphorylated residues in ICP0 protein were detected using microcapillary reverse-phase HPLC nano-electrospray tandem mass spectrometry. Using an in-house program, Enzyme Optimizer, the ICP0 protein sequence was evaluated for a dual enzyme strategy which would optimize for coverage of S/T/Y residues. The program considers peptide properties and experimental conditions that influence recovery and detection of a predicted peptide, rather than simple protein coverage. The band corresponding to ICP0 was then split in half for separate, in gel trypsin and chymotryptic digestions after reduction, and carboxyamidomethylation. The resultant digests were pooled just prior to LC-MS/MS injection. Phosphorylated peptide sequences were determined using a 75-μm reverse phase microcolumn terminating in a custom nano-electrospray source directly coupled to a Finnigan LCQ DECA XP+ quadrupole ion trap mass spectrometer (Thermo Electron). The flow rate was nominally 250 nl/min. The ion trap repetitively surveyed the range m/z 395-1600, executing data-dependent MS/MS on the four most abundant ions in each survey scan. MS/MS spectra were acquired with a relative collision energy of 30%, a 2.5 Da isolation width, and recurring ions dynamically excluded. Preliminary sequencing of peptides was facilitated by database correlation with the algorithm SEQUEST. The discovery of peptides carrying phosphorylation and subsequent manual validation of their MS/MS spectra were aided by the in-house programs Muquest and Fuzzylons, respectively.

Based on μLC-MS/MS analysis, each of the 3 phosphorylated regions of ICP0 that were identified lies within or overlaps domains reported to be important for ICP0's transactivating activity. Thus, the four mutations in the Phos1 region at positions 224, 226, 231, and 232 are adjacent to the RING-finger motif of ICP0, which is required for its E3 ubiquitin ligase and transactivating activities. This study has shown that the Phos1 form of ICP0 is impaired in its transactivating activity and in its ability to complement the replication of an ICP0 null mutant but not its ability to degrade and/or disperse ND10. Insertion and deletion mutations in region I (Phos 1 region) or between region I and ICP0's RING finger have been shown to diminish both the transactivating activity of ICP0 and its ability to co-localize with conjugated ubiquitin; the latter activity is consistent with ICP0's E3 ubiquitin ligase activity. Mutations in the RING finger motif (residues 116-156) and an adjacent region (residues 162-188) show a range of ND10-disrupting phenotypes that are distinct from the phenotype of WT ICP0. To date, however, the ND10-disrupting activities of the majority of ICP0 mutants with mutations that lie in region I and between region I and the RING finger motif have not been reported. Additionally, mutation of Asp-199 (which lies between region I and the RING finger motif) to alanine negates the binding of ICP0 to cyclin D3, accelerating the destabilization of cyclin D3. This mutation attenuates the pathogenesis of HSV-1. Residues 20-241 of ICP0 have been shown to interact with the cellular transcription factor, BMAL1. The interaction of ICP0 with BMAL1 is thought to facilitate synergistic transactivation of BMAL-1 responsive genes. Thus, it is possible that the effects we observed with the HSV-1 Phos1 in Vero cells result from alterations in these adjacent regions. Of interest is the fact that the phenotypes of Phos1 ICP0 are strikingly similar to the phenotypes of ICP0 synthesized in the presence of the cdk inhibitor, Rosco. Specifically, ICP0 synthesized in the presence of Rosco is impaired in its transactivating activity but not its ND10-disrupting activity. Thus, Rosco-sensitive cdk-mediated phosphorylation of phospho-acceptor sites in region I of ICP0, and especially Ser-224 which is a potential cdk-1 or -2 phosphorylation site, may contribute to ICP0's transactivating activity.

The mutations in Phos2 ICP0 at positions 365, 367, and 371 lie within a large proline-rich domain important for ICP0's transactivating activity. Phos2 was affected only in its capacity to disperse or degrade ND10-associated PML in a subset of Phos2 expressing cells; the transactivating- and 7134-complementing activities of Phos2 were only minimally affected relative to WT ICP0. A previous study noted a reduction in ICP0's transactivating activity in a mutant form of ICP0 lacking residues 263-448, which includes all of region II. Consistent with the transactivating potential of Phos2 ICP0, a report by Everett noted that an insertion in region II at residue 370 and deletion of residues 341-374 had marginal effects on ICP0-mediated transactivation in Vero cells. The ability of these deletion and insertion mutants to affect the dispersal or degradation of ND10-associated proteins (including PML) has not been reported. Notably, the magnitude of the impairment in the transactivating activity of these mutants correlates with the severity of their mutations.

Mutations in Phos3 ICP0 at positions 508, 514, 517, and 518 overlap the putative nuclear localization signal (NLS) of ICP0 and are adjacent to its multi-functional C-terminal domain. Phos3 was affected in its subcellular and nuclear localization and its ability to disperse or degrade PML in a subset of cells expressing Phos3; however, these mutations only minimally affected its ability to complement 7134 in Vero cells. The diminished transactivation potential of Phos3 may also be due to its altered subcellular and/or subnuclear localization. Similar observations have been reported for deletion mutants of ICP0 which eliminate its putative NLS. Notably, a proportion of cells expressing these deletion mutants co-localized with ND10-associated proteins in the cytoplasm similar to our observations with PML and Phos3 ICP0. Because the mutations in Phos3 ICP0 are directly adjacent to the putative NLS of ICP0 and because phosphorylation of the NLS may affect nuclear import, Phos3 ICP0 may be inefficiently transported to or from the nucleus as our immunofluorescence data suggest. In support of this possibility, mutagenesis of potential phosphorylation sites has been shown to regulate the subcellular localization of viral regulatory proteins from DNA-containing viruses including T-ag of SV40, pp 65 of human cytomegalovirus, latent nuclear antigen of Kaposi's sarcoma herpesvirus, IE63 protein of varicella zoster virus, and US11, an RNA-binding protein, and ICP27 of HSV-1. Of the viral regulatory proteins just mentioned with the exception of US11, CKII, cdk-1, and PKA have been implicated in their subcellular localization, and putative phosphorylation sites for these cellular kinases have been identified in region III of ICP0. The subcellular localization of Phos3 ICP0 may also indirectly affect the phosphorylation state of a portion of ICP0 molecules. For example, if ICP0 is efficiently phosphorylated by nuclear kinases which are required for its biological activities, then impairment of ICP0's nuclear translocation would prevent its phosphorylation by such kinases. Although the mutations in Phos3 ICP0 reduced its transactivating activity, they affected its 7134-complementating activity in Vero cells only minimally. These observations demonstrate that Phos3 ICP0 possesses sufficient transactivating activity to stimulate the replication of an ICP0 null mutant to levels similar to WT ICP0. This possibility is reinforced by two studies demonstrating that mutant forms of ICP0 exhibiting impaired transactivating activity are capable of supporting significant complementation of an ICP0 null mutant virus. Finally, although we examined the phenotypic effects of the Phos1 ICP0, Phos2 ICP0, and Phos3 ICP0 mutations in Vero cells, it is conceivable that these mutations may have cell type-specific effects in the functional assays used in this study, alter other known activities of ICP0 (e.g., E3 ubiquitin ligase activity, accumulation of conjugated ubiquitin, cell cycle-blocking activity), and/or have distinct phenotypes in the context of viral infection in vivo.

Example 6

Plasmid pIE3-CAT, which expresses the chloramphenicol acetyl transferase (CAT) gene under the control of the HSV-1 IE ICP4 promoter, was constructed as previously described in the art. Plasmid pAlter-1+ICP0 was constructed by isolating a 4.6 kb EcoRI to HindIII fragment containing the ICP0 gene from the plasmid pSH, and cloned into the vector pAlter-1 (Promega Corp. Madison, Wis.), using the same restriction enzyme sites. pAlter-1+ICP0 was subsequently used as the parental vector to mutate the putative phosphorylation sites of ICP0 to alanine using mutagenic primers (IDT, Coralville, Iowa) according to the manufacturer's protocol (Promega Corp., Madison, Wis.). The primers used for the mutagenesis are: Phos1 (S224A, T226A, T231A, T232A) 5'CTGGGGGGGCACACGGTGAGGGC-CCTagCGCCggCCCACCCTGAGCCggCCg CGGAC-GAGGATGACGACGACCTGGAC3' (SEQ ID NO: 5); Phos2 (S365A, S367A, S371A) 5'GCAAACAACAGAGAC-CCCATAGTGATCgcCGAtgCCCCCCCGGCCgCTCCCA CAGGCCCCCCGCGGCGCCC3' (SEQ ID NO: 6); and Phos3 (S508A, S514A, S517A, T518A) 5'GCGGTGCGTC-CGAGGAAGAGGCGCGGGgCcGGCCAG-GAAAACCCCgCCCC gCAGgCCgCGCGTC-CCCCCCTCGCGCCGGCAGGGG3' (SEQ ID NO: 7). Lower case letters in each primer indicate the nucleotides mutated relative to WT (strain KOS) ICP0 sequences. Putative mutants were identified by restriction enzyme analysis and confirmed by DNA sequencing.

Example 7

ICP0 proteins were prepared. Vero cells were plated at $5 \times 10^5$ cells per 60-mm dish, and at 2 hours prior to transfection (22 h post-plating), medium was changed. Twenty four hours after plating, transfections were performed with Lipofectamine 2000 (Invitrogen Corp., Carlsbad, Calif.) according to the manufacturer's protocol using 8 μg of plasmid or salmon sperm DNA and 16 μl of Lipofectamine 2000 diluted in Opti-MEM (Invitrogen Corp.). The DNA/Lipofectamine 2000 mixture was subsequently added to plates containing 5 ml of Opti-MEM in a dropwise manner and left on the cells for 4 hours at 37° C. Four hours after transfection, cells were pretreated for 1 hour with CHX [50 μg/ml] and mock-infected or infected with 5 PFU of KOS or 7134/cell for 1 hour at 37° C. in the presence of CHX. After 1 hour adsorption, inoculum was removed, cells were washed 3 times with PBS containing CHX, 4 ml of Vero cell medium plus CHX was added per dish, and dishes were incubated for 4.5 hours p.i. at 37° C. At t=5.5 hours p.i., cells were pre-incubated for 0.5 hours in phosphate- or methionine/cystine-free DMEM containing CHX. At t=6 hours p.i., medium was removed, and infected cells were washed three times with phosphate- or methionine/cystine-free DMEM containing 1% FCS. Cells were then labeled with 500 µCi of $^{32}P_i$ or 100 µCi [$^{35}$S]methionine/cysteine (PerkinElmer Life Sciences, Inc., Boston, Mass.) in phosphate-, or methionine/cystine-free DMEM containing 1% FCS, respectively, for an additional 6 hours. At t=12 hours p.i., cells were washed twice with ice-cold PBS, scraped into 1 ml of ice-cold RIPA lysis buffer containing protease inhibitors as described above in the "Partial purification of ICP0 for µLC-MS/MS sequencing". Extract preparation, immunoprecipitation of ICP0, and SDS-PAGE analysis were performed as described previously. Proteins were visualized, and their signal intensities were quantified by PhosphorImager analysis (Amersham Biosciences, Piscataway, N.J.).

Example 8

ICP0 protein was subjected to phosphotryptic peptide digestion and one-dimensional alkaline gel electrophoresis. $^{32}$P-labeled bands of WT ICP0 or its mutant forms were excised from the SDS-PAGE gel described above and washed two times for 5 min. in fresh ammonium bicarbonate (50 mM). Each gel piece was brought to a final volume of 500 µl with sodium bicarbonate, homogenized with a pestle grinder, and treated with 40 µg of TPCK-treated trypsin (Worthington Biochemicals, Lakewood, N.J.) while gently agitating at 34° C. overnight. An additional 25 µg of TPCK-treated trypsin was added per sample, incubating for a second time overnight at 34° C. Samples were spun at 20,800×g for 10 minutes at room temperature, and the resulting supernatant was removed. Remaining protein in the gel pieces was extracted twice by incubating the pieces in 400 µl of acetonitrile-formic acid (1:1) for 20 minutes. with gentle rocking at room temperature. The acetonitrile-formic acid extracts and the aqueous supernatant of the phosphotryptic digests were pooled (~1200 µl) and dried in a SpeedVac (Savant Instruments, Inc., Farmingdale, N.Y.). Phospholabeled peptides of ICP0 were suspended in 25 µl of sample buffer [0.125 M Tris-HCl buffer (pH 6.8) and 6 M Urea], loaded using equal Cherenkov counts (~1150 cpm), and separated on a 27-cm 30% (w/v) alkaline acrylamide gel as described previously at 10 mA for 44 hours. Phosphotryptic peptides from the alkaline gel electrophoresis were visualized by PhosphorImager analysis.

Example 9

Vero cells were stained for ICP0 immunofluorescence. Vero cells were plated on coverslips in 12 well plates, and 22 hours later, fresh Vero cell medium was added to each well 2 hours prior to transfection. Transfections were performed with Lipofectamine 2000 according to the manufacturer's protocol using 3 µg of plasmid DNA and 6 µl of Lipofectamine 2000 diluted in Opti-MEM (Invitrogen Corp.). The DNA/Lipofectamine 2000 mixture was then added to each well containing 500 µl Opti-MEM in a dropwise manner and left on cells for 5 hours at 37° C. Medium was removed and fresh medium added, incubating the monolayers for an additional 19 hours. Twenty-four hours post-transfection, medium was removed, and coverslips were washed twice with PBS. Transfected cells were fixed and permeabilized by formaldehyde and acetone treatments according to Zhu et al. Immunofluorescence staining for ICP0, its mutant forms, and PML was performed as previously described. The primary antibodies and the dilutions used for the dual staining of ICP0 and PML were: ICP0 [1:500] (H1112; mouse monoclonal antibody; Rumbaugh-Goodwin Institute for Cancer Research, Plantation, Fla.) and PML-14 [1:500] (rabbit polyclonal antibody; Gerd Maul, Wistar Institute, Philadelphia, Pa.). The following secondary antibodies and dilutions were used for each primary antibody: ICP0 (H1112) [1:100] (goat anti-mouse IgG conjugated with fluorescein isothiocyanate) and PML-14 [1:100] (goat anti-rabbit immunoglobulin G (IgG) conjugated with rhodamine red-X). All secondary antibodies were purchased from Jackson Immunoresearch (West Grove, Pa.). Following incubations with primary and secondary antibodies, coverslips were washed and 7 µl of Prolong Antifade Solution (Molecular Probes, Eugene, Ore.) was added per coverslip. Cells were viewed by fluorescence microscopy with a Nikon Eclipse TE300 Fluorescence microscope at ×400 magnification and photographed with an RT Slider digital camera (Diagnostic Instruments, Sterling Heights, Mich.), and images were processed in Adobe Photoshop (Adobe Systems Inc., Mountain View, Calif.). Images were assembled and labeled in Canvas 8 (Deneba Systems, Miami, Fl.).

At least 150 ICP0-stained cells from random fields were examined in each preparation and categorized as having nuclear only, nuclear and cytoplasmic, or cytoplasmic only staining. The percentage of cells in each category was determined by dividing the number of cells in a given category by the total number of cells counted in all three categories.

Example 10

Vero cells were transfected with genetic material encoding for ICP0. Vero cells (5×10$^5$ cells per 60-mm dish) were plated, and 2 hours before transfection (22 hours post-plating), the medium was changed. Twenty-four hours after plating, the transfections were performed with Lipofectamine 2000 according to the manufacturer's protocol using a total of 8 µg of DNA [1 µg of CAT expression vector, salmon sperm testis DNA, and/or increasing amounts plasmid DNA] and 16 µl of Lipofectamine 2000 diluted in Opti-MEM per dish. DNA/Lipofectamine 2000 was then added to dishes containing 5 µl of Opti-MEM in a dropwise manner and left on cells for 5 hours at 37° C. Medium was removed and fresh Vero cell medium added, incubating the monolayers for an additional 43 hours. At 48 hours post-transfection, cells were washed three times with tris buffered saline (TBS), harvested in 2 ml TBS, and pelleted at 800×g; the supernatant was removed. The resulting cell pellets were stored at −80° C. Samples were thawed on ice, re-suspended in 150 µl TBS, sonicated for 20 sec. at 80% power in a Misonix Sonicator 3000 (Misonix, Inc., Farmingdale, N.Y.), and cell debris was pelleted for 10 minutes. at 4° C. at 20,800×g. The resulting supernatant was assayed for CAT activity as performed as is known in the art.

Example 11

The plating efficiency of cells producing HSV-1 and/or ICP0 (wild type or mutant) were examined. Vero cells were plated at 2×10$^5$ cells per 35-mm dish. Twenty-two hours later, fresh medium was added to each well. Twenty four hours post-plating, the transfections were performed with FuGENE 6 (Roche Diagnostic Corporation, Indianapolis, Ind.) using a total of 3 µg DNA (0.5 µg of infectious HSV-1 KOS or HSV-1 7134 viral DNA, salmon sperm DNA, and/or 0.075 µg of plasmid DNA [pAlter-1 or WT ICP0- or Phos mutant-expressing plasmids]) and 12 µl of FuGENE 6 diluted in Opti-MEM. The DNA/FuGENE 6 mixture was divided in half, added dropwise to 35 mm dishes (for duplicate samples)

containing 2 μl of Opti-MEM, and left on the cells for 5 hours at 37° C. Medium was removed, fresh Vero cell medium added, and monolayers incubated for an additional 43 hours. Transfected cells were harvested 48 hours post-transfection and assayed for infectious virus by standard plaque assays on Vero cells for HSV-1 KOS or on L7 cells for HSV-1 7134.

For the HSV-1 7134 plating efficiency experiments, cells were transfected as described in the art, with the following modifications. Five hours post-transfection, medium was removed from each culture and replaced with 2.5 ml of medium containing 0.5% methylcellulose and 10% FCS in DMEM. Three days post-transfection, methylcellulose containing medium was removed from each plate, and cells were washed twice with PBS, fixed with 2% formaldehyde, and stained for β-galactosidase activity with X-gal as described in the art. X-gal staining was performed to note the spread of HSV-1 7134 infection (HSV-1 7134 contains the lacZ gene in place of both copies of ICP0) by counting CBF (cytopathic blue foci: clusters of 8 or more cells exhibiting cytopathic effect) per quadrant (¼ the area of each dish).

Example 12

ICP0 was partially purified. Four 100-mm dishes were seeded with 2×10⁶ Vero cells, and 23 hours after plating cells, were pretreated with cycloheximide (CHX [50 μg/ml]) for 1 hour and infected with 5 PFU of HSV-1 KOS/cell for 1 hour at 37° C. in the presence of CHX. After 1 hour adsorption, inoculum was removed, cells were washed three times with phosphate buffered saline (PBS) containing CHX. Five ml of Vero cell medium containing CHX was then added to each dish, and cells subsequently were incubated for 5 hours [t=6 hours post-infection (p.i.)] at 37° C. At t=6 hours p.i., medium was removed, and infected cells were washed three times with PBS and incubated for an additional 6 hours. At t=12 hours p.i., cells were washed twice with ice-cold PBS, scraped into 2 ml of ice-cold PBS, and pelleted at 800×g at 4° C. The supernatant fluid was removed, and the resulting cell pellets were stored at −80° C. Subsequently, samples were thawed on ice, and re-suspended in 2 ml of RIPA lysis buffer [150 mM NaCl, 50 mM Tris (pH 7.5), 0.1% sodium lauryl sulfate (SDS), 1% Nonidet P-40, and 0.5% deoxycholic acid] containing the protease inhibitors phenylmethysulfonylfluoride [1 mM], 1 μg of leupeptin/ml, and 1 μg of aprotinin/ml. Eight μl of J17, an ICP0 polyclonal rabbit antibody, was added per sample and the suspensions were gently agitated overnight at 4° C. The next day, 160 μl of protein A-agarose (Invitrogen Life Technologies, Carlsbad, Calif.) was added to each sample and agitated for 2 hours at 4° C. Immune complexes were pelleted by centrifugation for 2 minutes, 3,300×g at 4° C. The supernatant fluid was removed, and each pellet was washed and repelleted three times in RIPA buffer plus protease inhibitors. The resulting pellet was re-suspended in 60 μl of 1× Laemmli buffer plus 1 mM PMSF. Samples were heated at 100° C. for 5 minutes, placed on ice for 2 minutes, and centrifuged to pellet the protein A-agarose. The supernatants were analyzed by sodium dodecyl sulfate-polyacrylamide gel electrophoresis (SDS-PAGE) on a 0.75 mm 6% acrylamide gel. Proteins were visualized by Coomassie Blue staining and an estimate of the total amount of ICP0 protein isolated (1.5 μg) was determined relative to a standard curve of bovine serum albumin. Gel pieces containing ICP0 bands were marked, destained for Coomassie Blue dye, excised, and stored at −20° C. until further analysis.

Example 13

The HSV-2 recombinant viruses used in this study were derivative of HSV-2 MS (obtained from ATCC) and were all propagated in U2OS cells at 34° C. All HSV-2 viruses grow to ~100-fold lower titers than HSV-1. This is not unique to HSV-2 MS, but is also observed in HSV-2 strain G and 10 different clinical isolates of HSV-2 obtained from the STD clinic in the former Charity Hospital in New Orleans, La. (closed since Hurricane Katrina). To circumvent the fact that HSV-2 viruses grow to lower titers, three modifications to a standard HSV growth procedure were adapted: 1. HSV-2 viruses were grown in U2OS cells in which ICP0 is not necessary for efficient growth; 2. HSV-2 viruses were grown at 34° C. because this allowed higher titers of virus to be recovered relative to growth at 37° C.; and 3. cells were inoculated with HSV-2 viruses at a low multiplicity of infection (MOI) of 0.01 pfu per cell.

Plasmid Precursors of HSV-2 Recombinant Viruses

The construction of plasmid precursors of the HSV-2 recombinant viruses used in this study is described. A 12.5 kb Hind III-Kpn I DNA fragment which encompassed the long-internal repeat (IR$_L$) of the HSV-2 genome (117,071-128, 610; Genbank accession number NC_001798) was subcloned from HSV-2 (strain MS) into a pUC18 plasmid vector. The resulting plasmid, pHSV2-R$_L$ (UL56), contained the HSV-2 ICP0 gene but was too large for mutagenesis of the ICP0 gene. Excess DNA sequence was removed between Hind III and Mlu I restriction sites (bases 117,071-120,806) and between Age I and Kpn I restriction sites (bases 126,058-128,610) to create the plasmid, pUC-HSV2-ICP0, which contained bases 120,807-126,057 of the HSV-2 genome. This plasmid was used as a template for mutagenesis of the HSV-2 ICP0 gene, and each mutant allele of the ICP0 gene that was constructed is described below on a plasmid-by-plasmid basis.

i. p0Δ104: The plasmid p0Δ104 was created by replacing the Not I to Bam HI fragment that spans codons 19 to 104 of the HSV-2 ICP0 gene (bases 124,229-124, 893) with a GFP coding sequence flanked by matching Not I and Bam HI restriction sites. This GFP coding sequence was generated by PCR amplification off of the template peGFP-N1 (Clontech Laboratories) using the following oligonucleotide primers: Not 1-GFP-a primer: 5'-ccga GCGGCCGCtgagcaagggcgaggagctgt-3' (SEQ ID NO: 9) and Bam HI-GFP-b primer: 5'-ccaca GGATCCcagctcgtccatgccgagag-3' (SEQ ID NO: 10). Upon sub-cloning of the PCR-amplified GFP coding sequence into pUC-HSV2-ICP0, the resulting plasmid p0Δ104 possessed an open-reading-frame that encoded amino acids 1 to 18 of HSV-2 ICP0, 238 amino acids of GFP, and amino acids 19 to 825 of ICP0 (FIG. 15A).

Figure 15A:
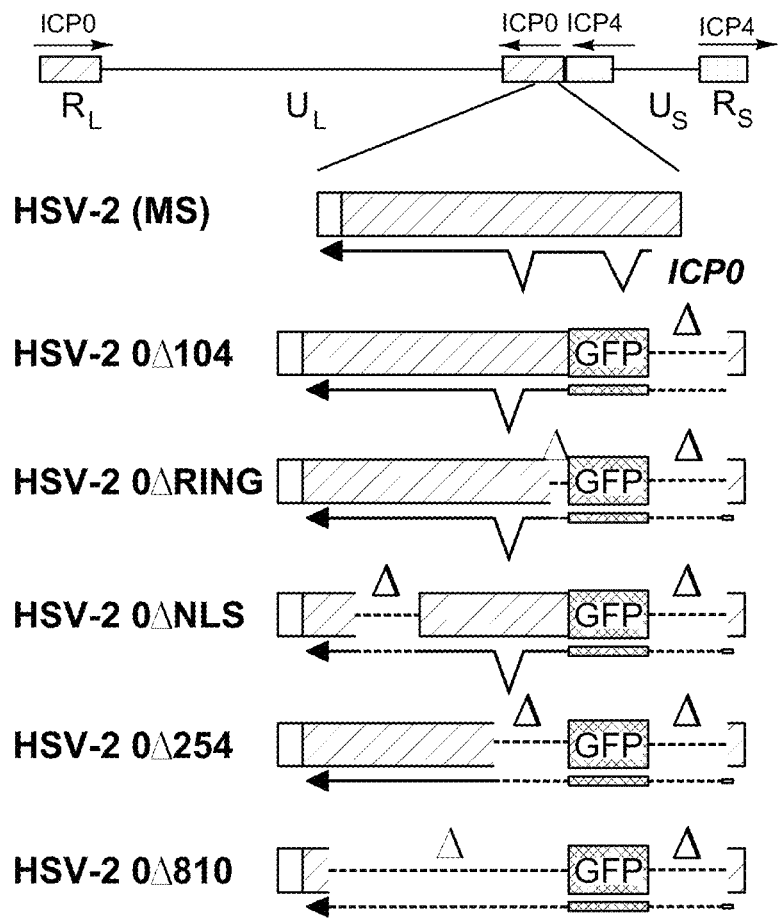
FIGS. 15A-15B show schematic illustrations of mutant ICP0 genes in a panel of HSV-2 ICP0− viruses and a corresponding Southern blot.
Figure 15B:
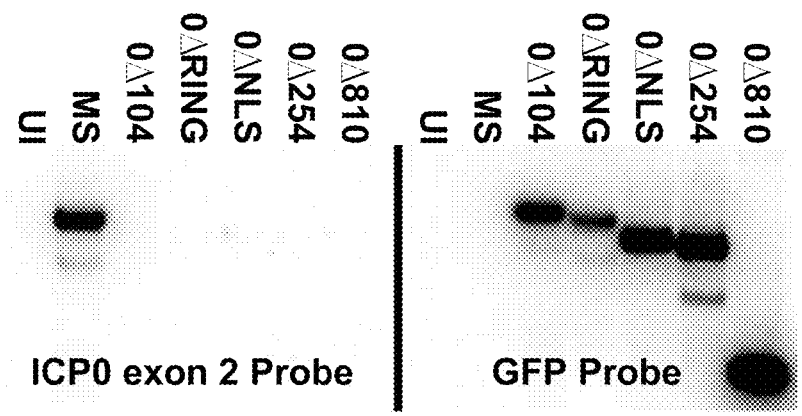
Figure 16A:
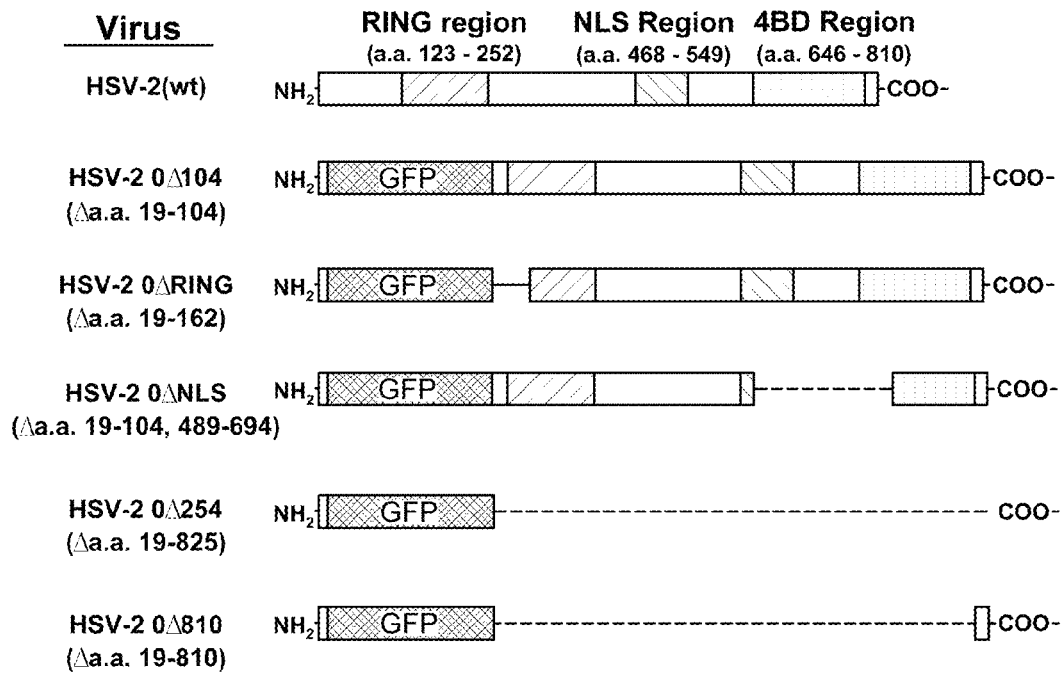
FIGS. 16A-16B show schematic illustrations of mutant ICP0 proteins encoded by a panel of HSV-2 ICP0− viruses and a corresponding Western Blot.
Figure 16B:
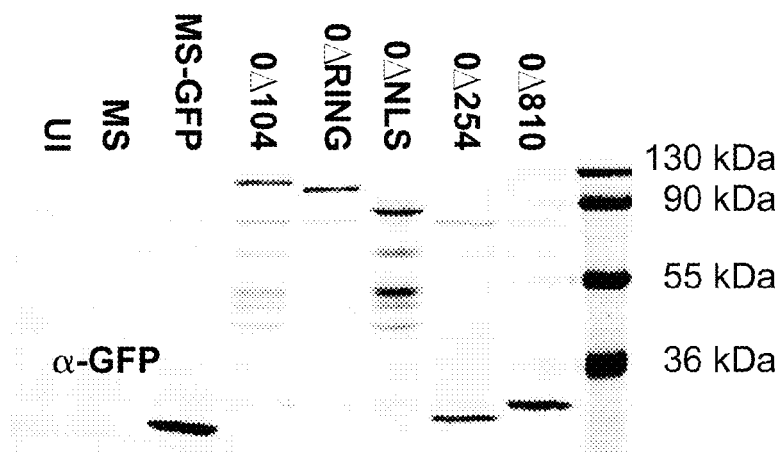

An HSV-2 virus was constructed, HSV-2 0Δ104, in which a region of poorly conserved amino acids was deleted from ICP0 and was replaced with green fluorescent protein (GFP) (FIGS. 15A, 16A). At the nucleotide level, intron 1 and part of exon 2 of the ICP0 gene were replaced in HSV-2 0Δ104 with an in-frame insertion of a GFP coding sequence (FIGS. 15A, 15B). At the protein level, ~240 amino acids of GFP replaced amino acids 19 to 104 of ICP0 (FIGS. 16A, 16B). Based on the lack of disruption of any of the conserved regions of the ICP0 protein, it was assumed that the GFP-tagged ICP0 protein encoded by HSV-2 0Δ104 might retain a significant amount of ICP0's biological activity.

ii. p0Δ125: The plasmid p0Δ125 was derived from p0Δ104 by replacing the DNA sequence between a Bam HI and Pml I restriction site that spanned codons 105 to 162 (bases 124, 055-124,229) with a dsDNA linker that contained codons 126 to 162 and whose DNA sequence was: tttGGATCC ggatgt-gccgtgtgcacggacgagatcgccccgccctgcgctgccagagttttccc-tgc-ctgcaccccttctgcatcccgtgcatgaagacctggattccgttgcgcaaCAC- GTGcatca (SEQ ID NO: 11). The resulting plasmid p0Δ125 possessed an open-reading-frame that encoded amino acids 1 to 18 of HSV-2 ICP0, 238 amino acids of GFP, and amino acids 126 to 825 of ICP0 (not shown).

iii. p0Δ127: The plasmid p0Δ127 was derived from p0Δ104 by replacing the DNA sequence between a Bam HI and Pml I restriction site that spanned codons 105 to 162 (bases 124,055-124,229) with a dsDNA linker that contained codons 128 to 162 and whose DNA sequence was: ttt GGATCCggagtgtgcacggacgagatcgccccgccccctgcgctgccagag-ttttccctgcctgcaccccttctgcatcccgtgcatgaagacctggattccgttgcg-caaCACGTGcatca (SEQ ID NO: 12). The resulting plasmid p0Δ127 possessed an open-reading-frame that encoded amino acids 1 to 18 of HSV-2 ICP0, 238 amino acids of GFP, and amino acids 128 to 825 of ICP0 (not shown).

iv. p0Δ129: The plasmid p0Δ129 was derived from p0Δ104 by replacing the DNA sequence between a Bam HI and Pml I restriction site that spanned codons 105 to 162 (bases 124,055-124,229) with a dsDNA linker that contained codons 130 to 162 and whose DNA sequence was: tttGGATCCggaacg-gacgagatcgccccgccccctgcgctgccagagttttccc-tgcctgcacccttct-gcatcccgtgcatgaagacctggattccgttgcgcaaCACGTGcatca (SEQ ID NO: 13). The resulting plasmid p0Δ129 possessed an open-reading-frame that encoded amino acids 1 to 18 of HSV-2 ICP0, 238 amino acids of GFP, and amino acids 130 to 825 of ICP0 (not shown).

v. p0ΔRING or p0Δ162: The plasmid p0ΔRING (i.e., p0Δ162) was derived from p0Δ104 by deleting the DNA sequence between a Bam HI and Pml I restriction site that spanned codons 105 to 162 (bases 124,055-124,229). The resulting plasmid p0ΔRING possessed an open-reading-frame that encoded amino acids 1 to 18 of HSV-2 ICP0, 238 amino acids of GFP, and amino acids 163 to 825 of ICP0 (FIGS. 15A, 15C).

vi. p0Δ254: The plasmid p0Δ254 was created by replacing the Bam HI to Pst I fragment that spans codons 105 to 254 in p0Δ104 (bases 123,607-124, 300) with the following dsDNA linker, which contained a translational stop: 5'-CCCTG GGATCCCTAGACTAGTCTAGCTGCAGTGGAC-3' (SEQ ID NO: 14). The resulting plasmid p0Δ254 possessed an open-reading-frame that encoded amino acids 1 to 18 of HSV-2 ICP0 and 238 amino acids of GFP (FIGS. 15A, 15C).

vii. p0Δ810: The plasmid p0Δ810 was created by replacing the Not I to Asc I fragment that spans codons 19 to 810 of the HSV-2 ICP0 gene (bases 121,927-124, 893) with a GFP coding sequence flanked by matching Not I and Asc I restriction sites. This GFP coding sequence was generated by PCR amplification off of the template peGFP-N1 (Clontech Laboratories) using the following oligonucleotide primers: Not 1-GFP-a primer: 5'-ccga GCGGCCGCtgagcaagggcgaggagctgt-3' (SEQ ID NO: 9) and Asc I-GFP-b primer: 5'-gcgcg GGCGCGCCcagctcgtccatgccgag-3' (SEQ ID NO: 15). Upon sub-cloning of the PCR-amplified GFP coding sequence into pUC-HSV2-ICP0, the resulting plasmid p0Δ810 possessed an open-reading-frame that encoded amino acids 1 to 18 of HSV-2 ICP0, 238 amino acids of GFP, and amino acids 811 to 825 of ICP0 (FIG. 15A).

viii. p0ΔNLS: The plasmid p0ΔNLS was derived from p0Δ104 by deleting DNA sequence between PpuMI and Xho I restriction sites that spanned codons 489 to 694 (bases 122,280-122,897). The plasmid p0ΔNLS possessed an open-reading-frame that encoded amino acids 1 to 18 of HSV-2 ICP0, 238 amino acids of GFP, amino acids 105 to 488 and amino acids 695 to 825 of ICP0 (FIG. 15A).

ix. p0Δ4BD: The plasmid p0Δ4BD was derived from p0Δ104 by deleting DNA sequence between Xho I and Asc I restriction sites that spanned codons 695 to 810 (bases 121, 922-122,275). The plasmid p0Δ4BD possessed an open-reading-frame that encoded amino acids 1 to 18 of HSV-2 ICP0, 238 amino acids of GFP, amino acids 105 to 694 and amino acids 811 to 825 of ICP0 (FIG. 15A).

x. pΔLAT-2 CMV-luciferase: The precursor plasmid pUC-HSV2-LAT was derived from pUC-HSV2 $R_L$ (UL56) and contained bases 117,071-122,280 of the HSV-2 genome. Mutagenesis steps were taken to replace a portion of the promoter of the LAT gene (bases 119,358-119,531) with a CMV promoter driving a firefly luciferase reporter gene.

xi. pΔLAT-2 CMV-GFP: The precursor plasmid pUC-HSV2-LAT was derived from pUC-HSV2 $R_L$ (UL56) and contained bases 117,071-122,280 of the HSV-2 genome. Mutagenesis steps were taken to replace a portion of the promoter of the LAT gene (bases 119,358-119,531) with a CMV promoter driving a green fluorescent protein (GFP) reporter gene derived from the plasmid vector peGFP-N1 (Clontech Laboratories).

Construction and Isolation of HSV-2 Recombinant Viruses

Infectious HSV-2 DNA was prepared by a protocol that relies upon dialysis to minimize shearing of genome-length HSV-2 DNA; this is a modification of a protocol that was generously provided by Karen Mossman (McMaster University, Hamilton, Ontario). Five 100 mm dishes of Vero cells ($3 \times 10^7$ cells) were inoculated with 2 pfu per cell of HSV-2 strain MS and were incubated overnight at 34° C. After 24 hours, cells were scraped, centrifuged, rinsed with PBS, resuspended in 7.0 ml of 200 mM EDTA pH 8.0, and transferred into a 15 ml conical. Proteinase K (75 μl of 10 mg/ml) and 375 μl of 10% SDS were added to virus-infected cells, and the tube was incubated in a rotisserie (hybridization) oven with slow rotation at 50° C. for 16 hours. Proteins were removed by phenol: chloroform extraction, DNA was transferred into a 0.5-3.0 mL Slide-a-lyzer cassette (10,000 MW cutoff; Pierce Chemical Co., Rockford, Ill.), dialyzed against 0.1× standard saline citrate for 24 hours, aliquoted and frozen at −80° C. until use.

Recombinant HSV-2 viruses were generated by co-transfecting a 60 mm dish containing $8 \times 10^5$ ICP0-complementing L7 cells with: 1.2 μg infectious HSV-2 MS DNA; and 2. 1 μg of each plasmid bearing a GFP⁺ mutant allele of the HSV-2 ICP0 gene. After 6 hours, co-transfection medium was replaced with complete DMEM containing 1% methylcellulose and GFP⁺ plaques were selected on the stage of a TE2000 fluorescent microscope (Nikon Instruments, Lewisville, Tex.). GFP⁺ recombinant viruses were repeatedly passed in ICP0-complementing L7 cells until a uniform population of viruses was obtained that produced 100% GFP⁺ plaques, at which time Southern blot analysis was used to confirm that the anticipated ICP0⁻ mutant allele was transferred into HSV-2.

Western Blot Analysis to Characterize GFP-Tagged, Mutant ICP0 Proteins

Vero cell cultures were established at a density of $3 \times 10^5$ cells per well in 12-well plates, and were infected at an MOI of 2.5 pfu per cell. After 18 hours incubation at 34° C., proteins were harvested using mammalian protein extraction reagent (Pierce Chemical Co., Rockford, Ill.) supplemented with 1 M dithiothreitol and protease inhibitor cocktail set I (Calbiochem, La Jolla, Calif.). After heat denaturation, 20 μg of each protein was resolved in a 10% polyacrylamide gel with a 4% stacking gel, and were transferred to nitrocellulose membranes. Protein blots were blocked in phosphate-buffered saline (PBS) containing 5% nonfat dry milk, and were incubated overnight at 4° C. in PBS+0.1% Tween-20+5% nonfat dry milk containing a 1:1000 dilution of a rabbit polyclonal anti-GFP antibody (Clontech Laboratories Inc.). Following incubation with primary antibody, membranes were washed four times with PBS+0.1% Tween-20 (PBS-T), and were then incubated for 1 hour with a 1:20,000 dilution of goat anti-rabbit IgG conjugated to the infrared fluorescent dye IRDye® 680 (LI-COR Bioscience, Lincoln, Nebr.). Protein blots were washed three times in PBS-T, rinsed in PBS (to remove Tween-20), and were scanned for two-color fluorescence using the Odyssey Infrared imaging system (LI-COR Bioscience). Data were analyzed using Odyssey application software version 3.0.16 (LI-COR Bioscience).

Southern Blot Analysis to Characterize ICP0 Gene in HSV-2 ICP0− Viruses

Cultures of L7 or Vero cells were established at a density of $1.5 \times 10^6$ cells per plate in 60 mm dishes, and inoculated with MOIs of 2.5 pfu per cell for 24 hours at a temperature of 34° C. DNA was isolated, digested with the restriction enzymes Sac I and Stu I, and was separated on 1.2% agarose gels, blotted onto Zeta Probe GT nylon membranes (Biorad Laboratories, Hercules, Calif.), and hybridized with radiolabeled oligonucleotides specific for exon 2 of the HSV-2 ICP0 gene 5'-tgaagg tcgtcgtcagagattcccacctcggtctcctcct-3' (SEQ ID NO: 16) or the GFP coding sequence (5'-atagacgttgtggctgt-tgtagttgtactccagcttgtgc-3' (SEQ ID NO: 17)). Oligonucleotides were end-labeled with [α-$^{32}$P] dATP using terminal deoxynucleotidyl transferase (Promega Corporation, Madison, Wis.) and were hybridized to their target sequence via 16 hours of hybridization at 37° C. in a solution containing 5 ng/ml labeled probe, 7% SDS, 120 mM NaH$_2$PO$_4$, and 250 mM NaCl. Excess probe was removed from membranes by sequential rinses in 0.1× standard saline citrate containing 0.1% SDS. Blots were exposed to phosphor screens, which were scanned and analyzed with a Cyclone PhosphorImager and OptiQuant software (Perkin Elmer, Boston, Mass.).

Inoculation of Mice with HSV-2 Viruses

Female ICR mice or rag2$^{-/-}$ mice were first inoculated with HSV-2 and/or vaccinated at 6- to 10-weeks of age, and were handled in accordance with the NIH Guide for the Care and Use of Laboratory Animals. Female ICR mice were obtained from Harlan Sprague Dawley (Indianapolis, Ind.) and female rag2$^{-/-}$ mice were obtained from Taconic Farms (Germantown, N.Y.).

Prior to viral inoculation by all routes, mice were anesthetized by i.p. administration of xylazine (7 mg/kg) and ketamine (100 mg/kg). Ocular inoculation of female mice with HSV-2 viruses was performed by scarifying the left and right corneas with a 26-gauge needle and by placing 4 µl complete DMEM containing 25,000 pfu/µl virus (100,000 pfu) on each eye. Viral titers in the ocular tear film of mice were determined at times after inoculation by swabbing the ocular surface of both eyes with a cotton-tipped applicator, and transferring the tip into 0.4 ml complete DMEM. Viral titers were determined by a 96-well plate plaque assay on the appropriate cell line cultured in complete DMEM containing 0.5% methylcellulose (i.e., Vero cells for wild-type HSV-2 and ICP0-complementing L7 cells for HSV-2 ICP0− viral mutants). After two to three days, the cell monolayers in these 96-well plates were stained with 20% methanol and 0.1% crystal violet.

Nasal inoculation with HSV-2 viruses was performed by pipetting 5 complete DMEM containing 25,000 pfu/µl of virus (125,000 pfu) into each nasal passage of anaesthetized mice. Footpad inoculation with HSV-2 viruses was performed by injecting 50 µl complete DMEM containing 25,000 pfu/µl of virus (1,250,000 pfu) into the left and/or right rear footpads of anaesthetized mice.

Vaginal inoculation with HSV-2 viruses was performed by first treating female mice on 7 and 3 days prior to vaginal inoculation with subcutaneous injections of 2 mg medoxyprogesterone acetate (Greenstone Ltd., Peapack, N.J.) delivered in a volume of 0.2 ml. Just prior to inoculation, mice were anaesthetized by i.p. administration of xylazine (7 mg/kg) and ketamine (100 mg/kg), the vagina was cleared of mucus by briefly introducing a cotton swab tip into the vagina. Upon removal of the swab, a pipettor was used to deliver 20 µl complete DMEM containing 25,000 pfu/µl of virus (500,000 pfu) into the vagina. Viral titers shed from the vaginas of mice were determined at times after inoculation by introducing a cotton swab tip into the vagina, and then transferring the tip into 0.4 ml complete DMEM. Viral titers were determined by a 96-well plate plaque assay on the appropriate cell line, as described above.

Visualization of Sites of HSV-2 Ms-GFP and Ms-Luciferase Replication in Mice

GFP fluorescence in the eyes of mice infected with HSV-2 ICP0− viruses or HSV-2 MS-GFP was visualized on a Nikon TE2000 inverted fluorescent microscope (Nikon Instruments, Lewisville, Tex.) and an Olympus DP72 digital camera (Olympus America Inc., Center Valley, Pa.). Images were collected at 2× or 4× magnification using identical exposure conditions within a given comparison group, and composite images of mouse faces were created by stitching together photographs that covered the face using Adobe Photoshop graphics editor. (Adobe Systems Incorporated). GFP fluorescence in the eyes and faces of living mice was obtained by placing anaesthetized mice on a petri dish on the stage of the microscope.

Luciferase expression in the face or anogenital regions of mice infected with HSV-2 MS luciferase was visualized by anaesthetizing mice, administering 3 mg of luciferin substrate (Gold Biotechnology, St. Louis, Mo.), and placing mice in an IVIS Lumina II bioluminescent imager (Caliper Life Sciences, Hopkinton, Mass.). Analysis of the resulting bioluminescent images was performed with Living Image version 4.0 software (Xengogen, Carlsbad, Calif.).

Purification of Recombinant HSV-2 gD 306T and GFP for Vaccinations and/or ELISA

The HSV-2 gD coating antigen consisted of amino acids 25 to 331 of the HSV-2 glycoprotein D (gD) protein was produced in Sf9 insect cells infected with a gD-2-expressing baculovirus (generously provided by Gary Cohen and Roslyn Eisenberg, University of Pennsylvania, Philadelphia). Specifically, a 500 ml suspension culture of Sf9 cells containing $1 \times 10^6$ cells per ml was inoculated with $1 \times 10^{10}$ pfu of the recombinant baculovirus gD-2 (306t) to achieve a multiplicity of infection of 2 pfu per cell. The gD-2 306t protein was engineered to allow for rapid and reproducible purification of the protein via: 1. a 25 amino-acid honeybee melittin secretion signal at the N-terminus of gD-2 306t; and 2. a 6 amino-acid His tag (SEQ ID NO: 45) at the C-terminus of gD-2 306t. Therefore, at 96 hours p.i., baculovirus-infected cell cultures were pelleted by centrifugation and the supernatant was collected and dialyzed against an appropriate buffer for purification on a nickel column (20 mM Tris pH 7.5, 300 mM NaCl, 10% glycerol, and 10 mM imidazole). The dialyzed fluid was purified. The purified gD-2 306t protein was eluted from the column buffer, diluted to a final concentration of 250 ng/µl, and frozen in 100 µl aliquots for later use as a recombinant protein subunit vaccine or as a coating antigen for antibody-capture ELISA measurements of gD-specific serum IgG titers in mice.

Comparison of Vaccination with Live HSV-2 Viruses Versus Recombinant Proteins

In comparative vaccination experiments, each mouse was vaccinated on Day 0 by a right, rear footpad injection with 50 µl that contained complete DMEM (no virus), 6.3×10⁵ pfu HSV-2 MS, 6.3×10⁵ pfu HSV-2 0ΔNLS, 2.5 µg recombinant gD-2 306t protein, or 2.5 µg recombinant GFP protein. Protein vaccinations were prepared by combining equal volumes of Imject® Alum (Thermo Scientific, Rockford, Ill.) with 100 ng/µl of: 1. recombinant gD-2 306t protein; or 2. recombinant GFP protein. After 30 minutes of intermittent mixing, the toll-like receptor 4 (TLR4) agonist monophosphorly lipid A (Avanti Polar Lipids, Alabaster, Ala.) was added to each protein-adjuvant mixture to achieve a final concentration of 200 µg per ml. Thus, each 50 µl footpad injection contained 2.5 µg of recombinant protein antigen and 10 µg of the TLR4 agonist monophosphoryl lipid A.

On Day 30, the immune response to each antigen was boosted by a left, rear footpad injection with 50 µl that contained complete DMEM (no virus), 6.3×10⁵ pfu HSV-2 MS, 6.3×10⁵ pfu HSV-2 0ΔNLS, 2.5 µg recombinant gD-2 306t protein, or 2.5 µg recombinant GFP protein. To ensure that 100% of mice survived their primary exposure to HSV-2 MS in the right, rear footpad, HSV-2 MS-vaccinated mice received 1 mg/ml oral acyclovir in their drinking water from Days −3 to +20 post-vaccination. Oral acyclovir was not administered to HSV-2 MS-vaccinated mice upon boosting in the left, rear foot on Day 30.

ELISA Measurement of HSV-2 gD-Specific IgG Titers

Enzyme-linked immunosorbent assay (ELISA) was used to measure HSV-2 gD-specific antibody titers in the serum of mice, as follows. Mice were bled on Day 60 post-vaccination (i.e., 10 days prior to challenge with wild-type HSV-2 MS) by collecting blood from the right retroorbital sinus with heparinized, Natelson blood collecting tubes (Fisher Scientific). The serum fraction was collected from centrifuged mouse blood samples at 18 hours post-collection and frozen at −80° C. until gD-specific IgG titers were determined by ELISA.

High-binding EIA 96-well plates (Costar catalog #9018, Corning, N.Y.) were coated overnight at 4° C. with 100 µl per well of sodium carbonate buffer (pH 9.6) containing 250 ng of recombinant gD-2 306t protein. Wells were blocked for 2 hours with 400 µl of 2% dry milk dissolved in PBS+0.02% Tween-20 (polyoxyethylene-20-sorbitan monolaurate), hereafter referred to as PBS-T buffer. During the protein block of ELISA plates, mouse serum was diluted 1:50 in PBS-FT buffer, which consisted of PBS+1% fetal bovine serum+ 0.02% Tween-20+0.1% sodium azide. After discarding blocking buffer from ELISA plates, duplicate 100-µl samples of 1:50 diluted mouse serum were added to gD-2-coated wells and were incubated overnight at 4° C. ELISA plates were rinsed seven times with an excess of PBS-T buffer prior to the addition of 100 µl of the detection antibody diluted 1:2500 in PBS-T buffer (i.e., antibody alkaline phosphatase-conjugated rabbit anti-mouse γ chain; Rockland Immunochemicals Cat #610-4512, Gilbertsville, Pa.). After allowing 1 hour at room temperature for binding of the detection antibody, plates were rinsed seven times with PBS-T buffer and 200 µl of p-nitrophenyl phosphate (Sigma Chemical Co., St. Louis, Mo.) was added to each well. Colorimetric development ($OD_{405}$) was measured in an ELISA plate reader (Bio-tek Instruments, Inc., Winooski, Vt.), and a standard curve was developed based on dilutions of a strongly positive pool of anti-HSV-2 mouse serum that spanned dilutions of 1:50 to 1:230,000. A hyperbolic tangent-based standard curve of the form x=arctan h (y) was used to calculate gD-specific IgG titer in each serum sample, where the value x was the gD-specific IgG titer that was calculated based on the $OD_{405}$/yellow color (y) that developed in each well. The goodness-of-fit of this standard curve ranged between 0.99 and 1.00, and the useful range of estimation of IgG titers was ~200-fold. The gD-specific IgG titer in each well was multiplied times the dilution-factor, 50, to calculate the gD-specific IgG titer in each serum sample.

Mutagenesis of the HSV-2 ICP0 Gene

A set of four HSV-2 (HSV-2 0ΔRING; HSV-2 0ΔNLS; HSV-2 0Δ254; HSV-2 0Δ810) viruses were constructed as described above in which the ICP0 gene bore two mutations (FIG. 15A). All of these viruses carried the same GFP marker that replaced amino acids 19 to 104 of ICP0. In addition, HSV-2 0ΔRING encoded an ICP0 protein deleted of amino acids 105 to 162 which constitute a critical portion of the RING finger region (FIG. 14A), which is necessary for ICP0's E3 ligase activity. Likewise, HSV-2 0ΔNLS encoded an ICP0 protein deleted of amino acids 489 to 694 which constitute a critical portion of the NLS region (FIG. 14A), which is critical for ICP0's capacity to localize to the nucleus and promote the efficient onset of HSV mRNA synthesis. Finally, HSV-2 0Δ254 and HSV-2 0Δ810 encoded little more than GFP from their mutant ICP0 loci (FIGS. 16A, 16B). Specifically, HSV-2 0Δ254 contained a deletion of codons 105 to 254 followed by a translational stop (FIGS. 15A, 15B); consequently, HSV-2 0Δ254 encoded amino acids 1-18 of ICP0 fused to GFP (FIGS. 16A, 16B). In contrast, HSV-2 0Δ810 contained a deletion of codons 105 to 810 of the ICP0 gene (FIGS. 15A, 15B); and consequently encoded a slightly larger GFP-tagged ICP0 peptide, which included amino acids 811-825 (FIGS. 16A, 16B).

Characterization of the Interferon-Sensitivity of HSV-2 ICP0⁻ Viruses

Figure 17A:
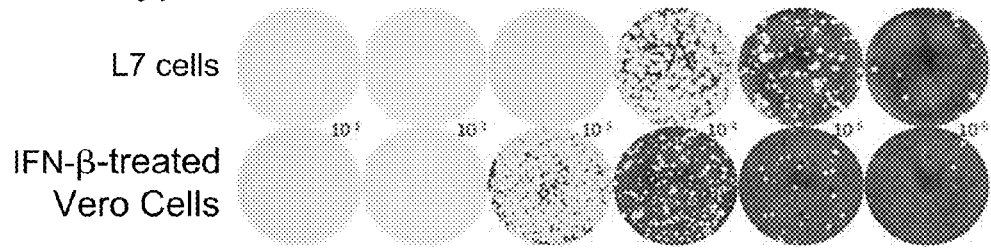
FIGS. 17A-17C show that HSV-2 0ΔRING, HSV-2 0Δ254, HSV-2 0Δ810, and HSV-2 0ΔNLS fail to efficiently form plaques in cells treated with human interferon-β. Representative results illustrating how the interferon-sensitivity of (FIG. 17A) wild-type HSV-2 MS or (FIG. 17B) HSV-2 0ΔNLS may be estimated by comparing the relative efficiency of plaque formation in ICP0-complementing L7 cells relative to Vero cells treated with human inteferon-β.
Figure 17B:
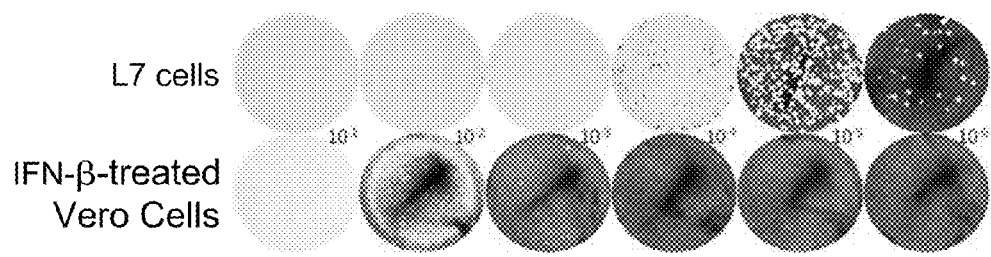
Figure 17C:
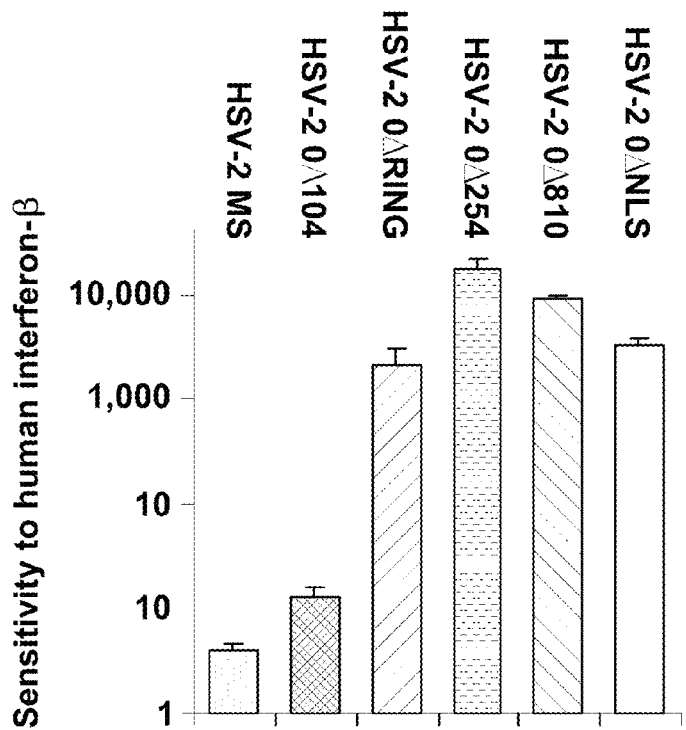

Wild-type HSV-2 ICP0⁻ mutant viruses were compared for their ability to form plaques in monolayers of ICP0-complementing L7 cells versus Vero cells pre-treated with 200 U/ml human interferon-β (FIGS. 17A-17C). This shows the sensitivity of HSV-2 ICP0⁻ viruses to human interferon-β as an index of safety. The interferon sensitivity of each virus was calculated as being equal to the actual titer of a virus stock (i.e., calculated in L7 cells)÷the apparent viral titer based on the efficiency of plaque formation in interferon-β treated Vero cells.

Wild-type HSV-2 MS had an average titer of 5.1×10⁷ pfu/ml in 3 independent plaque assays in ICP0-complementing L7 cells, and formed plaques at a 4±1-fold lower efficiency in interferon-β-treated Vero cells (FIGS. 17A, 17C). These results verified that HSV-2 MS is an inteferon-resistant virus. HSV-2 0ΔNLS had an average titer of 9.5×10⁷ pfu/ml in 4 independent plaque assays in ICP0-complementing L7 cells, and formed plaques at a 3300±600-fold lower efficiency in interferon-β treated Vero cells (FIGS. 17B, 17C). These results indicated that the HSV-2 0ΔNLS mutant virus was highly sensitive to inhibition by human interferon-ft Likewise, similar plaque assay measurements indicated that other HSV-2 ICP0⁻ mutant viruses HSV-2 0ΔRING, HSV-2 0Δ254, and HSV-2 0Δ810 were also highly sensitive to repression by human interferon-β (FIG. 17C). However, HSV-2 0Δ104 virus was interferon-resistant despite the removal of amino acids 19 to 104 from the ICP0 protein (FIG. 17C).

As a second, independent measure of interferon sensitivity, each HSV-2 virus was compared for its ability to produce new infectious virus in ICP0-complementing L7 cells, Vero cells, or interferon-β-treated Vero cells (FIGS. 18A-18F). This shows the sensitivity of HSV-2 ICP0⁻ viruses to human interferon-β as an index of safety. Wild-type HSV-2 grew to 6-fold lower titers in interferon-β treated Vero cells relative to ICP0-complementing cells L7 cells (FIG. 18A). HSV-2 0Δ104 grew to 100-fold lower titers in interferon-treated Vero cells relative to L7 cells (FIG. 18B). By contrast, the other HSV-2 ICP0⁻ viruses HSV-2 0ΔRING, HSV-2 0Δ254, HSV-2 0Δ810, and HSV-2 0ΔNLS were far more interferon-sensitive and grew to titers that were 5,000- to 31,000-fold lower in interferon-treated Vero cells relative to L7 cells (FIGS. 18C-18F). Therefore, synthesis of a functional ICP0 protein was essential for HSV-2 to sustain its ability to replicate in interferon-activated cells.

HSV-2 ICP0⁻ Viruses are Highly Attenuated in their Ability to Cause Disease in Mice Wild-type HSV-2 and HSV-2 ICP0⁻ mutant viruses were compared for their ability to replicate and cause disease in mice following inoculation of the right eye (FIGS. 19A-19D). These figures demonstrate that HSV-2 ICP0⁻ viruses replicate but do not cause disease. Mice were inoculated with 100,000 pfu/right eye of wild-type HSV-2 MS, HSV-2 0Δ104, HSV-2 0Δ254, HSV-2 0Δ810, or HSV-2 0ΔNLS. Mice inoculated with HSV-2 MS were untreated or were treated with the antiviral drug acyclovir (ACV) to reduce HSV-2's ability to spread and cause disease in animals.

Figure 19A:
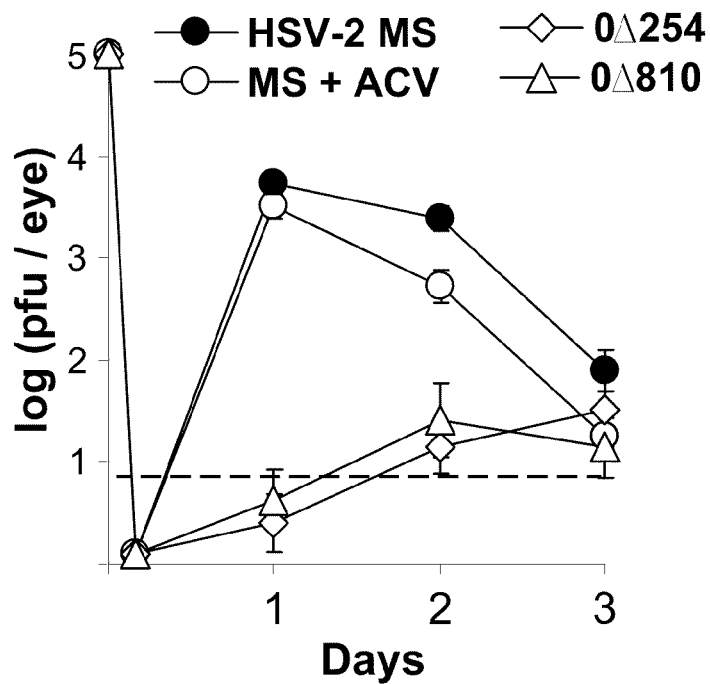
FIGS. 19A-19D show that HSV-2 0ΔRING, HSV-2 0Δ254, HSV-2 0Δ810, and HSV-2 0ΔNLS exhibit limited replication in mice without producing disease.
Figure 19B:
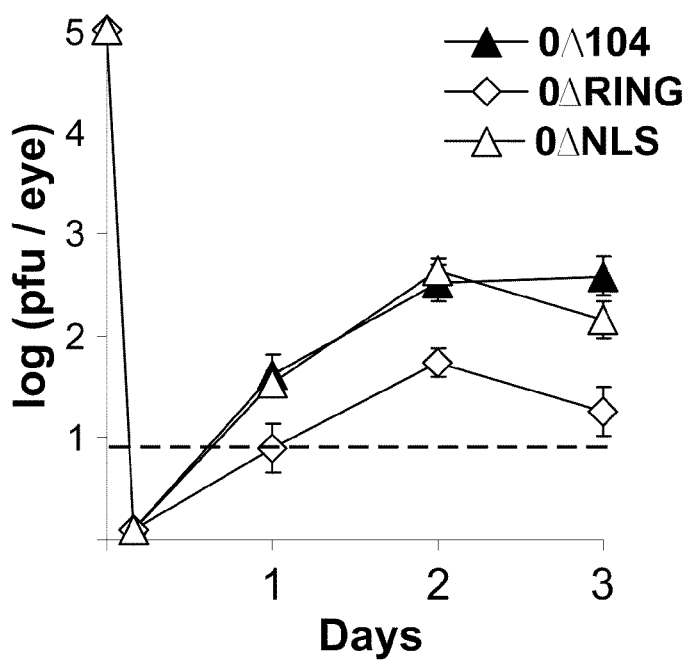

Mice inoculated with HSV-2 MS shed>1,000 pfu from the right eye at 24 and 48 hours post-inoculation (p.i.), and treatment with ACV only modestly reduced this level of viral shedding (FIG. 19A). In contrast, null mutations in the ICP0⁻ gene grossly attenuated HSV-2 0Δ254 and HSV-2 0Δ810 replication, such that mice inoculated with these viruses shed less than 30 pfu per eye at 24, 48, or 72 hours p.i. (FIG. 19A). More conservative mutations within the ICP0 gene that only excised portions of ICP0 resulted in more modest reductions in HSV-2 shedding. Specifically, mice inoculated with HSV-2 0Δ104, HSV-2 0ΔRING, or HSV-2 0ΔNLS shed 10- to 100-fold less virus at 24 and 48 hours p.i. relative to mice inoculated with wild-type HSV-2 MS (FIG. 19B versus 19A).

Figure 19C:
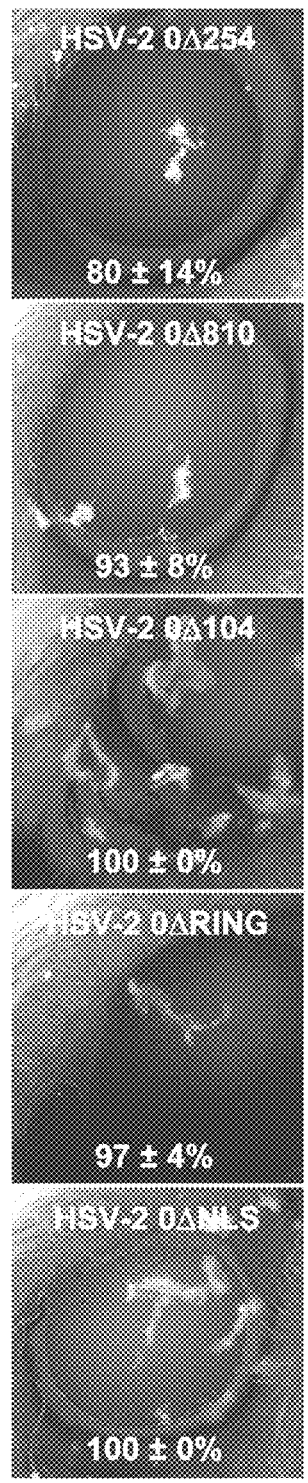

Fluorescent microscopic analysis was performed on mouse eyes inoculated with HSV-2 ICP0⁻ viruses at 60 hours p.i. to determine if the GFP-tagged ICP0 proteins expressed by each virus could be visualized (FIG. 19C). Sites of active HSV-2 replication were visualized in most eyes based on the presence of tracts of GFP⁺ cells in mouse corneas (FIG. 19C). However, only eyes inoculated with HSV-2 0Δ104 or HSV-2 0ΔNLS consistently showed evidence of viral replication in 100% of the n=25 mice tested in this manner (FIG. 19C).

Figure 19D:
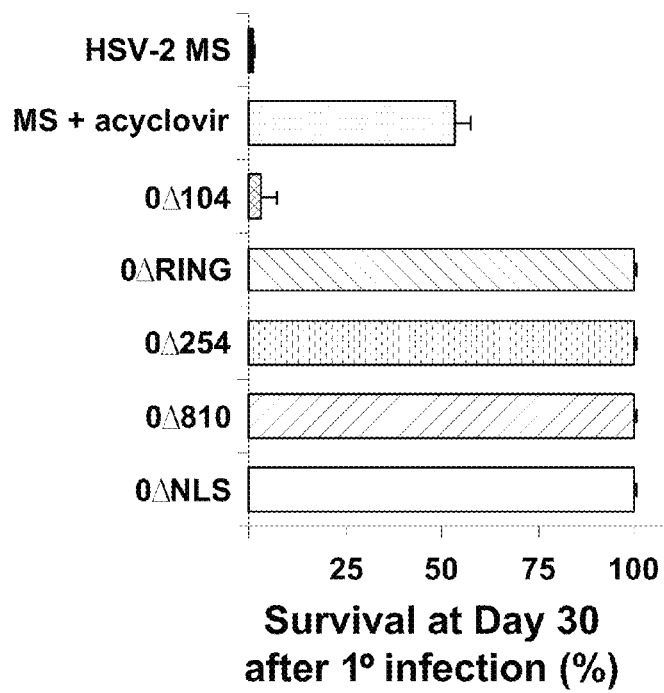

The frequency of survival of HSV-2 infected mice was compared at Day 30 p.i. Among mice inoculated with HSV-2 MS that were not treated with acyclovir, 0 of 25 mice survived (FIG. 19D). Treatment with high doses of acyclovir reduced mortality, but only 16 of 25 survived (FIG. 19D). The only HSV-2 ICP0⁻ mutant virus that was interferon-resistant, HSV-2 0Δ104, proved lethal and thus 0 of 25 mice survived ocular inoculation with HSV-2 0Δ104 (FIG. 19D). In contrast, each of the HSV-2 ICP0⁻ mutant viruses that was interferon-sensitive proved to be avirulent in animals. Specifically, 100% of the n=25 mice per group survived inoculation of the right eye with HSV-2 0ΔRING, HSV-2 0Δ254, HSV-2 0Δ810, or HSV-2 0ΔNLS (FIG. 19D), and these mice showed no visible signs of disease associated with the low-level HSV-2 infection that had occurred in the right eye.

Animals Exposed to HSV-2 0ΔNLS Acquire Immunity to Wild-Type HSV-2

For reference, the duration of survival of naïve mice following inoculation in the eyes with HSV-2 MS is shown (FIG. 20A). Based on many experiments, we have observed that 0% of HSV-2 MS-infected mice survive ocular inoculation unless they are treated with high doses of the antiviral drug acyclovir for the first 3 weeks after inoculation (FIGS. 19D, 20A). Secondly, the kinetics of disease onset and progression to death are highly reproducible following ocular inoculation with 100,000 pfu/eye of HSV-2 MS applied to the scarified corneas; mice inoculated in this manner consistently died between 6 and 8 days post-challenge with HSV-2 MS (FIG. 20A).

Figure 20C:
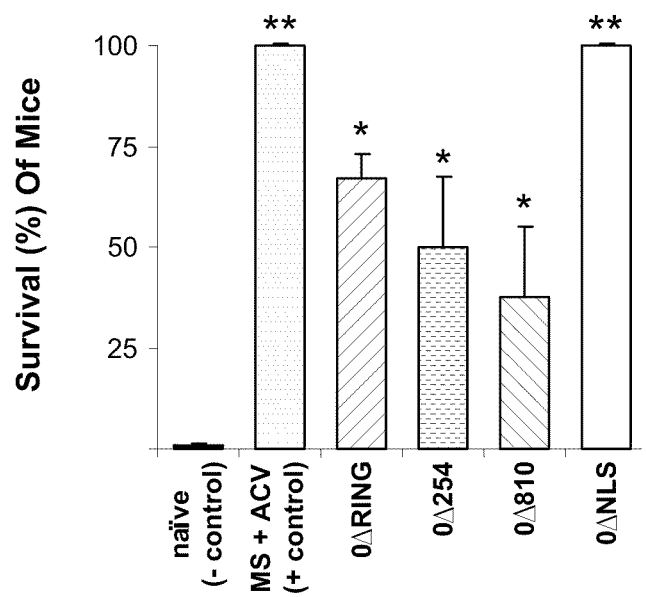
FIGS. 20A-20B show that mice exposed to HSV-2 MS (+ACV), HSV-2 0ΔRING, HSV-2 0Δ254, HSV-2 0Δ810, or HSV-2 0ΔNLS in the right eye are protected to varying degrees 70 days later against exposure to wild-type HSV-2 MS in the left eye.

On Day 70 after the initial exposure of mice to avirulent HSV-2 ICP0⁻ viruses in the right eye, these mice were secondarily challenged in the left eye with a lethal dose of HSV-2 MS (FIGS. 20B, 20C). As expected, 0 of 16 naïve control mice survived lethal ocular challenge with HSV-2 MS (FIGS. 20B, 20C). Also as expected, mice that survived a first exposure to HSV-2 MS in the right eye (with the aid of acyclovir, ACV) had acquired immunity to HSV-2, and thus 16 of 16 of these "MS+ACV" positive-control mice survived a second exposure to HSV-2 MS in the left eye (FIG. 20C). A first exposure to any of the HSV-2 ICP0⁻ viruses elicited some level of protection to lethal challenge with HSV-2 MS in the left eye (FIG. 20C). However, only exposure to HSV-2 0ΔNLS protected 16 of 16 mice challenged, and afforded a sufficiently high level of protection that most of the n=16 mice showed no symptoms of disease between 0 and 30 days post MS-challenge (FIGS. 20B, 20C).

FIGS. 20A-20C show that HSV-2 ICP0⁻ viruses can elicit protection against death caused by later exposure to the wild-type HSV. Based on this initial characterization, HSV-2 0ΔNLS became the focus of further studies to determine if this virus exhibited a safety and efficacy profile that was consistent with the properties of a live, attenuated viral vaccine strain.

Infection of HSV-2 0ΔNLS is Highly Attenuated Relative to Wild-Type HSV-2

Figure 21A:
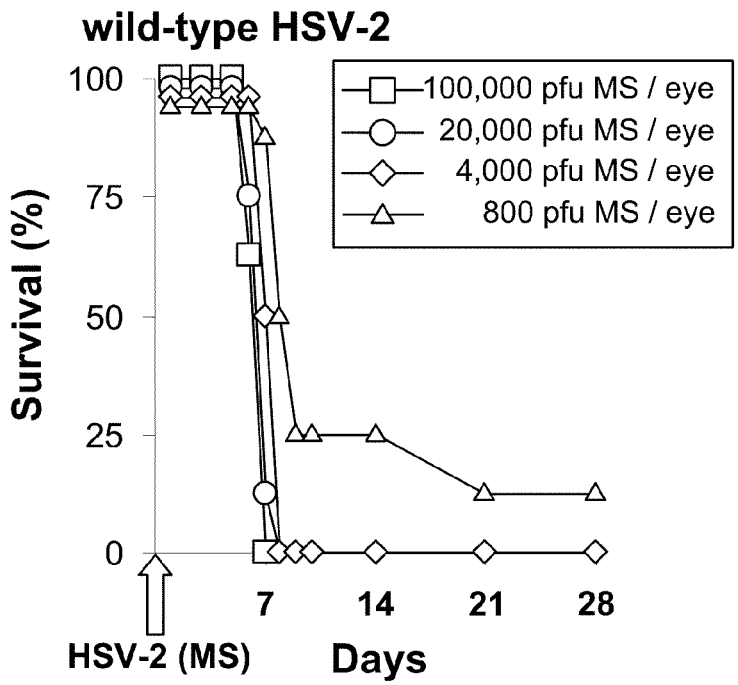
FIGS. 21A-21B show that HSV-2 0ΔNLS is grossly attenuated in its potential to cause ocular disease and/or death in immunocompetent ICR mice relative to wild-type HSV-2 MS.
Figure 21B:
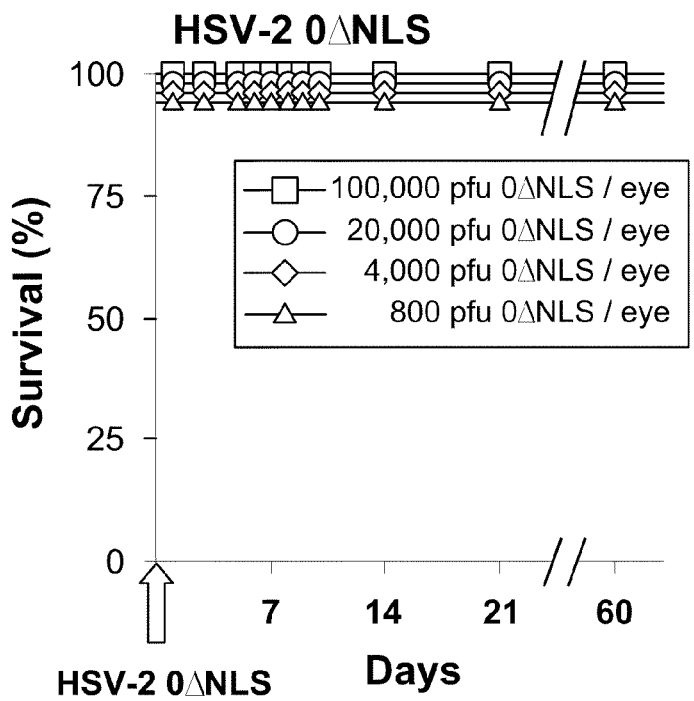

Wild-type HSV-2 and an ICP0⁻ mutant virus, HSV-2 0ΔNLS, were compared for their ability to replicate and cause disease in mice following inoculation of both the left and right eyes (FIGS. 21A-21B). These figures show that doses of 800 pfu per eye or higher of wild-type HSV-2 MS (ICP0⁺) are lethal in mice, whereas doses up to 100,000 pfu per eye of HSV-2 0ΔNLS does not cause disease. As such, FIGS. 21A-21B show that 100,000 pfu of HSV-2 0ΔNLS produces less disease than 800 pfu wild-type HSV-2. Nearly all mice inoculated with 0.8, 4, 20, or 100 thousand pfu/eye of wild-type HSV-2 shed high levels of virus between 1 and 3 days p.i. (not shown), and the infection was lethal in 31 of 32 infected mice (FIG. 21A). In contrast, all mice inoculated with 0.8, 4, 20, or 100 thousand pfu/eye of HSV-2 0ΔNLS did not develop symptoms at any point between 1 and 60 days p.i., and thus 32 of 32 infected animals survived ocular inoculation with HSV-2 0ΔNLS (FIG. 12B). HSV-2 0ΔNLS did not replicate to detectable levels in the eyes of mice inoculated with 800 or 4000 pfu/eye, but did replicate to detectable levels in the eyes of mice inoculated with 20,000 or 100,000 pfu/eye of HSV-2 0ΔNLS (not shown). Thus, consistent with previous HSV-1 findings, the minimum dose of HSV-2 ICP0⁻ mutant virus required to establish a robust infection in mouse eyes was ~100-fold higher than for wild-type HSV-2.

Figure 22A:
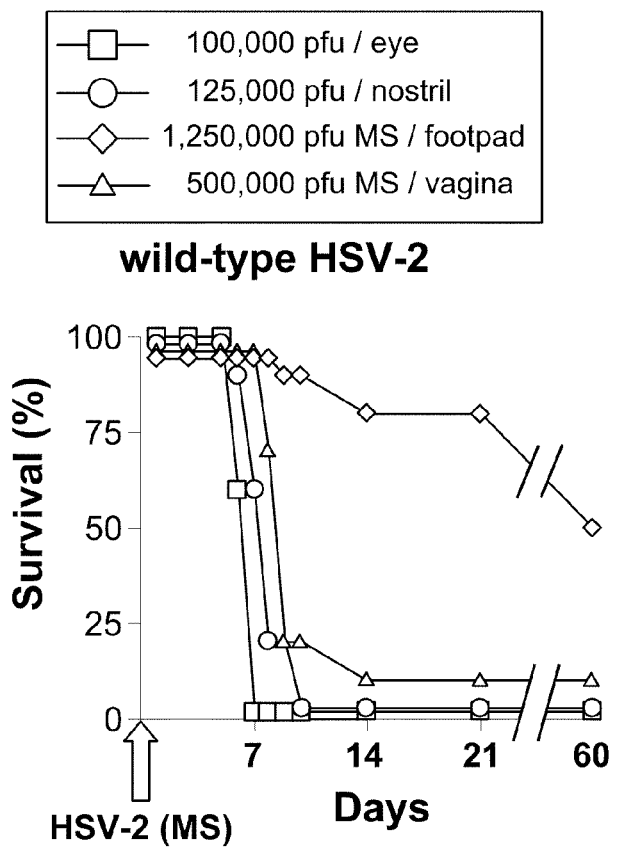
FIGS. 22A-22B show that HSV-2 0ΔNLS is grossly attenuated in its potential to cause disease and/or death relative to wild-type HSV-2 MS following inoculation of the eyes, nose, rear footpads, or vagina. Duration of survival of naïve mice following inoculation with equivalent doses of (FIG. 22A) HSV-2 MS or (FIG. 22B) HSV-2 0ΔNLS that were delivered to either the left and right eyes, left and right nostrils, both rear footpads, or the vagina.
Figure 22B:
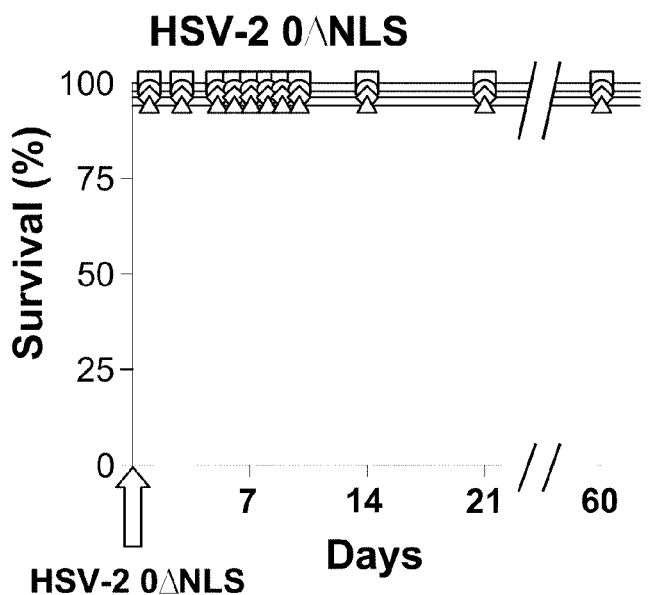
Figure 23A:
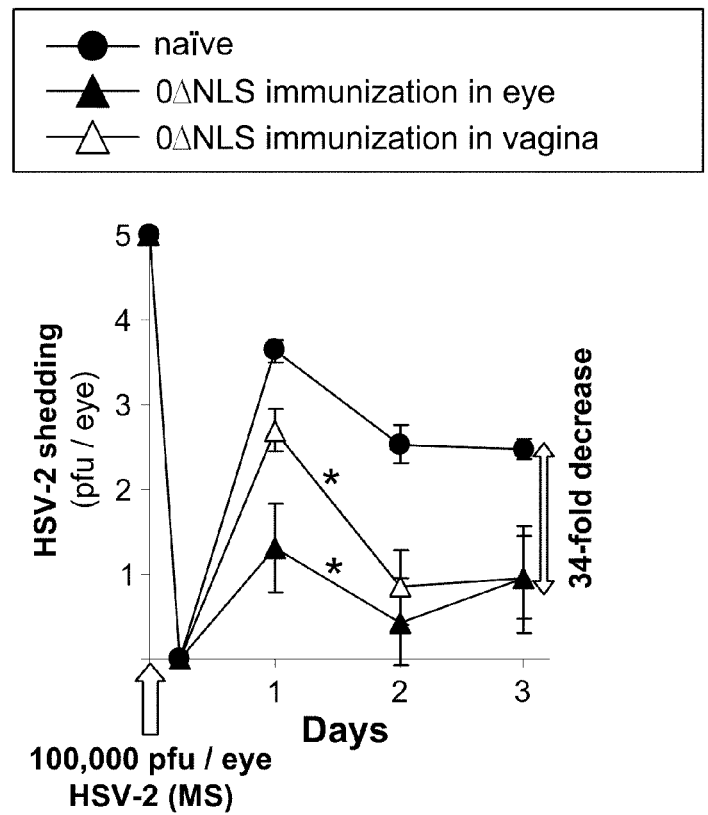
FIGS. 23A-23D show that mice exposed to HSV-2 0ΔNLS acquire systemic immunity to ocular or genital herpes. On Day 70 after exposure to HSV-2 0ΔNLS in the eyes, nose, feet, or vagina, mice were divided into two groups and challenged with either (FIG. 23A, FIG. 23C) 100,000 pfu/eye of HSV-2 MS applied to the left and right eyes or were challenged with (FIG. 23B, FIG. 23D) 500,000 pfu/vagina of HSV-2 MS.
Figure 23B:
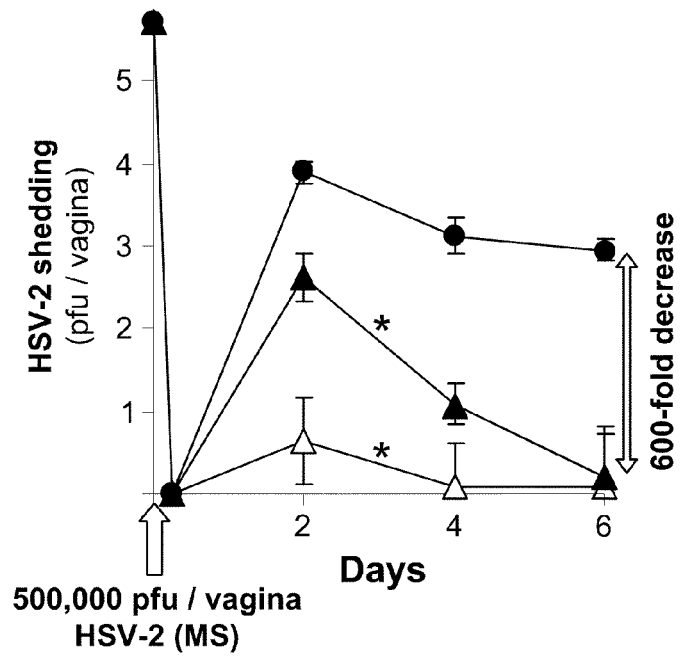
Figure 23C:
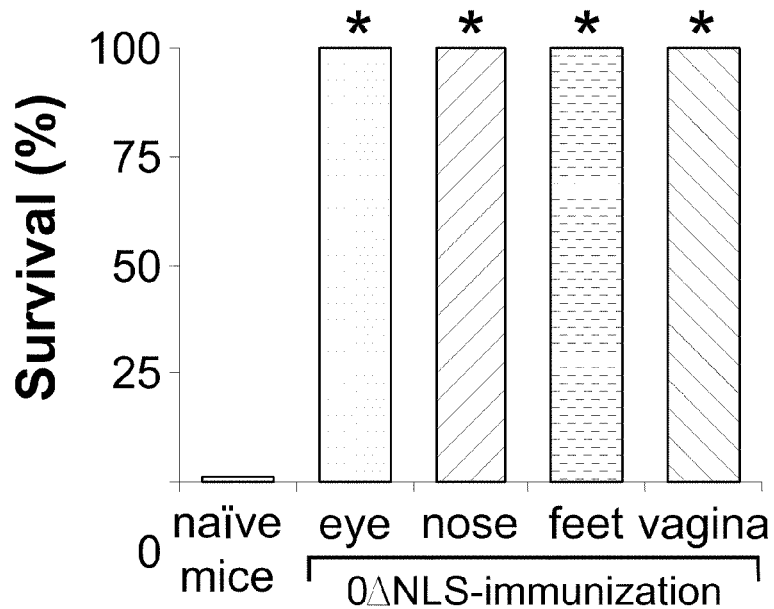
Figure 23D:
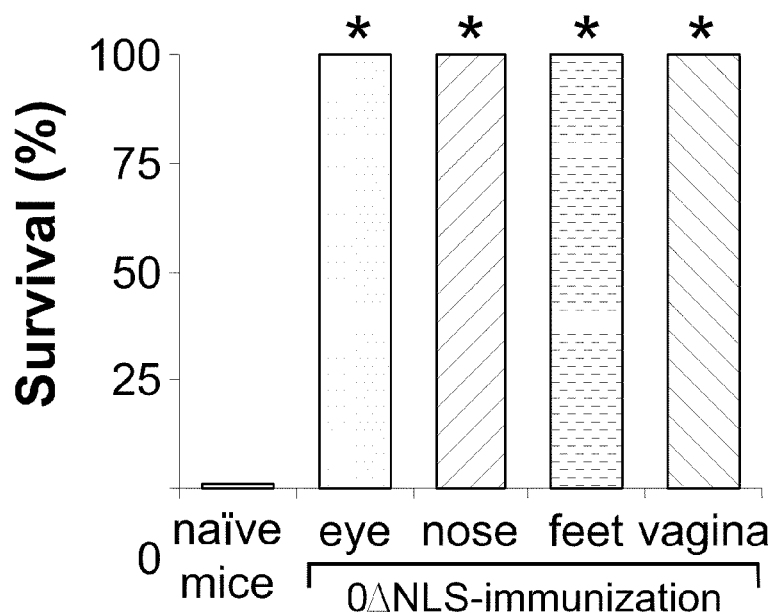
Figure 24A:
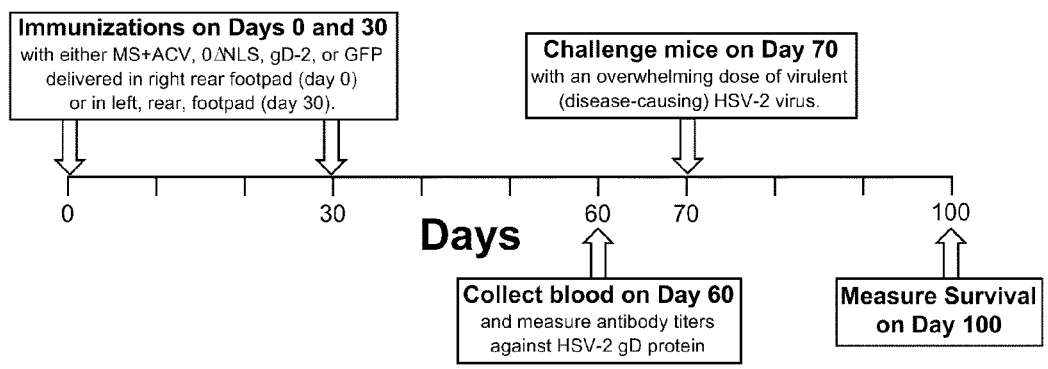
FIG. 24A shows a timeline for an immunization and subsequent challenge.
Figure 24B:
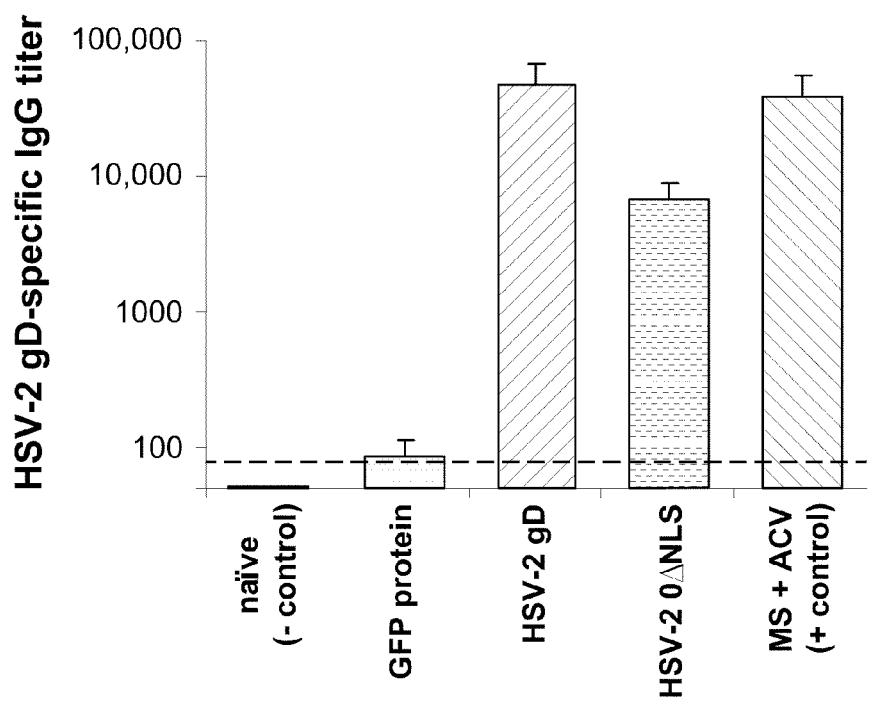
FIG. 24B shows evidence of immunogenicity of the HSV-2 0ΔNLS virus and HSV-2 gD protein subunit vaccines, and the results of ELISA tests to measure the titer of HSV gD-specific antibodies present in mouse serum on Day 60 following an initial vaccination of the right foot on Day 0, which was followed by a booster immunization delivered to the left foot on Day 30. These same groups of mice were used in the challenge experiments presented in FIGS. 25 and 26.

Wild-type HSV-2 and the ICP0⁻ mutant virus HSV-2 0ΔNLS were compared for their ability to cause disease in mice inoculated with overwhelming doses of virus by 1 of 4 routes of infection: i. left and right eyes, ii. left and right nasal passages, iii. left and right rear footpads, or iv. the vagina (FIGS. 22A-22B). FIGS. 22A-22B show that HSV-2 0ΔNLS does not produce disease following inoculation of eyes, nose, feet, or vagina. All mice inoculated in the eyes or nasal passages with HSV-2 MS rapidly succumbed to the infection (n=10 mice per group). The pathogenesis of HSV-2 MS vaginal challenge developed more slowly, and 1 of 10 mice survived HSV-2 MS vaginal challenge (FIGS. 22A-22B). Intriguingly, the pathogenesis of HSV-2 MS infection was greatly delayed when the rear footpads of mice were the site of inoculation, and 50% of the animals survived until Day 60 p.i. (FIGS. 22A-22B). The fact that the pathogenesis of HSV-2 MS infection could be reduced simply by using a different route of inoculation was exploited in later HSV-2 vaccine-challenge experiments.

Figure 25A:
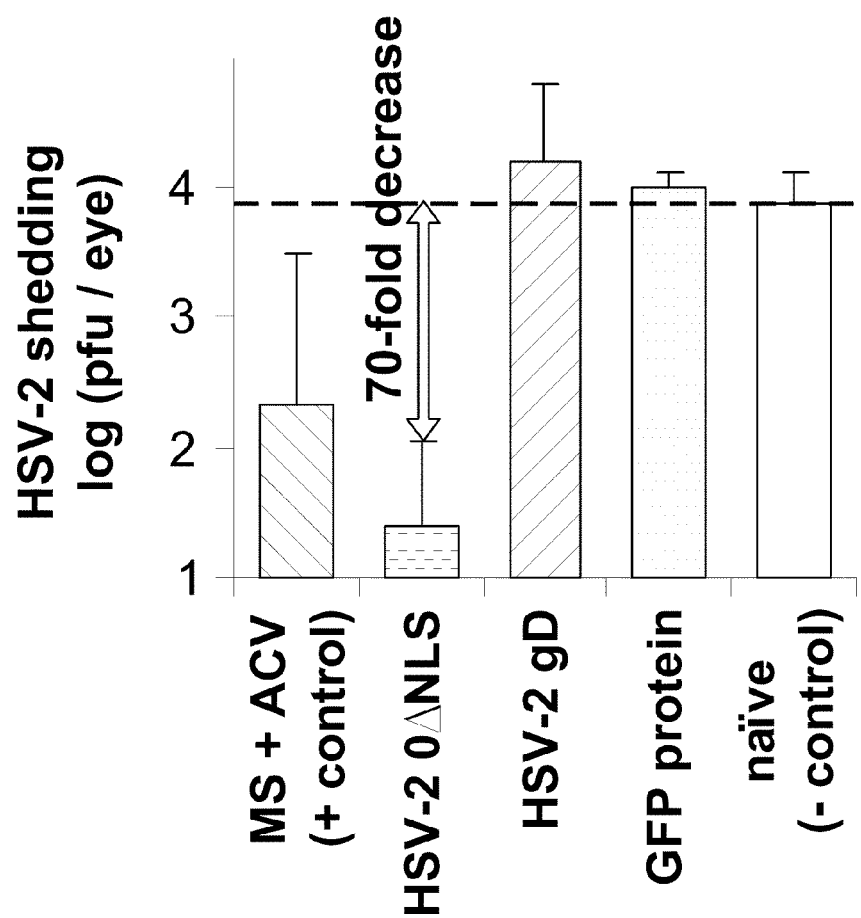
FIG. 25A-25C show that mice exposed to HSV-2 0ΔNLS virus, but not HSV-2 gD protein, acquire potent immunity to the spread of a 'glowing' HSV-2 MS luciferase virus from an ocular site of challenge. On Day 70 relative to the initial day of vaccination of the right, rear footpad with either HSV-2 MS (plus oral acyclovir to prevent disease), HSV-2 0ΔNLS virus, gD protein, an irrelevant GFP protein, or complete DMEM, mice were challenged with 100,000 pfu/eye of HSV-2 MS luciferase applied to both the left and right eyes.
Figure 25B:
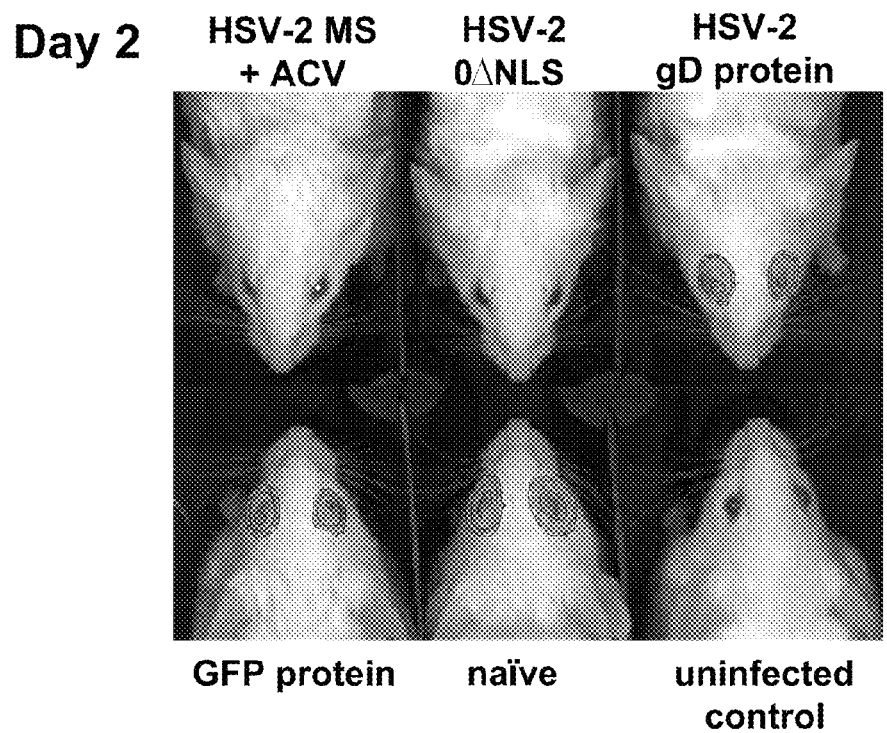
Figure 25C:
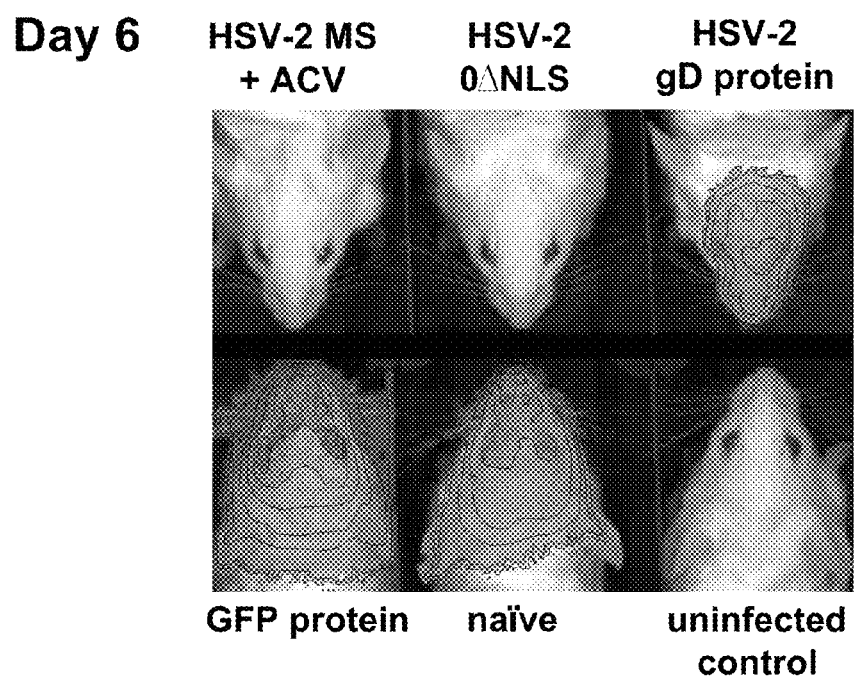

In contrast, none of the n=40 mice inoculated with HSV-2 0ΔNLS developed overt symptoms of disease between 1 and 60 days p.i. regardless of which route was used to introduce the HSV-2 0ΔNLS virus into the body (n=10 mice per group; FIG. 22B). Therefore, it was concluded that the specific mutation of the HSV-2 ICP0 gene contained in the HSV-2 0ΔNLS virus resulted in a severe attenuation of HSV-2's normal capacity to cause disease in animals. Thus, FIGS. 22A-22B show that wild-type HSV-2 MS (ICP0$^+$) is lethal in mice when delivered by any 1 of the 4 routes, whereas HSV-2 0ΔNLS does not cause disease in any of these routes.

HSV-2 0ΔNLS Vaccination Elicits Systemic Protection Against Ocular or Genital Herpes An HSV-2 challenge experiment was conducted to determine if animals exposed to HSV-2 0ΔNLS in the eyes, nose, rear footpads, or vagina acquired protective immunity to subsequent exposures to a lethal challenge with the wild-type HSV-2 MS virus (see FIG. 24A). It is possible that animals exposed to HSV-2 0ΔNLS in the eyes might only acquire immunity against ocular herpes disease caused by re-infection of the same site with HSV-2 MS. Alternatively, it is possible that animals exposed to HSV-2 0ΔNLS in the eyes, nose, feet, and vagina might all acquire immunity against ocular herpes disease because the history of immunology suggests that most effective vaccines elicit a protective immune response that is systemic in nature. Under this latter hypothesis, it might also be predicted that animals exposed to HSV-2 0ΔNLS in the eyes, nose, feet, and vagina would all acquire immunity against genital herpes disease following HSV-2 MS challenge of the vagina.

These predictions were tested on Day 70 relative to the time that mice were first exposed to HSV-2 0ΔNLS in the eyes, nose, feet, or vagina. On Day 70 post-vaccination, 0ΔNLS-vaccinated mice were divided into two groups that were either challenged with 100,000 pfu/eye of HSV-2 MS (FIGS. 23A, 23C) or were challenged with 500,000 pfu/vagina of HSV-2 MS (FIGS. 23B, 23D).

In the ocular HSV-2 challenge experiment, naïve control mice shed an average 3000 pfu/eye of HSV-2 MS at 24 hours post-challenge (FIG. 23A) and 0 of 10 naïve mice survived beyond 8 days p.i. (FIG. 23C). Quantitatively, there was a site-specific difference in the rapidity of immunity to HSV-2 MS challenge depending on the site of 0ΔNLS vaccination. Specifically, mice first exposed to 0ΔNLS in the eyes shed ~300-fold less HSV-2 MS at 24 hours post-challenge, whereas mice first exposed to 0ΔNLS in the vagina shed ~10-fold less HSV-2 MS at the same time point (FIG. 23A). However, these differences dissipated by days 2 and 3 post-challenge (FIG. 23A) and 20 of 20 0ΔNLS-vaccinated mice survived HSV-2 MS ocular challenge regardless of the specific anatomic site of vaccination (eyes, nose, feet, or vagina in FIG. 23C).

In the vaginal HSV-2 challenge experiment, equivalent results were obtained (FIGS. 23B, 23D). More specifically, naïve control mice shed an average 8000 pfu/vagina of HSV-2 MS at 48 hours post-challenge (FIG. 23B) and 0 of 10 naïve mice survived beyond 14 days p.i. (FIG. 23D). Mice first exposed to 0ΔNLS in the eyes shed ~20-fold less HSV-2 MS at 48 hours post-challenge, whereas mice first exposed to 0ΔNLS in the vagina shed ~1000-fold less HSV-2 MS at the same time point (FIG. 23B). However, these differences dissipated by days 4 and 6 post-challenge (FIG. 23B) and 20 of 20 0ΔNLS-vaccinated mice survived HSV-2 MS vaginal challenge regardless of the specific anatomic site of vaccination (eyes, nose, feet, or vagina in FIG. 23D).

These results provided a statistically robust argument that supported two conclusions: 1. It is possible via mutagenesis of the ICP0 gene to attenuate HSV-2 in a manner that would yield a live viral vaccine strain that is as safe, or likely safer, than other live viral vaccines that are currently administered to millions of children each year in doctor's offices; and 2. Recipients of a live HSV-2 $ICP0^-$ viral vaccine are protected against diseases caused by wild-type HSV-2. Thus, mice that receive HSV-2 0ΔNLS are resistant to ocular or genital herpes caused by wild-type HSV-2 MS regardless of the site of HSV-2 0ΔNLS vaccination.

Antibodies Against HSV-2's Attachment and Entry Protein, Glycoprotein D (gD)

FIG. 24A shows a timeline for immunizations and challenges. The results of ELISA (enzyme-linked immunosorbent assay) analysis indicated that mice vaccinated with a gD protein subunit, HSV-2 0ΔNLS, or HSV-2 MS all mounted a robust serum IgG antibody response against HSV-2's gD protein that was at least 50 times the lower limit of detection of the assay (FIG. 24B). The HSV-2 gD protein vaccination elicited a gD-specific antibody response that was at least 10 times higher than HSV-2 0ΔNLS (FIG. 24B). However, it is relevant to bear in mind that HSV-2 encodes ~75 other proteins that may also be necessary to elicit protective immunity against HSV-2. While the live HSV-2 viruses 0ΔNLS and MS encode all of HSV-2's proteins and may elicit an immune response against these antigens, mice immunized with HSV-2 gD are exposed to <2% of HSV-2's potential antigens. Further studies will be required to determine if HSV-2 0ΔNLS's capacity to elicit a B and T cell response against all of HSV-2's proteins is relevant in explaining why a live, attenuated HSV-2 virus elicits superior protection against diseases caused by wild-type HSV-2. Thus, mice that receive HSV-2 0ΔNLS vaccine, HSV-2 MS, and acyclovir control treatment, or HSV-2 glycoprotein D (gD) protein subunit vaccine all possessed serum IgG antibodies against one of the HSV-2 major antigens, the gD protein, and may be useful in immunogenic compositions.

HSV-2 0ΔNLS Vaccination Against Ocular and Genital Herpes

1. Ocular Herpes Challenge

On Day 70 post-vaccination, mice that received 1 of 5 treatments were compared for their ability to resist the replication and spread of HSV-2 MS luciferase following challenge with 100,000 pfu/eye (FIGS. 25A-25C). Naïve control mice shed an average 8000 pfu/eye of virus at 24 hours post-challenge (FIG. 25A). Vaccination with either GFP or HSV-2 gD proteins had no significant effect on the amount of HSV-2 challenge virus shedding from eyes at 24 hours post-challenge (FIG. 25A). In contrast, footpad vaccination with the live viruses, HSV-2 MS or HSV-2 0ΔNLS, was associated with an average ~70-fold decrease in HSV-2 challenge virus shedding at 24 hours post-challenge (FIG. 25A). The "glow" is shown as stipple in FIGS. 25B-25C, with more stipple density meaning more glow, and hence more viral infection.

This same trend was observed at 48 and 144 hours post-challenge when animals were injected with the luciferin substrate to track the spread of HSV-2 MS luciferase away from the initial site of challenge, the left and right eyes (FIGS. 25B, 25C). Specifically, vaccination with either GFP or HSV-2 gD proteins did not significantly alter HSV-2 MS luciferase spread as estimated by the distribution of luciferase enzyme in the eyes/faces of mice at 2 or 6 days post-challenge (FIGS. 25B, 25C). In contrast, vaccination with 2 shots of HSV-2 MS or HSV-2 0ΔNLS (in the rear footpads) completely prevented the spread of HSV-2 MS luciferase away from the site of challenge, the left and right eyes of mice. Consequently, HSV-2 MS luciferase did not cause disease or death in mice vaccinated with HSV-2 MS or HSV-2 0ΔNLS. In contrast, all naïve mice, GFP-vaccinated mice, and gD-vaccinated mice succumbed to the 'glowing' HSV-2 challenge virus, MS-luciferase. Thus, HSV-2 0ΔNLS vaccinated mice are far more resistant to spread of "glowing" HSV-2 MS luciferase from the initial site of challenge relative to mice vaccinated with HSV-2 glycoprotein D (gD) subunit vaccine.

2. Genital Herpes Challenge

Figure 26A:
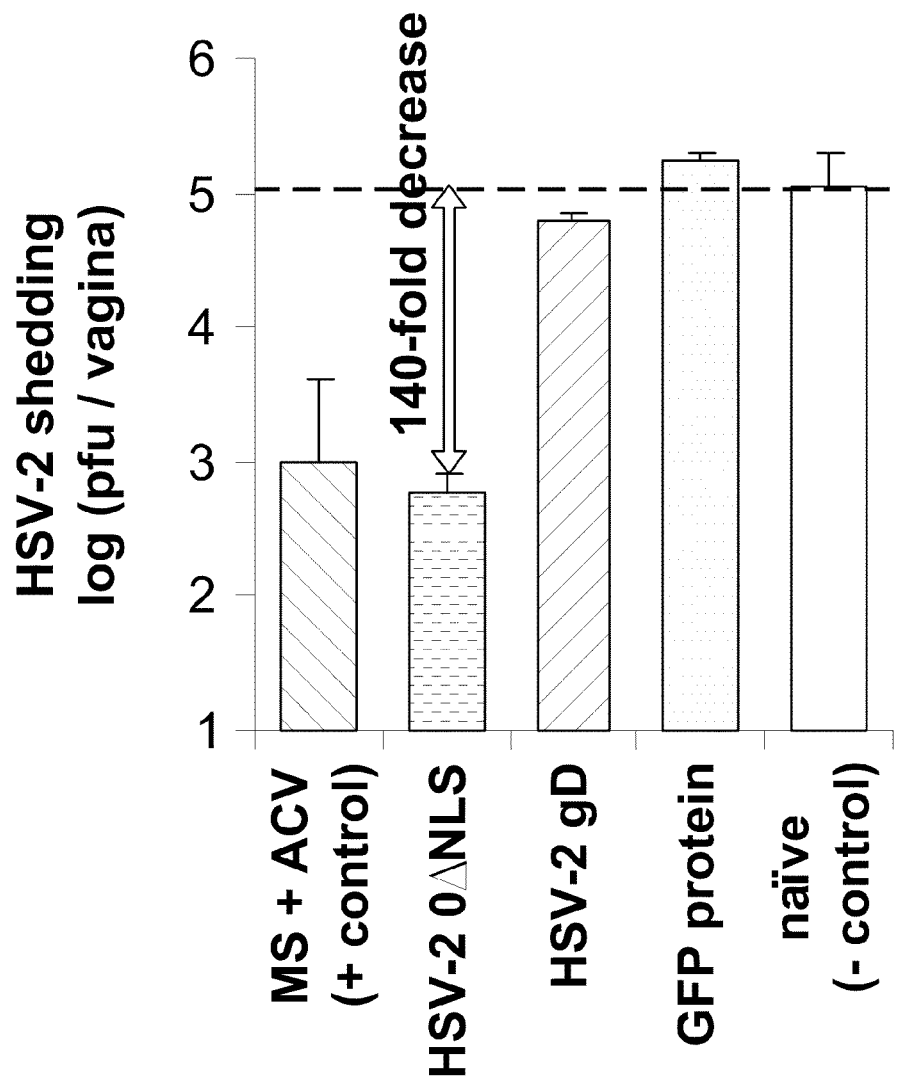
FIGS. 26A-26C show that mice exposed to HSV-2 0ΔNLS virus, but not HSV-2 gD protein, acquire potent immunity to the spread of a 'glowing' HSV-2 MS luciferase virus from a genital site of challenge. On Day 70 relative to the initial vaccination of the right, rear footpad with either HSV-2 MS (plus oral acyclovir to prevent disease), 0ΔNLS virus, gD protein, an irrelevant GFP protein, or complete DMEM, mice were challenged with 500,000 pfu/vagina of HSV-2 MS-luciferase delivered in a volume of 20 µl into the vagina.
Figure 26B:
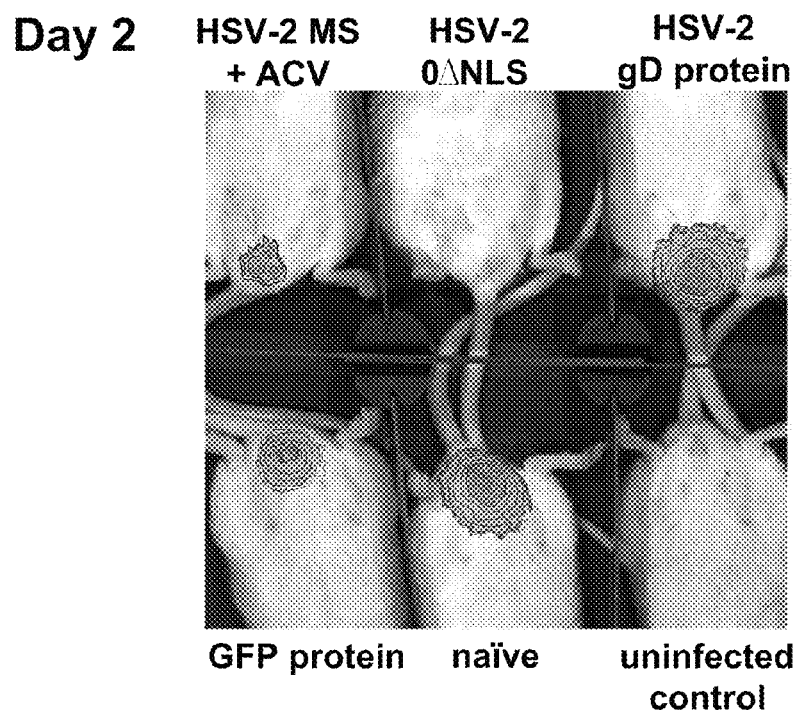
Figure 26C:
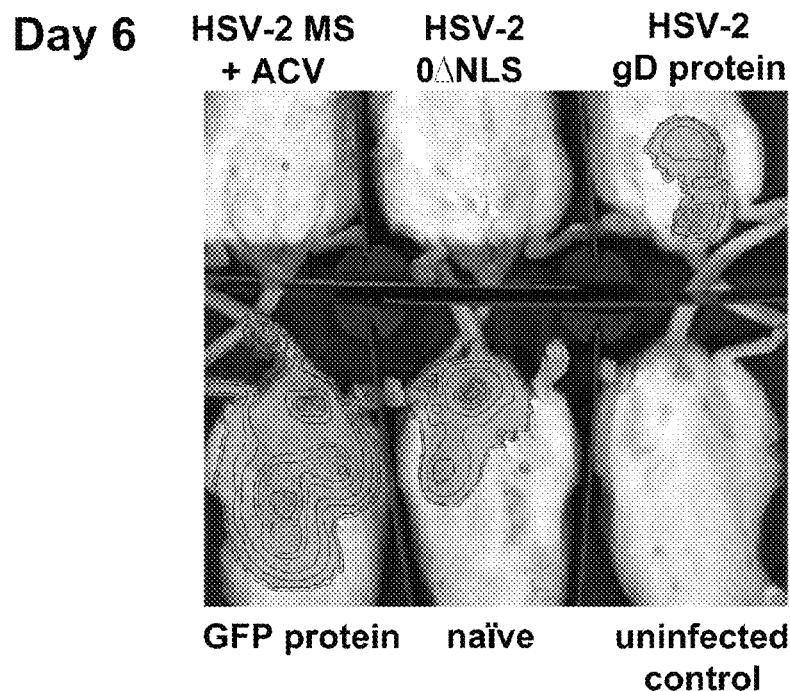

On Day 70 post-vaccination, mice that received 1 of 5 treatments were compared for their ability to resist the replication and spread of HSV-2 MS luciferase following challenge with 500,000 pfu/vagina (FIGS. 26A-26C). Naïve control mice shed an average 100,000 pfu/vagina of virus at 48 hours post-challenge (FIG. 26A). Vaccination with either GFP or HSV-2 gD proteins had little to no effect on the amount of HSV-2 challenge virus shed from vaginas at 48 hours post-challenge (FIG. 26A). In contrast, footpad vaccination with the live viruses, HSV-2 MS or 0ΔNLS, was associated with an average ~140-fold decrease in HSV-2 challenge virus shedding at 48 hours post-challenge (FIG. 26A).

A similar trend was observed at 48 and 144 hours post-challenge when animals were injected with the luciferin substrate to track the spread of HSV-2 MS luciferase away from the initial site of challenge, the vagina (FIGS. 26B, 26C). However, vaccination with HSV-2 gD protein had some protective effects on reducing HSV-2 MS luciferase spread as only 66% of the gD-vaccinated mice developed overt disease and/or died of the infection (not shown). In contrast, vaccination with 2 shots of HSV-2 MS or HSV-2 0ΔNLS (in the rear footpads) completely prevented the spread of HSV-2 MS luciferase away from the site of challenge, the vagina, in all mice tested (FIGS. 26B, 26C). The "glow" is shown as stipple in FIGS. 26B-26C, with more stipple density meaning more glow, and hence viral infection.

HSV-2 0Δ4BD-Vaccination Against the Spread of HSV-2 Infection.

1. HSV-2 0Δ4BD Vaccine-Induced Protection Against HSV-2 Ms-Luciferase

Side-by-side comparisons of two HSV-2 ICP0⁻ viruses, HSV-2 0Δ4BD and HSV-2 0ΔNLS, have been performed to compare their potential to function as safe and effective live HSV-2 viral vaccines. Unlike HSV-2 0ΔNLS, HSV-2 0Δ4BD produces visible symptoms in ~20% of mice following ocular inoculation. This does not necessarily mean that HSV-2 0Δ4BD could not be used safely as an effective human vaccine, particularly if it were used as the $2^{nd}$ or $3^{rd}$ shot in a booster series. However, it would appear at this juncture that HSV-2 0ΔNLS is the safer (less virulent) of the two HSV-2 ICP0⁻ viruses.

Several pilot experiments have been performed to initially evaluate the potential of HSV-2 0Δ4BD to elicit a protective immune response in vaccine recipients relative to the positive control of HSV-2 0ΔNLS, which we have now established as a treatment that elicits a robust protective immune response against HSV-2 MS challenge. The results of one such pilot experiment with HSV-2 MS luciferase challenge of the left and right eyes is shown.

Figure 27A:
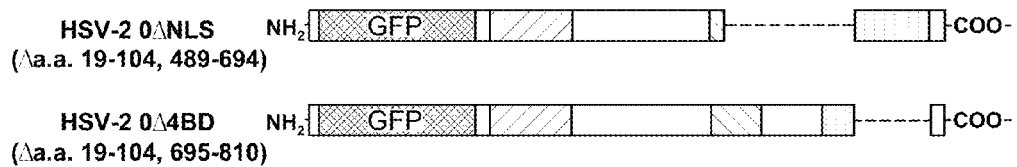
FIG. 27A shows a schematic representation of the ICP0 protein from HSV-2 0ΔNLS or HSV-2 0Δ4BD.
Figure 27B:
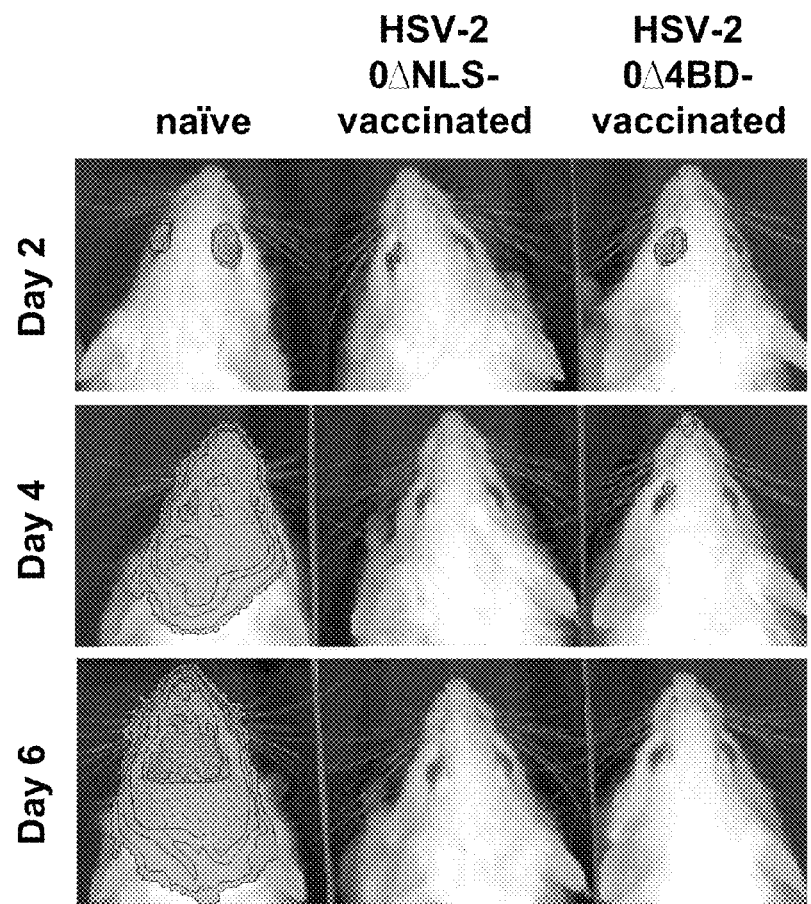
FIG. 27B shows that mice exposed to HSV-2 0ΔNLS or HSV-2 0Δ4BD virus acquire potent immunity to the spread of a 'glowing' HSV-2 MS luciferase virus from an ocular site of challenge.

On Day 70 post-vaccination, mice that received 1 of 3 treatments were compared for their ability to resist the replication and spread of HSV-2 MS luciferase following challenge with 100,000 pfu/eye (FIGS. 27A-27B). Consistent with previous experiments, HSV-2 MS luciferase spread in an uncontrolled fashion in naïve mice between Days 2 and 6 post-challenge (FIG. 27B) and produced lethal disease by Day 9 post-challenge. In contrast, vaccination with HSV-2 0ΔNLS or HSV-2 0Δ4BD in the rear footpads at Day 0 (with no booster shot) largely prevented the spread of HSV-2 MS luciferase away from the site of challenge (FIG. 27B). Small regions of HSV-2 MS-luciferase could be visualized in the eyes of mice at Days 2 and 4 post-challenge (FIG. 27B). However, extensive spread of HSV-2 MS-luciferase did not occur in HSV-20ΔNLS or HSV-20Δ4BD-vaccinated mice, and these animals developed no signs of overt disease at any time post-challenge. Thus, HSV-2 0ΔNLS or HSV-2 0Δ4BD vaccinated mice are highly resistant to spread of "glowing" HSV-2 MS luciferase from the initial site of challenge.

The "glow" is shown as stipple in FIG. 27B, with more stipple density meaning more glow, and hence viral infection.

2. HSV-2 0Δ4BD Vaccine-Induced Protection Against HSV-2 MS-GFP

On Day 70 post-vaccination, mice that received 1 of 3 treatments were compared for their ability to resist the replication and spread of HSV-2 MS GFP following challenge with 100,000 pfu/eye (FIG. 28). Consistent with previous experiments, HSV-2 MS GFP spread in an uncontrolled fashion in naïve mice between Days 1 and 7 post-challenge (FIG. 28) and produced lethal disease by Day 9 post-challenge. In contrast, vaccination with HSV-2 0ΔNLS or HSV-2 0Δ4BD in the rear footpads at Day 0 (with no booster shot) largely prevented the spread of HSV-2 MS-GFP away from the site of challenge (FIG. 28). Small regions of HSV-2 MS-GFP replication could be visualized in the eyes of mice at Days 1 and 2 post-challenge (FIG. 28). However, extensive spread of HSV-2 MS-GFP did not occur in 0ΔNLS or 0Δ4BD-vaccinated mice, and these animals developed no signs of overt disease at any time post-challenge.

ICP0 Sequence Alignment Between 16 Different Herpesviruses

It has now been found that there is also significant conservation in ICP0 protein between the different herpesviruses. Table 7 shows a summary of 16 different herpesviruses ICP0 protein based on BLAST analysis and sequence alignment. One aspect the data reveals is the significant conservation of the RING finger domain throughout the ICP0 proteins of different herpesviruses. For many of the ICP0 proteins encoded by herpesviruses, such as bovine herpesvirus 1 and pseudorabiesvirus for example, there is clear functional evidence in the published literature that all of these ICP0 proteins are functional counterparts of one another.

TABLE 7

| Genbank accession # | Virus | Protein | Score | E-value |
|---|---|---|---|---|
| Human viruses | | | | |
| 1. sp|P28284.1| | Herpes simplex virus 2 | ICP0 | 1573 | 0.0 |
| 2. gb|ACM62222.1| | Herpes simplex virus 1 | ICP0 | 539 | 7e−151 |
| 3. gb|AAF61662.1| | Varicella-zoster virus | ORF61 protein | 50.1 | 3e−10 |

TABLE 7-continued

| Genbank accession # | Virus | Protein | Score | E-value |
|---|---|---|---|---|
| Non-human primate viruses | | | | |
| 4. ref|YP_164442.2| | Cercopithecine herpesvirus 2 | ICP0 | 198 | 2e-48 |
| 5. gb|AAP41476.1| | Macacine herpesvirus | ICP0 | 197 | 4e-48 |
| 6. ref|YP_443846.2| | Papiine herpesvirus 2 | ICP0 | 184 | 4e-44 |
| 7. ref|NP_077475.1| | Cercopithecine herpesvirus 9 | ICP0 | 56.2 | 4e-12 |
| Viruses of cats, kangaroos, and dogs | | | | |
| 8. gb|AAB80763.1| | Felid herpesvirus 1 | ICP0 | 63.9 | 2e-14 |
| 9. gb|AAL14419.1| | Macropodid herpesvirus 1 | ICP0 | 130 | 5e-28 |
| 10. dbj|BAA95211.1| | Canid herpesvirus 1 | ICP0 | 55.1 | 6e-12 |
| Viruses of livestock | | | | |
| 11. gb|ABY55292.1| | Suid herpesvirus 1 | early protein 0 | 57.8 | 1e-12 |
| 12. dbj|BAD27395.1| | Equid herpesvirus 1 | ICP0 | 52.4 | 6e-11 |
| 13. ref|NP_045280.1| | Equid herpesvirus 4 | ORF63 protein | 50.4 | 3e-10 |
| 14. dbj|BAH02488.1| | Equid herpesvirus 9 | ICP0 | 52.0 | 9e-11 |
| 15. sp|P29836.1| | Bovine herpesvirus 1 | ICP0 | 68.2 | 5e-09 |
| 16. ref|NP_954951.1| | Bovine herpesvirus 5 | BICP0 | 69.7 | 5e-16 |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein by specific reference in their entirety.

The invention claimed is:

1. A mutant herpesvirus comprising:
   a mutated gene that encodes:
   a mutant infected cell protein 0 (ICP0) that includes at least one in-frame deletion in a nuclear localization signal (NLS) region of ICP0.

2. The mutant herpesvirus as in claim 1, wherein the herpesvirus is selected from herpes simplex virus 1 (HSV-1) and herpes simplex virus 2 (HSV-2).

3. The mutant herpesvirus as in claim 1, wherein the mutation is in the NLS region of ICP0 between:

amino acids corresponding to about amino acid 453 to about amino acid 531 of HSV-1 ICP0; or amino acids corresponding to about amino acid 468 to about amino acid 549 of HSV-2 ICP0.

4. The mutant herpesvirus as in claim 1, wherein the mutant herpesvirus is derived from a herpes simplex virus type 1 (HSV-1).

5. The mutant herpesvirus as in claim 1, wherein the mutant herpesvirus is derived from a herpes simplex virus type 2 (HSV-2).

6. An immunogenic composition comprising a mutant herpesvirus as in claim 1.

7. An immunogenic composition comprising:
a pharmaceutically acceptable carrier; and
a mutant herpes simplex virus comprising a gene that encodes:
a mutant infected cell protein 0 (ICP0) that includes at least one in-frame deletion in a nuclear localization signal (NLS) region of ICP0.

8. The immunogenic composition as in claim 7, wherein the at least one in-frame deletion is in the NLS region of ICP0 between:
amino acids corresponding to about amino acid 453 to about amino acid 531 of HSV-1 ICP0; or
amino acids corresponding to about amino acid 468 to about amino acid 549 of HSV-2 ICP0.

9. The immunogenic composition as in claim 7, wherein the immunogenic composition includes a mutant herpesvirus that is derived from a herpes simplex virus type 1 (HSV-1) having a mutant ICP0 gene.

10. The immunogenic composition as in claim 7, wherein the immunogenic composition includes a mutant herpesvirus that is derived from a herpes simplex virus type 2 (HSV-2) having a mutant ICP0 gene.

11. The mutant herpesvirus as in claim 1, wherein the mutant herpesvirus is characterized by one or more of:
being incapable of causing a herpes disease; or
being immunogenic for at least 100 days after administration.

12. A mutant herpes simplex virus 2 (HSV-2) comprising:
a mutated gene that encodes:
a mutant infected cell protein 0 (ICP0) that includes at least one in-frame deletion in one or more of a RING finger region or a nuclear localization signal (NLS) region of ICP0.

13. The mutant herpesvirus as in claim 12, wherein the mutation is in the RING finger region of ICP0 between amino acids corresponding to about amino acid 123 to about amino acid 252 of HSV-2 ICP0.

14. The mutant herpesvirus as in claim 12, wherein the mutation is in the NLS region of ICP0 between amino acids corresponding to about amino acid 468 to about amino acid 549 of HSV-2 ICP0.

* * * * *